US006571118B1

(12) United States Patent
Utzinger et al.

(10) Patent No.: US 6,571,118 B1
(45) Date of Patent: May 27, 2003

(54) COMBINED FLUORESCENCE AND REFLECTANCE SPECTROSCOPY

(75) Inventors: Urs Utzinger, Austin, TX (US); Anthony J. Durkin, Watertown, MA (US); Holger Fuchs, Tempe, AZ (US); Ann M. Gillenwater, Pearland, TX (US); Douglas L. Heintzelman, Plainfield, IN (US); Rebecca R. Richards-Kortum, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/304,922

(22) Filed: May 4, 1999

Related U.S. Application Data

(60) Provisional application No. 60/084,290, filed on May 4, 1998.

(51) Int. Cl.[7] .................................................. A61B 5/00

(52) U.S. Cl. ........................ 600/476; 600/478; 356/318

(58) Field of Search ................................... 600/473, 475, 600/476, 477, 310, 478; 250/339.01, 340, 338.1, 301; 356/300, 326, 317, 318

(56) References Cited

U.S. PATENT DOCUMENTS

| 4,966,458 | A | * | 10/1990 | Burns et al. ................. 356/328 |
| 5,205,291 | A | * | 4/1993 | Potter .......................... 600/476 |
| 5,384,589 | A | * | 1/1995 | Ulich et al. .................... 348/31 |
| 5,421,337 | A | * | 6/1995 | Richards-Kortum et al. ........................... 600/476 |
| 5,452,723 | A | * | 9/1995 | Wu et al. ..................... 600/473 |
| 5,491,344 | A | | 2/1996 | Kenny et al. ............. 250/461.1 |
| 6,026,319 | A | * | 2/2000 | Hayashi ....................... 600/476 |

OTHER PUBLICATIONS

Bigio and Mournat, "Ultraviolet and visible spectroscopies for tissue diagnostics: fluorescence spectroscopy and elastic–scattering spectroscopy," *Physics in Medicine & Biology*, 42:803–814, 1997.

Braichotte et al., "Clinical pharmacokinetic studies of photofrin by fluorescence spectroscopy in the oral cavity, the esophagus and the bronchi," *Cancer*, 75(11), 2768–78, 1995.

Chen et al., "Light–induced fluorescence spectroscopy: a potential diagnostic tool for oral neoplasia," *Proc. Nat. Scien. Counci, Rep. of China–Part B, Life Sci.*, 20(4): 123–30, 1996.

Cothren et al., "Gastrointestinal tissue diagnosis by laserinduced fluorescence spectroscopy at endoscopy," *Gastrointestinal Endoscopy*, 36:105–111, 1990.

Dhingra et al., "Early diagnosis of upper aerodigestive tract cancer by autofluorescence," *Arch. Otolaryngol Head Nec Surg.*, 122(11):1181–1186, 1996.

Dhingra et al., "Diagnosis of head and neck precancerous lesions in an animal model using fluorescence spectroscopy," *Laryngoscope*, 108:471–5, 1998.

(List continued on next page.)

*Primary Examiner*—Ruth S. Smith
(74) *Attorney, Agent, or Firm*—Fulbright & Jaworski, LLP

(57) ABSTRACT

Methods and apparatus for performing fluorescence and spatially resolved reflectance spectroscopy on a sample. A sample is irradiated with a fluorescence excitation fiber and radiation is collected from the sample with a fluorescence collection fiber and detected to form fluorescence spectra. The sample is also illuminated with a reflectance illumination fiber and reflected light from the sample is collected at a plurality of collection positions and detected to form spatially resolved reflectance spectra. The fibers may form a probe arranged in concentric sections. The spectra are analyzed by pre-processing and reducing the dimensionality of the spectral data.

48 Claims, 47 Drawing Sheets

OTHER PUBLICATIONS

Durkin and Richards–Kortum, "Comparison of methods to determine chromophore concentrations from fluorescence spectra of turbid samples," *Lasers in Surgery and Medicine,* 19:75–89, 1996.

Durkin et al., "Relation between fluorescence spectra of dilute and turbid samples," *Applied Optics,* 33(3):414–423, 1994.

Durkin et al., "Optically dilute, absorbing, and turbid phantoms for fluorescence spectroscopy of homogeneous and inhomogeneous samples," *Applied Spectroscopy,* 47:2114–2121, 1993.

Fahey et al., "Meta–analysis of pap test accuracy," *Amer. J Epidemiology,* 141(7), 680–689, 1995.

Fuchs et al., "Combined fluorescence and reflectance spectroscopy: in vivo assessment of oral cavity epithelial neoplasia," Abstract, *IEEE Opt. Soc. America,* 6:306–7, 1998.

Gillenwater et al., "Noninvasive diagnosis of oral neoplasia based on fluorescence spectroscopy and native tissue autofluoresence," *Arch. Otolaryngol. Head Neck Surg.,* 124(11):1251–1258, 1998.

Glassman et al., "Ultraviolet excited fluorescence spectra from non–malignant and malignant tissues of the gynecologic tract," *Lasers in Life Sciences,* 5(1–2):49–58, 1992.

Hung et al., "Autofluorescence of normal and malignant bronchial tissue," *Lasers in Surgery and Medicine,* 11(2), 99–105, 1991.

Kapadia et al., "Laser–induced fluorescence spectroscopy of human colonic mucosa," *Gastroenterology,* 99:150–157, 1990.

Koenig et al., "Laser induced autofluorescence diagnosis of bladder cancer," *J. Urology,* 156:1597–1601, 1996.

Kolli, et al. "Native cellular fluorescence of neoplastic upper aerodigestive mucosa," *Arch. Otolaryng. Head Neck Surg.,* 121(11):1287–92, 1995.

Kulapaditharom and Boonkitticharoen, "Laser–induced fluorescence imaging in localization of head and neck cancers," *Ann. Otol. Rhinol. Laryngol.,* 107:241–246, 1998.

Kurman et al. "Interim guidelines of management of abnormal cervical cytology," *JAMA,* 217:1866–1869, 1994.

Lam et al., "Detection of dysplasia and carcinoma in situ by ratio fluorimetry," *Am Rev Dis* 146:1458–1461, 1992.

Lam et al., "Detection and localization of early lung cancer by imaging techniques," *Chest,* 103:12s–14s, 1993.

Lin et al., "Measurement of tissue optical properties by the use of oblique–incidence optical fiber reflectometry," *Applied Optics,* 36(1):136–143, 1997.

Loh et al., "Oral versus intravenous administration of 5–aminolaevulinic acid for photodynamic therapy," *British Journal of Cancer,* 68(1), 41–51, 1993.

Mahadevan et al., "Study of the fluorescence properties of normal and neoplastic human tissue," *Lasers in Surgery & Medicine,* 13:647–655, 1993.

Mitchell "Accuracy of Colposcopy," *Clin. Consultations in Obstetrics and Gynecology,* 6(1), 70–73, 1994.

Mourant et al., "Spectroscopic diagnosis of bladder cancer with elastic light scattering," *Lasers in Surgery & Medicine,* 17:350–357, 1995.

Nichols et al., "Design and testing of a white–light, steady–state diffuse reflectance spectrometer of determination of optical properties of highly scattering systems," *Applied Optics,* 36:93–104, 1997.

Nishioka, "Laser–induced fluorescence spectroposcopy," *Gastrointestinal Endoscopy Clinics of North America,* 4:313–326, 1994.

Onizawa et al., "Fluorescence photography as a diagnostic method for oral cancer," *Cancer Lett.,* 108(1):61–6, 1996.

Ramanujam et al. "Development of a multivariate statistical algorithm to analyze human cervical tissue fluorescence spectra acquired in vivo," *Lasers Surg Med,* 19(1), 46–62, 1996.

Ramanujam et al., "Spectroscopic diagnosis of cervical intraepithelial neoplasia (CIN) in vivo using laser–induced fluorescence spectra at multiple excitation wavelenghts," *Lasers Surg Med,* 19(1), 63–74, 1996.

Ramanujam et al., "Cervical precancer detection using a multivariate statistical algorithim based on laser–induced fluorescence spectra at multiple excitation wavelenghts," *Photochemistry & Photobiology,* 64:720–735, 1996.

Richards–Kortum and Sevick–Muraca, "Quantitative optical spectroposcopy for tissue diagnosis," *Annual Review of Physical Chemistry,* 47:555–606, 1996.

Richards–Kortum et al., "Spectroscopic diagnosis of colonic dysplasia," *Photochemistry & Photobiology* 53:777–786, 1991.

Richards–Kortum, "Fluorescence spectroscopy of turbid media," In: *Optical–Thermal Response of Laser Irradiated Tissue,* Welch, Van Gemert (Eds.), Plenum Press, New York, Chapter 20, 1994.

Roy et al., "Diagnostic fluorescence spectroscopy of oral mucosa," SPIE, 2395: 135–142, 1995.

Schantz et al., "In vivo native cellular fluorescence and histological characteristics of head and neck cancer," *Clinical Cancer Research,* 4:1177–1182, 1998.

Schomacker et al., "Ultraviolet laser–induced fluorescence of colonic tissue: basic biology and diagnostic potential," *Lasers in Surgery & Medicine.* 12(1), 63–78, 1992.

Schomacker et al., "Ultraviolet laser–induced fluorescence of colonic polyps," *Gastrointerology,* 102:1155–1160, 1992.

Sterenborg et al., "In vivo fluorescence spectroscopy and imaging of human skin tumors," *Dermatologic Surgery,* 21:821–822, 1995.

Trujillio et al., "Method to determine tissue fluorescence efficiency in vivo and predict signal–to–noise ratio for spectrometers," *Applied Spectroscopy,* 52(7):943–951, 1997.

Utzinger et al., "Performance Estimation of Diagnostic Tests for Cervical Pre–Cancer Based on Fluorescence Spectroscopy: Effects of Tissue Type, Sample Size, Population and Signal–to–Noise Ratio," *IEEE Trans BME,* 46(11):1293–1303, 1999.

Wagnieres et al., "In Vivo Fluorescence Spectroscopy and Imaging for Oncological Applications," *Photochemistry and Photobiology* 68(5):603–632, 1998.

Wang and Jacques, "Use of a laserbeam with an oblique angle of incidence to measure the reduced scattering coeffiencnt of a turbid medium," *Applied Optics,* 34:2362–2366, 1995.

Welch et al., "Propagation of fluorescent light," *Lasers in Surgery and Medicine,* 21:166–178, 1997.

Wilkinson, "Pap Smears and screening for cervical neoplasia," *Clin Obstet Gynecol,* 33:817–825, 1990.

Wu et al., "Analytical model for extracting intrinsic fluorescence in turbid media," *Applied Optics,* 32(19):3585–3595, 1993.

Zangaro et al., "Rapid multiexcitation fluorescence spectroscopy system for in vivo tissue diagnosis," *Applied Optics,* 35:5211–5219, 1997.

Zuclich et al., "Rapid noninvasive optical characterization of the human lens," *Lasers in the Life Sciences,* 6:39–53, 1994.

Zuluaga et al., "Fluorescence excitation emission matrices of human tissue: A system for in vivo measurement and method of data analysis," *Applied Spectroscopy,* 53(3):302–310, 1999.

* cited by examiner

COMBINED FLUORESCENCE AND REFLECTANCE SPECTROSCOPY

This application claims priority to provisional patent application Ser. No. 60/084,290 filed May 4, 1998 entitled, "Combined Fluorescence and Reflectance Spectroscopy" by Rebecca Richards-Kortum, Urs Utzinger, Holger Fuchs, Ann M. Gillenwater, and Doug Heintzehnan. The entire text of the above-referenced disclosure is specifically incorporated by reference herein without disclaimer.

The United States government has rights to the present invention pursuant to a grant from the National Institutes of Health.

BACKGROUND OF THE INVENTION

1. Field of the Invention

The present invention relates generally to the fields of optical imaging. More particularly, it concerns apparatus and methods for combining fluorescence and reflectance spectroscopy for the imaging of samples, including both in situ and ex situ imagining of body tissues.

2. Description of Related Art

Cancer is one of the leading causes of death in the United States and in the world. In the United States alone, deaths from cancer are estimated to number 560,000 in 1997 (American Cancer Society Online. Cancer Facts & Figures). Currently, diagnosis and treatment of cancer follow histopathologic evaluation of directed biopsies. However, the tissue removal necessitated by these techniques not only may alter the progression of the disease (Robbins and Kumar, 1984) but is also very costly. Improving the capability for in situ monitoring of disease progression could greatly enhance the ability to detect and treat cancer and precancer (Kelloff et al., 1992).

A growing number of clinical studies have demonstrated that fluorescence spectroscopy may be used to distinguish normal and abnormal human tissues in vivo in the skin, head and neck, genito-urinary tract, gastro-intestinal tract, breast, and brain. It is well known that fluorescence intensity and lineshape are a function of both the excitation and emission wavelength in samples containing multiple chromophores, such as human tissue. A complete characterization of the fluorescence properties of an unknown sample requires measurement of a fluorescence excitation emission matrix, in which the fluorescence intensity is recorded as a function of both excitation and emission wavelength. The field of analytical chemistry has exploited the fluorescence properties of different compounds to identify and quantify them in mixtures.

Most clinical studies reported to date have measured fluorescence emission spectra at only a small number of excitation wavelengths (typically one to three) due to clinical requirements imposed on the size, speed and sensitivity of instrumentation. The choice of excitation wavelength has been based on factors which vary from study to study, but include laser availability and predictions of chromophores thought to be present in normal and abnormal tissues and measurements of fluorescence excitation emission matrices (EEM) of normal and abnormal tissues in vitro. While in vitro measurements of tissue EEMs are feasible using commercially available scanning fluorimeters, several studies have demonstrated that the optical properties of tissue change significantly when tissue is examined in vitro due in part to interruption of the blood supply, oxidation and small size of biopsies. Thus, in vitro studies to select excitation wavelengths are of limited value.

Several recent studies have suggested that differences in optical properties, assessed using diffuse reflectance spectroscopy, may be used to discriminate normal and abnormal human tissues in vivo in the urinary bladder and the skin. Furthermore, measuring both fluorescence and diffuse reflectance spectra may provide additional information of diagnostic value.

A system capable of measuring spatially resolved reflectance spectra and fluorescence excitation emission matrices in vivo would remove limitations of many previous studies, potentially enabling prediction of excitation wavelengths that provide greatest discrimination of normal and abnormal tissues, as well as a better understanding of the relative diagnostic ability of changes in absorption, scattering and fluorescence properties of tissue. Although fiber optic systems to record fluorescence EEMs and reflectance spectra at a single spatial location have been reported, such systems have measured data from only a single spatial location, and have thus not been able to perform spatially resolved spectroscopy. Additionally, previous systems have not been well-adapted for in-vivo studies of various tissues.

SUMMARY OF THE INVENTION

In one respect, the invention is an apparatus for performing fluorescence and spatially resolved reflectance spectroscopy on a sample, and it includes a light source, a monochromator, a reflectance illumination fiber, a fluorescence excitation fiber, an imaging spectrograph, a fluorescence collection fiber, a reflectance collection fiber, and a detector. The monochromator is in optical communication with the light source. The reflectance illumination fiber is in optical communication with the light source. The fluorescence excitation fiber is in optical communication with the monochromator. The fluorescence collection fiber is in optical communication with the imaging spectrograph. The reflectance collection fiber is in optical communication with the imaging spectrograph and is in spaced relation with the reflectance illumination fiber. The detector is in optical communication with the imaging spectrograph.

In other aspects, the light source may include a Xe arc lamp. The monochromator may include a double monochromator. The detector comprises a thermo-electrically cooled CCD camera. The fluorescence excitation fiber and the fluorescence collection fiber may be integral. One or more of the fibers may be positioned flush with the sample. The apparatus may also include a spacer positioned between one or more of the fibers and the sample. The reflectance illumination fiber, the fluorescence excitation fiber, the fluorescence collection fiber, and the reflectance collection fiber may define a fiber optic probe. The probe may be configured to be positioned within a trocar. The probe may include a center section and an outer section, and the fluorescence excitation fiber and the fluorescence collection fiber may be positioned in the center section, and the reflectance illumination fiber and the reflectance collection fiber may be positioned in the outer section. The apparatus may include a plurality of fluorescence excitation and collection fibers arranged in a circular bundle. The apparatus may include a plurality of reflectance collection fibers defining a plurality of collection positions. The plurality of collection positions may be spaced between about 0 and about 10 millimeters from the reflectance illumination fiber. The reflectance collection fiber may define a collection position at about 180 degrees relative to the reflectance illumination fiber. The reflectance collection fiber may define a collection position at about 90 degrees relative to the reflectance illumination fiber. The reflectance collection fiber may define a collection position at about 45 degrees relative to the reflectance illumination fiber. The apparatus may include one or more fibers in optical communication with the light source and configured to illuminate the sample during operation of the apparatus. The apparatus may include a plurality of fluorescence excitation fibers arranged in one or more rows adjacent the monochromator. The apparatus may include a plurality of fluorescence excitation fibers and a plurality of reflectance collection fibers arranged in a single row adjacent the imaging spectrograph. The apparatus may include one or more unconnected fibers interspersed with the plurality of fluorescence excitation fibers and the plurality of reflectance collection fibers. The apparatus may include a fiber connected from the light source to the imaging spectrograph to monitor spectral output of the light source. The apparatus may include a controller coupled to the detector.

In another respect, the invention is an apparatus for measuring fluorescence and spatially resolved reflectance spectra of a sample. The apparatus includes a light source, a monochromator, a fiber optic probe, an imaging spectrograph, and a detector. The monochromator is in optical communication with the light source. The fiber optic probe is in optical communication with the light source and with the monochromator. The probe includes a plurality of fluorescence excitation and collection fibers in spaced relation and a plurality of reflectance collection fibers in spaced relation with a reflectance illumination fiber. The imaging spectrograph is in optical communication with the plurality of fluorescence collection fibers and with the plurality of reflectance collection fibers. The detector is in optical communication with the imaging spectrograph.

In other aspects, the plurality of reflectance collection fibers and the reflectance illumination fiber may be positioned concentrically about the plurality of fluorescence excitation and collection fibers. At least one of the plurality of reflectance collection fibers may define a collection position at about 180 degrees relative to the reflectance illumination fiber. At least one of the plurality of reflectance collection fibers may define a collection position at about 90 degrees relative to the reflectance illumination fiber. At least one of the plurality of reflectance collection fibers may define a collection position at about 45 degrees relative to the reflectance illumination fiber. The plurality of collection positions may be spaced between about 0 and about 10 millimeters from the reflectance illumination fiber. The probe may include between twenty-one and forty-six optical fibers.

In another respect, the invention is a method for combined fluorescence and spatially resolved reflectance spectroscopy of a sample. The method includes directing radiation to the sample with a fluorescence excitation fiber, collecting radiation from the sample with a fluorescence collection fiber, directing the radiation from the sample to an imaging spectrograph and a detector, illuminating the sample with a reflectance illumination fiber, collecting reflected light from the sample with a reflectance collection fiber in spaced relation with the reflectance illumination fiber, and directing the reflected light from the sample to an imaging spectrograph and a detector.

In other aspects, the step of collecting reflected light may include collecting reflected light from a plurality of collection positions with a plurality of reflectance collection fibers. The step of collecting reflected light may include collecting reflected light from the sample with a reflectance collection fiber defining a collection position at about 180 degrees relative to the reflectance illumination fiber. The step of collecting reflected light may include collecting reflected light from the sample with a reflectance collection fiber defining a collection position at about 90 degrees relative to the reflectance illumination fiber. The step of collecting reflected light may include collecting reflected light from the sample with a reflectance collection fiber defining a collection position at about 45 degrees relative to the reflectance illumination fiber. The sample may include ovarian, head and neck, or cervical tissue. The method may also include analyzing spectral data from the detector to characterize the sample. The step of analyzing may include pre-processing the data and reducing a dimension of the data using principal component analysis. The step of analyzing may also include selecting one or more diagnostic principal components of the data and forming one or more algorithms. The step of analyzing may also include forming one or more composite algorithms. The step of analyzing may also include evaluating at least on of the algorithms using a cross-validation technique.

In another respect, the invention is a method for combined fluorescence and spatially resolved reflectance spectroscopy of a sample. The method includes directing radiation to the sample with a fluorescence excitation fiber, collecting radiation from the sample with a fluorescence collection fiber, directing the radiation from the sample to an imaging spectrograph and a detector, illuminating the sample with a reflectance illumination fiber, collecting reflected light at a plurality of collection positions from the sample with a plurality of reflectance collection fibers arranged in spaced relation, directing the reflected light from the sample to an imaging spectrograph and a detector to produce spectral data, pre-processing the data, and reducing a dimension of the data using principal component analysis.

The method may also include selecting one or more diagnostic principal components of the data and forming one or more algorithms. The method may also include forming one or more composite algorithms. The method may also include evaluating at least one of the algorithms using a cross-validation technique.

In another respect, the invention is a method for analyzing spectroscopy data to define an optimized reduced data set. The method includes pre-processing the spectroscopy data, reducing a dimension of the spectroscopy data using principal component analysis, and selecting one or more diagnostic principal components of the spectroscopy data.

In other aspects, the spectroscopy data may include combined fluorescence and spatially resolved reflectance spectroscopy data. The step of pre-processing may include normalization of the spectroscopy data. The step of pre-processing may include mean scaling the spectroscopy data. The step of pre-processing may include calculating one or more derivatives on the spectroscopy data. The method may also include eliminating redundant data from the spectroscopy data. The method may also include forming one or more algorithms and evaluating at least one of the algorithms using a cross validation technique. The method may also include forming one or more composite algorithms.

Applications for the methods and apparatus described herein are vast and include, but are not limited to, analysis and detection of disease including cancers and pre-cancers (such as cervical, head and neck, colon, lung, esophageal, ovarian) and atherosclerosis. Applications also include industry, including, but not limited to, the semiconductor industry.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
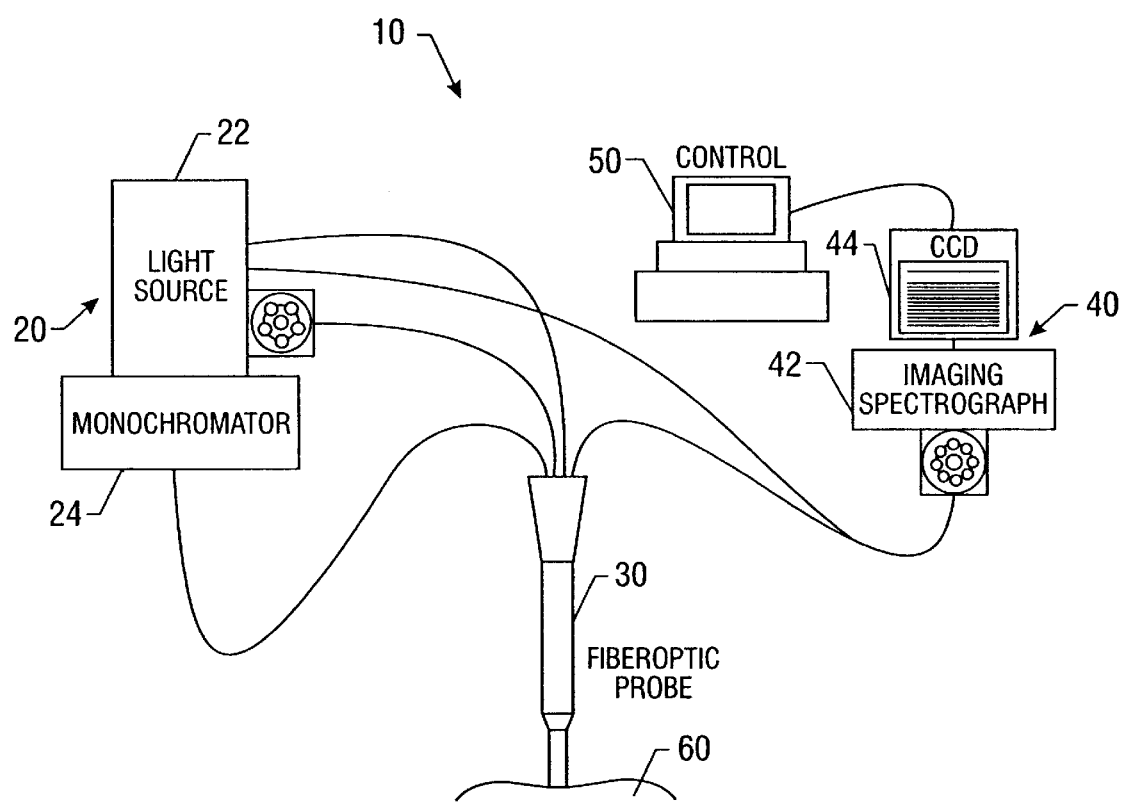
FIG. 1 Block diagram of a Fast EEM system according to one embodiment of the present disclosure.
Figure 2A:
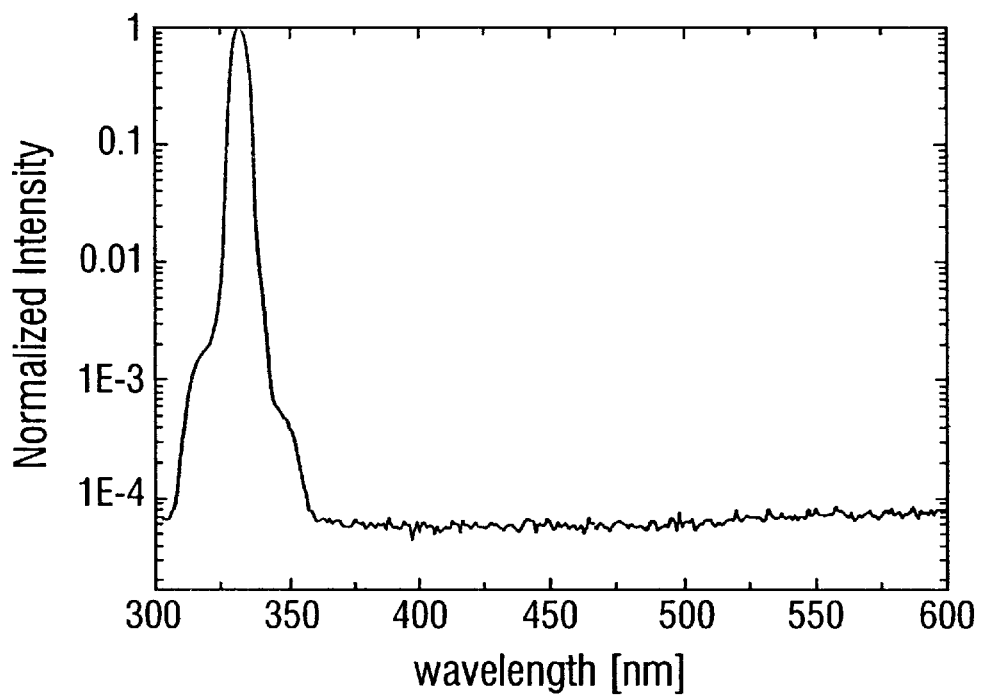
FIG. 2 Probe output at 332 nm according to one embodiment of the present disclosure.
Figure 2B:
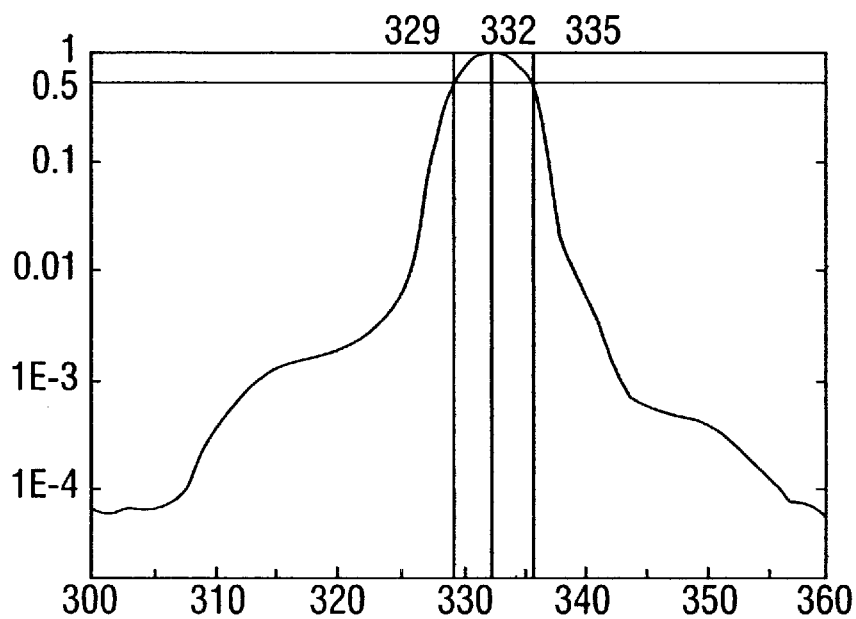

FIG. 1 shows one embodiment of an apparatus 10 according to the present disclosure. The apparatus is adapted to measure both reflectance and fluorescence data, and may be referred to as a Fast-EEM system (where EEM stands for excitation emission matrix) system. Fast EEM system 10, in one embodiment, may include four main components, although those having skill in the art will recognize that more or fewer components may be utlized: The components are: (a) an excitation source 20, which may include an arc lamp 22 and a monochromator 24 for monochromatic and broad band excitation, (b) a fiber optic probe 30, which may be configured to deliver excitation light to and collect remitted fluorescence from a sample 60, (c) a detection apparatus 40, which may include a filter wheel, an imaging spectrograph 42, and a CCD camera 44 and that spectrally resolves a collected signal, and (d) a control unit 50, which may be a personal computer used to run Fast EEM system 10 and to acquire data.

Excitation Source 20

The light source 22 for Fast EEM system 10, which may provide both quasi-monochromatic excitation for fluorescence and broad band illumination for reflectance, may be, in one embodiment, a 150 W ozone free Xe arc lamp (Spectral Energy Corp., Westwood N.J.) with a spherical rear reflector.

Figure 9A:
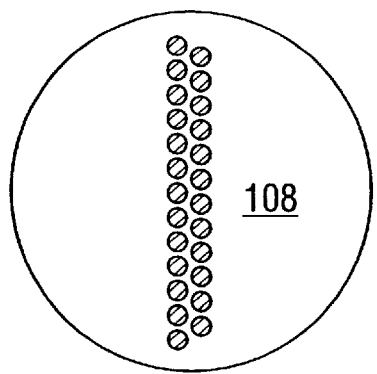
FIGS. 9A–9C. Monochromator and spectrograph connector with fluorescence and reflectance collection fibers according to one embodiment of the present disclosure.

A condenser system including two piano convex quartz lenses may be used to couple light into a monochromator 24. With the benefit of the present disclosure, those having skill in the art will understand that any optical filter or device suitable for creating bandpass filtered light may be used for monochromator 24. In one embodiment, monochromator 24 may be a single monochromator. A manual shutter (not shown) may be located between condensing optics and monochromator 24 and may be closed to prevent fluorescence excitation light from reaching sample 60 during reflectance measurements. The scanning speed of monochromator 24 may be, in one embodiment, about 10 nm/sec. Light may be coupled from the output slit of monochromator 24 into probe 30 via a fiber optic adapter (Spectral Energy, GMA 257) (not shown) that includes a quartz plano-convex lens and a 5× quartz microscope objective. The light passing through the objective may be focused to an appropriate shape to fill one or more fibers of probe 30. In one embodiment, light passing through the objective may be focused onto a vertical line onto twenty-five fibers of probe 30, the twenty-five fibers being arranged in two columns and placed at the focal plane of the objective (See FIG. 9A).

Figure 16A:
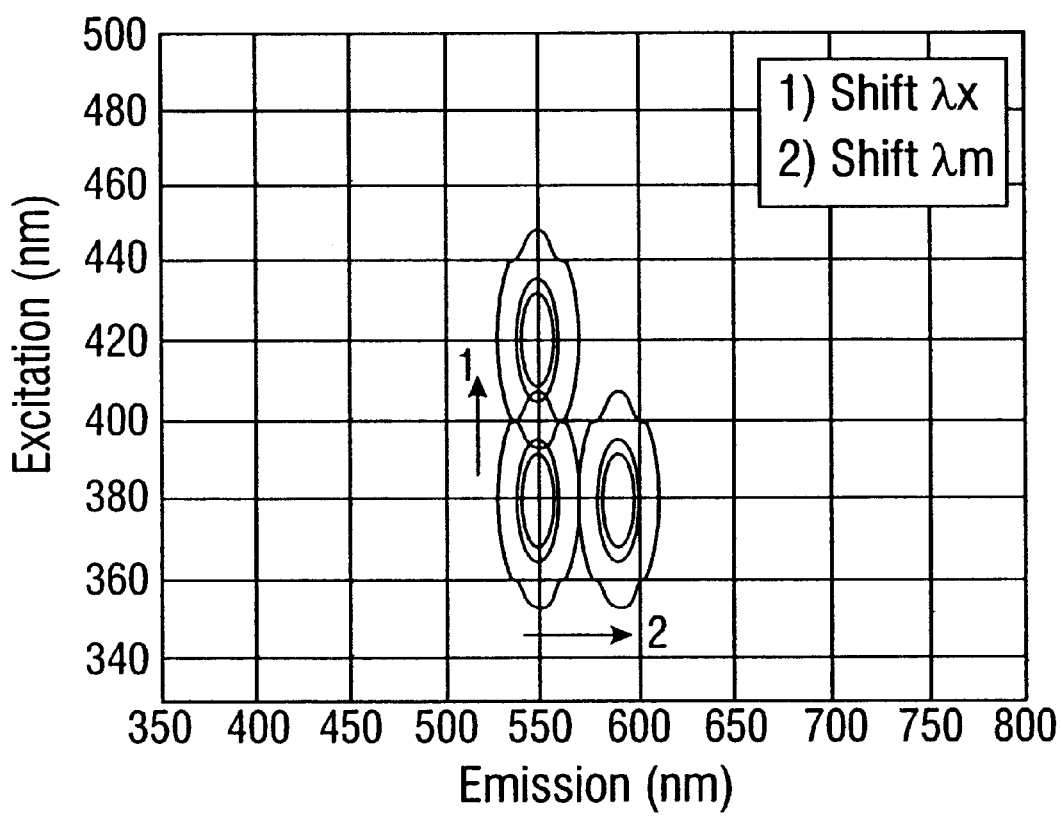
FIG. 16A Simulated EEM with peak shifting in [1] excitation wavelength [2] and emission wavelength.
Figures 1, 16B:
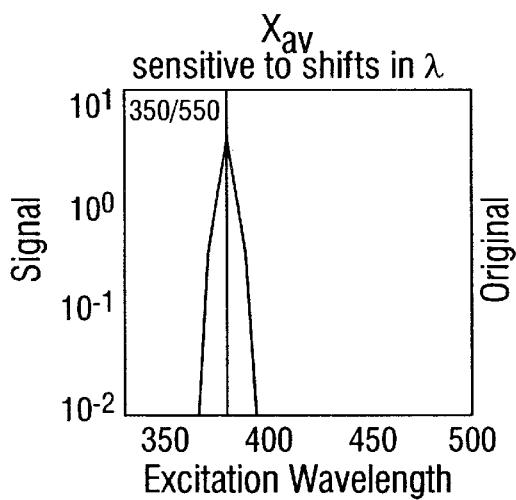
FIG. 16B Simulated EEM with peak shifting in [1] excitation wavelength [2] and emission wavelength. Calculated $x_{av}$ and $m_{av}$ for the simulated EEM. $x_{av}$ is sensitive to changes in the excitation position of the peak and $m_{av}$ is sensitive to the emission position.
Figures 4, 16B:
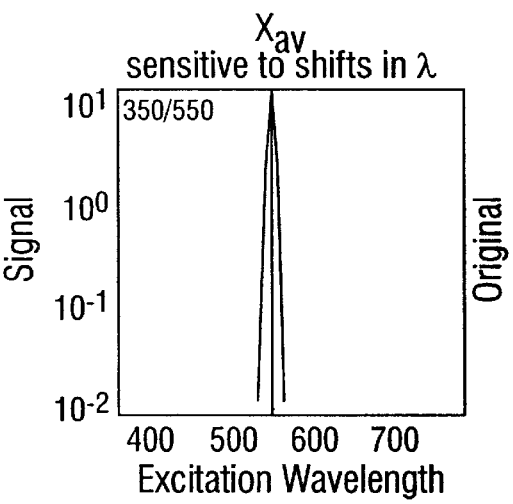

A reflectance excitation fiber (See, e.g., FIG. 6) may be coupled to the lamp housing of light source 22 via a micropositioner (not shown). Broadband light exiting the lamp housing through an exiting hole may be coupled to a reflectance illumination fiber using a quartz plano-convex lens (NA=0.24). A five position illumination filter wheel (not shown) placed between the lamp and the lens may include three long pass filters with 50% transmission at 295 nm, 515 nm and 715 nm, respectively. One of the filter positions may be blocked and may act as a shutter to prevent white light from reaching sample 60 during fluorescence measurements.

In another embodiment, the light source 22 for Fast EEM system 10, which may provide both quasi-monochromatic excitation for fluorescence and broad band illumination for reflectance, may be an ozone-free 450 W Xe arc lamp (FL-1007, Instruments SA, Edison, N.J.).

Light used for monochromatic fluorescence excitation may be focused with a spherical mirror (not shown) onto the input slit of monochromator 24. In this embodiment, monochromator 24 may be a double monochromator (DDD 180, Instruments SA, Edison, N.J.). A spherical rear reflector (not shown) may redirect light that is exiting the lamp in the opposite direction into the opposite direction onto the spherical mirror. The slit may be covered with a sapphire window, which may prevent hot air from flowing out of the lamp housing into the monochromator 24. A double monochromator may be chosen for monochromator 24 because of its higher stray light rejection compared to a single monochromator. A double monochromator may be configured in additive mode, which means that the dispersions of the two holographic gratings are added. Stray light in such a configuration may be so slight as to be negligible. The focal length of each of the two monochromators may be about 18 cm and the high throughput may be f/3.9. The two holographic gratings may have about 1200 grooves/mm and may be blazed at 500 nm. In this embodiment, the system's maximal resolution may be about 0.3 nm with an accuracy of about 0.5 nm. The scanning speed in this emboidment may be about 150 nm/s, and the usable wavelength range may be from about 300 to about 1000 nm. Wavelength scanning may be achieved with a direct digital steppermotor with a worm drive mechanism (not shown). Three computer-controlled slits (entrance, middle, and exit) may be opened between 0 and 7 mm in steps of 12.5 $\mu$m. In one embodiment, a slit-width of about 2 mm may be chosen for both the entrance and the exit slits. The middle slit twice may be opened as wide as the entrance and the exit slit to achieve an optimal performance. These settings guaranteed a spectral resolution of about 6 nm FWHM.

Figures 2, 16B:
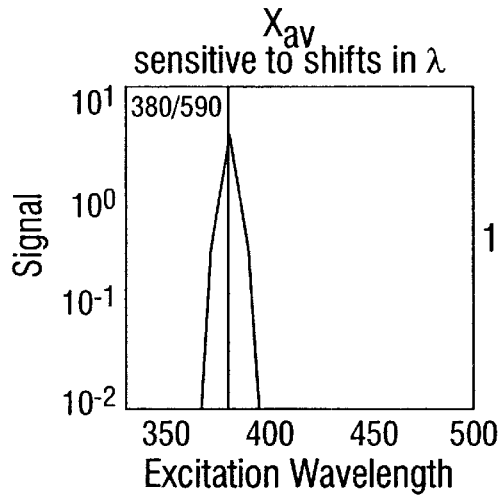

FIG. 2 shows a spectrum taken at 332 nm by coupling light through probe 30 through a fiber optic adapter into a scanning spectrofluorimeter (SPEX, Fluorolog II, Edison, N.J.). An emission scan from 300 nm to 600 nm was performed to collect the relative intensity of the probe output.

In one embodiment, the coupling of light into a fluorescence excitation bundle (See, e.g., FIG. 6 and FIG. 7) was done using a fiber-optic interface kit (220F, Instruments SA, Edison, N.J.). Two plano-convex lenses (different focal lengths) may be matched to different NAs of the exit slit and of a fiber bundle of probe 30 to minimize coupling losses. A computer-controlled shutter (LS6, Vincent Associates, Rochester, N.Y.) may be mounted in front of the probe connector to block fluorescence excitation light during reflectance measurements.

Light source 22 may be customized to provide white light output. White light may be needed (a) for reflectance measurements, (b) for visual observation of a measurement site by a physician, and (c) to monitor the lamp output.

Figure 3:
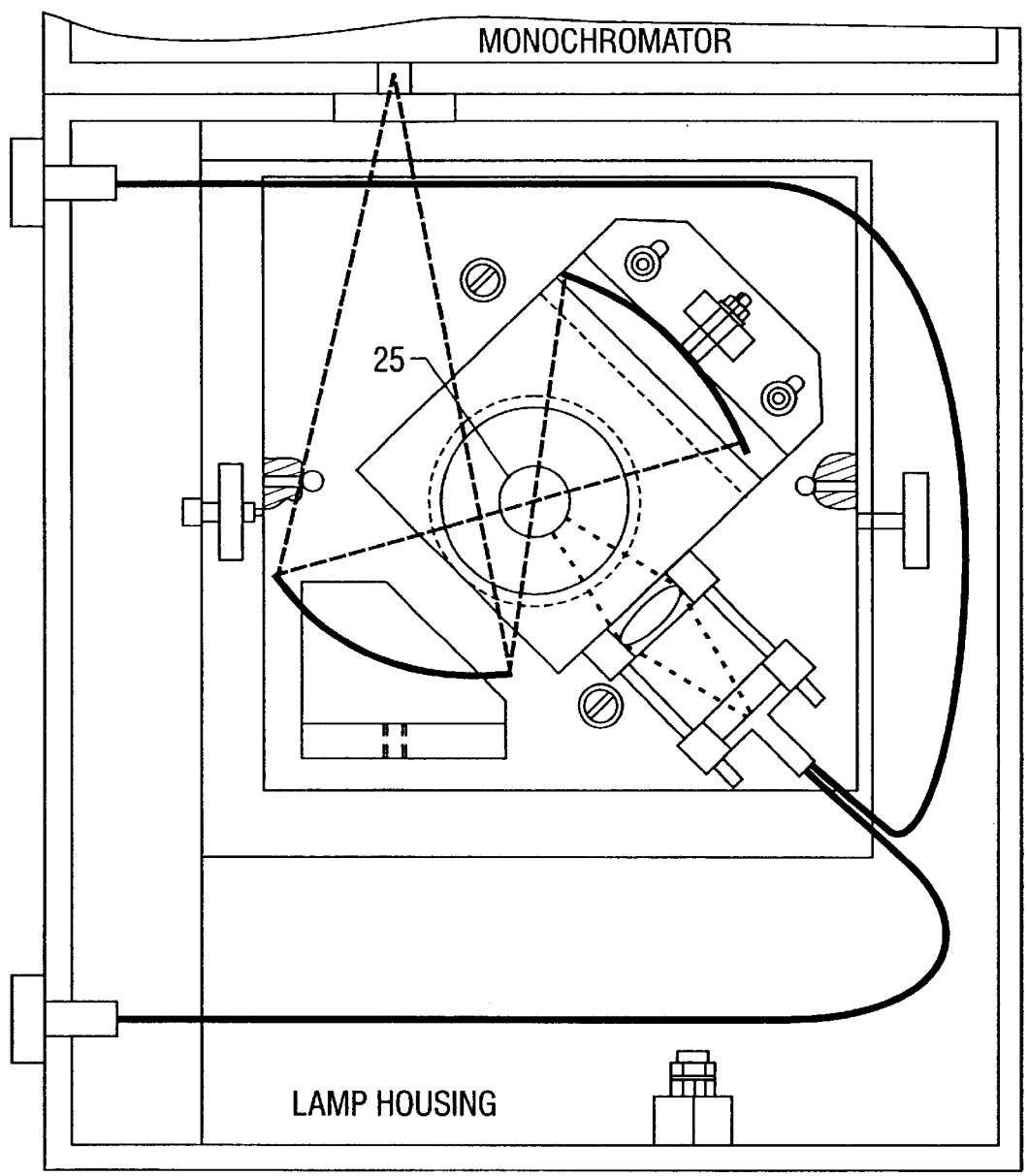
FIG. 3 Inside of a light source according to one embodiment of the present disclosure.
Figure 4:
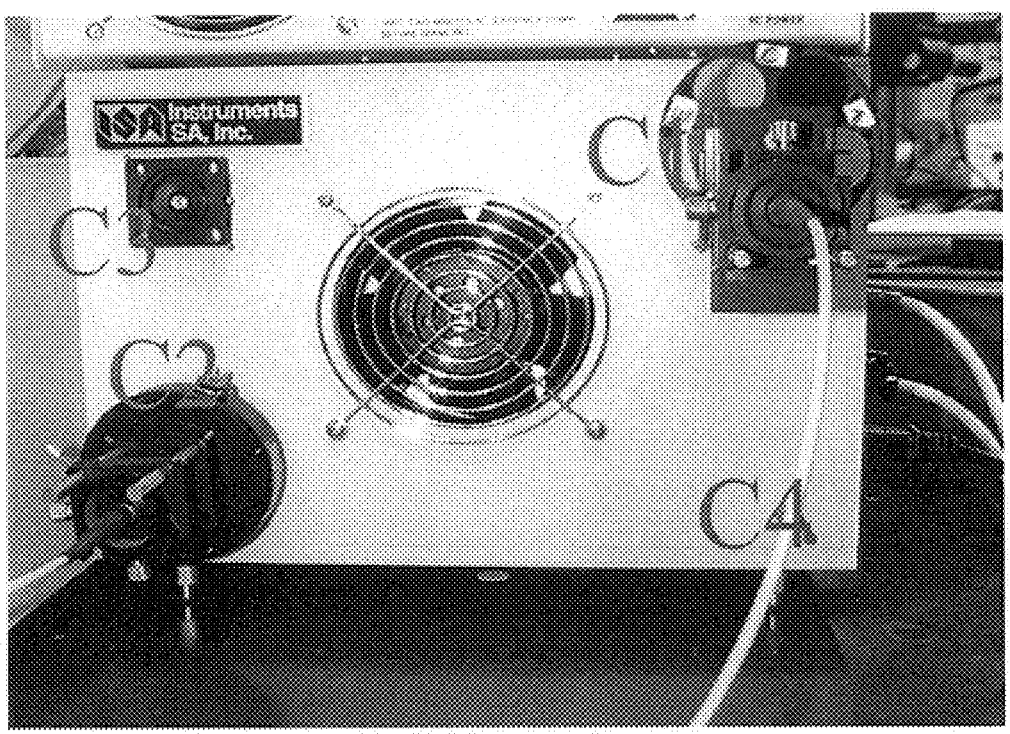
FIG. 4 Outside connectors of the light source according to one embodiment of the present disclosure.
Figure 5A:
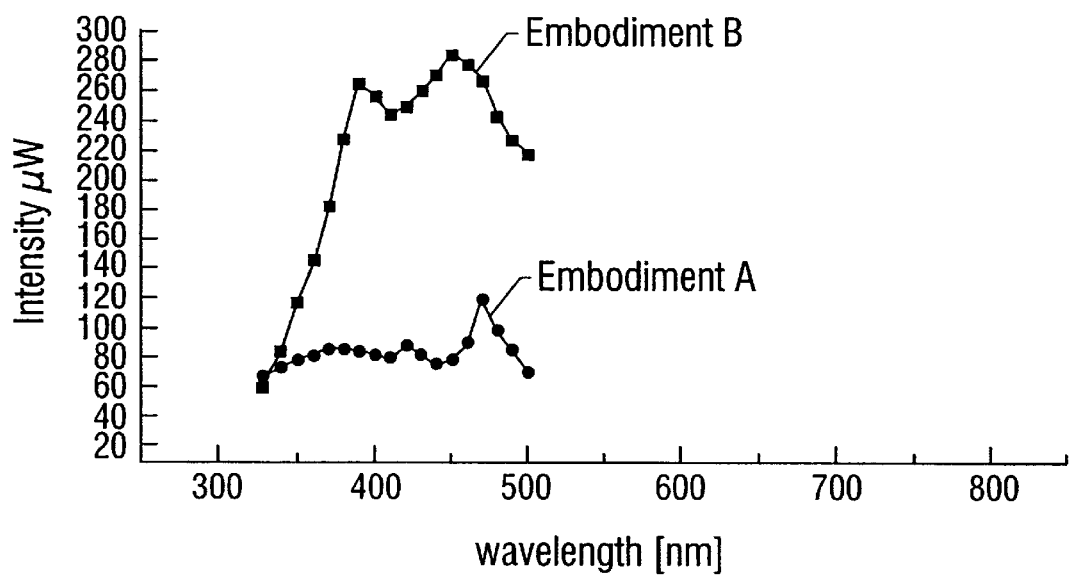
FIG. 5 Comparison between the monochromator and the spectral lamp output.
Figure 5B:
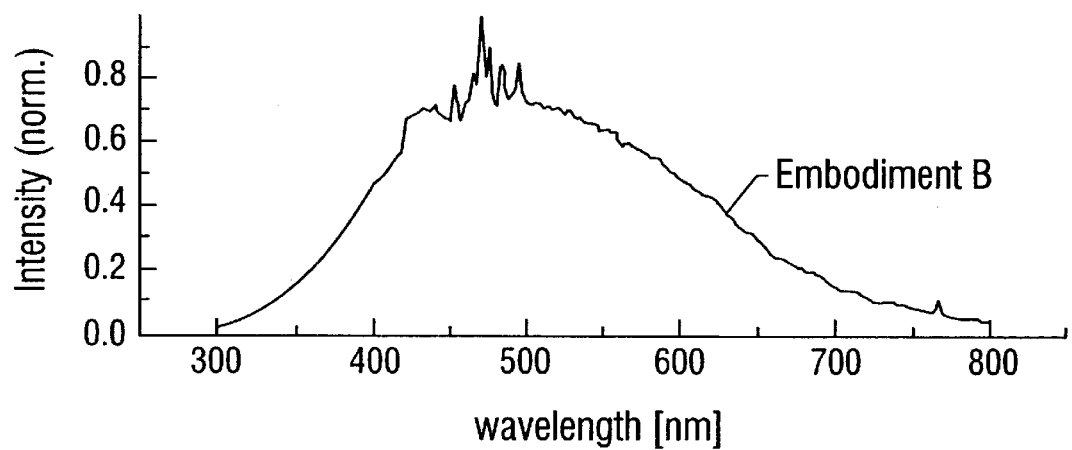

FIG. 3 shows a top view drawing of the inside of the lamp housing according to one embodiment. Light bulb 25 and ray traces (dashed lines) for the monochromator light are shown. In one embodiment, the optimal solution to provide white light output to the outside of the housing involved the use a bundle of quartz fibers. One biconvex lens, mounted in a custom-made rack inside the lamp housing, coupled light into a bundle of three 600 $\mu$m and one 50 $\mu$m high-temperature quartz fibers (Thermocoat, Fiberguide Industries, Stirling, N.J.). The light rays are indicated by the dotted line in FIG. 3. These fibers transported white light to four connectors on the outside of the housing (See FIG. 4). The first connector C1 may provide excitation light used for reflectance measurements. The five-position illumination filter wheel described previously may be placed between two biconvex quartz lenses (focal length=20 mm). The second connector C2 may be equipped with one quartz lens (focal length=20 mm) that focuses light onto the illumination fiber bundle. A second shutter (LS6, Vincent Associates, Rochester, N.Y.) may be placed between the connector and the lens, which may be closed during data acquisition and may otherwise be held open to deliver light to the in illumination fibers of probe 30. The third 600 $\mu$m fiber output C3 may be used for other purposes, or not at all. The 50 $\mu$m fiber output C4 may couple light into a fiber that is directly connected to imaging spectrograph 42 to record the lamp spectrum for every measurement. In one embodiment, however, this option is not used.

Figures 5, 16B:
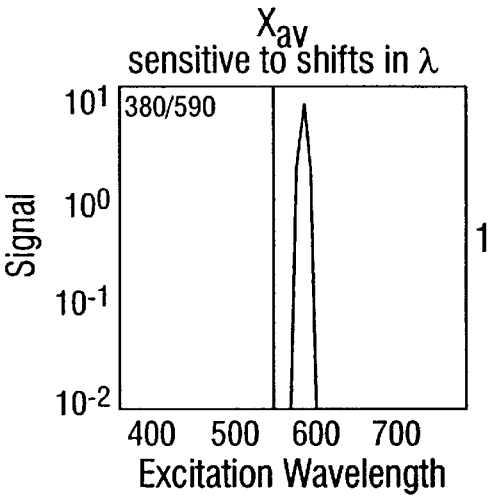
Figures 3, 16B:
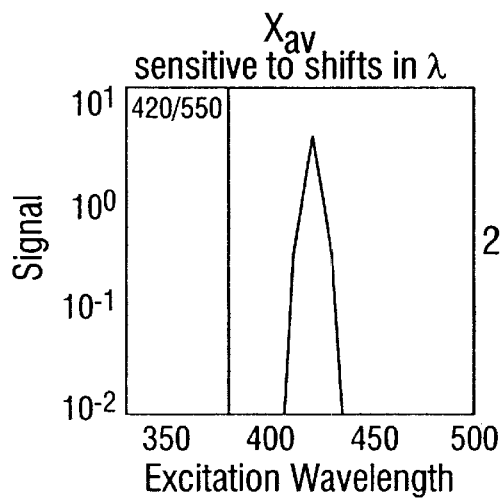
Figures 6, 16B:
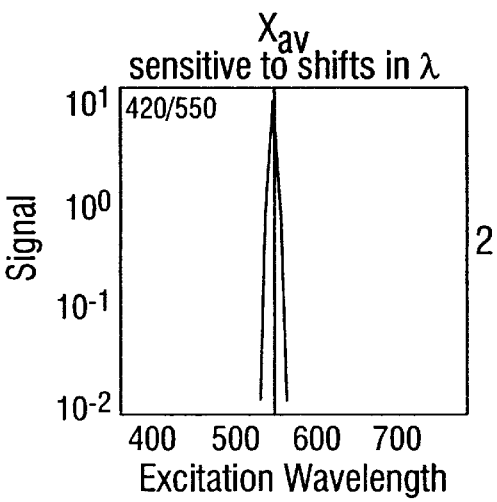

FIG. 5 illustrates the power output of two monochromatic illumination systems (one using a 150 W ozone free Xe arc lamp and the other using an ozone-free 450 W Xe arc lamp). The output was measured through probe 30 using a calibrated power meter (818-UV, Newport, Irvine, Calif.) and represents the flux (W) that is provided to sample 60, which may be a tissue sample. Above about 400 nm, an improvement in power of a factor of four is noticeable. Note that the lamp performed poorly below 400 nm. The light output at about 330 nm is only about 20% of the peak performance at 460 nm. The low UV output may be due to the fact that lamp is an ozone-free model. The light bulb is made out of UV blocking glass since Ozone is mainly produced in the surrounding air within this spectral region. In order to have a useful S/N ratio prolonged exposure times in the spectral region below 400 nm may become a necessity.

Probe 30

The combined spatial reflectance and fluorescence probe 30 of the present disclosure may be built to meet the following criteria. First, the tissue volume probed by the reflectance and fluorescence measurements may overlap. Second, because the collected fluorescence intensity may be typically three orders of magnitude lower than the reflectance intensity, a detector with a high dynamic range may be required. Weakening the reflectance excitation light by using a smaller excitation fiber or using a number of fluorescence excitation fibers may, however, alleviate this problem. Third, the total diameter of the probe may be small enough so that it is possible to cover an area of only one tissue type; for example, dysplastic lesions around a tumor are likely to be only a few millimeters wide. Finally, a probe 30 small in diameter may give the opportunity to use it for minimal invasive surgeries through trocars. According to one embodiment, probe 30 may fit into a trocar. In one embodiment, it is designed to fit into a trocar (Reflex STR, 5 mm, Richard-Allan Inc.) that is commonly used in the Gynecology Department at The University of Texas M. D. Anderson Cancer Center, Houston, Tex., (UT MDACC).

One embodiment of a combined reflectance and fluorescence probe 30 includes a total of 21 quartz fibers (200 $\mu$m core diameter, NA=0.22). With the benefit of the present disclosure, however, those of skill in the art will recognize that more or fewer fibers may be used. Additonally, although the present disclosure refers to embodiments of a probe including "fibers", it will be understood that any channel suitable for transmission of light may be substituted therewith. In one embodiment, a ring of twelve fluorescence collection fibers 70 surround a circle of seven fluorescence excitation fibers 72. In one embodiment (not shown), at least one fluorescence fiber may be an integral fluorescence excitation and collection fiber. At the distal end of fluorescence excitation and collection fibers may be a quartz rod (about 1.5 mm diameter, about 7 mm thick) 74 located to ensure an overlap at the sample surface between fluorescence excitation and collection fibers. One reflectance excitation fiber 76 and one reflectance collection fiber 78 (both about 90 μm core diameter) may be placed outside of the quartz rod and flush to the sample, which may be tissue, on opposite sides. The reflectance fibers may be about 1.7 mm apart from each other, and light may be scattered through the same tissue volume that is examined for fluorescence.

In one embodiment, a probe 30 may have a total length of about 28 cm to about 35 cm, which allows the probe to pass a trocar shaft. With the benefit of the present disclosure, however, those having skill in the art will recognize that the probe 30, and other components described herein, may be made of different size (and materials) according to need or desire.

Figure 7A:
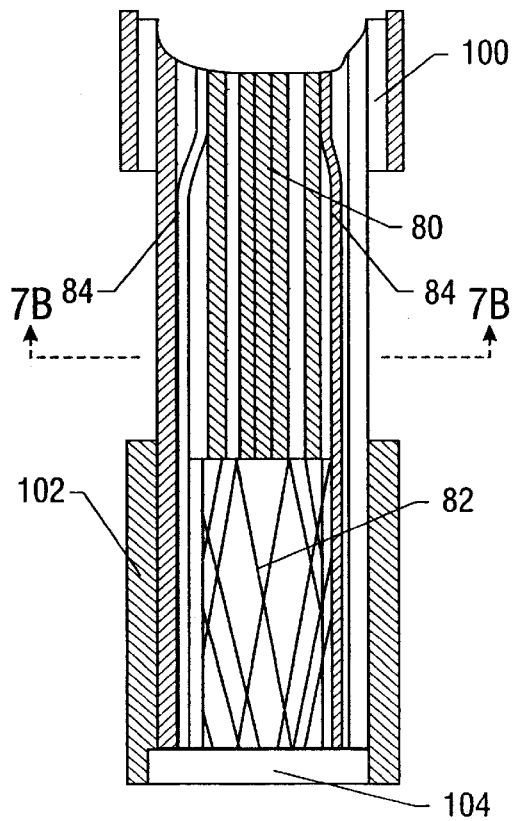
FIG. 7 Probe according to the present disclosure showing fluorescence fibers, a quartz rod, reflectance fibers, illumination fibers, a protection shield, and a quartz shield.
Figure 7B:
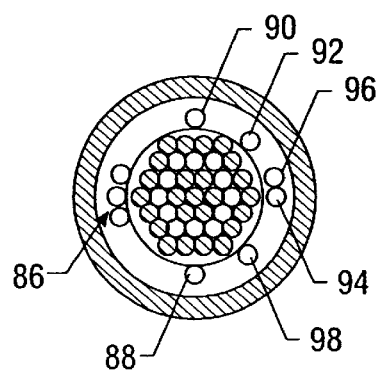
Figure 8:
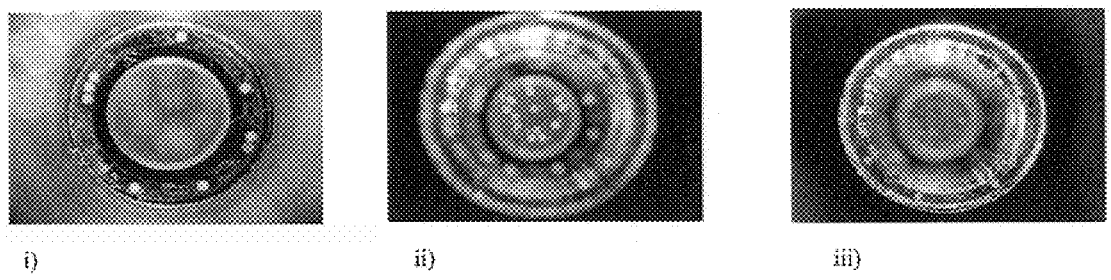
FIG. 8 Tip of a probe according to the present disclosure showing illumination of i) reflectance ii) fluorescence and iii) illumination fibers.

Turning to FIG. 7 and FIG. 8, it may be seen that the diagnostic portion of probe 30 may include forty-six optical fibers (about 200 μm, NA=0.22) in two concentric sections. With the benefit of the present disclosure, however, those of skill in the art will recognize that more or fewer fibers may be used. The center bundle 80 (See FIG. 7) may contain twenty-five fluorescence excitation fibers and twelve fluorescence collection fibers. At the distal end of the probe 30, these fibers may be arranged randomly in central bundle 80 and may be placed in mechanical contact with a short piece (about 1.5 cm long) of thick quartz fiber 82. Light sent through this rod may be distributed over an examined area. The rod's length may be determined by the radius of the rod and the NA of the fibers and may be calculated by taking twice the radius and dividing it by the fiber NA.

Nine fibers for illumination and collection of diffuse reflectance may be arranged in a ring around the fluorescence fibers (See element 84, FIG. 7). Three collection fibers 86 may be located at about 180°, two fibers 88 and 90 may be located at about 90°, and two fibers 92 and 98 may be located at about 45° from the illumination fiber 94. A single collection fiber 96 may be placed directly beside the reflectance excitation fiber in to measure single backscattered light. Fibers 92 and 98 may have a distance to the excitation source of about 1.4 mm, fibers 88 and 90 of about 2.4 mm, and fibers 86 of about 3.3 mm. The distal ends of the reflectance fibers may be flush with the tip of the central fiber and placed in contact with the sample surface.

For measurements that take longer than about 30 s, an optical feedback mechanism for the probe operator may need to be provided to avoid a displacement of the instrument. Therefore, a third ring of seven fibers 100, with an offset of about 2 cm (for a 28 cm probe) and about 5 cm (for a 35 cm probe) from the tip may be added for illumination purposes. Probe 30 may have a screw-on protection shield 102 at the tip of the probe. Specularly reflected light between a quartz shield 104 and the probe 30, however, may lead to an uncorrectable biasing of the probe performance, and therefore protection shield 102 may optionally not be used. A 30-minute soaking of probe 30 in a disinfecting solution like Cidex™ (Johnson and Johnson Inc.) allows the probe to be used in the sterile environment of an operating room.

Figure 9B:
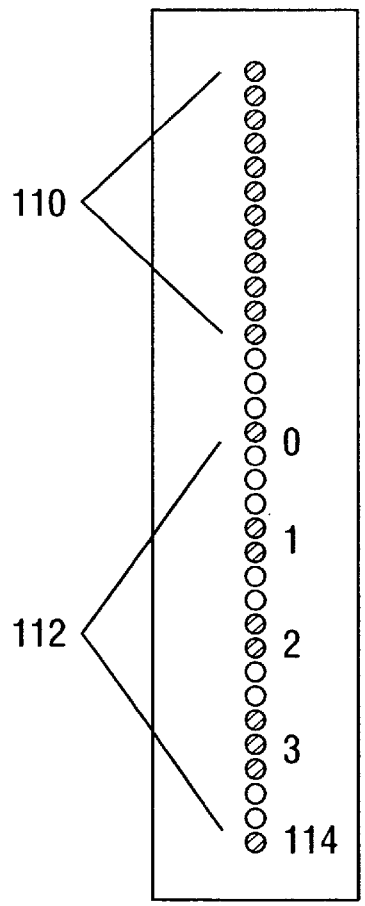
Figure 9C:
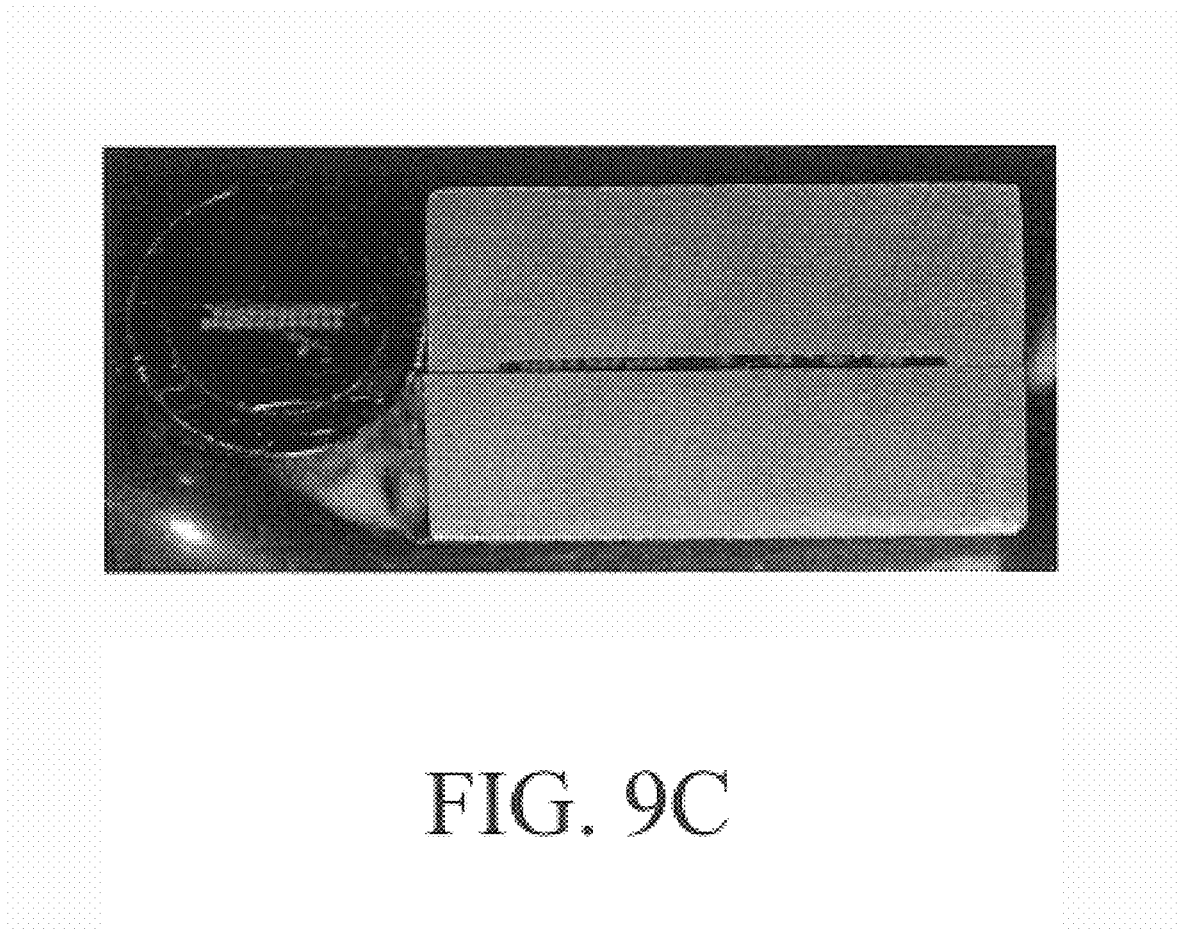

The arrangement of fibers at the monochromator 24 and the spectrograph 42 connectors, according to one embodiment, are shown in FIG. 9 The fluorescence excitation fibers 108 may be arranged in two rows for optimally filling by a rectangular output beam of the monochromator 24. The fibers on the spectrograph 42 end may be lined up in a single row, as shown. Fibers 110 are fluorescence collection fibers, and fibers 112 (represented by darkened circles) are the reflectance collection fibers. Because saturation in one fiber location may bloom to adjacent pixels on the detector, additional spacing, realized by unconnected fibers (illustrated by un-darkened circles), reduced this problem. In this embodiment, the spectrograph connector contains fiber 114 that may be connected directly to a white light output of light source 22, which may be a Xe lamp, to monitor the spectral output of the light source over time.

Figure 10:
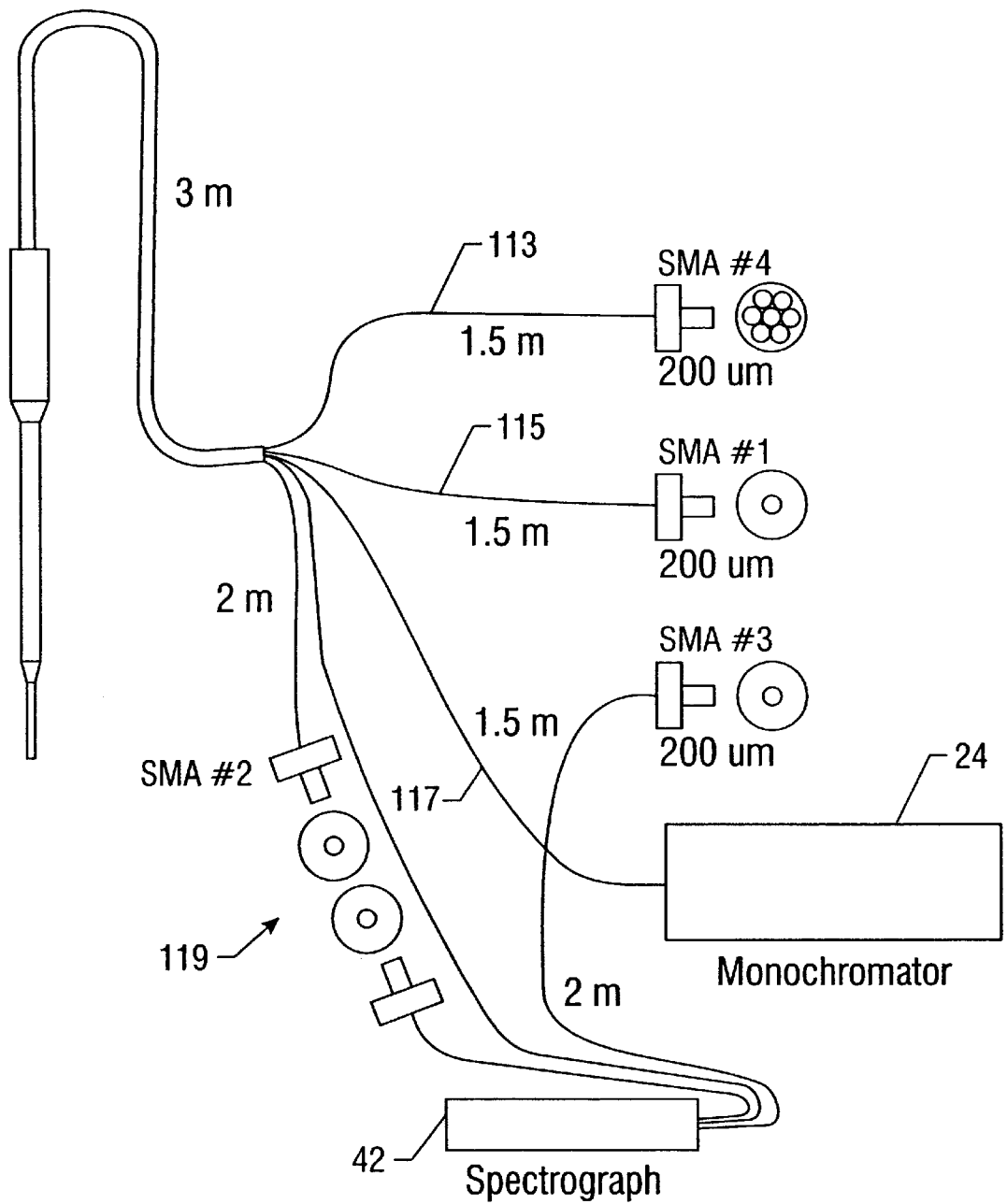
FIG. 10 Probe including fiber connectors according to one embodiment of the present disclosure. Shown are visual illumination fiber 113, reflectance excitation fiber 115, fluorescence excitation fiber 117, and reflectance collection position 119.

FIG. 10 illustrates an entire probe 30, according to one embodiment, including connectors and connecting fibers. Note that reflectance collection fiber 94 (See FIG. 8), the position right next to the excitation fiber, may be interrupted by disconnecting SMA connector #2. This feature was created in this embodiment in case the directly backscattered light signal was too strong and needed attenuation.

Spectrograph 42 and Filter Wheel

Imaging spectrograph 42, in one embodiment, may be a commercial imaging spectrograph (Chromex 250 IS, Albuquerque, N.Mex.). A grating of about 100 grooves/mm, blazed at about 450 nm may be used. With the benefit of the present disclosure, however, those of skill in the art will understand that any optical filter or device suitable for analyzing spectral content of light from one or mutliple sources simultaneously may be used for imaging spectrograph 42.

Light collected by fluorescence and reflectance fibers and the excitation light guided directly from the source may be coupled through an 8-position, computer controlled collection filter wheel (Optomechanics Research, Inc., Vail, Ariz.), into imaging spectrograph 42. The filter wheel blocks the fluorescence excitation light from entering the spectrograph 42. The spectrograph may contain a holographic grating blazed at about 380 nm with about 100 grooves/mm. The fibers may be projected onto an entrance slit (about 250 μm) to yield a spectral resolution of about 7 nm.

Figure 11:
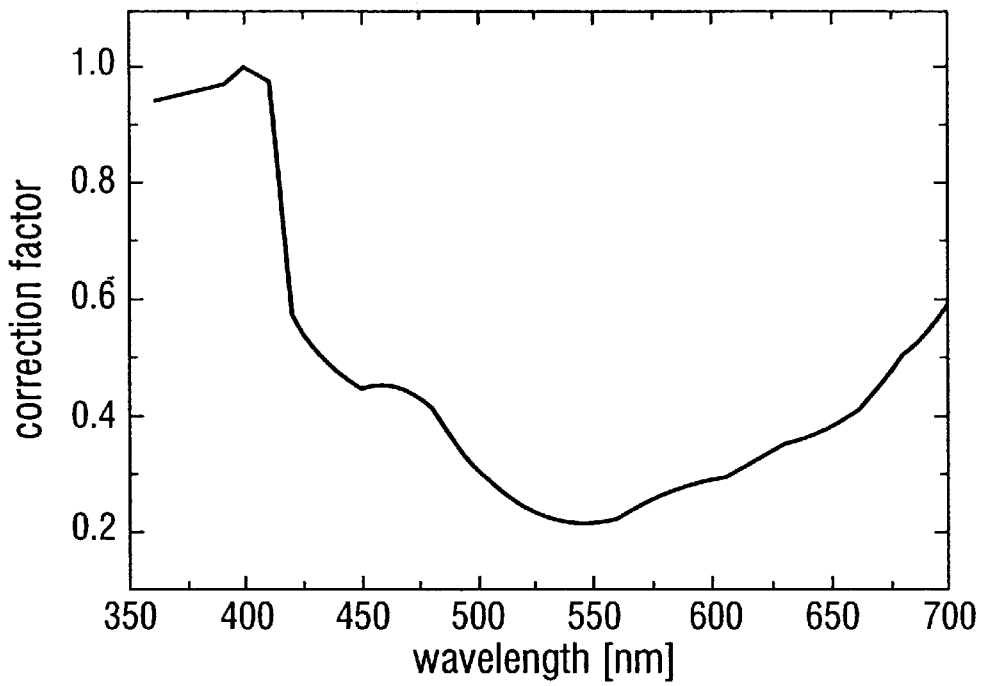
FIG. 11 Correction factors for the spectrograph.

The non-uniform spectral response of the system may be corrected as shown in FIG. 11. These correction factors may be determined from measurements of calibration sources; in the visible, a N.I.S.T traceable tungsten ribbon filament lamp, and in the UV, a deuterium lamp may be used (550C and 45D, Optronic Laboratories Inc., Orlando, Fla.).

Variations in the intensity of fluorescence excitation light source at different excitation wavelengths may be corrected using measurements of the intensity at each excitation wavelength at the probe tip using a calibrated photodiode (818-UV, Newport).

CCD Camera 44

A thermo-electrically cooled CCD camera 44 (Spectrasource HPC-1, Westlake Village, Calif.) may be operated at about −30° C. and may be located at the back focal plane of the imaging spectrograph 42. Chip dimensions may be about 13.8×9.2 mm with 1536×1024 pixels (Kodak KAF-1600 grade 2), to yield a nominal spectral range of about 410 nm for a single grating position. Each fiber may take up about 40 pixels. The dark current of the CCD chip, in this embodiment, was specified and confirmed as 0.25 electrons/pixel/sec when operated at −30° C. Quantum efficiency of the lumogen-coated chip may range from a peak of about 40% at about 550 nm to a low of about 15% at about 250 nm.

Binning Pixels

The HPC-1 CCD camera 44 allows a user to perform on-chip binning of pixels. Binning means that neighboring pixels may be added together to represent only one data point. This feature is attractive for at least two reasons: (1) it allows a reduction in the time required to read data from the chip, and (2) it increases the signal-to-noise ratio by reducing the effective read out and shot noise.

Although a useful feature, excessive binning may diminish the resolution of the system. Furthermore, because the full well capacity of the pixels and shift register is limited, it is possible to exceed this capacity by either grouping too many pixels together or by encountering an unexpectedly strong signal (blooming). When blooming occurs, a charge in excess of the full well capacity of a capacitive element may spill into adjacent pixels. This can essentially fill the pixels with charge and render them unavailable for signal detection or perhaps give a false indication of signal where none exists.

Figure 12:
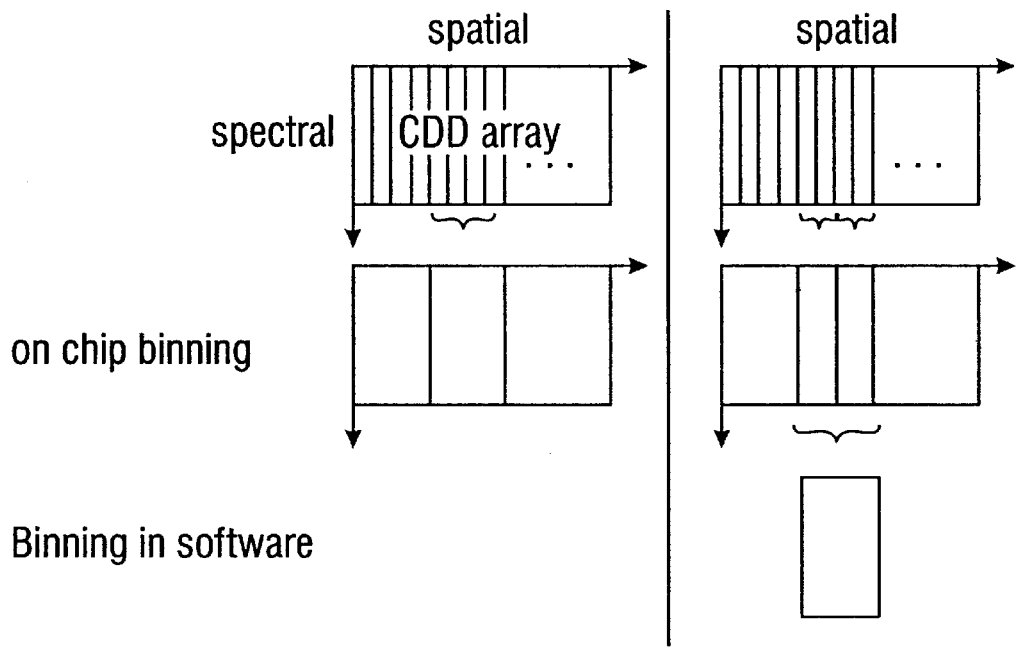
FIG. 12 Schematic of Binning techniques: On chip binning (left), On chip and software binning (right).

In one embodiment, binning was only electronically implemented in the spatial direction on the chip. The 12 fluorescence excitation fibers filled 480 pixels and were all binned together. For the reflectance excitation, a combined binning in hardware and software was used in one embodiment. This technique had two advantages: (1) it increased the dynamic range compared to a full binning in hardware, and (2) it increased the data transfer rates as compared to non-binned data. FIG. 12 shows the two different binning techniques.

In one embodiment, the camera 44 and the readout electronics did not operate in a reliable manner. Long-term testing showed that counts on every pixel can vary from exposure to exposure when the shutter remains closed. A DC offset variation on the chip, resulting in an average count of 700/pixel/s to 1500/pixel/s was monitored during a 12 hour period. The origin of this behavior was expected to be either a cooling problem of the CCD camera 42 or an unstable DC offset supplied to the A/D converter. In an attempt to cure at least some of the problems, a higher number of pixels were digitized that were actually physically present. The count of these fake pixels reflected the DC offset of the signal and was found to be independent of the detector temperature. Testing showed that the count of these fake pixels varied the same way as the real pixels did. In this embodiment, monitoring of the background was required at every single measurement, since a low fluorescence signal may lie in this range. The background could be subtracted from the acquired data. In the embodiment, another problem was discovered with the readout of the chip. The first electronically binned line that was read out was always corrupted and had to be discharged. This meant that the double amount of pixels were binned into two columns from which the first corrupted one was dumped.

Software and Control

In one embodiment, National Instruments Labview Version 3.0 (Austin, Tex.) a graphical programming development environment based on the G (Graphic) programming language may be used to control Fast EEM system 10. The platform for the control software may be any suitable control device or computer 50. In one embodiment, a laptop 486/75 MHz personal computer with docking station (Austin Inc., Austin, Tex.) was used as computer 50. Communication with the excitation monochromator may be provided via an RS-232 control module that is interfaced to the COM port of the docking station of computer 50. A camera control card may be mounted in the docking station. The imaging spectrograph 42 may be operated using a National Instruments GPIB IEEE-488 board that is also located inside the docking station of computer 50.

In another embodiment, a desktop computer was chosen (Optiplex 233GXa, Dell Computer Corporation, Round Rock, Tex.) equipped with a Windows95™ operating system as computer 50. All mentioned cards in this embodiment may be connected to the ISA-bus of computer 50. A double monochromator 24 and spectrograph 42 controls may be connected by a GPIB IEEE-488 interface (AT-GPIB/TNT, National Instruments, Austin, Tex.). The two shutters and the filter wheel may be controlled with a digital I/O card (PC-DIO-24, National Instruments, Austin, Tex.). The CCD camera 44 may have its own ISA-bus interface card. The readout rate of the chip in this embodiment was greater than about 65,000 pixels/s. This gave a readout time of about 24 s for the whole chip if no binning was used. In this embodiment, no on board RAM was available to buffer acquired data.

In one embodiment, Labview V.5.0 (National Instruments, Austin, Tex.) was chosen as the software to control the entire Fast EEM system 10. In this embodiment, the goal of software development was to create an easy to use interface that made the system controllable by an operator with basic computer knowledge after only a few days of training.

Such software may be designed using a small number of basic sub-Vi's (Vi: virtual instrument. National Instruments' expression for software units). Operator interaction may be minimized to avoid human errors. Automation of file saving and auto-naming of saved files may be implemented to prevent loss of data by mislabeling or accidentally overwriting certain files. Such automation may also speed up the interaction time of an operator with the software between measurements.

In one embodiment, stored fluorescence data was loaded immediately after storage and could be visually inspected in the center of the screen. Such a routine may be added as a quality-ensuring feature, and it may also help to prevent data loss caused by saving errors or misalignment of the system if the operator was experienced in interpreting the acquired data.

Software Structure

Figure 13:
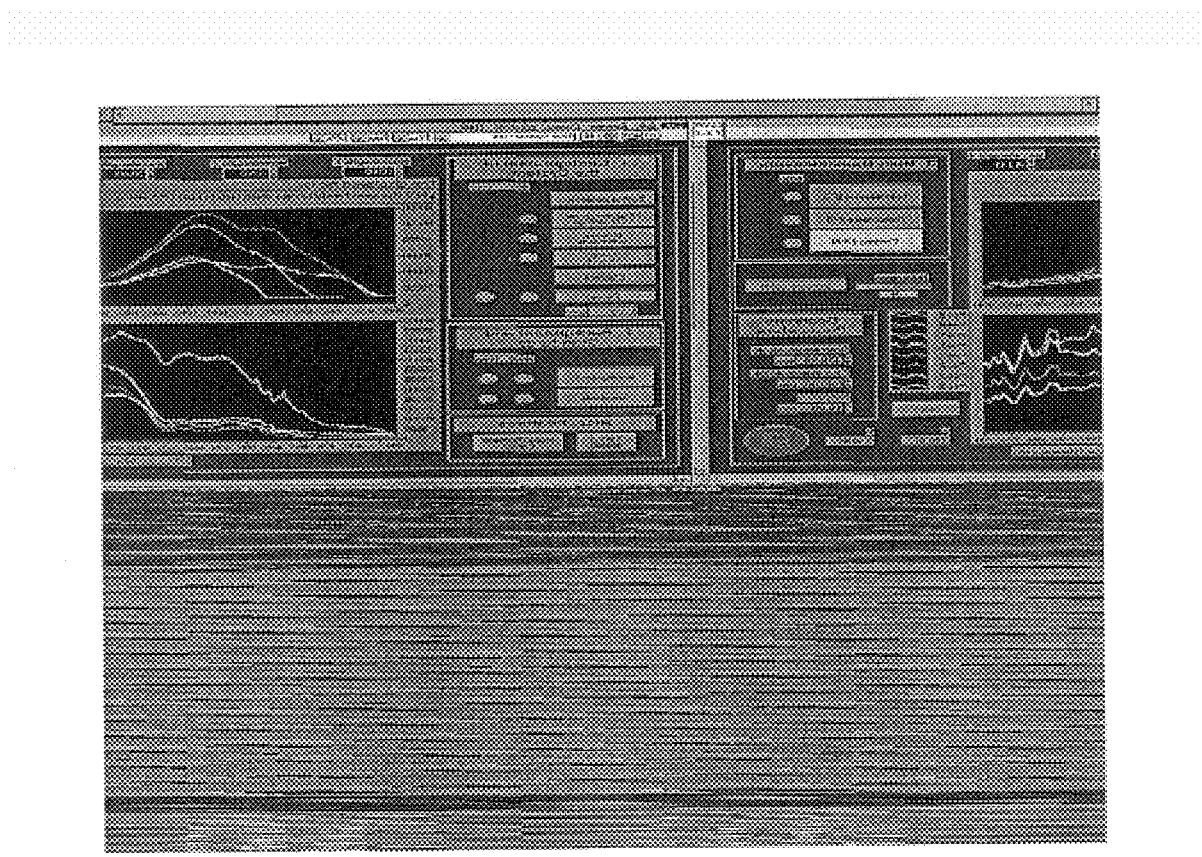
FIG. 13 Main screen of a Fast-EEM user interface according to one embodiment of the present disclosure.

FIG. 13 shows a main user interface according to one embodiment from which the Fast EEM system 10 may be controlled. With the benefit of the present disclosure, those having skill in the art will understand that there are numerous ways in which system 10 may be controlled and that the interface shown in FIG. 13 is but only one of those ways. Other user interfaces may be implemented as is known in the art. In FIG. 13, the center displays show four spectra of the last fluorescence measurement (top graph) and the acquired reflectance data (bottom). The excitation wavelengths of the displayed spectra may be changed online. Around this screen, different buttons may be present, which allow access to the certain main features.

In the configuration component of the software interface illustrated in FIG. 13, all the configurations were accessible and controllable. In the 'Saving parameter' sub program, a patient number and the directory path may be defined. The integration time for the individual exposures and the settings of the CCD camera 44 may be stored in the corresponding subroutine. The Spectrograph settings may be changed in the 'Chromex'-Vi. The buttons for the mercury calibration, the lamp monitoring, and the power output of the probe may also be associated with the configuration settings of the software.

In regard to acquiring date, individual switches for starting the background and the standards measurements may be placed on the left side of the spectra display. The fluorescence, reflectance and combined reflectance and fluorescence measurements may be initiated in the 'Main Measurements' box. Naming of files with the acquired data may be dependent on which kind of measurement is chosen. In one embodiment, no manual naming of files by the operator was necessary.

Many additional features may be added to the software and user interface. For example, an image of the whole CCD chip with all possible settings and binnings may be achieved.

The monochromator 24 may be moved to any desired wavelength. The center wavelength of the spectrograph 42 may be set manually, too. The camera's 44 exposure time may be adjusted, and it may possible to choose if the shutter of the spectrograph 42 should open or if it should remain closed to image the dark current. Another sub Vi may be designed to change all the settings of the monochiomator 24, such as wavelength, and slit width. Emission and reflectance spectra may be loaded and visually compared on the screen. It may be possible to turn on and off the probe's illumination light from the main screen. It shall be understood that none of these extra features need influence the settings for the main measurements. Default values may always be restored when measurements are started. When exiting the software, a protocol file may be created that contains all the important settings, the date, file names and the name of the operator. In one embodiment, about 112 individual Vi's were created to design a reliable, easy-to-use and fault-proof system, although it will be understood that more or fewer routines may be implemented according to the needs or desires of the user. In other embodiments, for instance, a simpler or more complicated user interface may be easily implemented as is known in the art.

Temporal Performance

Table 2.1 compares the temporal performance of the two embodiments of Fast EEM systems described above—one utilizing a 150 W ozone free Xe arc lamp, single monochromator, and twenty-one fiber probe (Embodiment A); and the other system using a 450 W ozone free Xe arc lamp, a double monochromator, and a forty-six fiber probe (Embodiment B). Overall, the time to obtain a complete EEM in Embodiment B between 330 nm and 500 nm excitation in steps of 10 nm was cut down to less than 45 s, a temporal improvement of 105 seconds over Embodiment A. To obtain the same amount of counts on the CCD chip, the exposure times may be cut down from 1500 ms to 200 ms, depending on the excitation wavelength. An exposure time of 375 ms may be expected since the amount of light delivered to the tissue may increase by a factor of 4. The alignment on the emission side was improved in Embodiment B, so that the throughput was almost twice as much as before. The monochromator's scanning speed may be decreased from 34 s for an entire scan and resetting to the starting wavelength to less than 3 s. A faster computer and the use of a 32-bit operating system in Embodiment B cut down the computation time by almost 50%. However, it still required about 2 s per exposure to transfer the data from the camera to the computer. This value adds up to 42 s, 75% of the whole data acquisition time. This handicap may be further improved by replacing the readout electronics of the CCD chip. The control of the illumination shutter, a new feature of the system, did not add any extra time to the measurements. The shutter opened and closed in less than 5 ms.

In embodiment B, reflectance measurements may be sped up by using a 200 μm fiber for the excitation light instead of a 80 μm fiber, since more light is provided to the sample 60, which may be a tissue. A more intense white light output of the system may serve the same purpose. By using a different imaging spectrograph 42 with a grating with lower spectral dispersion, a wider spectrum may be covered on the CCD chip. To cover the desired spectral range for reflectance measurements, only two (instead of three) sub-range exposures may be necessary. Overall data acquisition time over 2 wavelength ranges and four positions may be achieved in 31 s in Embodiment B, which is about three times faster than that in Embodiment A, in which only 3 spatial positions had to be exposed.

TABLE 2.1

Comparison of Temporal Performance:

|  | Embodiment A | Embodiment B |
| --- | --- | --- |
| Fluorescence |  |  |
| Scanning time: <br> 2 × 500 nm – 300 nm | 2 × 170 nm/ <br> 10 nm/s = 34 s | 2 × 70 nm/ <br> 150 nm/s = 2.7 s |
| Exposure time | 18 × 1.5 s = 27 s | 20 exposures: Σ = 6.0 s <br> (see 3.1.2) |
| Moving filter wheel | 8 × 1 s = 8 s | 8 × 1 s = 8 s |
| Camera shutter, data transport | 18 × 4.5 s = 81 s | 21 × 2 s = 42 s |
| illumination shutter |  | <1 s |
|  | Σ = 150 s | Σ = 53.7 s |
| Reflectance |  |  |
| Exposure time | 9 exposures: 27 s | 8 exposures: 6 s |
| Camera shutter, data transport | 63 s | 25 s |
|  | Σ = 90 s | Σ = 31 s |

In summary, a combined reflectance and fluorescence measurement with the Embodiment B may be obtained in 85 s, about three times faster than with the Embodiment A. This temporal improvement may benefit the patient and may also minimize the chance that the physician moves the probe during measurements.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Fluorescence Excitation Emission Matrices of Human Tissue: A System for In Vivo Measurement and Method of Data Analysis This example describes a Fast EEM system capable of measuring spatially resolved reflectance spectra from 380–950 nm and fluorescence excitation emission matrices from 330–500 nm excitation and 380–700 nm emission in vivo. System performance was compared to a standard scanning spectrofluorimeter. This FastEEM system was used to interrogate human normal and neoplastic oral cavity mucosa in vivo. Measurements were made through a fiber optic probe and required about 4 minutes total measurement time. This example also presents a method based on autocorrelation vectors to identify excitation and emission wavelengths where the spectra of normal and pathologic tissues differ most. The FastEEM system provides a tool with which to study the relative diagnostic ability of changes in absorption, scattering and fluorescence properties of samples, including tissue samples.

Figure 14:
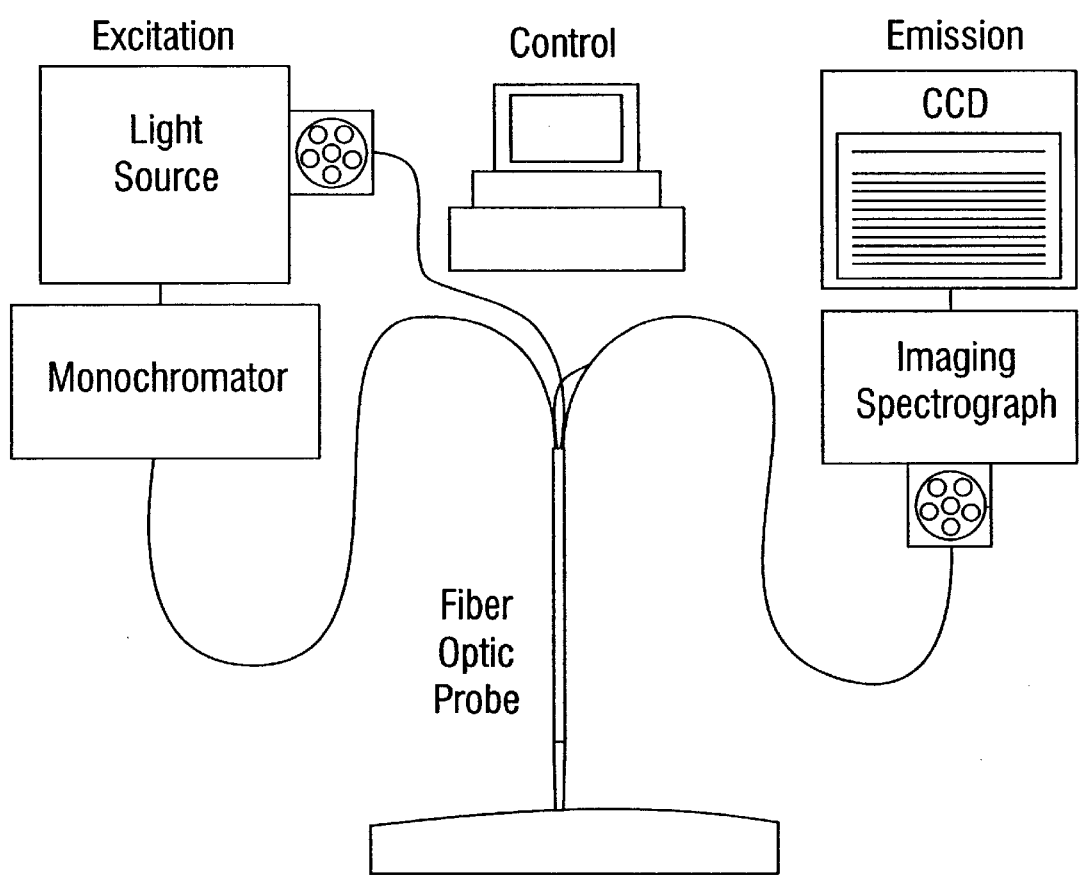
FIG. 14 System block diagram showing a variable excitation light source, a fiber optic delivery and collection probe, and a spectral multichannel analyzer according to one embodiment of the present disclosure.
Figure 15A:
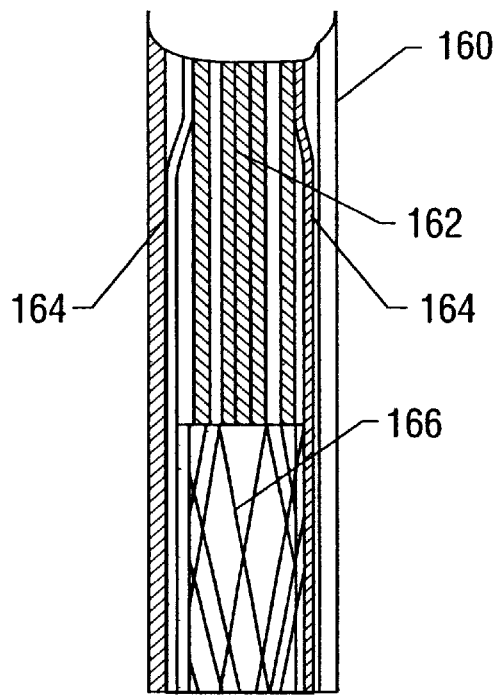
FIG. 15 (left) Schematic diagram of the distal ends of the probe: [a] outer shaft, [b] fluorescence excitation and emission fibers, [c] reflectance collection and illumination fibers, [d] mixing element, [E] reflectance excitation fiber, [1–3] reflectance collection locations, (Right) Schematic diagram of the proximal ends of the probe.
Figure 15C:
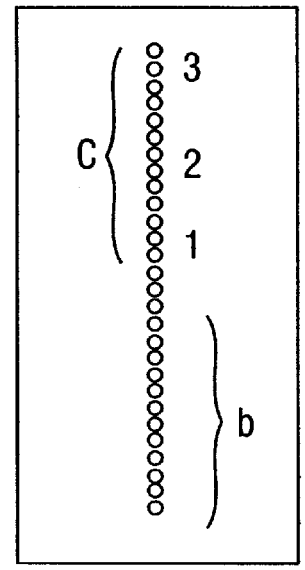
Figure 15B:
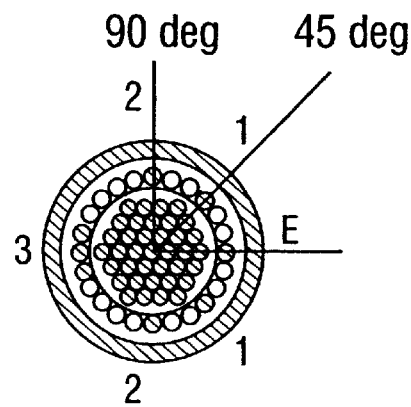
Figure 15D:
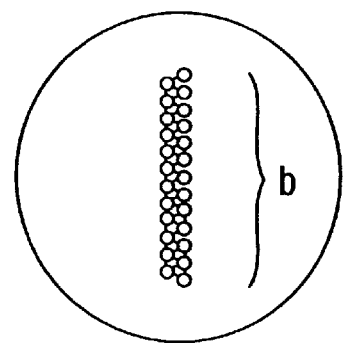

Materials and Methods:

FIG. 14 illustrates a block diagram of a Fast EEM system 10 in accordance with the present disclosure. This system includes at least three main components: (1) an arc lamp 22, stepper motor driven monochromator 24 and filter wheel, which provides monochromatic and broad band excitation, (2) a fiber optic probe 30 which directs excitation light to the sample 60, which may be a tissue sample, and collects remitted fluorescence from, in this embodiment, one location and diffusely reflected light from, in this embodiment, three locations, and (3) a filter wheel, imaging spectrograph 42 and CCD camera 44 which detects the spectrally resolved reflectance and fluorescence signals. Excitation monochromator position, filter wheel position, spectrograph grating position, CCD operation and data acquisition are controlled using a laptop personal computer 50 mated to a docking station. The specifications of each sub-system are described below.

The probe 30, illustrated in FIG. 15, included a total of forty-six optical fibers (200 $\mu$m diameter, NA=0.2) arranged in two concentric bundles. The center bundle contained twenty-five fluorescence excitation fibers and twelve fluorescence collection fibers. The proximal ends of the fluorescence excitation fibers were arranged in two vertical lines at the exit slit of the excitation monochromator 24 to maximize the coupling of the light into the sample. The proximal ends of the fluorescence collection fibers were arranged in a single vertical line at the entrance slit of the imaging spectrograph 42. At the distal end of the probe 30, the fibers that excite and collect fluorescence were arranged randomly in a central bundle and placed in contact with a short piece of a thick quartz fiber (2 mm diameter, 15 mm long, NA=0.2). The distal tip of this fiber was placed in contact with the sample surface 60, and ensured that the area from which fluorescence was collected was the same as that directly illuminated.

The nine fibers for illumination and collection of diffuse reflectance were arranged in a concentric ring around the thick quartz fluorescence measurement fiber. The distal ends of these fibers were flush with the tip of the central fiber and were placed in contact with the sample surface 60. White light from a port on the side of the lamp housing was coupled to the proximal end of a single illumination fiber (80 $\mu$m, NA 0.2). Photons that scatter through the tissue and exit the surface were collected at four different positions with seven collection fibers; three located 180° from the illumination fiber (3 mm distance), two located 90° from the illumination fiber (2.1 mm) and two located 45° from the illumination fiber as shown (1.1 mm) (See FIG. 15). The proximal ends of the reflectance collection fibers were situated at the top of the vertical line of fluorescence collection fibers, separated by dummy fibers as shown in FIG. 15.

The light source 22 for the instrument, which provided both quasi-monochromatic excitation for fluorescence and broad band illumination for reflectance, was a 150 W ozone free Xe arc lamp (Spectral Energy Corp., Westwood N.J.) with a spherical rear reflector. A condenser system consisting of two plano-convex quartz lenses was used to couple light into monochromator 24. The primary condenser was 1.5 inches in diameter with an aperture ratio of f/1.5. The secondary condenser was also 1.5 inches in diameter, but was masked to provide numerical aperture matching to the monochromator 24. A manual shutter was located between the condensing optics and monochromator 24 and was closed to prevent fluorescence excitation light from reaching the sample 60 during reflectance measurements. The monochromator 24 had an aperture ratio of f/3.6 (Spectral Energy, GM 252) and was used with an ion-etched holographic grating (ISA, Edison, N.J., 240 nm blaze, 1180 grooves/mm, dispersion=3.3 nm/mm). An RS-232 controlled stepper motor drove the monochromator 24 with a maximum stepping rate of about 400 step/sec (about 10 nm/sec). A bandwidth of 6.6 nm was selected by setting the entrance slit of the monochromator to about 2.0 mm. Light was coupled from the monochromator 24 into the probe 30 via a fiber optic adapter (Spectral Energy, GMA 257) consisting of a quartz plano-convex lens and a 5×quartz microscope objective. The light passing through the objective was focused onto a vertical line of 25 fibers in two columns, placed at the focal plane of the objective (See FIG. 15). The reflectance excitation fiber was attached to the lamp housing via a micropositioner. Broadband light exiting the lamp housing through an existing hole was coupled to the reflectance illumination fiber using a quartz plano-convex lens (NA= 0.24). A five position illumination filter wheel placed between the lamp and the lens contained three long pass filters with 50% transmission at 295 nm, 515 nm and 715 nm. One of the filter positions was blocked and acted as a shutter to prevent white light from reaching the sample during fluorescence measurements.

Light collected by fluorescence and reflectance fibers was coupled through an 8 position, computer controlled collection filter wheel, into a Chromex 250 IS (Albuquerque, N.Mex.) imaging spectrograph 42 containing a holographic grating blazed at 380 nm with 150 grooves/mm and a reciprocal linear dispersion (RLD) of 20 nm/mm. The fibers were projected onto an entrance slit (250 $\mu$m) which yielded a spectral resolution of about 5 nm. A thermo-electrically cooled CCD camera 44 operated at about −30° C. (Spectrasource HPC-1, Westlake Village, Calif.) was located at the back focal plane of the imaging spectrograph 42. Chip dimensions were 13.8×9.2 mm with 1536×1024 pixels (Kodak KAF-1600 grade 2), yielding a nominal spectral range of about 276 nm for a single grating position. Dark current was specified as 0.25 electrons/pixel/sec when operated at −30° C. The quantum efficiency of the lumogen coated chip ranged from a peak of 40% at 550 nm to a low of 15% at 250 nm.

The detector and imaging spectrograph were wavelength calibrated by measuring the room light spectra that showed three Mercury peaks at 404.7, 436 and 546 nm. The relation between pixels and wavelength was then linearly fitted through these points.

Fluorescence and reflectance measurements were obtained sequentially. Prior to fluorescence measurements, the white light port was closed and pixels illuminated by the fluorescence fibers were selected to be read from the CCD 44. Dark current and A/D conversion offset was measured with the same setting as the subsequent measurement but with a closed camera shutter. These were subtracted from all fluorescence and reflectance measurements. The first excitation wavelength was selected by scanning the excitation monochromator, the emission filter wheel was rotated to select the appropriate long pass filter and the spectrograph grating was adjusted to record signal over the desired emission wavelength range. The monochromator 24 and camera shutters were then opened for the desired exposure time to record the fluorescence emission spectrum (1.5 seconds). The excitation wavelength was then incremented, and the process repeated until all desired excitation wavelengths have been measured. The excitation wavelengths were incremented from 330 to 500 nm in 10 nm steps. Table 1 contains a list of the excitation wavelengths and corresponding long pass filters and emission wavelength ranges used in this Example.

Following collection of fluorescence spectra, diffuse reflectance spectra were then measured. For these measurements, the monochromator shutter was closed, the emission filter wheel was set to the lowest filter position and the pixels illuminated by the corresponding reflectance collection fibers were selected to be read from the CCD 44. Dark current and A/D conversion offsets were measured and stored for subtraction of the following measurements. The reflectance spectrum was collected over three illumination wavelength ranges. Prior to measurement of each range, the appropriate long-pass filter was selected in the illumination filter wheel, and the spectrograph grating was adjusted to record signal over the desired wavelength range. The lamp and camera shutters were then opened for the desired exposure time to record the reflectance spectrum (0.4–4.8 seconds). The illumination wavelength range was then incremented, and the process repeated until all desired wavelength ranges have been measured. Exposure times were determined empirically to achieve a signal to noise ratio greater than 20. Table 1 contains a list of the illumination wavelength ranges and corresponding long pass filters used for diffuse reflectance measurements. The high dynamic range of the reflectance measurements, spanning over three orders of magnitude, required that each spatial position be read out individually from the CCD 44. This prevented saturation and blooming artifacts.

There are no accepted safety standards for illumination of mucosal surfaces other than skin and cornea. However, the exposure of solar radiation that is equivalent to the exposure received when a measurement is made with this system has been calculated. The method compares the spectral irradiance [$W/cm^2$ nm] of the excitation source with solar irradiance data obtained from [NSF Polar Programs UV Spectroradiometer Network 1994–1995 Operations Report; NSF UV Radiation Monitoring Network 1994 to 1995 Volume 5.0 Data Set. Available at WWW.BIOSPHERICAL.COM.]. The comparison includes a point-wise division of the irradiance from the FastEEM system to the solar irradiance at the same wavelength. This ratio gives a relative solar exposure factor. The solar data is for a sunny day in San Diego, Calif. Irradiation during fluorescence excitation is less than 7 times solar exposure at all wavelengths. Given that fluorescence excitation times were 1.5 seconds, this corresponds to exposure to solar radiation for less than 11 seconds in any given wavelength band. During diffuse reflectance measurements, the lamp exposure is maximum at 300 nm, where the relative exposure is a factor of 25 that of the sun. Since the total exposure time for this wavelength band is 14 seconds, the exposure corresponds to 350 seconds or less than 6 minutes. All other wavelengths have relative exposure factors of 10 or less resulting in a shorter equivalent total solar exposure.

Prior to every patient measurement the probe output was measured with a calibrated power meter (Newport, Irvine, Calif., 818-UV) at 400 nm excitation wavelength. An average output of 86 $\mu$W+/−12 $\mu$W was achieved at this wavelength with a bandwidth of 6.6 nm. Background fluorescence spectra were measured with the probe dipped in a non-fluorescent bottle containing distilled water. This background EEM was subtracted from all subsequently acquired EEMs to correct for room lights and probe autofluorescence. The non-uniform spectral response of the system was corrected using correction factors determined from measurements of calibration sources; in the visible a N.I.S.T traceable tungsten ribbon filament lamp and in the UV a deuterium lamp were used (550C and 45D, Optronic Laboratories Inc., Orlando, Fla.). Variations in the intensity of fluorescence excitation light source at different excitation wavelengths were corrected using measurements of the intensity at each excitation wavelength at the probe tip using a calibrated photodiode (818-UV, Newport). Background spectra to correct reflectance measurements for room light contributions were measured with all parameters set as for tissue measurements except the white light shutter was closed. These measurements were subtracted from all subsequent reflectance spectra.

Fluorescence and reflectance standards were measured before each patient measurement. The fluorescence intensity was reported relative to the fluorescence intensity of a solution of 2 mg/L Rhodamine 610 (Exciton, Dayton, Ohio) in ethylene glycol at 460 nm excitation and 580 nm emission. Reflectance data are reported relative a 2.68% by volume solution of 1.072 micron diameter polystyrene microspheres (Polyscience Inc., Warrington, Pa.). The microsphere standard was used for its well-characterized optical properties. The total integrated reflectance of this standard was measured on a double beam spectrophotometer (U-3300 Hitachi, Tokyo, Japan) with an integrating sphere attachment (Labsphere Inc., North Sutton, N.H.). This was used to correct the reflectance standard measurements made with the FastEEM system. Tissue spectra at each collection fiber position were divided pointwise by the corrected standard reflectance spectrum at the corresponding fiber position.

The EEMs were assembled offline from each series of fluorescence emission scans. Data processing and plotting were performed with Matlab, (The Math Works Inc., Natick, Mass.). Reflectance spectra were assembled from three wavelength areas giving a range from 380 to 950 nm. The wavelength range was further reduced (380–800 nm) to comply with the range of calibration measurements of the reflectance standards on the U-3300. Reflectance data were reported between 380 and 595 nm, a range where the possible influence of room lights in the measurement was minimized.

System Validation

System performance was assessed using two fluorescence standards. The first standard was a 2 mg/L Rhodamine 610 (Exciton Inc., Dayton, Ohio) ethylene glycol solution that is non-scattering, but has peak fluorescence intensity approximately twice the average intensity of human cervix. The second standard mimics the optical properties of tissue and consists of 20 $\mu$M Flavin Adenine Dinucleotide (FAD, Kodak, Rochester, N.Y.), 0.625 vol % polystyrene micro spheres (Polyscience Inc., diameter=1.072 $\mu$m).

Both standards were measured with the FastEEM system 10 and a scanning spectrofluorimeter (SPEX, Fluorolog II, Edison, N.J.). The EEMs measured with the SPEX were considered as standards since the performance of the system is well documented (dynamic range=$10^5$, spectral resolution 5 nm, corrected for non-uniform spectral response). The excitation light was incident perpendicular to the sampling cuvette and the emitted light was collected at approximately a 20 degree angle with respect to excitation light. A front focus arrangement with a 10 mm cuvette was used in the SPEX. 60 minutes were required to collect a full EEM from each sample with the SPEX.

Clinical Studies

In vivo data were obtained from a group of patients with a known or suspected premalignant or malignant lesions of the oral cavity. The studies were reviewed and approved by the Internal Review Board of the University of Texas at Austin and the Surveillance Committee at the UT MD Anderson Cancer Center (Houston). Informed consent was obtained from each person in the study. Before using the probe, it was disinfected with Metricide (Metrex Research Corp.) in accordance with the standard clinical protocol. Background fluorescence EEM and reflectance spectra were measured by dipping the fiber optic probe in a nonfluorescent bottle filled with deionized water. These EEMs and spectra correspond to the system autofluorescence, and were subtracted from all subsequently acquired EEMs for that patient. Next an EEM was measured from a Rhodamine calibration standard and a reflectance spectrum was measured from a polystyrene solution calibration standard. The probe was then guided to the tissue site to be examined and its tip positioned flush with the tissue. A fluorescence EEM and reflectance spectra were obtained from sites within a lesion and a clinically normal site. Post-spectroscopy, a 2–4 mm biopsy of the tissue was taken from normal and abnormal sites where the probe measured spectra. These specimens were evaluated by an experienced pathologist, Bonnie Kemp, M.D., using light microscopy and classified using standard diagnostic criteria.

Data Analysis

One of the goals of the Fast EEM instrument 10 is to provide information for the identification of excitation wavelengths suitable for the differentiation of tissue of differing pathological characteristics, as well as identification of the chromophores responsible for the differences. While all such information is present in the EEMs collected, it can be difficult to extract due to the dimensionality of the data set. A method was devised to separately characterize the excitation and emission characteristics of the data set.

Given that the EEM has dimensions corresponding to ($\lambda_x$, $\lambda_m$), the following autocorrelation vectors are defined:

$$x_{av}(\lambda_x) = \sum_{i=1}^{N} EEM(\lambda_x, \lambda_{m_i}) \cdot EEM(\lambda_x, \lambda_{m_i})$$

$$m_{av}(\lambda_m) = \sum_{i=1}^{N} EEM(\lambda_{x_i}, \lambda_m) \cdot EEM(\lambda_{x_i}, \lambda_m)$$

where $x_{av}(\lambda_x)$ is the excitation autocorrelation vector and $m_{av}(\lambda_m)$ is the emission autocorrelation vector. Essentially, the emission autocorrelation vector is the diagonal of the product of the EEM with its transpose, and the excitation autocorrelation vector is the diagonal of the product of the transpose of the EEM with the EEM. Note that in signal processing terms, the autocorrelation vectors, $x_{av}$ and $m_{av}$, are a measure of the average signal of the EEM at each excitation or emission wavelength, respectively. In this way they provide qualitative information about and EEM.

An example with simulated data is presented in FIGS. 16A and 16B to illustrate how autocorrelation vectors reflect changes in fluorescence peak positions in EEMs. Two kinds of changes are simulated in the modeled data: a shift in the excitation wavelength at which a fluorescence peak appears, and a shift in the emission wavelength at which a fluorescence peak appears. The original peak in the EEM was modeled as a single gaussian at 380 nm excitation, 550 nm emission with a FWHM of 35 nm in emission and excitation wavelengths. The original peak was then shifted by 30 nm in excitation as shown by arrow 1 in FIG. 16A. The shift in emission wavelength is shown by arrow 2 in FIG. 16A, and corresponds to a 30 nm shift in the emission peak of the original data. Three sets of autocorrelation vectors were computed: one for the EEM with the original peak, one for the EEM with the excitation wavelength-shifted peak, and one for the EEM with the emission wavelength-shifted peak. The autocorrelation vectors are shown in FIG. 16B. Comparing the vectors for the original EEM (row 1 in FIG. 16B) with the vectors from the EEM with the excitation wavelength-shifted EEM (row 2 in FIG. 16B), it is seen that the excitation autocorrelation vector is sensitive to the change in excitation wavelength but not in emission wavelength. Similarly, comparing the autocorrelation vectors for the original EEM with the vectors from the EEM with the emission wavelength shift in the peak (row 3 in FIG. 16B) shows that the emission autocorrelation vector is sensitive to the changes in emission wavelength but not excitation wavelength.

It is sometimes desirable to normalize the autocorrelation vectors to facilitate comparisons between different sets of measurements. Normalized autocorrelation vectors have been calculated by dividing these vectors by their RMS value, in effect forcing the area of the vector to one unit of signal energy. The normalized emission autocorrelation vector is well suited for the identification of differential features in EEMs, such as the shifting or broadening of fluorescence peaks.

Figure 17A:
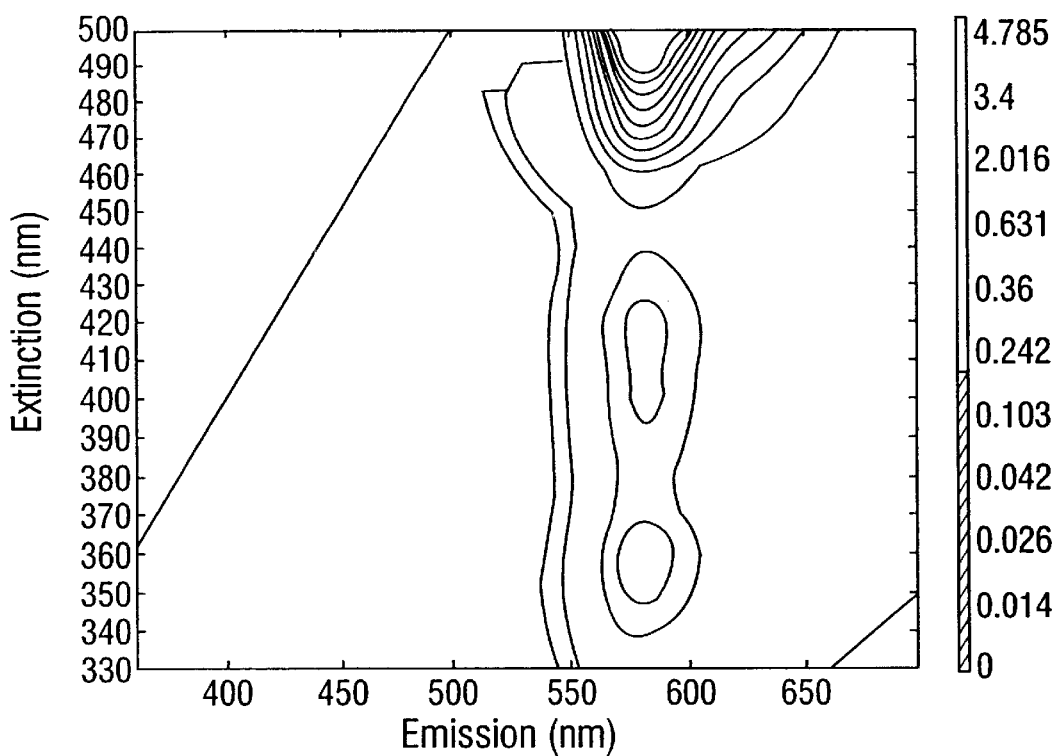
FIG. 17A EEM of Rhodamine standard solution.
Figure 17B:
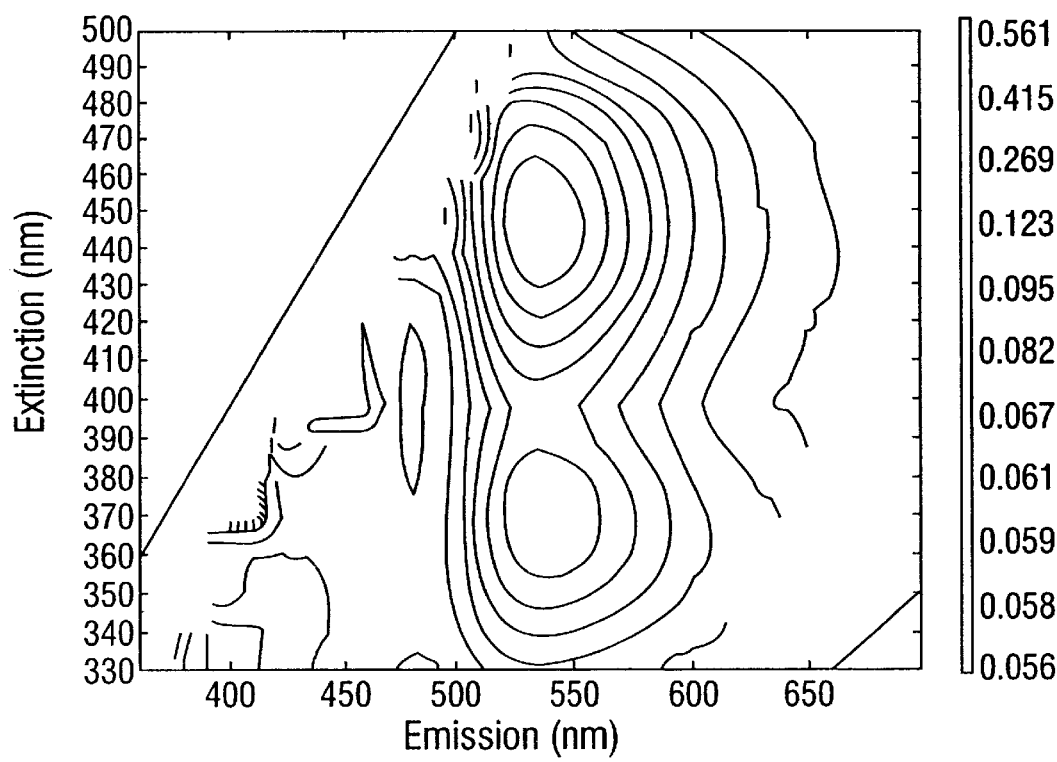
FIG. 17B EEM of an FAD and microspheres-based tissue phantom measured using a FastEEM system.
Figure 18A:
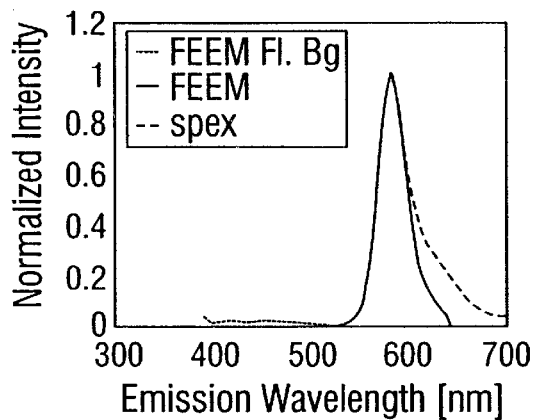
FIGS. 18A–18D (A) Emission spectra at 360 nm excitation of the Rhodamine calibration standard measured with the FastEEM system and SPEX Fluorolog II fluorimeter. (B) Emission spectra at 360 nm excitation of the scattering tissue phanthom containing FAD and polystyrene microspheres measured with the FastEEM system and SPEX Fluorolog II fluorimeter. (C) Emission spectra at 450 nm excitation of the Rhodamine calibration standard measured with the FastEEM system and SPEX Fluorolog II fluorimeter. (D) Emission spectra at 450 nm excitation of the scattering tissue phantom containing FAD and polystyrene microspheres measured with the FastEEM system and SPEX Fluorolog II fluorimeter.
Figure 18B:
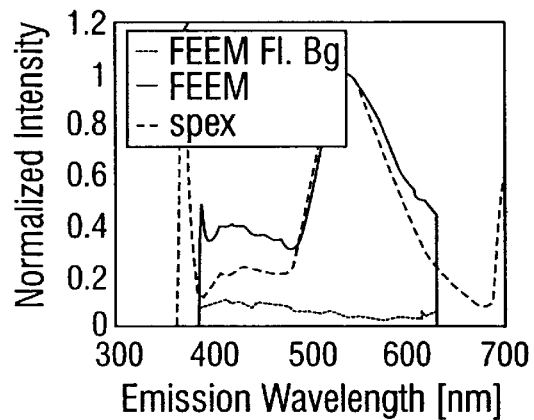
Figure 18C:
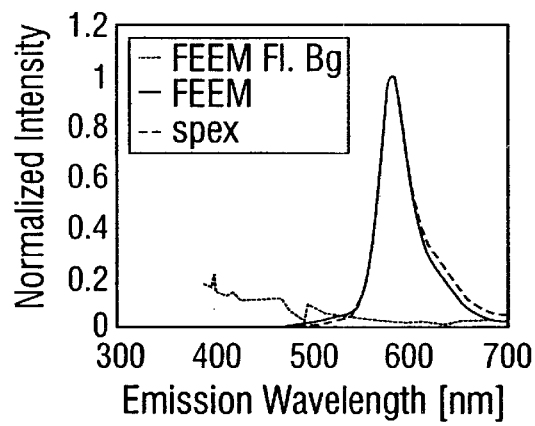
Figure 18D:
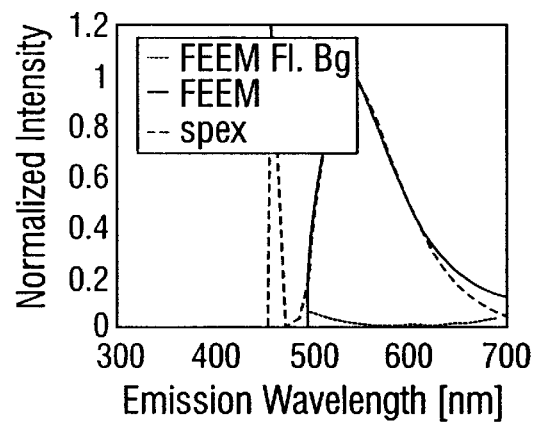

Results and Discussion:

FIGS. 17A and 17B show fluorescence EEMs of the non-scattering Rhodamine standard and the scattering FAD phantom obtained with a FastEEM system 10. Intensities are reported relative the Rhodamine intensity measured at 460 nm excitation and 580 nm emission wavelength. FIGS. 18A and 18B show fluorescence emission spectra of the Rhodamine standard obtained at 370 and 450 nm excitation with the SPEX and the FastEEM system 10 as well as the fluorescence background. FIGS. 18B and 18D show the same spectra for scattering FAD phantom obtained at the same excitation wavelengths. The spectra are normalized at their maximum. Note the presence of Rayleigh scattering peaks from the excitation source in the data taken with the SPEX. In general, from non-scattering samples (FIGS. 18A, 18C) the FastEEM system 10 collects less light above 600 nm than the SPEX. This may be due to the different collection efficiencies of the FastEEM probe and the front face collection geometry of the SPEX. Under scattering conditions and with lower fluorescence signal, the influence of background fluorescence becomes more critical. At 370 nm excitation wavelength the FastEEM system 10 measures more fluorescence below 500 nm. A comparison with the measured fluorescence background however shows that the additional signal has the same shape as the background. It has been hypothesized that the background may have been underestimated by measuring it in a non-scattering non-fluorescent media.

In-vivo fluorescence EEMs of the oral cavity were measured from 71 sites and in-vivo reflectance spectra were measured from 49 sites. These were obtained from patients in two studies. The first study included patients with abnormal oral lesions identified in a previous medical examination (17 patients). The second study, contributing nine patients, was of normal volunteers. All sites interrogated spectroscopically in patients with lesions were biopsied and submitted for histopathological analysis. Spectra and biopsies were also obtained from a contralateral site with no lesion in these patients with abnormal lesions. These biopsies were also evaluated histopathologically. No biopsies were taken from the normal volunteers. In this Example, we show representative EEMs from tissue found to be histopathologically normal and malignant to illustrate spectral features detectable with the FastEEM system.

Figure 19A:
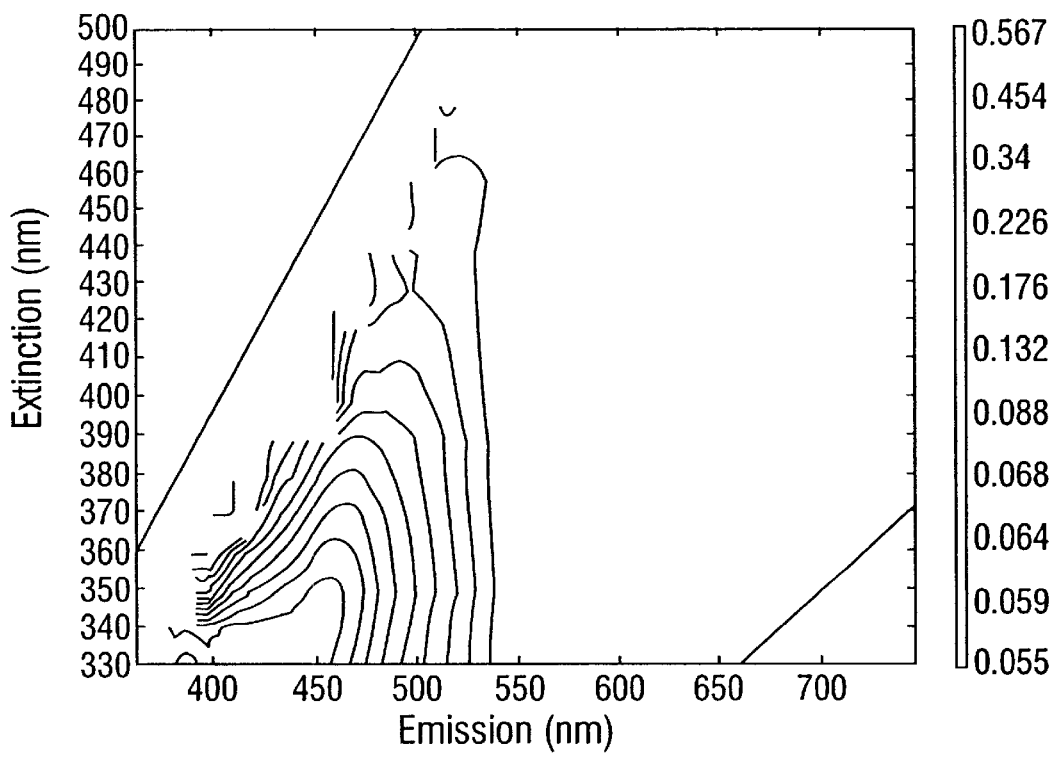
FIGS. 19A and 19B In-vivo fluorescence measurements with the FastEEM system: (A) Fluorescence EEM of a normal site of the tongue. (B) Fluorescence EEM of a diseased site of the tongue, containing a moderately differentiated squamous cell carcinoma.
Figure 19B:
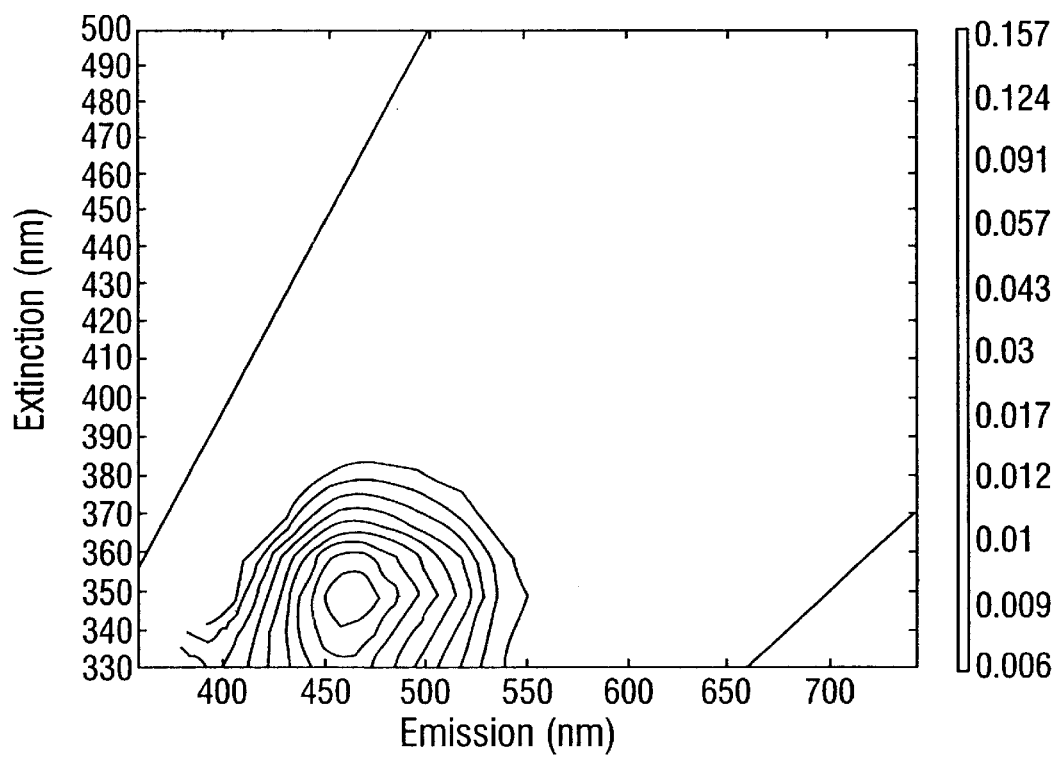

Two EEM contour plots from a normal and an abnormal area of the tongue are presented in FIGS. 19A and 19B, respectively. In the normal sample, fluorescence is observed throughout the whole collection range, with a peak located at 330/380 (excitation/emission) and a ridge extending from 340/450 to 450/500. Table II lists excitation-emission maxima pairs of endogenous tissue chromophores. Comparison of the observed peaks with Table II shows these peaks are consistent with the emission of structural proteins such as collagen and elastin, pyridine nucleotides (NADH) and flavoproteins (FAD). The normal site shows overall increased fluorescence with respect to the abnormal site shown in FIG. 19B. The abnormal site, assessed by a pathologist as being moderately differentiated squamous cell carcinoma, also shows broad fluorescence throughout. Peaks are observed at 330/380, 350/460, 460/520 and 500/630. A valley is seen at 420 nm excitation between 560 and 580 emission. This valley is seen to extend along the 420 nm excitation line as well as the 580 nm emission line. Table III suggests that these features are produced by hemoglobin reabsorption. Hemoglobin reabsorption may also in part account for the shift in the peaks of the abnormal EEM relative to the normal EEM. A summary of the excitation and emission maxima for the peaks observed in the normal and abnormal sites measured is presented in Table IV.

Figure 20A:
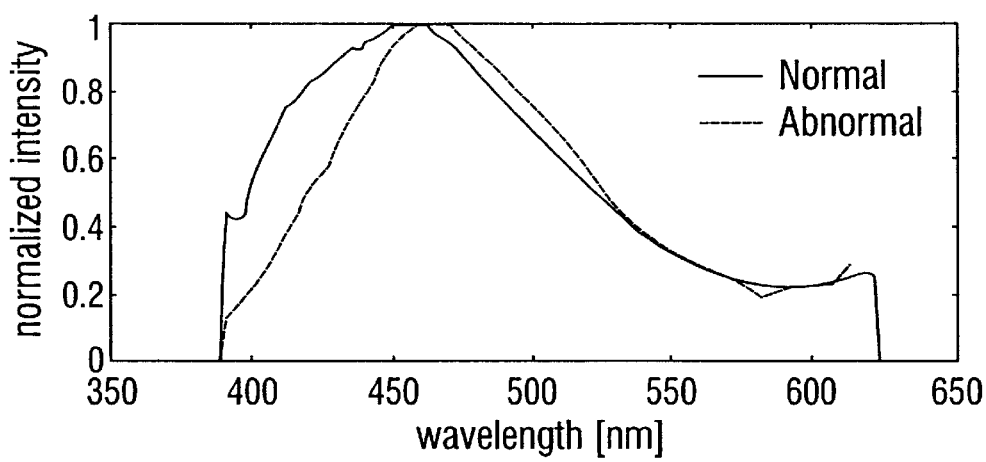
FIG. 20 Fluorescence emission spectra of normal and moderately differentiated squamous cell carcinoma of the tongue from FIG. 6. The spectra were normalized to the peak fluorescence at 350 nm excitation. (a) Fluorescence emission spectra at 350 nm excitation. (b) Fluorescence emission spectra at 410 nm excitation. (c) Fluorescence emission spectra at 460 nm excitation.
Figure 20B:
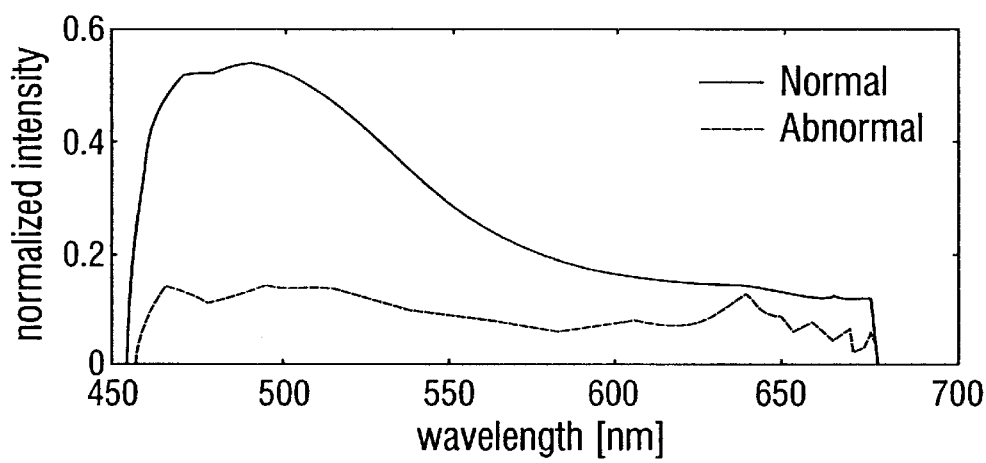
Figure 20C:
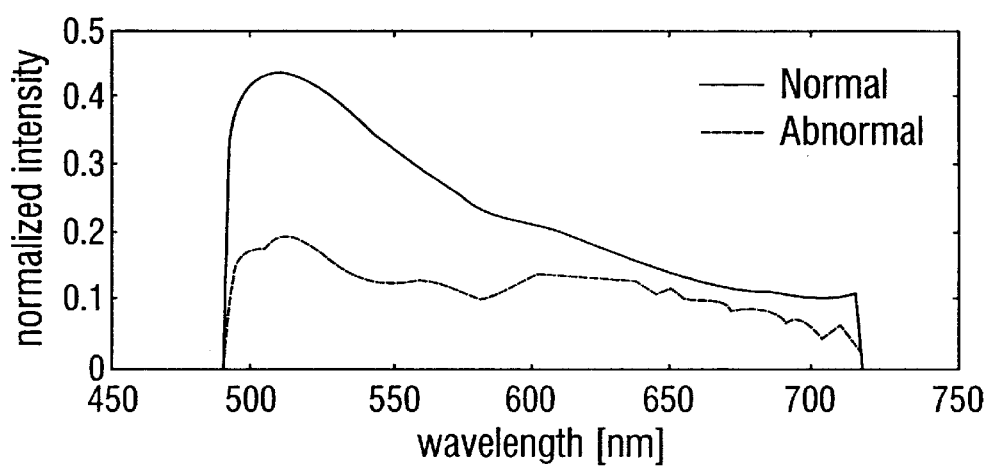

Fluorescence emission spectra at three selected excitation wavelengths are shown in FIG. 20, illustrating changes in relative intensities of fluorescence emission. For comparison purposes each set (normal/abnormal) was normalized to the maximum at 350 nm excitation. FIG. 20(a) shows the emission spectra at 350 nm excitation. Fluorescence from the normal site is seen as a broad peak with a maximum at 455 nm. The peak from the abnormal site is seen to be narrower and red-shifted. Examination of this spectrum at 410, 540 and 580 nm suggests that the change in lineshape is due to oxygenated hemoglobin. The general line shapes of the fluorescence observed at 410 nm excitation (FIG. 20(b)) are seen to be similar for both sites in the 450–575 nm excitation range, with a broad peak at 500 nm. The abnormal site shows a significantly lower fluorescence intensity, as well as an extra, narrow fluorescence peak at 640 nm, attributed to porphyrin fluorescence. FIG. 20(c) shows the emission spectra at 460 nm excitation. The normal site shows a broad peak at 520 nm and clear modulation from hemoglobin reabsorption at 540 and 580 nm. Fluorescence from the abnormal site shows an even more marked hemoglobin reabsorption; also the overall fluorescence intensity is reduced.

Figure 21A:
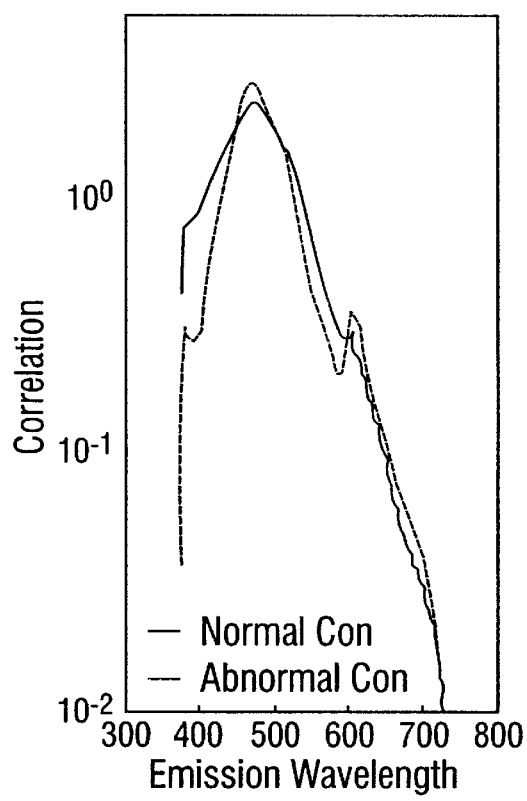
FIGS. 21A and 21B Emission and excitation autocorrelation vectors of normal and moderately differentiated squamous cell carcinoma of the tongue from FIGS. 18. (A) Emission autocorrelation vectors. (B) Excitation autocorrelation vectors.
Figure 21B:
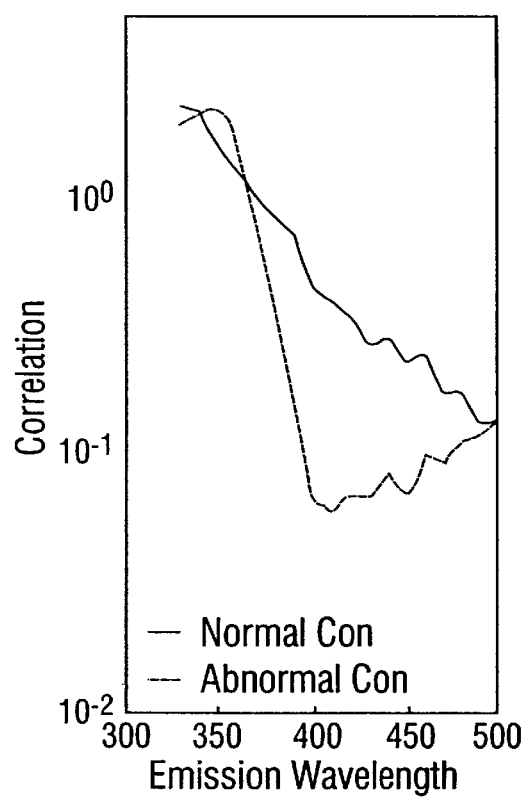

FIGS. 21A and 21B show the emission and excitation autocorrelation vectors for the same measurements. Note that the plots have a logarithmic y-axis. The emission autocorrelation vectors have a large broad peak at 460 nm corresponding to the main fluorescence peak observed in the EEMs. The vectors show the effect of hemoglobin absorption around 410, 540 and 580 nm in the abnormal site and the presence of additional fluorescence in the UV in the normal sample (FIG. 21A). This autocorrelation vector also highlights the peak at 610 nm in the abnormal sample. The excitation autocorrelation vectors show different line shapes. The curve corresponding to the normal site decreases steadily from 330 nm to 500 nm excitation. The curve from the abnormal site shows a peak at 350 nm and a minimum at 410 nm. The latter illustrates the greater influence of hemoglobin reabsorption in the abnormal sample also shown in FIG. 20.

Figure 22A:
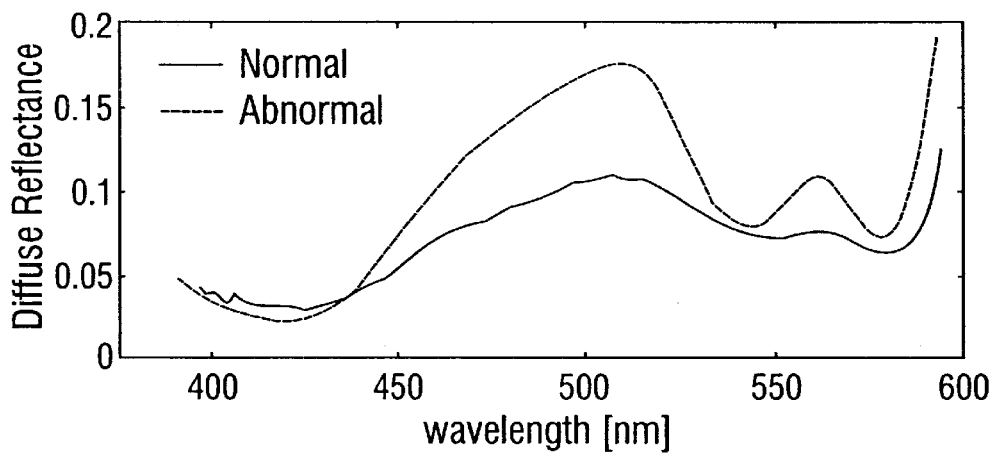
FIGS. 22A–22C. Reflectance measurements of normal and moderately differentiated squamous cell carcinoma of the tongue at three different separations from the source fiber. (A) Position 1, 1.1 mm separation. (B) Position 2, 2.1 mm separation. (C) Position 3, 3 mm separation.
Figure 22B:
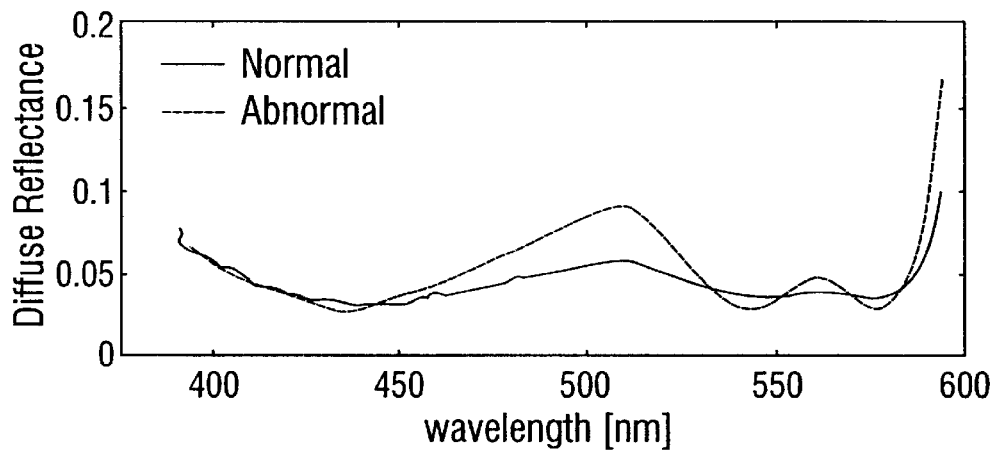
Figure 22C:
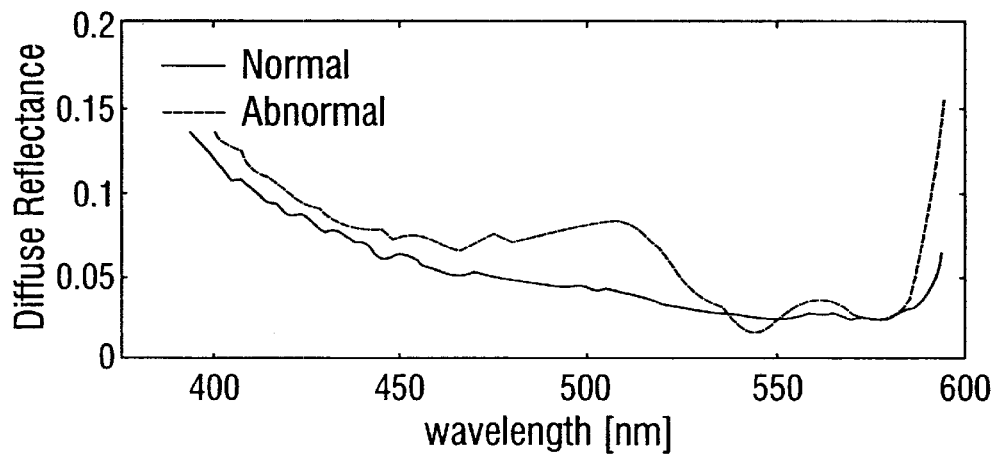

The corresponding reflectance data is shown in FIGS. 22A–22C. Position 1 corresponds to the collection fibers closest to the source fiber and position 3 to those furthest from the source fiber as shown in FIG. 15. The difference in position allow for spatially resolved reflectance measurements. Differences induced by the fluorescence reabsorption of oxygenated hemoglobin in the normal site and abnormal site are shown. The modulation of the spectrum by the 540 and 580 absorption bands is seen to be significantly stronger in the abnormal sample; this is consistent with the increased reabsorption seen in the fluorescence spectrum of the abnormal sample. The reflectance in the blue range (450–500 nm) of the abnormal site is consistently higher than that of the normal site. Below 450 nm the reflectance seems not to differ between the normal and abnormal samples.

Conclusions

The total data acquisition time for the data presented here was 2.5 minutes for a fluorescence EEM, and 1.5 minutes for the spatially resolved reflectance measurements. However, only 29 seconds of this time represented fluorescence collection. Actual reflectance collection time was 26 seconds. The most time consuming process was changing the excitation wavelength using the stepper motor controlled excitation spectrograph and changing the corresponding long-pass filter using the remotely controlled filter wheel. Worm drive based monochromators are available (DDD180, ISA) which require less than 10 seconds to scan our entire wavelength range in 10 nm steps, and could substantially reduce the total measurement time. Using a higher power lamp may further reduce acquisition time of both fluorescence and reflectance.

This Example has demonstrated the acquisition of EEMs in combination with spatially resolved reflectance measurements of tissue phantoms and in the oral cavity in vivo with good signal to noise ratio. The system features easy and arbitrary selection of excitation wavelengths in the UV and visible range. The system is also portable, and capable of functioning in a hospital operating room. Probes used in the Fast EEM system incorporate channels to measure spatially resolved reflectance and fluorescence, and are built small enough (less than about 5 mm) to be used during endoscopic surgical procedures. Autocorrelation vectors $x_{av}$ and $m_{av}$ are a suitable method to reduce the data set while preserving information about the wavelength bands carrying information. Based on the representative data shown here, fluorescence emission and excitation as well as reflectance data appear promising for the identification of tumors of the oral cavity. The Fast EEM system is an ideal tool to identify a subset of the most promising optical features to identify pathological findings in large clinical studies.

TABLE I

Fluorescence long-pass and diffuse reflectance filters used. Fluorescence long-pass filters are shown with the corresponding fluorescence excitation wavelength. Diffuse reflectance filters are shown with the corresponding measurement range.

| Fluorescence long-pass filter | Fluorescence excitation wavelengths (nm) |
|---|---|
| (1) GG 375 | 330, 340 |
| (2) GG 395 | 350, 360 |
| (3) GG 420 | 370, 380, 390 |
| (4) GG 445 | 400, 410, 420 |
| (5) GG 475 | 430, 440 |
| (6) OG 495 | 450, 460 |
| (7) OG 515 | 470, 480 |
| (8) OG 530 | 490, 500 |

| Reflectance filter | Possible reflectance measurement range |
|---|---|
| (1) WG 295 + GG 375 | 350–628 |
| (2) OG 515 + GG 375 | 500–778 |
| (3) RG 715 + GG 375 | 700–978 |

TABLE II

Summary of excitation/emission maxima of endogenous tissue chromophores.

| Chromophores | Excitation/emission (nm) |
|---|---|
| NADH | 340/450[11] |
| FAD | 450/515[11] |
| FAD | 370/535[11] |
| Porphyrin | 420/640[11] |
| Collagen I | 340/410[41] |
| Collagen I | 500/520[41] |
| Elastin | 330/405[41] |

TABLE III

Summary of absorption maxima of oxy- and deoxy-hemoglobin.

| Absorbers | Absorption wavelength (nm) |
|---|---|
| Oxygenated hemoglobin | 415[22] |
| Oxygenated hemoglobin | 542[41] |
| Oxygenated hemoglobin | 577[44] |
| Deoxygenated hemoglobin | 430[44] |
| Deoxygenated hemoglobin | 555[44] |

TABLE IV

Summary of excitation/emission maxima for peaks in the fluorescence EEMs of normal and abnormal oral cavity samples. The intensity is reported relative to the rhodamine standard at 460/580 nm.

Figure 6A:
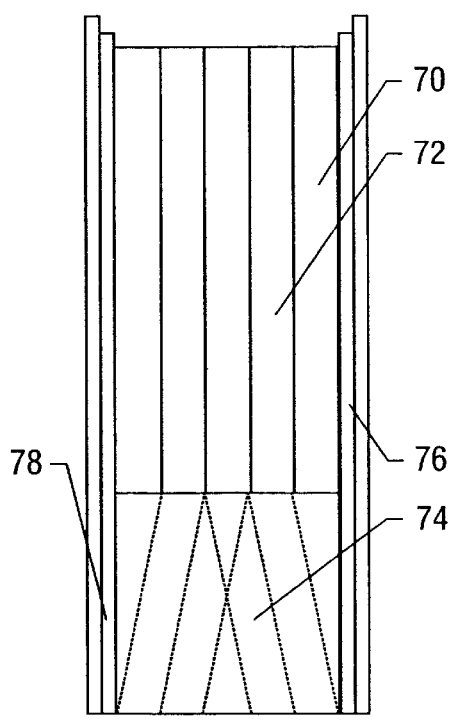
FIG. 6 A probe according to the present disclosure showing fluorescence excitation fibers, fluorescence collection fibers, a quartz rod, a reflectance excitation fiber, and reflectance collection fibers.
Figure 6B:
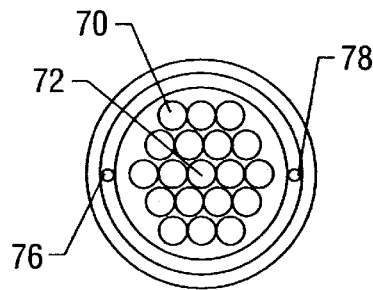

| Peak location [Excitation/emission nm] | Fluorescence intensity (Relative to rhodamine standard at 460/580 nm) |
|---|---|
| Normal site (FIG. 6A) | |
| 330/380 | 0.597 |
| 340/450 | 0.583 |
| 450/500 | 0.238 |
| Abnormal site (FIG. 6B) | |
| 330/380 | 0.082 |
| 350/460 | 0.166 |
| 460/520 | 0.031 |
| 500/630 | 0.032 |

EXAMPLE 2

Cervical Pre-Cancer Detection Using A Multivariate Statistical Algorithm Based On Laser Induced Fluorescence Spectra At Multiple Excitation Wavelengths A portable fluorimeter was developed and utilized to acquire fluorescence spectra from 381 cervical sites in 95 patients at 337, 380 and 460 nm excitation immediately prior to colposcopy. A multivariate statistical algorithm was used to extract clinically useful information from tissue spectra acquired in vivo. Two full-parameter algorithms were developed using tissue fluorescence emission spectra at all three excitation wavelengths (161 excitation-emission wavelength pairs) for cervical pre-cancer (squamous intraepithelial lesion (SIL)) detection: a screening algorithm which discriminates between SILs and non SILs with a sensitivity of 82%±1.4 and specificity of 68%±0.0, and a diagnostic algorithm which differentiates high grade SILs from non high grade SILs with a sensitivity and specificity of 79%±2 and 78%±6, respectively. Multivariate statistical analysis was also employed to reduce the number of fluorescence excitation-emission wavelength pairs needed to re-develop algorithms that demonstrate a minimum decrease in classification accuracy. Two reduced-parameter algorithms which employ fluorescence intensities at only 15 excitation-emission wavelength pairs were developed: the screening algorithm differentiates SILs from non SILs with a sensitivity of 84%±1.5 and specificity of 65%±2 and the diagnostic algorithm discriminates high grade SILs from non high grade SILs with a sensitivity and specificity of 78%±0.7 and 74%±2, respectively. Both the full-parameter and reduced-parameter screening algorithms discriminate between SILs and non SILs with a similar specificity (±5%) and a substantially improved sensitivity relative to Pap smear screening. A comparison of the full-parameter and reduced-parameter diagnostic algorithms to colposcopy in expert hands indicated that all three have a very similar sensitivity and specificity for differentiating high grade SILs from non high grade SILs.

This paper presents the development and application of a detection technique for human cervical pre-cancer based on laser induced fluorescence spectroscopy. A portable fluorimeter consisting of two nitrogen pumped-dye lasers, a fiber-optic probe and a polychromator coupled to an optical multi-channel analyzer was utilized to acquire fluorescence spectra from 381 cervical sites in 95 patients at three excitation wavelengths: 337, 380 and 460 nm. A general multivariate statistical algorithm was then used to analyze and extract clinically useful information from tissue spectra acquired in vivo. First, a screening algorithm was developed to discriminate between SILs and non SILs (normal squamous and columnar epithelia and inflammation); second, a diagnostic algorithm was developed to differentiate HG SILs from non HG SILs (LG SILs, normal epithelia and inflammation). The retrospective and prospective accuracy of both the screening and diagnostic algorithms were compared to the accuracy of Pap smear screening and to colposcopy in expert hands.

The general multivariate statistical algorithm was initially developed and tested using cervical tissue spectra acquired at 337 nm excitation from 476 cervical sites in 92 patients. This algorithm could be used to differentiate SILs and normal squamous tissues with an average sensitivity and specificity of 91%±2 and 78%±3, respectively. A limitation however is that spectra of normal columnar tissues and inflammation were indistinguishable from those of SILs at this single excitation wavelength. Furthermore, a multivariate statistical algorithm based solely on spectra at 337 nm excitation could not discriminate between HG SILs and LG SILs effectively.

However, multivariate statistical analysis of cervical tissue fluorescence spectra acquired in vivo at 380 nm and 460 nm excitation from a subset of the 92 patients indicated that spectra at these excitation wavelengths can overcome the limitations of spectra at 337 nm excitation. Spectra at 380 nm excitation from 165 sites in a first group of 40 patients could be used to differentiate SILs from normal columnar epithelia and inflammation with a sensitivity and specificity of 77%±1 and 72%±9, respectively; spectra at 460 nm excitation from 149 sites in a second group of 24 patients could be used to differentiate HG SILs from LG SILs with a sensitivity and specificity of 80%±4 and 76%±5, respectively.

The results from previous clinical studies suggested that an algorithm based on normalized, mean-scaled spectra at 337 nm excitation may be used to differentiate between SILs and normal squamous tissues, while an algorithm based on similarly pre-processed spectra at 380 nm excitation may be used to differentiate SILs from normal columnar tissues and samples with inflammation. Finally, a third algorithm based on normalized tissue spectra at 460 nm excitation may be used to discriminate between LG SILs and HG SILs. These results suggest that (1) a composite screening algorithm based on a combination of the first two constituent algorithms may be used to differentiate between SILs and non SILs (normal epithelia and inflammation) and (2) a composite diagnostic algorithm which combines all three constituent algorithms may be used to differentiate HG SILs from non HG SILs (LG SILs, normal tissues and inflammation).

The primary goal of the clinical study described in this Example was to evaluate the accuracy of constituent and composite algorithms which address certain limitations of previous clinical studies. Fluorescence spectra acquired in vivo at all three excitation wavelengths from 381 cervical sites in 95 patients were analyzed to determine if the accuracy of each of the three constituent algorithms previously developed may be improved using tissue spectra at a combination of two or three excitation wavelengths rather than at a single excitation wavelength. A second goal of the analysis was to integrate the three independently developed constituent algorithms that discriminate between pairs of tissue types into composite screening and diagnostic algorithms that may achieve discrimination between many of the clinically relevant tissue types. The effective accuracy of a composite screening algorithm for the identification of SILs and a composite diagnostic algorithm for the identification of HG SILs was evaluated.

The final goal of the analysis was to determine if fluorescence intensities at a reduced number of excitation-emission wavelength pairs may be used to re-develop constituent and composite algorithms that may achieve classification with a minimum decrease in predictive ability. A significant reduction in the number of required fluorescence excitation-emission wavelength pairs may enable the development of a cost-effective clinical fluorimeter. The accuracy of the constituent and composite algorithms based on the reduced emission variables was compared to the accuracy of those that utilize entire fluorescence emission spectra.

Instrumentation

Figure 23A:
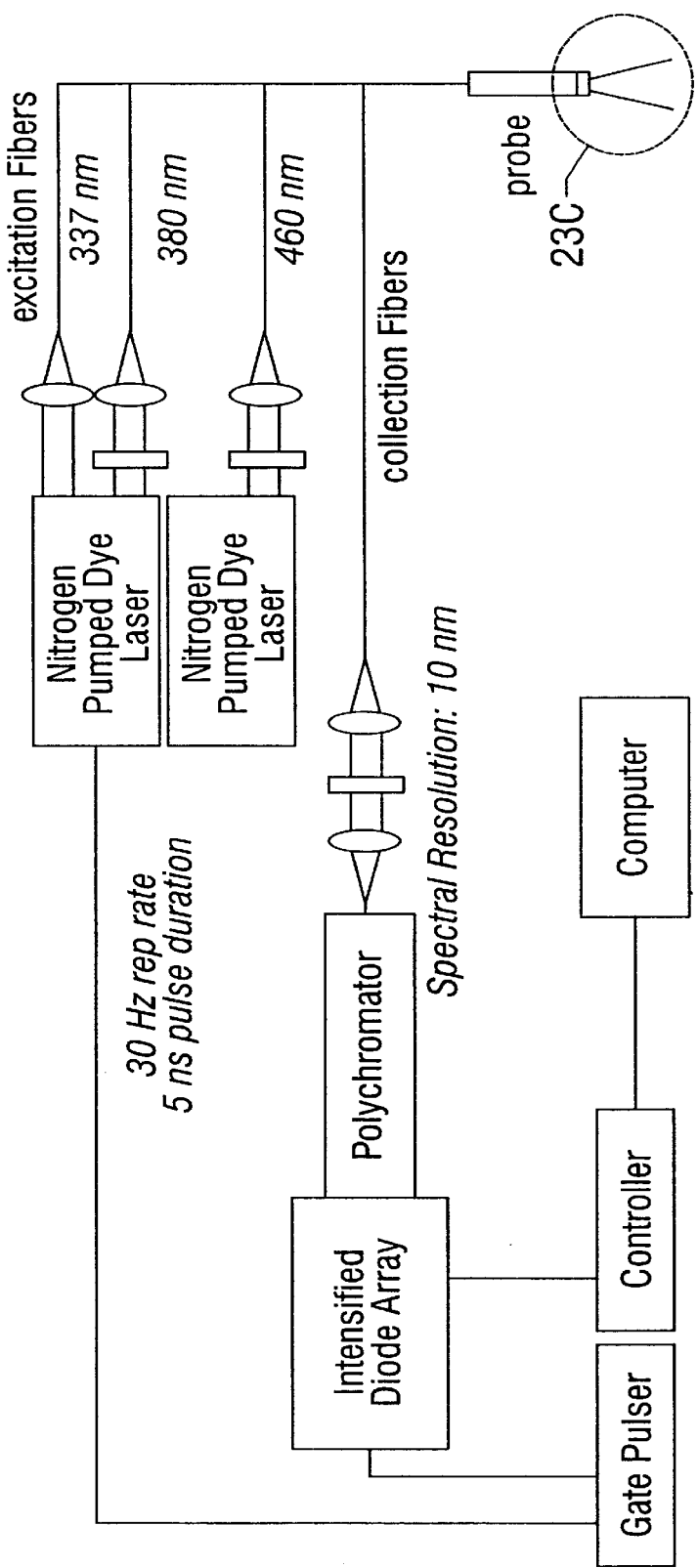
FIG. 23 A schematic of the portable fluorimeter used to measure cervical tissue fluorescence spectra at three excitation wavelengths.
Figure 23C:
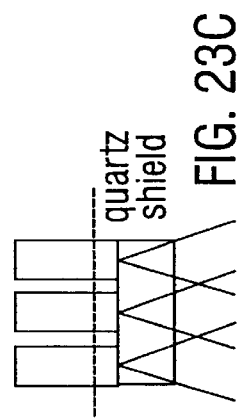
Figure 23B:
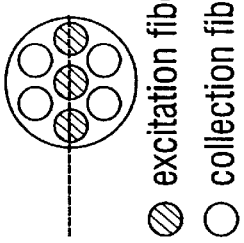

A schematic of the portable fluorimeter which was used to acquire cervical tissue fluorescence spectra at three excitation wavelengths is shown in FIG. 23(a). The fiber-optic probe (Valdor Fiber Optics, VSC/FER/4SMA-1/7-BUN) included a central fiber surrounded by a circular array of six fibers; all seven fibers having the same characteristics (0.22 NA, 200 $\mu$m core diameter, 245 $\mu$m diameter with cladding). Three fibers along the diameter of the distal end of the probe (FIG. 23(b)) were used for excitation light delivery. The purpose of the remaining four fibers was to collect the emitted fluorescence from the area directly illuminated by the probe. A quartz shield (3 mm in diameter and 2 mm thick) at the tip of the distal end of the probe that is in direct tissue contact (FIG. 23(c)) provided a fixed distance between the optical fibers and the tissue surface so fluorescence intensity can be measured in calibrated units.

An area, 1 mm in diameter was illuminated by each excitation fiber. The overlap of the illumination area viewed by the three excitation fibers and the four collection fibers was approximately 80% at the outer surface of the quartz shield. Note that the central excitation fiber has four adjacent collection fibers whereas the two excitation fibers in the periphery of the probe have only two adjacent collection fibers (FIG. 23(b)). However, due to the large overlap of the optical fibers at the outer face of the quartz shield, this difference in the excitation-emission configuration relates only to a small difference in the collection efficiency of the fluorescence generated due to excitation delivered by the central and peripheral excitation fibers. The difference in collection efficiency is accounted for by normalizing tissue fluorescence spectra to the peak fluorescence intensity of a Rhodamine 610 calibration standard measured using the same probe configuration.

Two nitrogen pumped-dye lasers (laser characteristics: 5 ns pulse duration, 30 Hz repetition rate) (Laser Photonics, LN300C) were used to provide illumination at three different excitation wavelengths: one laser served to deliver excitation light at 337 nm (fundamental) and had a dye module which was used to generate light at 380 nm using the fluorescent dye, BBQ (1E-03 M in 7 parts toluene and 3 parts ethanol). The dye module of the second laser was used to provide illumination at 460 nm, using the fluorescent dye, Coumarin 460 (1E-02 M in ethanol). Laser illumination at each excitation wavelength, 337, 380 and 460 nm was coupled into each of the three excitation fibers of the probe. Note that two 10 nm bandpass filters, one centered at 380 nm and the other centered at 460 nm were placed between the excitation fiber and the dye module used to generate illumination at 380 and 460 nm, respectively to prevent leakage from the fundamental at 337 nm. In this Example, the average fluence per pulse at 337, 380 and 460 nm excitation were 15.2, 11.5 and 18 $\mu$J/mm$^2$, respectively. The pulse energy at 337 nm excitation was intentionally reduced so that the measured fluorescence signal did not exceed the dynamic range of the detector.

The proximal ends of the four collection fibers were arranged in a circular array and imaged at the 500 $\mu$m wide entrance slit of a f/3.8 spectrograph equipped with a 300 ln/mm grating (Jarrell Ash, Monospec 18) coupled to a 1,024 intensified diode array controlled by a multi-channel analyzer (Princeton Instruments, OMA). The collection optics between the proximal end of the four emission collection fibers and the polychromator included two quartz plano convex lenses. Between these lenses was a filter wheel assembly containing long pass filters with 50% transmission at 360 (GG360), 400 (GG400) and 475 (GG475) nm which are used to block scattered excitation light at 337, 380 and 460 nm excitation, respectively from the detector. The purpose of the filter wheel was to position the appropriate long pass filter in the optical path during fluorescence measurements at each excitation wavelength. The nitrogen pumped-dye lasers were used to externally trigger a pulser (Princeton Instruments, PG200) which served to synchronize the 200 ns collection gate of the detector to the leading edge of the laser pulse. The gating of the detector eliminated the effects of the colposcope's white light illumination during fluorescence measurements. Data acquisition was computer controlled.

Clinical measurements

A randomly selected group of non-pregnant patients referred to the colposcopy clinic of the University of Texas MD Anderson Cancer Center on the basis of abnormal cervical cytology was asked to participate in the in vivo fluorescence spectroscopy study. Informed consent was obtained from each patient who participated and the study was reviewed and approved by the Institutional Review Boards of the University of Texas, Austin and the University of Texas, MD Anderson Cancer Center. Each patient underwent a complete history and a physical examination including a pelvic exam, a Pap smear and colposcopy of the cervix, vagina and vulva. After colposcopic examination of the cervix, but before tissue biopsy, fluorescence spectra were acquired on average from two colposcopically abnormal sites, two colposcopically normal squamous sites and 1 normal columnar site (if colposcopically visible) from each patient. Tissue biopsies were obtained only from abnormal sites after they had been identified by colposcopy and then analyzed by the probe. Tissue biopsies were not obtained from normal squamous or columnar sites analyzed by the probe to comply with routine patient care procedure. All tissue biopsies were fixed in formalin and submitted for histologic examination. Hemotoxylin and eosin stained sections of each biopsy specimen were evaluated by a panel of four board certified pathologists and a consensus diagnosis was established using the Bethesda classification system. This classification system which has previously been used to grade cytologic specimens has now been extended to classification of histology samples. Samples were classified as normal squamous, normal columnar, inflammation, LG SIL or HG SIL. Samples with multiple diagnoses were classified into the most severe histo-pathologic category.

Prior to each patient study, the probe was disinfected and a background spectrum was acquired at all three excitation wavelengths consecutively with the probe dipped in a nonfluorescent bottle containing distilled water. The background spectrum indicated no fluorescence due to optical components of the fluorimeter or the disinfectant and was subtracted from all subsequently acquired spectra at corresponding excitation wavelengths for that patient. Next, with the probe placed on the face of a quartz cuvette containing a solution of Rhodamine 610 dissolved in ethylene glycol (2 mg/L), 50 fluorescence spectra were measured at each excitation wavelength. After calibration, fluorescence spectra were acquired from the cervix: 10 spectra for 10 consecutive pulses were acquired at 337 nm excitation; next, 50 spectra for 50 consecutive laser pulses were measured at 380 nm excitation and then at 460 nm excitation. The data acquisition time was 0.33 s at 337 nm excitation and 1.67 s at each 380 and 460 nm excitation per cervical site. The time required to switch between the two nitrogen pumped-dye lasers and the three long pass filters was approximately 5 s. Hence, the total time required to record fluorescence emission spectra at all three excitation wavelengths from one cervical site was approximately 10 s. Spectra were collected in the visible region of the electromagnetic spectrum with a resolution of 10 nm (full width at half maximum) and a signal to noise ratio of 100:1 at the fluorescence maximum at each excitation wavelength.

All spectra were corrected for the non-uniform spectral response of the detection system using correction factors obtained by recording the spectrum of an N.I.S.T traceable calibrated tungsten ribbon filament lamp. Spectra from each cervical site at each excitation wavelength were averaged to obtain a single spectrum per site. The fluorescence spectra obtained at each excitation wavelength from the Rhodamine 610 calibration standard were also averaged to obtain a single spectrum per excitation wavelength. The average tissue spectra were then normalized to the average peak fluorescence intensity of the Rhodamine 610 calibration standard at the corresponding excitation wavelength for that patient; absolute fluorescence intensities are reported in these calibrated units. In this clinical study, fluorescence spectra were acquired at all three excitation wavelengths from each cervical site from a total of 381 sites in 95 patients during colposcopy.

Development of Screening and Diagnostic Algorithms

Figure 24:
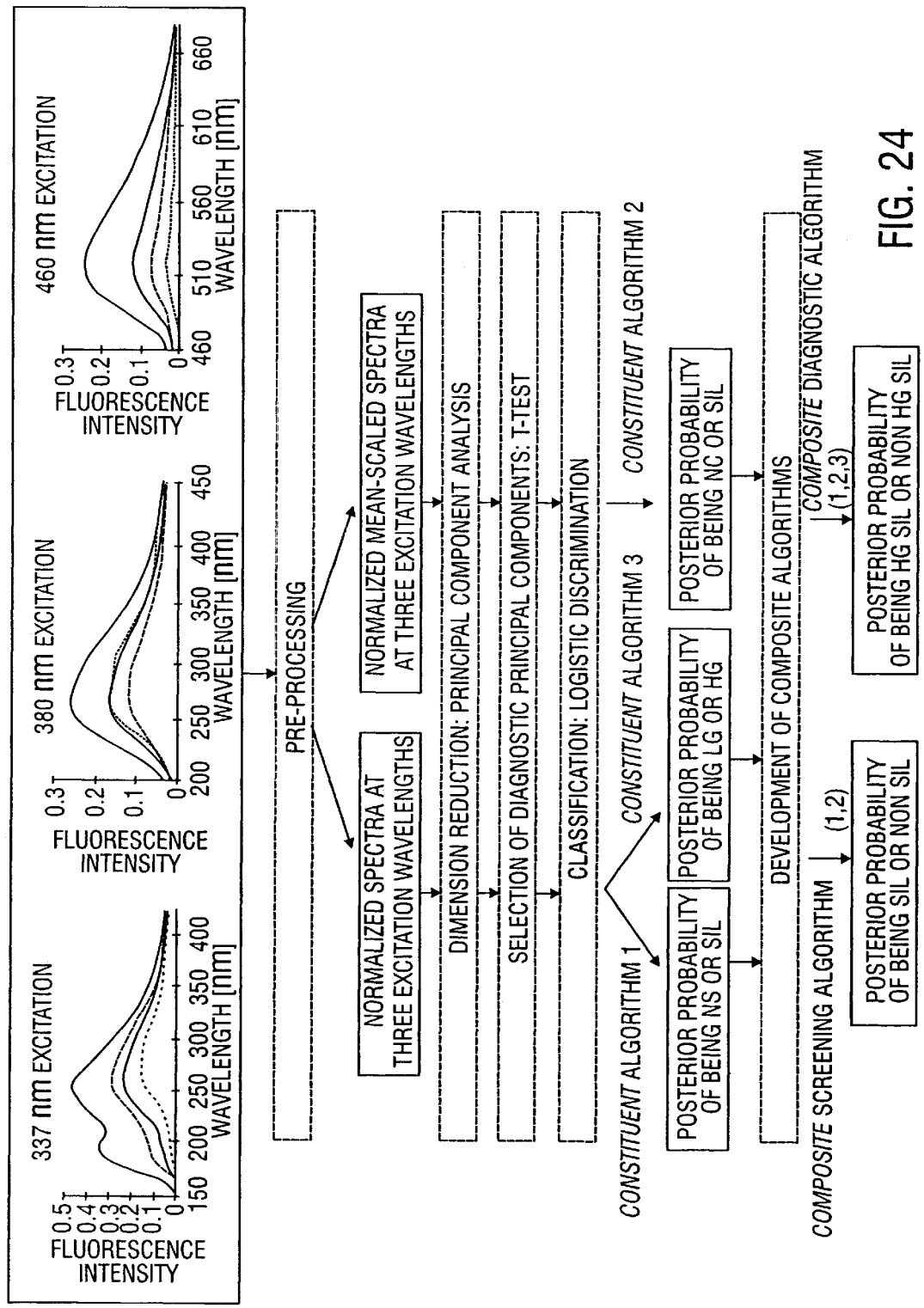
FIG. 24 A schematic of formal analytical process used to develop the screening and diagnostic algorithms. The text in the dashed-line boxes represent mathematical steps implemented on the spectral data and the text in the solid line boxes represent outputs after each mathematical step (NS—normal squamous, NC—normal columnar, LG—LG SIL and HG—HG SIL).

FIG. 24 illustrates a schematic of the formal analytical process used to develop screening and diagnostic algorithms for the differential detection of SILs, in vivo. In FIG. 24, the text in the dashed-line boxes represent the mathematical steps implemented on the spectral data, and the text in the solid-line boxes represent the output after each mathematical process. There are four primary steps involved in the multivariate statistical analysis of tissue spectral data (FIG. 24). The first step is to pre-process spectral data to reduce inter-patient and intra-patient variation within a tissue type; the pre-processed spectra are then dimensionally reduced into an informative set of principal components that describe most of the variance of the original spectral data set using Principal Component Analysis (PCA). Next, the principal components that contain diagnostically relevant information are selected using an unpaired, one-sided student's t-test, and finally a classification algorithm based on logistic discrimination is developed using these diagnostically relevant principal components.

In summary, three constituent algorithms were developed using multivariate statistical analysis (FIG. 24): constituent algorithm (1) discriminates between SILs and normal squamous tissues, constituent algorithm (2) discriminates between SILs and normal columnar tissues and finally, algorithm (3) differentiates HG SILs from LG SILs. The three constituent algorithms were then combined to develop two composite algorithms (FIG. 24): constituent algorithms (1) and (2) were combined to develop a composite screening algorithm which discriminates between SILs and non SILs. All three constituent algorithms were then combined to develop a composite diagnostic algorithm which differentiates HG SILs from non HG SILs.

Multivariate Statistical Analysis of Cervical Tissue Spectra

As a first step, three methods of pre-processing were applied to the spectral data at each excitation wavelength: (1) normalization (2) mean-scaling and (3) a combination of normalization and mean-scaling. Similarly pre-processed spectra at each excitation wavelength were combined to create spectral inputs at the following combinations of excitation wavelengths: (337, 460) nm, (337, 380) nm, (380, 460) mm and (337, 380, 460) nm. Pre-processing of spectral data resulted in four types of spectral inputs (original and three types of pre-processed spectral inputs) at three single excitation wavelengths and at four possible combinations of multiple excitation wavelengths. Hence, there were a total of 12 spectral inputs at single excitation wavelengths and 16 spectral inputs at multiple excitation wavelengths which were evaluated using the multivariate statistical algorithm.

Prior to PCA, the input data matrix, D (r×c) was created so each row of the matrix corresponded to the pre-processed fluorescence spectrum of a sample and each column corresponded to the pre-processed fluorescence intensity at each emission wavelength. Spectral inputs at multiple excitation wavelengths were created by arranging spectra at each excitation wavelength in series in the original spectral data matrix. PCA was used to dimensionally reduce the pre-processed spectral data matrix into a smaller orthogonal set of linear combinations of the emission variables that account for most of the variance of the spectral data set.

Average values of principal component scores were calculated for each principal component of each tissue type. An unpaired, one-sided student's t-test was employed to determine the diagnostic content of each principal component. The hypothesis that the means of the principal component scores of two tissue types are different was tested for (1) normal squamous epithelia and SILs, (2) normal columnar epithelia and SILs and (3) inflammation and SILs. The t-test was extended a step further to determine if there were any statistically significant differences between the means of the principal component scores of HG SILs and LG SILs. Principal components for which the hypothesis stated above was statistically significant (P<0.05) were retained for further analysis.

Next, a statistical classification algorithm was developed using the diagnostically useful principal components to calculate the posterior probability that an unknown sample belongs to each tissue type under consideration. The posterior probability of an unknown sample belonging to each tissue type was calculated using logistic discrimination. The posterior probability is related to the prior and conditional joint probabilities and to the costs of misclassification of the tissue types under consideration. The prior probability of each tissue type was determined by calculating the observed proportion of cases in each group. The cost of misclassification of a particular tissue type was varied from 0 to 1 in 0.1 increments, and the optimal cost was identified when the total number of misclassified samples based on the classification algorithm was a minimum. If there was more than one cost at which the total number of misclassified samples was a minimum, the cost that maximized sensitivity was selected. The conditional joint probabilities were developed by modeling the probability distribution of each principal component of each tissue type using the normal probability density function, which is characterized by $\mu$ (mean) and $\sigma$ (standard deviation). The best fit of the normal probability density function to the probability distribution of each principal component (score) of each tissue type was obtained in the least squares sense, using $\mu$ and $\sigma$ as free parameters of the fit. The normal probability density function was then used to calculate the conditional joint probability that an unknown sample, given that it is from tissue type i, will exhibit a set of principal component scores, X.

The multivariate statistical algorithm was developed and optimized using a calibration set and then tested on a prediction set of approximately equal prior probability (Table 1). The purpose of testing the algorithm on the prediction set was to determine (1) an unbiased estimate of the algorithm's classification accuracy and (2) if the number of sample spectra within each category in the calibration set is sufficient to describe the spectral data in the prediction set. The calibration and prediction sets were developed by randomly assigning the spectral data into the two sets with the condition that both contain roughly equal number of samples from each histo-pathologic category. The random assignment ensured that not all spectra from a single patient were contained in the same data set.

Development of Constituent Algorithms

The multivariate statistical algorithm was developed and optimized using all 28 types of pre-processed spectral inputs from the calibration set. The algorithm was used to identify spectral inputs which provide the greatest discrimination between the following pairs of tissue types: (1) SILs and normal squamous epithelia, (2) SILs and normal columnar epithelia, (3) SILs and inflammation, and (4) HG SILs and LG SILs. The optimal spectral input for differentiating between two particular tissue types was identified when the total number of samples misclassified from the calibration set using the multivariate statistical algorithm was a minimum. The algorithm based on the spectral input that minimized misclassification between the two tissue types under consideration was implemented on the prediction data set.

Three multivariate statistical constituent algorithms were developed using tissue spectra at three excitation wavelengths. Constituent algorithm (1) was developed to differentiate between SILs and normal squamous epithelia; constituent algorithm (2) was developed to differentiate between SILs and normal columnar epithelia and constituent algorithm (3) could be used to discriminate between LG SILs and HG SILs. A constituent algorithm which can discriminate between SILs and tissues with inflammation could not be developed using spectral data from the current clinical study.

Development of Composite Algorithms

Each of the independently developed constituent algorithms was intended to discriminate only between pairs of tissue types. A combination of these constituent algorithms was required to provide discrimination between several of the clinically relevant tissue types. Therefore, two composite algorithms were developed: a composite screening algorithm was developed to differentiate between SILs and non SILs (normal squamous and columnar epithelia and inflammation) using constituent algorithms (1) and (2) and a composite diagnostic algorithm was developed to differentiate HG SILs from non HG SILs (LG SILs, normal epithelia and inflammation) using all three constituent algorithms.

The composite screening algorithm was developed in the following manner. First, constituent algorithms (1) and (2) were developed independently using the calibration data set. The classification outputs from both constituent algorithms were used to determine if a sample being evaluated is SIL or non SIL: first, using constituent algorithm (1), samples were classified as non SIL if they had a probability that is less than 0.5; otherwise, they were classified as SIL. Next, only samples that were classified as SIL based on the algorithm (1) were tested using algorithm (2). Again, samples were classified as non SIL if their posterior probability was less than 0.5; otherwise they were classified as SIL. The spectral data from the prediction set was evaluated using the composite screening algorithm in an identical manner.

The composite diagnostic algorithm was implemented in the following manner. The three constituent algorithms were developed independently using the calibration set. Algorithms (1) and (2) were implemented on each sample from the calibration data set, as described previously. Only samples that were classified as SIL based on algorithms (1) and (2) were tested using algorithm (3). If samples evaluated using algorithm (3) had a posterior probability greater than 0.5, they were classified as HG SIL; otherwise they were classified as non HG SIL. The spectral data from the prediction set was evaluated using the composite diagnostic algorithm in an identical manner.

Results

Constituent Algorithms (1), (2) and (3)

Table 2 summarizes the components of the optimal set of three constituent algorithms. Constituent algorithm (1) can be used to differentiate between SILs and normal squamous epithelia; algorithm (2) differentiates between SILs and normal columnar epithelia and algorithm (3) discriminates between LG SILs and HG SILs.

Pre-processing

Figure 25A:
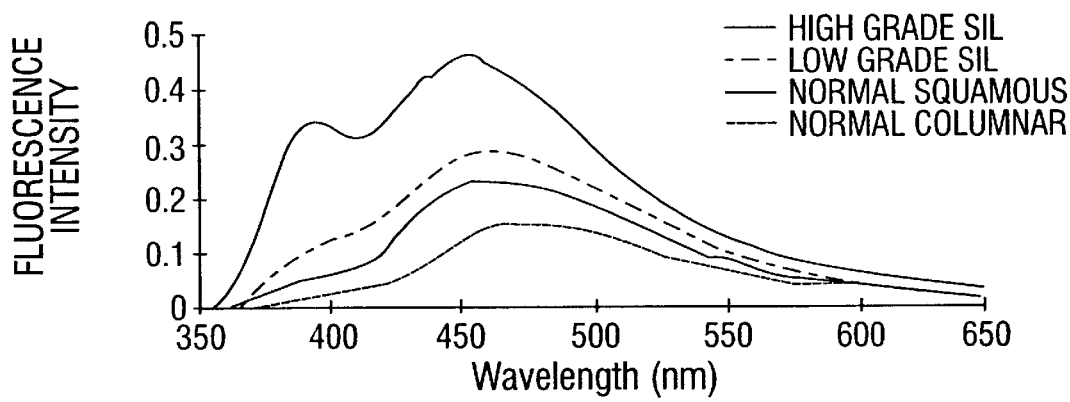
FIG. 25 (a) Original and corresponding (b) normalized and (c) normalized, mean-scaled spectra at 337 nm excitation from a typical patient.
Figure 25B:
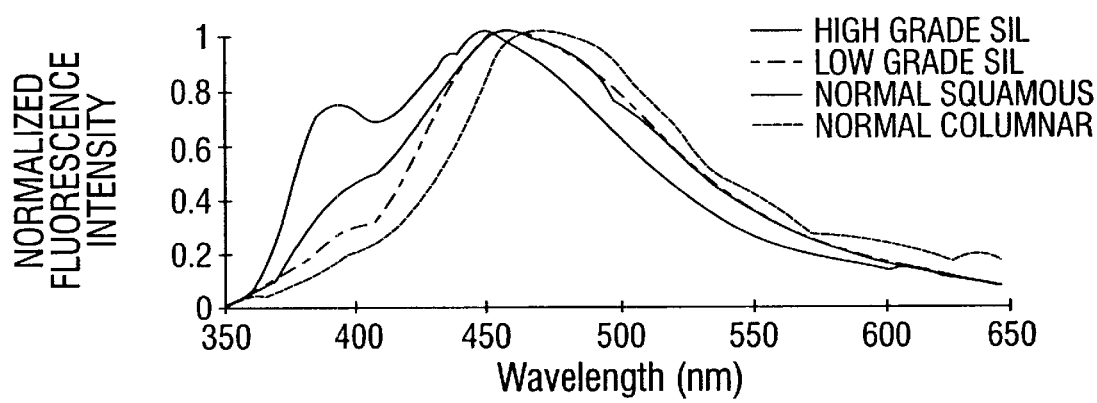
Figure 25C:
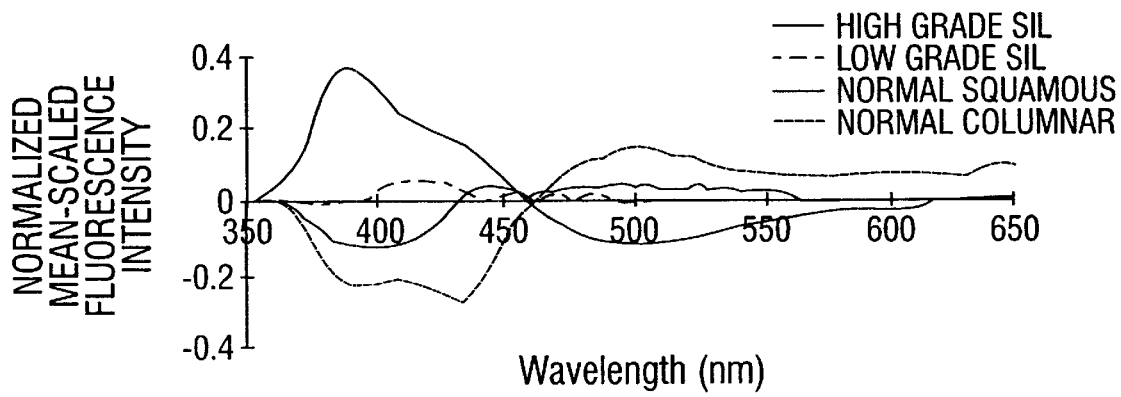

FIG. 25(a) illustrates average fluorescence spectra per site acquired from cervical sites at 337 nm excitation from a typical patient. All fluorescence intensities are reported in the same set of calibrated units. Corresponding normalized and normalized, meanscaled spectra are illustrated in FIG. 25(b) and 25(c), respectively. Evaluation of the original spectra at 337 nm excitation (FIG. 25(a)) indicates that the fluorescence intensity of SILs is less than that of the corresponding normal squamous tissue and greater than that of the corresponding normal columnar tissue over the entire emission spectrum. Examination of normalized spectra from this patient (FIG. 25(b)) indicates that following normalization, the fluorescence intensity of the normal squamous tissue is greater than that of corresponding SILs over the wavelength range 360 to 450 nm only; between 460 and 600 nm, the fluorescence intensity of SILs is greater than that of the corresponding normal squamous tissue which in part reflects the longer peak emission wavelength of SILs. A comparison of the spectral line shape of SILs to that of the normal columnar tissue illustrates the opposite phenomenon. The normalized fluorescence intensity of SILs is greater than that of the corresponding normal columnar tissue over the wavelength range 360 to 450 nm; however, between 460 and 600 nm, the fluorescence intensity of the normal columnar tissue is greater than that of the SILs; this spectral difference reflects the longer peak emission wavelength of the normal columnar tissue relative to that of SILs. Further evaluation of normalized spectra in FIG. 25(b) indicates that there are spectral line shape differences between LG SILs and HG SILs over the wavelength range 360 to 420 nm.

The corresponding normalized, mean-scaled spectra of this patient, shown in FIG. 25(c) displays differences in the normalized fluorescence spectrum (FIG. 25(b)) from a particular site with respect to the average normalized spectrum (the average of all normalized spectra obtained from this patient). As the average normalized spectrum has been subtracted from each normalized spectrum obtained from this patient, the mean now lies at Y=0 over the entire emission wavelength range. Evaluation of FIG. 25(c) indicates that between 360 and 450 nm, the normalized, mean-scaled fluorescence intensity of the normal squamous tissue is greater than the mean, and that of the normal columnar tissue is less than the mean. Above 460 nm, the opposite phenomenon is observed; the fluorescence intensity of the normal squamous tissue is less than the mean, while that of the normal columnar tissue is greater than the mean. The fluorescence intensity of SILs lies close to the mean and is bounded by the intensities of the two normal tissue types. In addition, between 360 and 420 nm, the normalized, mean-scaled fluorescence intensity of the LG SIL is slightly greater than the mean, while that of the HG SIL is less than the mean.

Figure 26A:
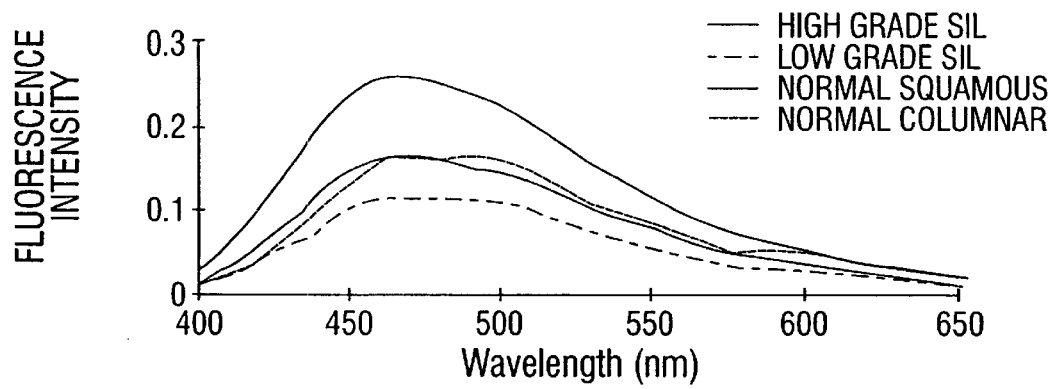
FIG. 26 (a) Original and corresponding (b) normalized and (c) normalized, mean-scaled spectra at 380 nm excitation from the same patient.
Figure 26B:
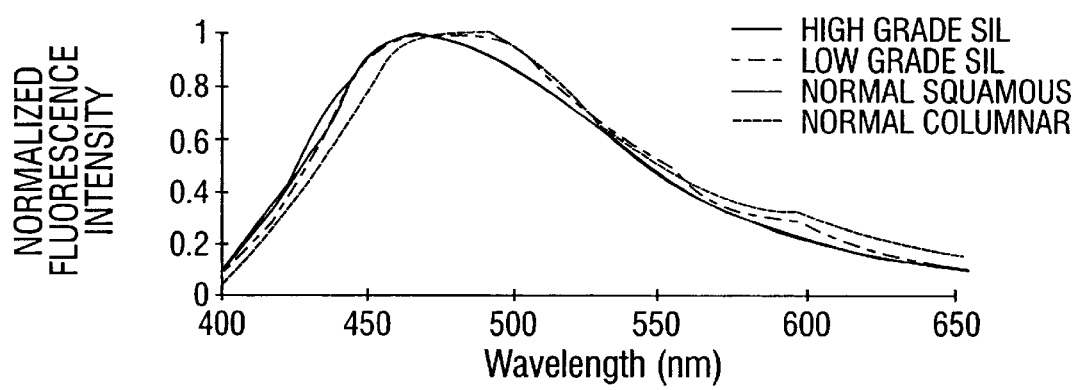
Figure 26C:
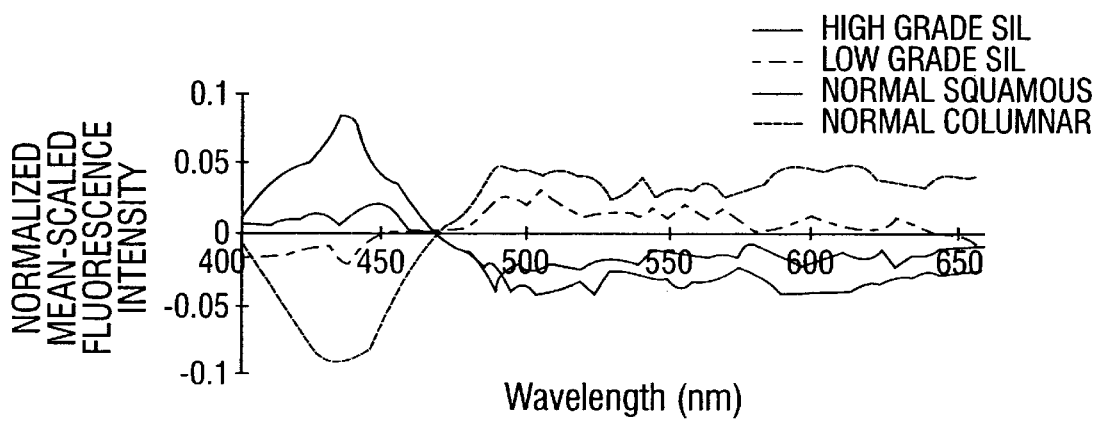

FIG. 26(a) illustrates average fluorescence spectra per site acquired from cervical sites at 380 nm excitation, from the same patient. FIGS. 26(b–c) show the corresponding normalized, and normalized, mean-scaled spectra, respectively. In FIG. 26(a), the fluorescence intensity of SILs is less than that of the corresponding normal squamous tissue, with the LG SIL exhibiting the weakest fluorescence intensity over the entire emission spectrum. Note that the fluorescence intensity of the normal columnar sample is indistinguishable from that of the HG SIL. Normalized spectra at 380 nm excitation, (26(b)), indicate that over the wavelength range 400 to 450 nm, the fluorescence intensity of the normal squamous tissue is slightly greater than that of SILs and that of the normal columnar tissue is less than that of SILs. The opposite phenomenon is observed above 580 nm. A careful examination of the spectra of the LG SIL and HG SIL indicates that between 460 and 580 nm, the normalized fluorescence intensity of the LG SIL is higher than that of the HG SIL. The normalized, mean-scaled spectra (FIG. 26(c)) enhances the previously observed normalized spectral line shape differences by displaying them relative to the average normalized spectrum of this patient. FIG. 26(c) indicates that between 400 to 450 nm, the fluorescence intensity of the normal squamous tissue is greater than the mean and that of the normal columnar tissue is less than the mean. The opposite phenomenon is observed above 460 nm. The fluorescence intensity of the SILs is bounded by the intensities of the two normal tissue types over the entire emission spectrum. The LG SIL and HG SIL also show spectral line shape differences; above 460 nm, the normalized, mean-scaled fluorescence intensity of the LG SIL lies above the mean and that of the HG SIL lies below the mean.

Figure 27A:
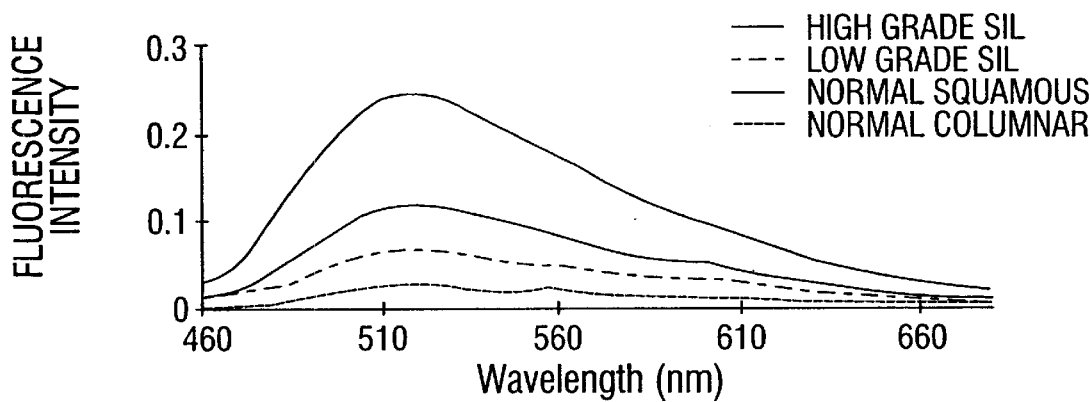
FIG. 27 (a) Original and corresponding (b) normalized and (c) normalized, mean-scaled spectra at 460 nm excitation from the same patient.
Figure 27B:
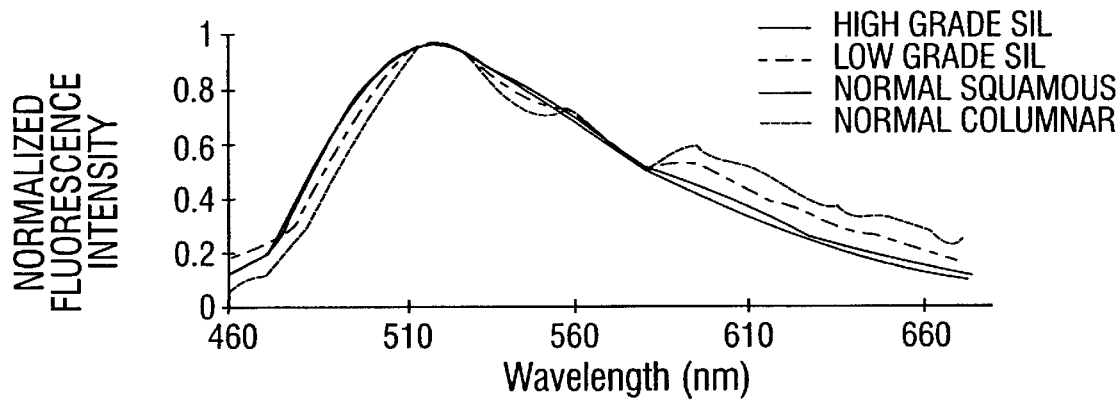
Figure 27C:
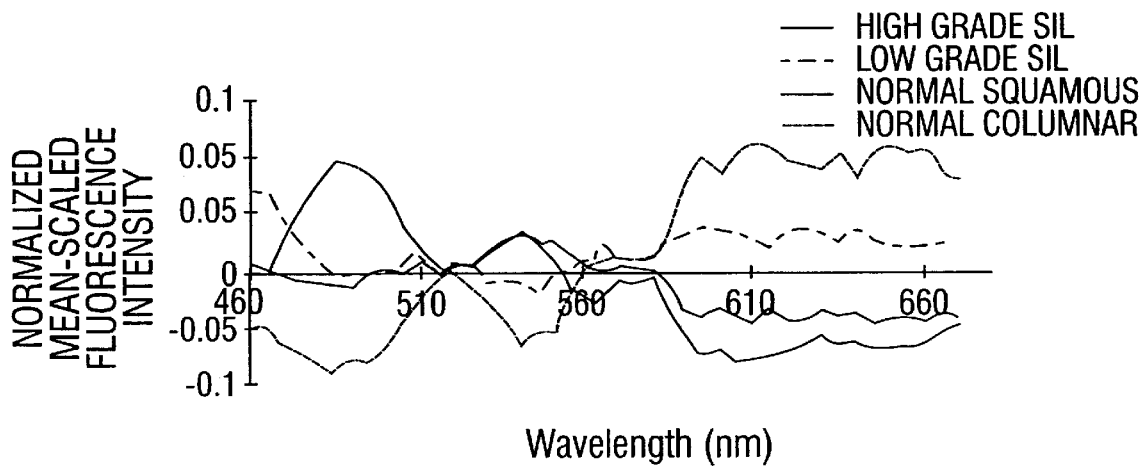

FIGS. 27(a–c) illustrate original, normalized and normalized, mean-scaled spectra, respectively at 460 nm excitation from the same patient. Evaluation of FIG. 27(a) indicates that the fluorescence intensity of SILs is less than that of the corresponding normal squamous tissue and greater than that of the corresponding normal columnar sample over the entire emission spectrum. Evaluation of normalized spectra at this excitation wavelength (FIG. 27(b)) demonstrates that below 510 nm, the fluorescence intensity of SILs is less than that of the normal squamous tissue and greater than that of the corresponding normal columnar tissue. Above, 580 nm, the normalized fluorescence intensity of SILs is less than that of the normal columnar tissue and greater then that of normal squamous tissue. Note that there are spectral line shape differences between the LG SIL and HG SIL between 580 and 660 nm; the normalized fluorescence intensity of the LG SIL is greater than that of the HG SIL. The normalized, mean-scaled spectra shown in FIG. 27(c) reflects the differences observed in the normalized spectra relative to the average normalized spectrum of this patient. Below 510 nm, the fluorescence intensity of the normal squamous tissue is greater than the mean, while that of the normal columnar tissue is less than the mean. Above 580 nm, the opposite phenomenon is observed. The fluorescence intensity of the SILs lies between those of the two normal tissue types. Above 580 nm, the fluorescence intensity of the LG SIL is greater than the mean and that of the HG SIL is less than the mean.

Figure 28:
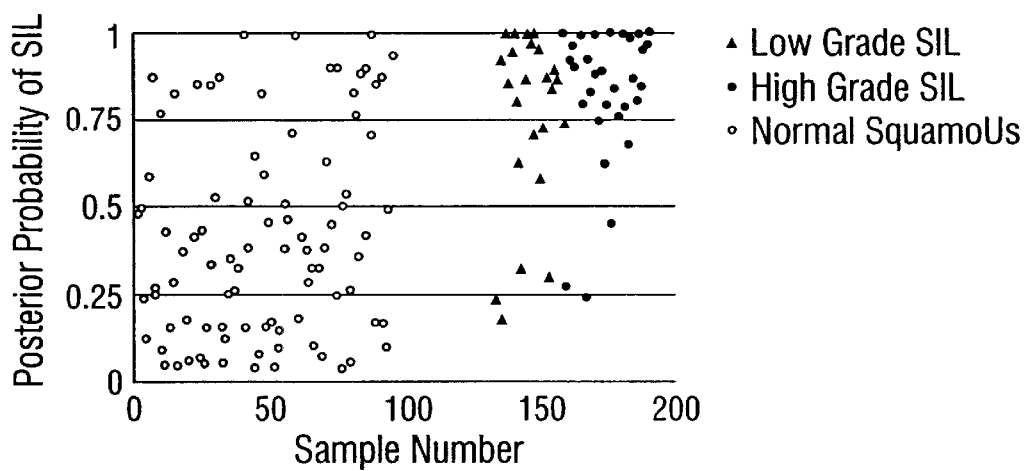
FIG. 28 A plot of the posterior probability of belonging to the SIL category of all SILs and normal squamous epithelia from the calibration set. Evaluation of the misclassified SILs indicates that one samples with CIN III, two with CIN II, two with CIN I and two with HPV are incorrectly classified.

Principal Component Analysis and Logistic Discrimination Constituent Algorithm (1) which Differentiates SILs from Normal Squamous Tissues A constituent algorithm based on normalized spectra arranged in series at all three excitation wavelengths provided the greatest discrimination between SILs and normal squamous tissues. The algorithm demonstrated an incremental improvement in sensitivity without sacrificing specificity relative to the previously developed constituent algorithm (1) that employed normalized, mean-scaled spectra at 337 nm excitation only. Multivariate statistical analysis of normalized tissue spectra at all three excitation wavelengths, indicated three principal components show statistically significant differences between SILs and normal squamous tissues (Table 2). These three principal components account collectively for 65% of the total variance of the spectral data set. Logistic discrimination was used to develop a classification algorithm to discriminate between SILs and normal squamous epithelia based on these three informative principal components. Prior probabilities were determined by calculating the percentage of each tissue type from the data set: 62% normal squamous tissues and 38% SILs. The cost of misclassification of SIL was optimized at 0.7. Posterior probabilities of belonging to each tissue type were calculated for all samples from the data set, using the known prior probabilities, cost of misclassification of SILs and the conditional joint probabilities calculated from the normal probability density function. FIG. 28 illustrates the retrospective accuracy of the algorithm applied to the calibration data set. The posterior probability of being classified into the SIL category is plotted for all SILs and normal squamous epithelia. FIG. 28 indicates that 92% of HG SILs and 83% of LG SILs are correctly classified with a posterior probability greater than 0.5. Approximately 70% of colposcopically normal squamous epithelia are correctly classified with a posterior probability less than 0.5.

The confusion matrix in Table 3 compares the retrospective accuracy of the algorithm on the calibration data set to its prospective accuracy on the prediction set. In the confusion matrix, the first row corresponds to the histo-pathologic classification and the first column corresponds to the spectroscopic classification of the samples. A prospective evaluation of the algorithm's accuracy indicates that there is a small increase in the proportion of correctly classified LG SILs and no change in the proportion of correctly classified HG SILs or normal squamous tissues. Note that the majority of normal columnar tissues and samples with inflammation from both calibration and prediction sets are misclassified as SIL using this algorithm. Evaluation of the misclassified SILs from the calibration set indicates that one sample (out of 19) with CIN III, two samples (out of 16) with CIN II, two samples (out of 16) with CIN I and two samples (out of 7) with HPV are incorrectly classified. From the prediction set, two samples (out of 19) with GIN III, one samples (out of 16) with GIN II, two samples (out of 16) with CIN I and one sample (out of 8) with HPV are incorrectly classified as non SIL.

Figure 29:
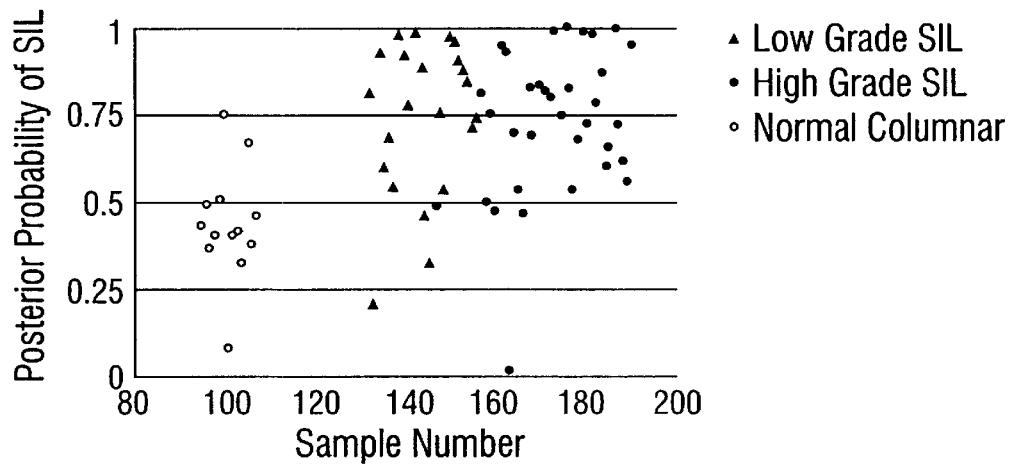
FIG. 29 A plot of the posterior probability of belonging to the SIL category of all SILs and normal columnar epithelia from the calibration data set. Evaluation of the misclassified SILs indicates that three samples with CIN II, three with CIN I and one with HPV are incorrectly classified.

Constituent Algorithm (2) which Differentiates SILs from Normal Columnar Tissues The greatest discrimination between SILs and norm al columnar epithelia was achieved using a constituent algorithm based on normalized, mean-scaled spectra at all three excitation wavelengths. This algorithm demonstrated a substantially improved sensitivity for a similar specificity relative to the previously developed constituent algorithm (2) which used normalized, mean-scaled spectra at 380 nm excitation, only. Multivariate statistical analysis of a combination of normalized, mean-scaled tissue spectra at all three excitation wavelengths resulted in four principal components that demonstrate statistically significant differences between SILs and normal columnar epithelia (Table 2). These four principal components collectively account for 80% of the total variance of the spectral data set. Logistic discrimination was employed to develop a classification algorithm to discriminate between SILs and normal columnar epithelia. The prior probabilities were determined to be: 28% normal columnar tissues and 72% SILs. The optimized cost of misclassification of SIL was equal to 0.58. Posterior probabilities of belonging to each tissue type were calculated for all samples from the data set. FIG. 29 illustrates the retrospective accuracy of the algorithm applied to the calibration data set. The posterior probability of being classified into the SIL category is plotted for all SILs and normal columnar samples examined. FIG. 29 graphically indicates that 91% of HG SILs and 83% of LG SILs have a posterior probability that is greater than 0.5. Seventy-six percent of colposcopically normal columnar epithelia are correctly classified with a posterior probability less than 0.5.

The confusion matrix in Table 4 compares the retrospective accuracy of the constituent algorithm on the calibration data set to its prospective accuracy on the prediction set. The prospective accuracy of the algorithm (Table 4) indicates that there is a small increase in the proportion of correctly classified LG SILs and a small decrease in the proportion of correctly classified HG SILs; there is approximately a 10% decrease in the proportion of correctly classified normal columnar tissues. Note that the majority of normal squamous tissues and samples with inflammation from both the calibration and prediction sets are misclassified as SIL using this algorithm. Evaluation of the misclassified SILs from the calibration set indicates that three samples (out of 16) with CIN II, three samples (out of 16) with CIN I and one sample (out of 7) with HPV are incorrectly classified. From the prediction set, two samples (out of 19) with CIN III, three samples (out of 16) with CIN II, and three samples (out of 16) with CIN I are incorrectly classified.

Constituent Algorithm (3) which Differentiates HG SILs and LG SILs

Figure 30:
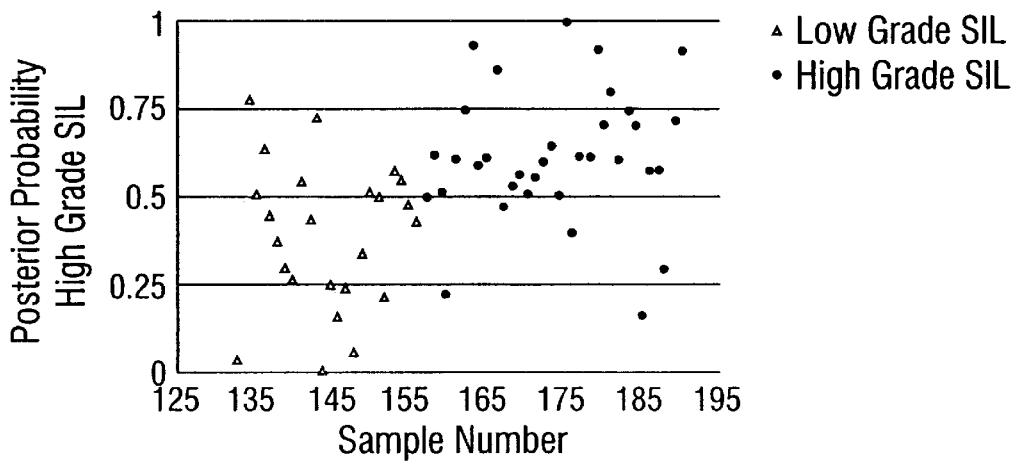
FIG. 30 A plot of the posterior probability of belonging to the HG SIL category of all SILs from the calibration set. Evaluation of the misclassified HG SILs indicates that three samples with CIN III and three with CIN are incorrectly classified as LG SILs; five samples with CIN I and two with HPV are misclassified as HG SIL.

A combination of normalized spectra at all three excitation wavelengths significantly enhanced the accuracy of the previously developed constituent algorithm (3) which differentiated HG SILs from LG SILs using normalized spectra at 460 nm excitation. Multivariate statistical analysis of normalized spectra at all three excitation wavelengths resulted in four statistically significant principal components, that account collectively for 67% of the total variance of the spectral data set (Table 2). Again, a probability based classification algorithm was developed to differentiate HG SILs from LG SILs. The prior probability was: 40% LG SILs and 60% HG SILs. The optimal cost of misclassification of HG SIL was equal to 0.51. Posterior probabilities of belonging to each tissue type were calculated. FIG. 30 illustrates the retrospective accuracy of the algorithm applied to the calibration data set. The posterior probability of being classified into the HG SIL category is plotted for all SILs evaluated. FIG. 30 indicates that 83% of HG SILs have a posterior probability greater than 0.5, and 70% of LG SILs have a posterior probability less than 0.5.

The confusion matrix in Table 5 compares the retrospective accuracy of the constituent algorithm on the calibration set to its prospective accuracy on the prediction set. Its prospective accuracy indicates that there is a 5% decrease in the proportion of correctly classified LG SILs and no change in the proportion of correctly classified HG SILs. From the calibration set, six HG SILs are misclassified; three samples (out 19) with CIN III and three samples (out of 16) with CIN II are misclassified as LG SIL. The misclassified LG SILs comprise of five samples (out of 16) with CIN I and two samples (out of 7) with HPV. From the prediction set, five HG SILs are misclassified; two samples (out of 19) with CIN III and three (out of 16) with CIN II. There were ten misclassified LG SILs from the prediction set: seven with CIN I (out of 16) and three (out of 8) with HPV.

"Full-parameter" Composite Screening and Diagnostic Algorithms

A composite screening algorithm was developed to differentiate SILs and non SILs (normal squamous and columnar epithelia and inflammation) and a composite diagnostic algorithm was developed to differentiate HG SILs from non HG SILs (LG SILs, normal epithelia and inflammation). The effective accuracy of both composite algorithms were compared to those of the constituent algorithms from which they were developed and to the accuracy of current detection modalities.

A Composite Screening Algorithm which Discriminates Between SILs and Non SILs

A composite screening algorithm to differentiate SILs from non SILs was developed using a combination of the two constituent algorithms: algorithm (1) which differentiates SILs from normal squamous tissues and algorithm (2) which differentiates SILs from normal columnar epithelia. The optimal cost of miclassification of SIL was equal to 0.66 for constituent algorithm (1) and 0.64 for constituent algorithm (2). Only the costs of misclassification of SIL of the two constituent algorithms was altered for the development of the composite screening algorithm. These costs were selected to minimize the total number of misclassified samples.

The accuracy of the composite screening algorithm on the calibration and prediction data sets is illustrated in the confusion matrix in Table 6. Examination of the confusion matrix indicates that the algorithm correctly classifies approximately 90% of HG SILs and 75% of LG SIL from the calibration data set. Furthermore, approximately, 80% of normal squamous tissues and 70% of normal columnar epithelia from the calibration set are correctly classified. Evaluation of the prediction set indicates that there is a small change in the proportion of correctly classified HG SILs and LG SILs. There is a negligible change in the correct classification of normal squamous and columnar tissues. Note that while 80% of samples with inflammation from the calibration set are incorrectly classified as SIL, only 43% of these samples from the prediction set are incorrectly classified.

A comparison of the accuracy of the composite screening algorithm (Table 6) to that of each of the constituent algorithms (1) (Table 3) and (2) (Table 4) on the same spectral data set indicates that in general, there is less than a 10% decrease in the proportion of correctly classified SILs using the composite screening algorithm relative to using either of the constituent algorithms independently. Note however that the proportion of correctly classified normal (squamous and columnar) epithelia is substantially higher using the composite algorithm relative to using either of the constituent algorithms independently. These results confirm that utilization of a combination of the two constituent algorithms, significantly reduces the false-positive rate relative to that using each algorithm independently. Evaluation of the spectroscopically misclassified SILs from the calibration set (Table 6) indicates that only one sample (out of 19) with CIN III, three samples (out of 16) with CIN II, two samples (out of 16) with CIN I and four samples (out of 7) with HPV are incorrectly classified. From the prediction data set (Table 6), two samples (out of 19) with CIN III, four samples (out of 16) with CIN II, three samples (out of 16) with CIN I and one sample (out of 8) with HPV are incorrectly classified.

A Composite Diagnostic Algorithm which Differentiates HG SILs from Non HG SILs

A composite diagnostic algorithm which differentially detects HG SILs was developed using a combination of all three constituent algorithms: algorithm (1) which differentiates SILs from normal squamous tissues, algorithm (2) which differentiates SILs from normal columnar epithelia and algorithm (3) which differentiates HG SILs from LG SILs. The optimal costs of miclassification of SIL was equal to 0.87 for algorithm (1) and 0.65 for algorithm (2); the optimal cost of misclassification of HG SIL was equal to 0.49 for algorithm (3). Only the costs of misclassification of SIL of constituent algorithms (1) and (2) and the cost of misclassification of HG SIL of constituent algorithm (3) were altered during development of the composite diagnostic algorithm. These costs were selected to minimize the total number of misclassified samples.

The results of the composite diagnostic algorithm on the calibration and prediction sets are shown in the confusion matrix in Table 7. The algorithm correctly classifies 80% of HG SILs, 74% of LG SILs and more than 80% of normal epithelia. Evaluation of the prediction set using this composite algorithm indicates that there is only a 3% decrease in the proportion of correctly classified HG SILs and a 7% decrease in the proportion of correctly classified LG SILs. There is less than a 10% decrease in the proportion of correctly classified normal epithelia. A comparison between the calibration and prediction sets indicates that while more than 70% of samples with inflammation from the calibration data set are incorrectly classified as HG SIL, only 14% of samples with inflammation from the prediction set are incorrectly identified. Due to the relatively small number of samples examined in this histo-pathologic category, the results presented here do not conclusively establish if the algorithm is capable of correctly identifying inflammation.

A comparison of the accuracy of the composite diagnostic algorithm to that of constituent algorithm (3) which differentiates HG SILs from LG SILs (Table 5) indicates there is less than a 5% decrease in the proportion of correctly classified HG SILs and a 5% increase in the proportion of correctly classified LG SILs using the composite diagnostic algorithm relative to using the constituent algorithm (3). Evaluation of the HG SILs from the calibration set (Table 7) that were incorrectly classified indicates that three samples (out of 19) with CIN III and four samples (out of 16) with CIN II are incorrectly classified. From the prediction set, four samples (out of 19) with CIN III and five samples (out of 16) with CIN II are incorrectly classified.

"Reduced-parameter" Composite Screening and Diagnostic Algorithms

Component Loadings: A component loading represents the correlation between each principal component and the original pre-processed fluorescence emission spectra at a particular excitation wavelength. FIGS. 31(a–c) illustrate component loadings of the diagnostically relevant principal components of constituent algorithm (1) obtained from normalized spectra at 337, 380 and 460 nm excitation, respectively. FIGS. 32(a–c) display component loadings that correspond to the diagnostically relevant principal components of constituent algorithm (2) obtained from normalized, mean-scaled spectra at 337, 380 and 460 nm excitation, respectively. Finally, FIGS. 33(a–c) display the component loadings corresponding to the diagnostically relevant principal components of constituent algorithm (3), obtained from normalized spectra at 337, 380 and 460 nm excitation, respectively. In each graph shown, the abscissa corresponds to the emission wavelength range at a particular excitation wavelength and the ordinate corresponds to the correlation coefficient of the component loading. Correlation coefficients of the component loading above 0.5 and below −0.5 are considered to be significant.

Figure 31A:
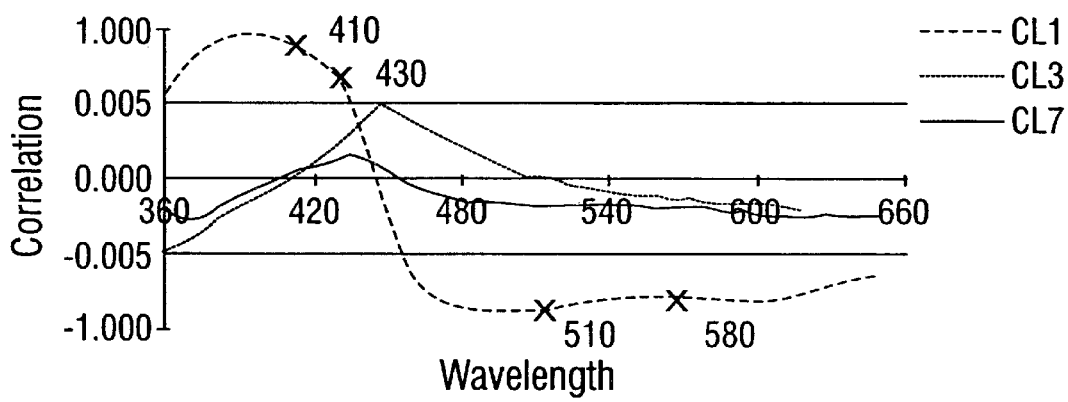
FIG. 31 Component loadings (CL) of diagnostic principal components of constituent algorithm (1), obtained from normalized spectra at (a) 337 (b) 380 and (c) 460 nm excitation, respectively.
Figure 32A:
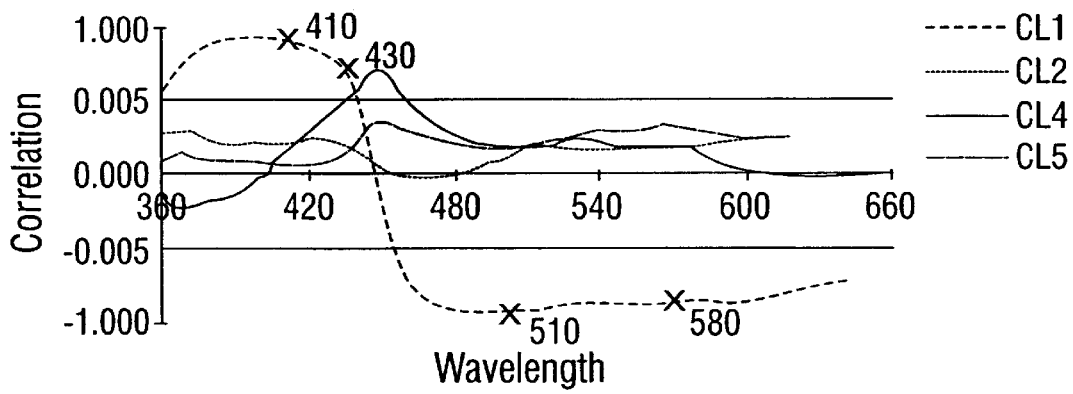
FIG. 32 Component loadings (CL) of diagnostic principal components of constituent algorithm (2), obtained from normalized, mean-scaled spectra at (a) 337 (b) 380 and (c) 460 nm excitation, respectively.
Figure 33A:
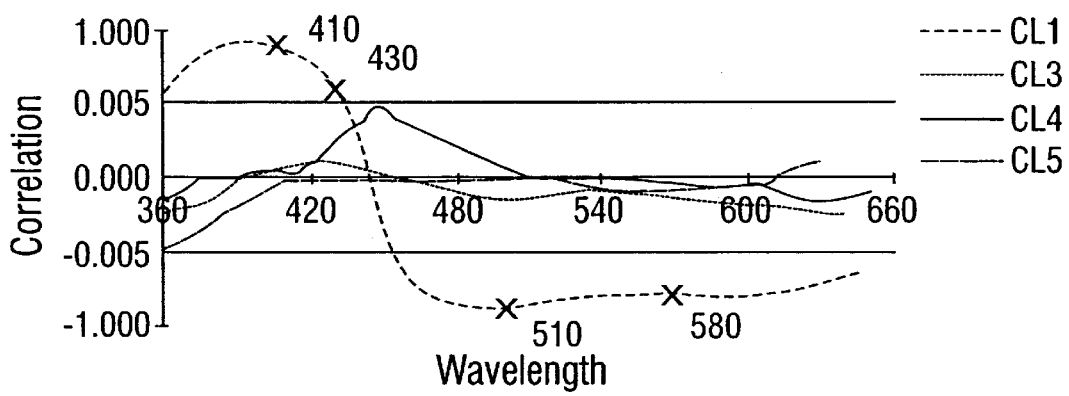
FIG. 33 Component loadings (CL) of diagnostic principal components of constituent algorithm (3), obtained from normalized spectra at (a) 337 (b) 380 and (c) 460 nm excitation, respectively.

FIGS. 31(a), 32(a) and 33(a) display component loadings of principal components of constituent algorithms (1), (2) and (3), respectively, obtained from pre-processed spectra at 337 nm excitation. A closer examination indicates that component loading 1 is nearly identical for all three algorithms. Evaluation of this loading indicates that it is positively correlated with corresponding emission spectra over the wavelength range 360–440 nm and negatively correlated with corresponding emission spectra over the wavelength range 460–660 nm. All remaining principal components of all three algorithms display a correlation between −0.5 and 0.5, except component loading 4 of algorithm (2) (FIG. 32(a)) which displays a positive correlation of 0.75 with the corresponding emission spectra at 460 nm.

Figure 31B:
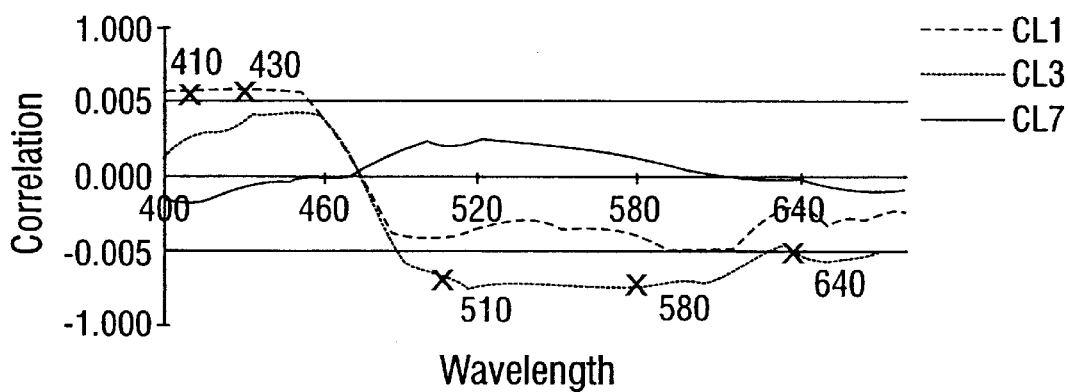
Figure 31C:
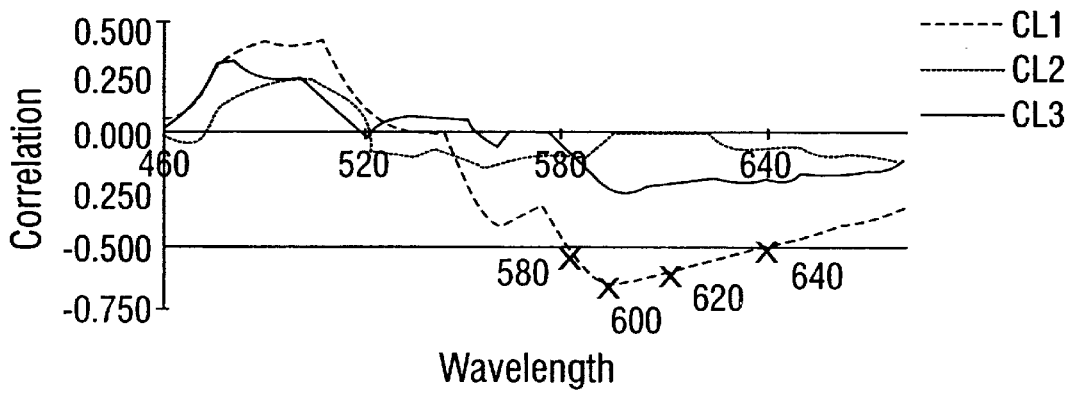
Figure 32B:
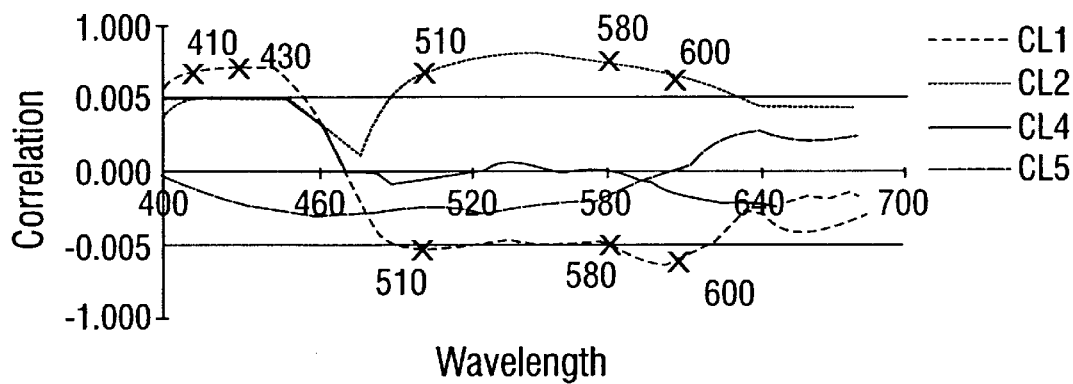
Figure 32C:
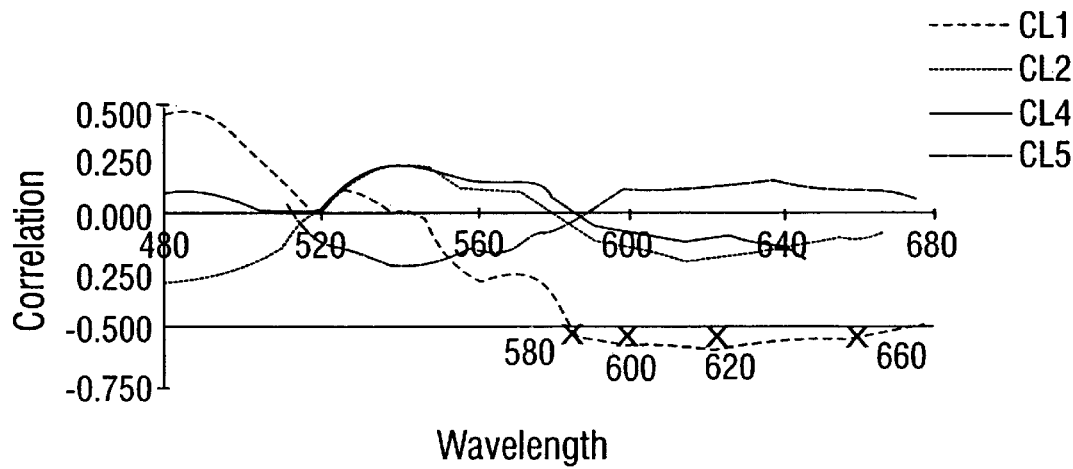
Figure 33B:
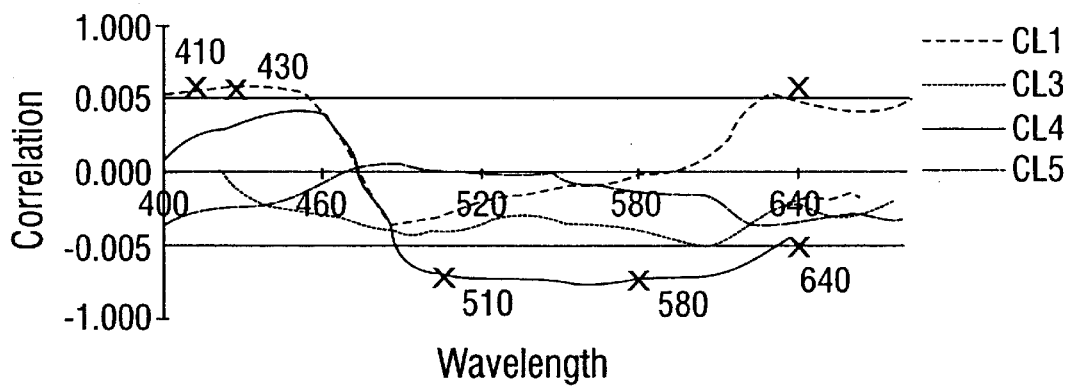

FIGS. 31(b), 32(b) and 33(b) display component loadings that correspond to the diagnostically relevant principal components of constituent algorithms (1), (2) and (3), respectively obtained from pre-processed spectra at 380 nm excitation. Component loading 1 of all three algorithms is positively correlated with corresponding emission spectra over the wavelength range, 400–450 nm. Between 500–600 nm, component loading 1 of algorithm (2) (FIG. 32(b)) is correlated negatively with corresponding emission spectra. Examination of component loading 3 of algorithm (1) (FIG.

Figure 33C:
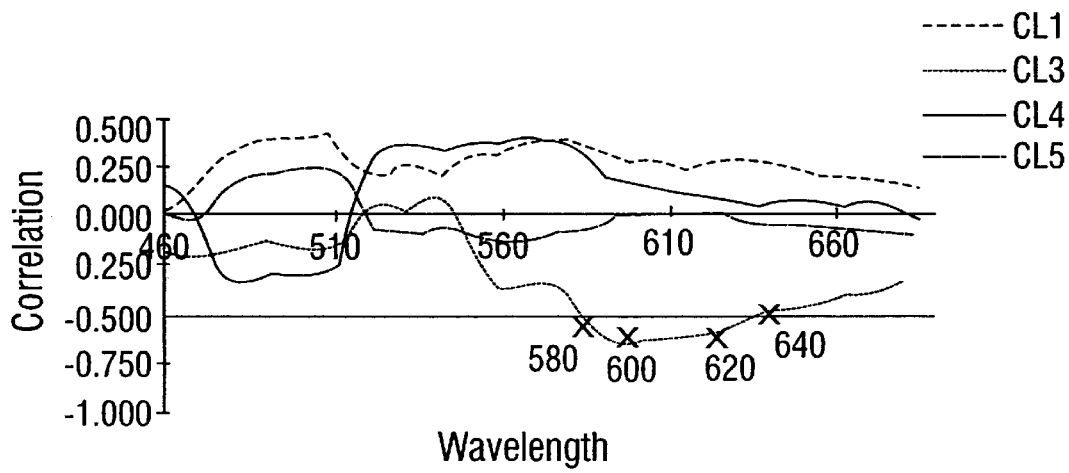
Figure 34A:
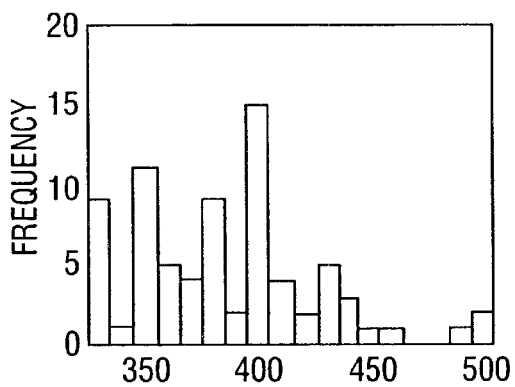
FIG. 34 Plots of Frequency of occurrence vs. emission wavelength in top 25 performing combinations of three wavelengths: (a) ESL=65%, (b) ESL=75%, (c) ESL=85%, and (d) ESL=95%
Figure 34B:
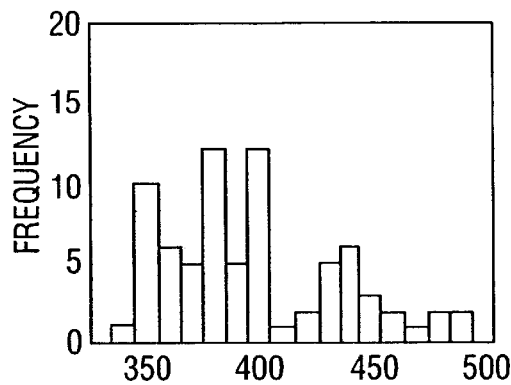
Figure 34C:
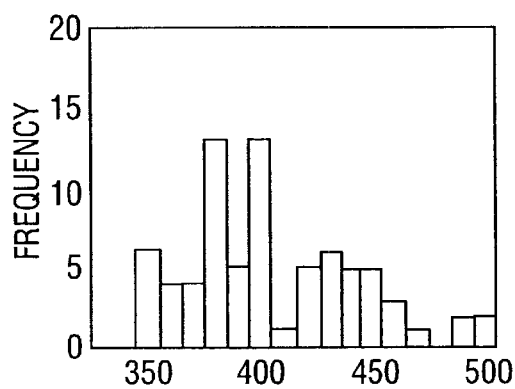
Figure 34D:
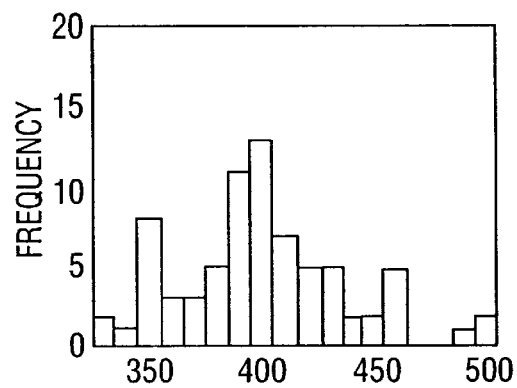
Figure 35:
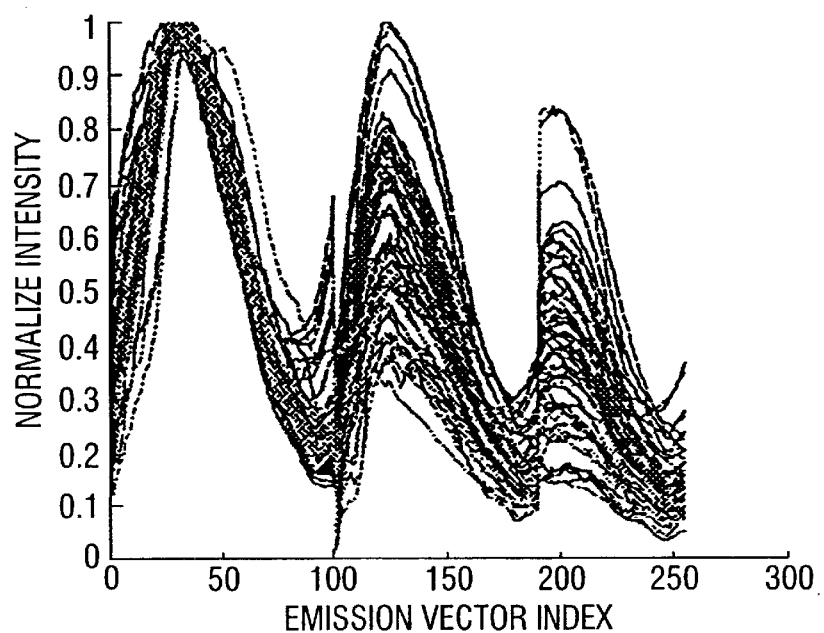
FIG. 35 Fluorescence emission spectra normalized by the peak intensity of the concatenated vector for all 62 sites at 350, 380 and 400 nm excitation. Red lines indicate histologically cancerous, green lines indicate histologically dysplastic, and blue lines indicate visually and/or histologically normal sites.

31(*b*)) and algorithm (3) (FIG. 33(*b*)) indicates that they are also negatively correlated with corresponding emission spectra from 500–600 nm. Only component loading 2 of algorithm (2) (FIG. 32(*b*)) is positively correlated with corresponding emission spectra from 500–600 nm. Also note that component loading 3 of algorithm (1) (FIG. 31(*b*)) and component loadings 3 and 6 of algorithm (3) (FIG. 33(*b*)) display a correlation with corresponding emission spectra at approximately 640 nm.

FIGS. 31(*c*), 32(*c*) and 33(*c*) display component loadings that correspond to the diagnostic principal components of constituent algorithms (1), (2) and (3), respectively obtained from pre-processed spectra at 460 nm excitation. Note that only component loading 1 displays a negative correlation (<−0.5) with corresponding emission spectra for all three algorithms. This component loading is correlated with corresponding emission spectra over the wavelength range 580–660 nm. The remaining principal components of all three algorithms display a correlation between −0.5 and 0.5.

The component loadings at all three excitation wavelengths of all three constituent algorithms were evaluated to select fluorescence intensities at a minimum number of excitation-emission wavelength pairs required for the previously developed constituent and composite algorithms to perform with a minimal decrease in classification accuracy. Portions of the component loadings of the three constituent algorithms most highly correlated (correlation>0.5 or <−0.5) with corresponding emission spectra at each excitation wavelength were selected and the reduced data matrix was then used to regenerate and evaluate the constituent and composite algorithms. It was iteratively determined that fluorescence intensities at a minimum of 15 excitation-emission wavelength pairs are required to re-develop constituent and composite algorithms that demonstrate a minimum decrease in classification accuracy. At 337 nm excitation, fluorescence intensities at two emission wavelengths between 360–450 nm and intensities at two emission wavelengths between 460–660 nm were selected. At 380 nm excitation, intensities at two emission wavelengths between 400–450 nm and intensities at four emission wavelengths between 500–640 nm were selected. Finally, at 460 nm excitation, fluorescence intensities at five emission wavelengths over the range 580–660 nm was selected. Table 8 lists these excitation-emission wavelength pairs for each of the three constituent algorithms, (1), (2) and (3). These excitation-emission wavelength pairs are also indicated on the component loading plots in FIGS. 31–33. The bandwidth at each emission wavelength is 10 nm.

Reduced-parameter Composite Algorithms

Using the fluorescence intensities only at the selected excitation-emission wavelength pairs, the three constituent algorithms were re-developed using the same formal analytical process as was done previously using the entire fluorescence emission spectra at all three excitation wavelengths (FIG. 24). The three constituent algorithms were then independently optimized using the calibration set and tested prospectively on the prediction data set. They were combined as described previously into composite screening and diagnostic algorithms. The effective accuracy of these reduced-parameter composite algorithms were compared to that of the full-parameter composite algorithms developed previously using fluorescence emission spectra at all three excitation wavelengths.

Table 9 displays the accuracy of the reduced-parameter composite screening algorithm (based on fluorescence intensities at 15 excitation-emission wavelength pairs) which discriminates between SILs and non SILs applied to the calibration and prediction sets. A comparison between the calibration and prediction data sets indicates that there is less than a 10% decrease in the proportion of correctly classified SILs and normal squamous tissues from the prediction set. Note however that there is a 20% increase in the proportion of correctly classified normal columnar epithelia and a 40% increase in the proportion of correctly classified samples with inflammation from the prediction set.

The accuracy of the reduced-parameter composite screening algorithm (Table 9) was compared to that of the full-parameter composite screening algorithm (Table 6) applied to the same spectral data set. A comparison indicates that in general there is less than a 10% decrease in the accuracy of the reduced-parameter composite algorithm relative to that of the full-parameter composite screening algorithm, except for a 20% decrease in the proportion of correctly classified normal columnar epithelia from the calibration set tested using the reduced-parameter composite screening algorithm (Table 9).

Table 10 displays the accuracy of the reduced-parameter composite diagnostic algorithm that differentially identifies HG SILs from the calibration and prediction sets. A comparison of sample classification between the calibration and prediction data sets indicates that there is negligible change in the proportion of correctly classified HG SILs, LG SILs and normal squamous epithelia. Note that there is approximately a 20% increase in the proportion of correctly classified normal columnar epithelia and samples with inflammation from the prediction set.

A comparison of the composite diagnostic algorithm based on the reduced emission variables (Table 10) to that using fluorescence emission spectra at all three excitation wavelengths (Table 7) applied to the same spectral data set indicates that in general, the accuracy of the reduced-parameter composite diagnostic algorithm is within 10% of that reported for the full-parameter composite diagnostic algorithm; however, a comparison between Tables 7 and 10 indicates that there is approximately a 15% decrease and a 20% increase in the proportion of correctly classified normal columnar epithelia from the calibration and prediction sets (Table 10), respectively which were tested using the reduced-parameter composite diagnostic algorithm. The opposite trend is observed for samples with inflammation tested using the reduced-parameter composite diagnostic algorithm (Table 10).

Table 11 compares the sensitivity and specificity of the full-parameter and reduced-parameter composite algorithms to that of Pap smear screening and colposcopy in expert hands. Table 11 indicates that the composite screening algorithms have a similar specificity and a significantly improved sensitivity relative to Pap smear screening. A comparison of the sensitivity of the composite screening algorithms to that of colposcopy in expert hands for differentiating SILs from non SILs indicates that these algorithms demonstrate a 10% decrease in sensitivity, but a 20% improvement in specificity. The composite diagnostic algorithms and colposcopy in expert hands discriminate HG SILs from non HG SILs with a very similar sensitivity and specificity. Also note that the variability (standard deviation) of both Pap smear screening and colposcopy in expert hands is substantially higher than that of the full-parameter and reduced-parameter screening and diagnostic algorithms. A comparison between the full-parameter and reduced-parameter composite algorithms indicates that the algorithms based on the reduced emission variables demonstrate a minimal decrease in classification accuracy relative to those that employ fluorescence emission spectra at all three excitation wavelengths.

Discussion and Conclusions

Cervical tissue fluorescence spectra recorded at 337, 380 and 460 nm excitation can be used to develop composite screening and diagnostic algorithms for the differential detection of SILs in vivo. The composite screening algorithm discriminates between SILs and non SILs with a similar specificity and a substantially improved sensitivity relative to standard Pap smear screening. When compared to colposcopy in expert hands, the composite screening algorithm displays a 10% decrease in sensitivity but almost a 20% improvement in specificity. A comparison between the composite diagnostic algorithm and colposcopy in the hands of expert practitioners indicates that both have a very similar sensitivity and specificity for discriminating between HG SILs and non HG SILs. Note that as spectroscopic interrogation of diseased and non-diseased cervical tissue sites in the current clinical study was directed by colposcopic impression, the sensitivity of the spectroscopic algorithms could not exceed the sensitivity of colposcopy. In other words, if there were histologically diseased cervical tissue sites that were overlooked by colposcopy, these false-negatives were not be evaluated spectroscopically. As a result, the potential of fluorescence spectroscopy to correctly classify these false-negatives could not be determined.

The full-parameter composite algorithms were re-developed using fluorescence intensities at 15 excitation-emission wavelength pairs, to generate reduced-parameter composite algorithms. The fluorescence intensities at these reduced number of excitation-emission wavelength pairs were selected using a parameter called the component loading calculated from the principal components. Evaluation of the reduced-parameter composite algorithms indicates that they display a minimal decrease in sensitivity and specificity relative to the full-parameter composite algorithms. The reduction in the number of excitation-emission wavelength pairs from 161 to 15 implies reduction in the complexity and cost of the portable fluorimeter which would be used to measure cervical tissue fluorescence. For example, if fluorescence intensities at only 15 excitation-emission wavelength pairs need to be measured, the polychromator and intensified diode array can be replaced by a mechanical filter assembly and a single channel detector. This represents a substantial decrease in cost and complexity of this instrumentation at the expense of less than a 1% decrease in sensitivity.

Several significant improvements and refinements have been made in previously developed constituent algorithms using tissue spectra at all three excitation wavelengths. Previously, the constituent algorithm (1) which differentiates SILs from normal squamous epithelia was developed using normalized, mean-scaled spectra at a single excitation wavelength: 337 nm. Spectra at this excitation wavelength had to be mean-scaled in order to calibrate for the significant inter-patient variation in spectral line shape. This algorithm demonstrates the greatest classification accuracy when the patient being evaluated has equal numbers of diseased and non-diseased tissue sites. This restriction clearly reduces the clinical effectiveness of this algorithm. The new algorithm which is based on normalized emission spectra at all three excitation wavelengths, minimizes this inter-patient variation and hence obviates the need for mean-scaling, while maintaining a slightly improved classification accuracy. Inclusion of spectra at additional excitation wavelengths represents a significant improvement in the clinical effectiveness of this algorithm as it can be applied to a much wider population of patients.

The accuracy of previously developed constituent algorithm (2) which discriminates between SILs and normal columnar epithelia was significantly improved by using normalized, mean-scaled spectra at all three excitation wavelengths rather than at a single excitation wavelength. Despite the significant improvement in these results, this algorithm is also based on tissue spectra that require mean-scaling at each excitation wavelength. A multivariate statistical algorithm based on normalized spectra only, at all three excitation wavelengths differentiates SILs from normal columnar epithelia with a significantly poorer sensitivity than the algorithm that uses normalized, mean-scaled spectra at all three excitation wavelengths. Therefore, mean-scaling is essential for the optimal operation of this algorithm.

Finally, an improvement that is significant is the development of the third constituent algorithm which discriminates between LG SILs and HG SILs using tissue spectra at all three excitation wavelengths. The utilization of spectra at all three excitation wavelengths results in a substantial improvement in sensitivity relative to using the constituent algorithm (3) which is based on a single excitation wavelength. Furthermore, spectra required for this algorithm do not have to be mean-scaled for inter-patient variation in spectral line shape.

Each of the three constituent algorithms developed using spectral data from the current clinical study discriminate between a specific pair of tissue types. Using each constituent algorithm, a posterior probability assignment of an unknown sample to a particular tissue category is calculated using a set of diagnostically relevant principal components that demonstrate statistically significant differences between the two tissue types under consideration. The posterior probability output of the constituent algorithms are then combined to develop composite screening and diagnostic algorithms that discriminate between many of the clinically relevant tissues types. Hence, development of the two composite algorithms is based on the prior development of the three constituent algorithms.

To test the feasibility of an alternate approach, the two composite algorithms were developed directly from diagnostically relevant principal components of their corresponding constituent algorithms, thereby by-passing the constituent algorithm development phase. The composite screening algorithm which discriminates between SILs and non SILs was developed using logistic discrimination based on the diagnostically relevant principal components of constituent algorithms (1) and (2); the posterior probability of an unknown sample being classified as either SIL or non SIL was calculated. The composite diagnostic algorithm which discriminates between HG SILs and non HG SILs was developed using logistic discrimination based on the diagnostically relevant principal components of constituent algorithms (1), (2) and (3); the posterior probability of an unknown sample being classified as either HG SIL or non HG SIL was calculated. The composite algorithms developed directly from the diagnostically relevant principal components of their corresponding constituent algorithms demonstrated a poorer classification accuracy relative to composite algorithms that were developed using a combination of corresponding constituent algorithms. Therefore, composite screening and diagnostic algorithms were developed using a combination of independently developed constituent algorithms.

Pre-processing to remove inter-patient and intra-patient variation prior to the development of the multivariate statistical algorithm may remove the spectral variations that may be significant from a biological standpoint. However, in the development of multivariate statistical screening and diagnostic algorithms that can successfully identify disease in any given patient, the intra-patient and inter-patient spectral variations must be removed if they do obscure the important inter-category differences that the algorithm needs to extract. If a sophisticated physical model can be developed to describe the biological basis of the spectral data as well as the inter-patient and intra-patient spectral variations accurately, then this information can be used to develop better methods of pre-processing or direct the need for additional measurements to calibrate for these variations. This is an important issue to address and is currently the subject of study in our laboratory.

In spite of the successful development of algorithms that can differentiate (1) SILs from normal tissues and (2) HG SILs from non HG SILs and normal epithelia, these algorithms do not consistently classify samples with inflammation as non SIL; this results in a decrease in their specificity. Although the number of samples examined in this histopathologic category is limited, analysis from previous and current clinical studies indicates that it relatively difficult to correctly classify these samples. A plausible explanation for this is that (1) the current excitation wavelengths used may not be optimum for identification of fluorophores that are unique to inflammation and/or (2) the penetration depth of the light may not be sufficiently long to spectroscopically interrogate the underlying stromal layers where inflammation develops.

The specificity of fluorescence spectroscopy for the detection of cervical neoplasia may be improved by using fluorescent photosensitizers to enhance the contrast between neoplastic and non-neoplastic tissues in vivo. The use of photosensitizers such as photofrin, hematoporphyrin derivative or 5-ALA may potentially enhance the spectroscopic differences between neoplastic and non-neoplastic (normal and inflammatory) cervical tissues and hence contribute to an improved specificity of the spectroscopic algorithms.

Another limitation is that the portable fluorimeter described in this Example to measure in vivo tissue fluorescence spectra utilizes a single-pixel probe that interrogates a 1 mm diameter area on the cervix. Although the single-pixel probe that we have used provides the capability to determine whether a small region of cervical tissue contains pre-cancerous changes, mapping the entire cervix with this system is extremely time consuming, making wide-scale application of this technology impractical. To address this limitation, a multi-pixel probe that can be used to acquire fluorescence spectra from multiple sites on the cervix, simultaneously may be used. This may provide to a user not only information regarding the presence of pre-cancer but can also indicate. its location and extent.

In summary, in vivo fluorescence spectroscopy has the capability to significantly improve the sensitivity of Pap smear screening and the specificity of colposcopy in expert hands. Hence, this technique may play an important clinical role as a screening/re-screening tool (to screen women who have already had an initial positive Pap smear, but who have not undergone colposcopy and directed biopsy) and as an adjunct to colposcopy in expert hands. Advantages realized by using this technique include, but are not limited to: (1) screening and diagnostic information may be obtained in near real-time and (2) this technique may be easily automated hence reducing the need for subjective interpretation. Furthermore, while the Pap smear examines only exfoliated cervical epithelial cells, fluorescence spectroscopy may interrogate the full thickness of the epithelium.

TABLE 1

Histopathologic classification of samples from the calibration and prediction sets. Note, biopsies for histologic evaluation were not obtained from colposcopically normal squamous and columnar tissue sites to comply with routine patient care procedure

| Histo-pathology | Calibration set | Prediction set |
| --- | --- | --- |
| Normal squamous | 94 | 94 |
| Normal columnar | 13 | 14 |
| Inflammation | 15 | 14 |
| LG SIL | 23 (7 HPV, 16 CIN I) | 24 (8 HPV, 16 CIN I) |
| HG SIL | 35 (16 CIN II, 19 CIN III) | 35 (16 CIN II, 19 CIN III) |

TABLE 2

Components of an optimal set of three constituent algorithms. Algorithm 1 discriminates between SIL and normal squamous tissues, algorithm 2 discriminates between SIL and normal columnar tissues and algorithm 3 differentiates HG SIL from LG SIL

| Constituent algorithms | Excitation wavelengths | Preprocessing method | Principal component analysis PC* | (%)† | Logistic discrimination $(\mu, \sigma)$‡ | PP§ |
| --- | --- | --- | --- | --- | --- | --- |
| 1 SIL vs normal | 337, 380, 460 | Normalization | PC1 | 51 | NS: (3.59, 0.843); SIL: (2.514, 0.671) | NS: 62% |
| | | | PC3 | 11 | NS: (2.631, 0.292); SIL: (2.535, 0.427) | SIL: 38% |

TABLE 2-continued

Components of an optimal set of three constituent algorithms. Algorithm 1 discriminates between SIL and normal squamous tissues, algorithm 2 discriminates between SIL and normal columnar tissues and algorithm 3 differentiates HG SIL from LG SIL

| Constituent algorithms | Excitation wavelengths | Preprocessing method | Principal component analysis | | Logistic discrimination | |
|---|---|---|---|---|---|---|
| | | | PC* | V (%)† | ($\mu$, $\sigma$)‡ | PP§ |
| squamous (NS) | | | PC7 | 3 | NS: (2.850, 0.145); SIL: (2.775, 0.209) | |
| 2 SIL vs normal columnar (NC) | 337, 380, 460 | Normalization mean-scaling | PC1 | 59 | NC: (2.479, 0.444); SIL: (2.737, 0.482) | NC: 28% |
| | | | PC2 | 12 | NC: (2.894, 0.330); SIL: (2.990, 0.367) | SIL: 72% |
| | | | PC4 | 6 | NC: (3.006, 0.186); SIL: (3.051, 0.167) | |
| | | | PC5 | 3 | NC: (3.004, 0.101); SIL: (2.994, 0.199) | |
| 3 HG SIL (HG) vs LG SIL (LG) | 337, 380, 460 | Normalization | PC1 | 51 | LG: (2.755, 0.663); HG (2.353, 0.759) | LG: 40% |
| | | | PC3 | 11 | LG: (2.549, 0.394); HG (2.453, 0.497) | HG: 60% |
| | | | PC6 | 3 | LG: (2.042, 0.180); HG (2.100, 0.180) | |
| | | | PC8 | 2 | LG: (2.486, 0.223); HG (2.550, 0.130) | |

*Principal component.
†Variance accounted for by principal component.
‡Mean ($\mu$) and standard deviation ($\sigma$) of principal component scores of tissue types under consideration.
§Prior probabilities of tissue types under consideration.

TABLE 3

Accuracy of constituent algorithm 1, which differentiates SIL and normal squamous tissues from the calibration and prediction sets. The first column corresponds to the spectroscopic classification and the first row corresponds to the histopathologic classification

| | Normal squamous | Normal columnar | Inflammation | LG SIL | HG SIL |
|---|---|---|---|---|---|
| | Classification in calibration set | | | | |
| Non-SIL | 68% | 8% | 7% | 17% | 9% |
| SIL | 32% | 92% | 93% | 83% | 91% |
| | Classification in prediction set | | | | |
| Non-SIL | 68% | 29% | 21% | 12% | 9% |
| SIL | 32% | 71% | 79% | 88% | 91% |

TABLE 4

Accuracy of constituent algorithm 2, which differentiates SIL and normal columnar tissues from the calibration and prediction sets. The first column corresponds to the spectroscopic classification and the first row corresponds to the histopathologic classification

| | Normal squamous | Normal columnar | Inflammation | LG SIL | HG SIL |
|---|---|---|---|---|---|
| | Classification in calibration set | | | | |
| Non-SIL | 7% | 77% | 27% | 17% | 9% |
| SIL | 93% | 23% | 73% | 83% | 91% |
| | Classification in prediction set | | | | |
| Non-SIL | 5% | 64% | 27% | 13% | 14% |
| SIL | 95% | 36% | 73% | 87% | 86% |

TABLE 5

Accuracy of constituent algorithm 3, which differentiates HG SIL and LG SIL from the calibration and prediction sets. The first column corresponds to the spectroscopic classification and the first row corresponds to the histopathologic classification

| | LG SIL | HG SIL |
|---|---|---|
| | Classification in calibration set | |
| LG SIL | 69% | 17% |
| HG SIL | 31% | 83% |
| | Classification in prediction set | |
| LG SIL | 63% | 19% |
| HG SIL | 37% | 81% |

TABLE 6

Accuracy of the full-parameter composite screening algorithm that differentiates SIL and non-SIL from the calibration and prediction sets. The first column corresponds to the spectroscopic classification and the first row corresponds to the histopathologic classification

| | Normal squamous | Normal columnar | Inflammation | LG SIL | HG SIL |
|---|---|---|---|---|---|
| | Classification in calibration set | | | | |
| Non-SIL | 79% | 69% | 20% | 26% | 11% |
| SIL | 21% | 31% | 80% | 74% | 89% |
| | Classification in prediction set | | | | |
| Non-SIL | 75% | 69% | 57% | 25% | 14% |
| SIL | 25% | 31% | 43% | 75% | 86% |

TABLE 7

Accuracy of the full-parameter composite diagnostic algorithm that discriminates between HG SIL and non-HG SIL from the calibration and prediction sets. The first column corresponds to the spectroscopic classification and the first row corresponds to the histopathologic classification

|  | Normal squamous | Normal columnar | Inflammation | LG SIL | HG SIL |
|---|---|---|---|---|---|
| Classification in calibration set | | | | | |
| Non-HG SIL | 84% | 77% | 27% | 74% | 20% |
| HG SIL | 16% | 23% | 73% | 26% | 80% |
| Classification in prediction set | | | | | |
| Non-HG SIL | 85% | 69% | 86% | 67% | 23% |
| HG SIL | 15% | 31% | 14% | 33% | 77% |

TABLE 8

Fluorescence intensities at 15 excitation-emission wavelength pairs needed to redevelop the three constituent algorithms 1, 2 and 3 with a minimal decrease in classification accuracy

| Algorithm 1 ($\lambda_{exc}$, $\lambda_{em}$) | Algorithm 2 ($\lambda_{exc}$, $\lambda_{em}$) | Algorithm 3 ($\lambda_{exc}$, $\lambda_{em}$) |
|---|---|---|
| 337, 410 nm | 337, 410 nm | 337, 410 nm |
| 337, 430 nm | 337, 430 nm | 337, 430 nm |
| 337, 510 nm | 337, 510 nm | 337, 510 nm |
| 337, 580 nm | 337, 580 nm | 337, 580 nm |
| 380, 410 nm | 380, 410 nm | 380, 410 nm |
| 380, 430 nm | 380, 430 nm | 380, 430 nm |
| 380, 510 nm | 380, 510 nm | 380, 510 nm |
| 380, 580 nm | 380, 580 nm | 380, 580 nm |
| 380, 640 nm | 380, 600 nm | 380, 640 nm |
| 460, 580 nm | 460, 580 nm | 460, 580 nm |
| 460, 600 nm | 460, 600 nm | 460, 600 nm |
| 460, 620 nm | 460, 620 nm | 460, 620 nm |
| 460, 640 nm | 460, 660 nm | 460, 640 nm |

TABLE 9

Accuracy of the reduced-parameter composite screening algorithm that differentiates SIL and non-SIL from the calibration and prediction sets. The first column corresponds to the spectroscopic classification and the first row corresponds to the histopathologic classification

|  | Normal squamous | Normal columnar | Inflammation | LG SIL | HG SIL |
|---|---|---|---|---|---|
| Classification in calibration set | | | | | |
| Non-SIL | 73% | 46% | 13% | 17% | 15% |
| SIL | 27% | 54% | 87% | 83% | 85% |
| Classification in prediction set | | | | | |
| Non-SIL | 72% | 64% | 50% | 25% | 11% |
| SIL | 28% | 36% | 50% | 75% | 89% |

TABLE 10

Accuracy of the reduced-parameter composite diagnostic algorithm that differentiates HG SIL and non-HG SIL from the calibration and prediction sets. The first column corresponds to the spectroscopic classification and the first row corresponds to the histopathologic classification

|  | Normal squamous | Normal columnar | Inflammation | LG SIL | HG SIL |
|---|---|---|---|---|---|
| Classification in calibration set | | | | | |
| Non-HG SIL | 79% | 62% | 40% | 65% | 23% |
| HG SIL | 21% | 38% | 60% | 35% | 77% |
| Classification in prediction set | | | | | |
| Non-HG SIL | 82% | 86% | 64% | 63% | 20% |
| HG SIL | 18% | 14% | 36% | 37% | 80% |

TABLE 11

Comparison of accuracy of composite screening and diagnostic algorithms to that of Pap smear screening and colposcopy in expert hands

| Classification | SIL vs Non-SIL | | HG SIL vs Non-HG SIL | |
|---|---|---|---|---|
|  | Sensitivity | Specificity | Sensitivity | Specificity |
| Pap smear screening | 62 ± 23% | 68 ± 21% | N/A* | N/A |
| Colposcopy in expert hands | 94 ± 6% | 48 ± 23% | 79 ± 23% | 76 ± 13% |
| Full-parameter composite algorithm | 82 ± 1.4% | 68 ± 0.0% | 79 ± 2% | 78 ± 6% |
| Reduced-parameter composite algorithm | 84 ± 1.5% | 65 ± 2% | 78 ± 0.7% | 74 ± 2% |

*N/A = not applicable.

EXAMPLE 3

Head and Neck Analysis—Fluorescence

Analysis of fluorescence data collected in a clinical head and neck study has been analyzed in accordance with the present disclosure. The Example that follows describes analysis of these data.

Materials and Methods

Fluorescence excitation emission matrices were measured in vivo from sixty two sites in 9 normal volunteers and 11 patients with a known or suspected premalignant or malignant oral cavity lesion. Excitation wavelength ranged from 330 to 500 nm and emission wavelength ranged from 340 to 600 nm. Fluorescence data were analyzed to determine which excitation and emission wavelengths contained the most diagnostically useful information and to estimate the performance of diagnostic algorithms based on this information. Algorithms were developed based on combinations of emission spectra at various excitation wavelengths in order to determine which excitation wavelengths contained the most diagnostic information. Then, at those excitation wavelengths, algorithms were developed based on reduced numbers of emission wavelengths to determine whether complete emission spectra were required or whether accurate diagnosis could be made using multi-spectral measurements at a few excitation/emission wavelength combinations. The algorithm development process, consisted of the following steps: (1) data pre-processing to reduce inter-patient variations, (2) data reduction to reduce the dimensionality of the data set, (3) feature selection and classification to develop algorithms which maximize diagnostic performance and minimized the likelihood of over-training in a training set, (4) unbiased evaluation of these algorithms using the technique of cross-validation.

Results

The optimal excitation wavelengths for the in vivo detection of oral cancers with fluorescence spectroscopy were found to be 350, 380 and 400 nm. An unbiased estimate of an algorithm based on the entire emission spectra at these excitation wavelengths yields a sensitivity of 100% and specificity of 88%. Increasing the number of excitation wavelengths did not improve algorithm performance. Better algorithm performance was obtained when data were normalized to the peak emission intensity of the concatenated vector than when each emission spectrum was normalized to its own peak emission wavelength. The number of emission wavelengths could be significantly reduced without compromising algorithm performance. When only a single emission wavelength of 472 nm, common to all three excitation wavelengths, was used algorithm performance on cross validation was 90% sensitivity and 88% specificity. The unbiased performance estimate for the diagnostic algorithms based on fluorescence spectroscopy have a higher sensitivity than current visual screening techniques done by experts.

Study Subjects 9 normal volunteers and 11 patients with a known or suspected premalignant or malignant oral cavity lesion were recruited to participate in the study at the Head and Neck Surgery Clinical at The University of Texas M.D. Anderson Cancer Center. Written informed consent was obtained from each person in the study.

Instrument

A FastEEM system in accordance with the present disclosure was used for this study. Briefly, the system measured fluorescence emission spectra at 18 excitation wavelengths, ranging from 330 nm to 500 nm in 10 nm increments. The system incorporated a fiberoptic probe, a Xenon arc lamp coupled to a monochromator to provide excitation light and a polychromator and thermo-electrically cooled CCD camera to record fluorescence intensity as a function of emission wavelength.

Calibration

A background EEM, to be subtracted from the acquired patient data, was obtained with the probe immersed in a non-fluorescent bottle filled with distilled water at the beginning of each measurement day. Then a fluorescence EEM was measured with the probe placed on the surface of a quartz cuvette containing a solution of Rhodamine 610 (Exciton, Dayton, Ohio) dissolved in ethylene glycol (2 mg/mL).

To correct for the non-uniform spectral response of the detection system, the spectra of two calibrated sources were measured; in the visible an NIST traceable calibrated tungsten ribbon filament lamp was used and in the UV a deuterium lamp was used (550C and 45D, Optronic Laboratories Inc, Orlando, Fla.). Correction factors were derived from these spectra. Background subtracted EEMs from patients were then corrected for the non-uniform spectral response of the detection system. Variations in the intensity of the fluorescence excitation light source at different excitation wavelengths were corrected using measurements of the intensity at each excitation wavelength at the probe tip made using a calibrated photodiode (818-UV, Newport Research Corp.). Finally, corrected fluorescence intensities from each site were divided by the fluorescence emission intensity of the Rhodamine standard at 460 nm excitation, 580 nm emission. Thus, data illustrated in this paper are not the absolute fluorescence intensities of tissue but rather the intensities relative to the Rhodamine standard.

Data Aquisition

Before the probe was used it was disinfected with Metricide (Metrex Research Corp.) in accordance with standard protocol. The probe was then guided into the oral cavity and its tip positioned flush with the mucosa. Then fluorescence EEMs were measured.

Fluorescence EEMs were measured from 9 volunteers with no history of oral cavity neoplasia at 35 clinically normal sites in the oral cavity (Table 1). No biopsies were obtained from volunteers. Following visual screening in 11 patients with a known or suspected premalignant or malignant oral cavity lesion, fluorescence EEMs were measured from 27 sites (Table 1). The physician placed the fiber optic probe on a lesion or suspected lesion and the fluorescence of that site was measured. In addition to the three to five visually abnormal sites, fluorescence EEMs were measured from one to three contralateral normal sites. Post-spectroscopy, abnormal sites were tattooed with India Ink where the probe measured the spectra. A clinical diagnosis of each lesion as normal, abnormal (not dysplastic), abnormal (dysplastic) or cancerous was recorded by an experienced head and neck surgeon (AMG) or dental oncologist (RJ). During follow up surgery, a 2–4 mm biopsy of the tissue was taken from the tattooed area. These specimens were evaluated by an experienced pathologist (BK) using light microscopy and classified as normal, mucosal reactive atypia (MRA), dysplasia or cancer using standard diagnostic criterion. Biopsies with multiple diagnoses were classified according to the most severe pathological diagnosis. The pathologist and clinicians were blinded to the results of the spectroscopic analyses.

Data Review

A total of 88 sites were measured from 26 subjects. All spectra were reviewed by a single investigator blinded to the pathologic results (DLH). Spectra were discarded if files were not saved properly due to software error (8 sites), instrument error (2 sites), operator error (4 sites), probe movement (3 sites), and the presence of room light artifacts at wavelengths below 600 nm (3 sites) in at least one of the emission spectra. From the remaining sites, spectra from six sites were excluded because the tattoo could not be located and consequently reliable histologic diagnosis was not available for these sites. Therefore, fluorescence EEMs from 62 sites from 20 subjects were available for further analysis (Table 1).

Data Analysis

Fluorescence data were analyzed to determine which excitation and emission wavelengths contained the most diagnostically useful information and to estimate the performance of diagnostic algorithms based on this information. Algorithms based on multi-variate discriminant analysis were considered. Algorithms based on combinations of emission spectra at various excitation wavelengths were developed in order to determine which excitation wavelengths contained the most diagnostic information. Then, at those excitation wavelengths, spectra based on reduced numbers of emission wavelengths were developed to determine whether complete emission spectra were required or whether accurate diagnosis could be made using multi-spectral measurements at a few excitation/emission wavelength combinations.

In each case, the algorithm development process, described in detail below, included the following major steps: (1) data pre-processing to reduce inter-patient variations, (2) data reduction to reduce the dimensionality of the data set, (3) feature selection and classification to develop algorithms which maximized diagnostic performance and minimized the likelihood of over-training in a training set, (4) unbiased evaluation of these algorithms using the technique of cross-validation.

Diagnostic Categories

Multi-variate discriminant algorithms were sought to separate two tissue categories: normal and abnormal. The abnormal class contained sites with dysplasia, carcinoma in situ and squamous cell carcinoma; the normal class contained sites which were clinically and/or histologically normal as well as benign changes such as inflammation.

Data Pre-Processing

Fluorescence data from a single measurement site is represented as a matrix containing calibrated fluorescence intensity as a function of excitation and emission wavelength. Columns of this matrix correspond to emission spectra at a particular excitation wavelength; rows of this matrix correspond to excitation spectra at a particular emission wavelength. Each excitation spectrum contains 18 intensity measurements; each emission spectrum contains between 50 and 130 intensity measurements depending on the excitation wavelength. Most multi-variate data analysis techniques require vector input rather than matrix input, so the column vectors containing the emission spectra at excitation wavelengths selected for evaluation were concatenated into a single vector in order to explore which excitation wavelengths contained the most diagnostic information.

Our previous work illustrated that spectra of oral cavity obtained in vivo show large patient to patient variations in intensity that can be greater than the inter-category differences. Therefore, we explored pre-processing methods to reduce the inter-patient variations, while preserving inter-category differences. While many different methods of pre-processing are possible, two methods were selected for evaluation here: (1) normalization of all emission spectra of a given excitation wavelength combination to the maximum intensity contained within that combination, and (2) normalization of each emission spectra to its maximum intensity.

Reduction of Excitation Wavelength Number

In this study, fluorescence emission spectra were measured at 18 different excitation wavelengths. One goal of data analysis was to determine which combination of excitation wavelengths contains the most diagnostic information. We considered combinations of up to four emission spectra. Limiting the number of wavelengths to four allows for construction of a reasonably cost-effective clinical spectroscopy system. Two strategies were considered to identify the optimal wavelength combination. The first was to identify the single wavelength which gives the best diagnostic performance, then the wavelength of those remaining that most improves diagnostic performance, and so forth until performance no longer improves or four wavelengths have been selected. The second method was to evaluate all possible combinations of up to four wavelengths chosen from the 18 possible excitation wavelengths. This equates to 18 combinations of one, 153 combinations of two, 816 combinations of three, and 3,060 combinations of four excitation wavelengths, for a total of 4,047 combinations. While the first method requires less computational time, it is only appropriate for normalization methods that remove relative intensity information. Otherwise, the best single wavelength may not be part of the best wavelength pair that exploits differences in relative intensity. The second method can be used with either normalization scheme and in addition, provides a tool to rank the top wavelength combinations, rather than identifying the single best wavelength combination, so this method was pursued.

Algorithm Development

For each of the 4,047 combinations of one to four excitation wavelengths, spectra from the entire data set were used as a training set to develop multi-variate algorithms to separate normal and abnormal tissues based on their fluorescence emission spectra at all possible wavelength combinations. Algorithm development included of three steps: (1) pre-processing, (2) data reduction and (3) development of a classification algorithm which maximized diagnostic performance. Data were pre-processed using the two normalization schemes described above. For each normalization, principal component analysis was performed using the entire dataset and eigenvectors accounting for 65, 75, 85, and 95% of the total variance were retained. Principal component scores associated with these eigenvectors were calculated for each sample. Discriminant functions were then formed to classify each sample as normal or abnormal. The classification was based on the Mahalanobis distance, which is a multivariate measure of the separation of a point from a dataset in n-dimensional space. Each sample was held out one at a time and the Mahalanobis distances between to the held out sample and the remaining normal and abnormal samples were calculated; the sample was classified according to the category corresponding to the smallest distance. The sensitivity and specificity of the algorithm were then evaluated relative to diagnoses based on histopathology (in patients suspected to have oral cavity malignancy) or clinical impression (in normal volunteers). Overall diagnostic performance was evaluated as the sum of the sensitivity and the specificity, thus minimizing the number of misclassifications (when prevalence of disease and normal are approximately equal). The performance of the diagnostic algorithm depended on the principal component scores which were included. Four different diagnostic algorithms were developed using principal component scores derived from eigenvectors accounting for increasing amounts of total variance. From the available pool of principle component scores, the single principal component score yielding the best initial performance was identified, and then the principal component score that most improved this performance was selected. This process was repeated until performance is no longer improved by the addition of principal components scores, or all available scores were selected. The pool of available eigenvectors is specified by a variance criterion, eigenvector significance level (ESL), that represents the minimum variance fraction accounted for by the sum of the n largest eigenvalues. In this work we examined 4 ESLs, corresponding to 65%, 75%, 85% and 95% of the total variance.

Comparing Performance of Various Excitation Wavelength Combinations

At each ESL, the wavelength combinations were ranked in order of decreasing performance, based upon the sum of sensitivity and specificity. The combinations were ranked and evaluated based upon training performance. However, as the ESL approaches 100%, over-training becomes more likely, since the available pool of eigenvectors will account for nearly 100% of the variance, including variance due to noise. The magnitude of diagnostically important variances is unknown.

The risk of over-training risk was assessed at the top 25 wavelength combinations of two, three, and four excitation wavelengths, by comparing the training set performance to the performance of an algorithm developed from the same data after the diagnoses corresponding to each measurement site had been randomized. This provides a dataset with the same variance structure as the original dataset, but where the diagnostic performance is not expected to exceed that of chance. In order to make equivalent comparisons, the disease prevalence in the real sample was maintained in the randomly assigned diagnoses. Diagnostic algorithms were then developed again which minimized the number of misclassified samples at a specified eigenvector significance level (ESL). Random diagnoses were assigned fifty times for each wavelength combination and the average and standard deviation of the sum of the sensitivity and specificity were calculated. Ideally, for completely normally distributed data, the sum of the sensitivity and specificity should be one for the randomized diagnosis at all levels of training significance. However, if over-training occurs, this sum will be greater than one. The top 25 wavelength combinations were then ranked again based on the absolute difference between the training set performance and random diagnosis assignment. This method allows the top wavelength combinations to be ranked in order of their robustness, or lack of propensity to over-train. For a given number of wavelengths per combination, the differences were ranked across all four eigenvector significance levels. The largest difference, usually seen at ESL values of 65%, was selected as the optimal wavelength combination. This criterion selects the wavelength combination that is least prone to over-training.

Validation of Algorithm Performance

Although the optimal wavelength combination has been identified based upon comparison of its performance to that which can be achieved when the tissue diagnoses have been randomized, our estimates of algorithm performance are still biased since they are based on the same training set used to develop the algorithm. An unbiased performance estimate must be made to assess the true potential of this wavelength combination. The effects of over-training in performance estimation can be minimized by using separate training and validations sets, or by using the method of cross-validation. The data set here was not sufficiently large to divide into separate training and validation sets, therefore we used the cross-validation method. In this method, all data from one patient are temporarily removed from the data set, the algorithm is developed using the remaining data set, and then the new algorithm is applied to the left out sites. This is repeated until data from each patient has been left out once. Cross validation was used to provide an unbiased estimate of the performance of the top three combinations of excitation wavelengths with each normalization.

Reduction of Emission Wavelength Number

We investigated whether effective diagnostic algorithms could be developed using reduced numbers of emission wavelengths at the top performing excitation wavelength combinations. We calculated the component loadings associated with the eigenvectors corresponding to the principal component scores selected in these algorithms. A component loading represents the correlation between each principal component and the original pre-processed fluorescence emission spectra at each excitation wavelength. The component loadings at each excitation wavelength were evaluated to select fluorescence intensities at a minimum number of excitation-emission wavelength pairs required for the algorithms to perform with a minimal decrease in classification accuracy. Portions of the component loadings most highly correlated (correlation >0.5 or <−0.5) with corresponding emission spectra at each excitation wavelength were selected and the reduced data matrix was then used to regenerate and evaluate the algorithms.

Results

Fluorescence EEMs from 62 sites from 20 subjects were available for further analysis (Table 1). Of these 62 sites, 37 were measured from the tongue, eight from the floor of mouth (FOM), seven from the buccal mucosa, four from the gingiva, one from the palate, and five from the lip. There were 52 normal, four dysplastic, and six cancerous sites. The data set consisted of two types of normal sites: adjacent normals and normals from a population without oral cancer. Adjacent normals are the visually normal sites taken from patients that have suspected lesions elsewhere in the oral cavity. In this data set there were 17 adjacent normal (histologically normal) sites from eleven patients, and 35 visually normal sites taken from nine patients.

The visual screening accuracy of the head and neck physicians for this data set was 100% sensitivity and 83% specificity. This performance was determined by comparing the visual impressions of the clinicians to the histologic findings upon excision. Results of the analysis of the spectroscopic data are presented according to the normalization method used.

Normalization by Peak Emission Intensity of the Concatenated Vector

The top 25 combinations of one to four excitation wavelengths were ranked in order of the largest difference in the sum of the sensitivity and the specificity in the training set and the average performance with randomly assigned diagnoses. The top 3 combinations correspond to the following excitation wavelength combinations: (350 380 400 480), (350 380 400 490), and (350 380 400). All of these combinations demonstrate approximately the same training set performance, with 100% sensitivity and 90% specificity. These combinations have three wavelengths in common. Since no performance benefit was observed when a fourth wavelength was added for the top performing combinations, combinations of four wavelengths were not pursued any further. The top 25 combinations of three excitation wavelengths, ranked in order of the largest difference in the sum of the sensitivity and the specificity in the training set and the average performance with randomly assigned diagnoses are given in Table 2. The ranking of each combination based upon training set performance is given as well. Table 2 gives the diagnostic performance of each combination for both the training set and the average performance for the data set with randomized diagnosis. The random diagnosis performance demonstrated that the combinations showed varying propensities to over-train.

A histogram depicting the frequency at which each wavelength appeared in the top 25 combinations from Table 2 is shown in FIG. 34 for various ESLs. At low ESL values of 65%, 75% and 85% the diagnostic importance of excitation at 350, 380, and 400 nm is evident. This is seen in the histograms for wavelength combinations of two and four as well (data not shown).

To provide an unbiased estimate of performance of these algorithms, the diagnostic performance of the top wavelength combinations was evaluated by using the method of cross-validation using the full data set. The wavelength combination (350, 380, 400 nm) demonstrated a cross validation performance of 100% sensitivity and 88% specificity. The other two combinations (350, 380, 400, 480 nm) (350, 380, 400, 490 nm) demonstrated identical performance upon cross validation with a sensitivity of 100% and a specificity of 90%.

Figure 36:
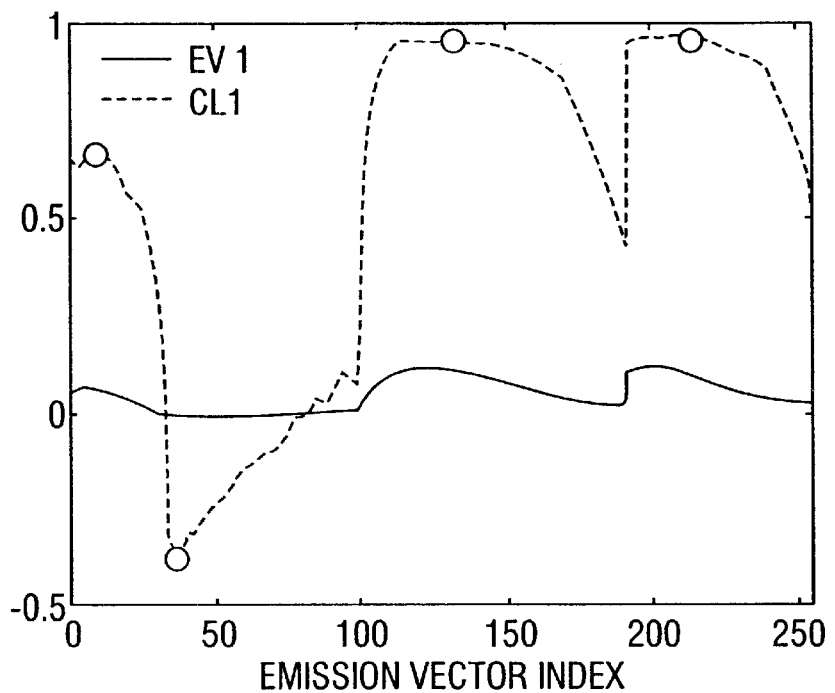
FIG. 36 Plot of the only eigenvector of diagnostic importance at ESL=65% for wavelength combination (350 380 400) (lower line at vector index=200) and the corresponding component loading (upper line at vector index=200).

The emission spectra corresponding to all 62 sites at the three excitation wavelengths common to these combinations are shown in FIG. 36. Visual examination of FIG. 36 confirms the diagnostic potential of this wavelength combination. The identified combinations demonstrate the importance of the relative intensities as seen following normalization to the maximum intensity in the concatenated emission vector. With this normalization, the normal sites demonstrate greater fluorescence intensity at 380 nm excitation, 450 nm emission than the abnormal sites. Additionally, the remaining emission peaks tend to be more intense in normal sites than for abnormal sites in most instances. The normal sites misclassified as abnormal are easily seen in FIG. 36. Histologically, these sites demonstrated increased vascularity, suggesting that the increased hemoglobin absorption is one cause of the reduced relative fluorescence intensity from these sites.

Figure 37:
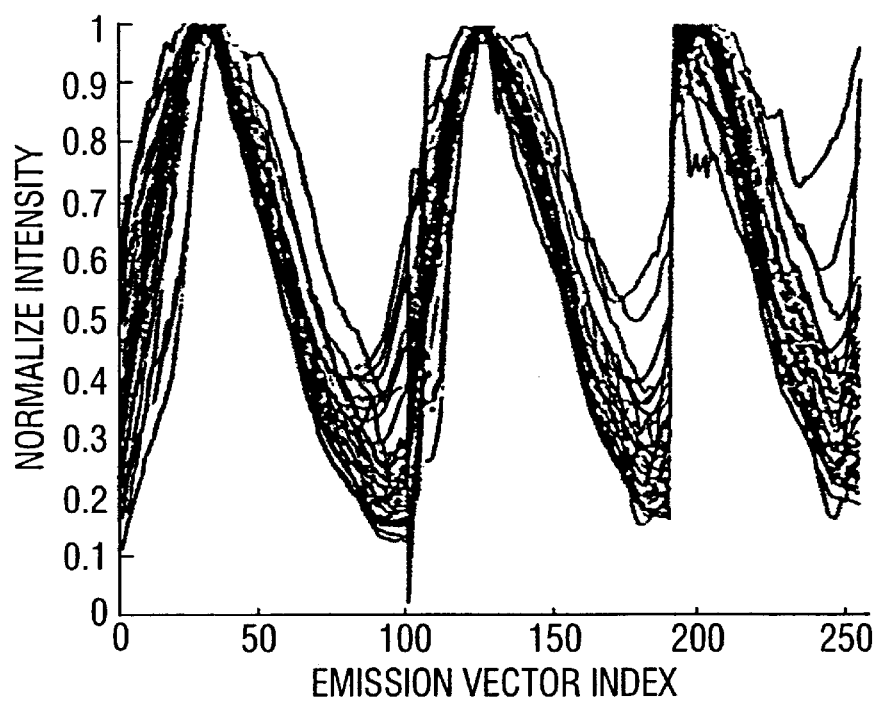
FIG. 37 Plot of emission vector for a wavelength combination of three excitation wavelengths (350, 380, 400 nm) normalized by the peak intensity of each emission spectra.

The algorithm based on the combination of 350, 380 and 400 nm excitation wavelengths selected only a single principal component score, associated with the eigenvector that accounted for most of the total variance. FIG. 37 shows this eigenvector and the associated component loading. The eigenvector depicts the general lineshape of the normalized spectra shown in FIG. 37. The component loading shows that the principal component score for this eigenvector is highly correlated to approximately four regions of the concatenated emission vector. Single emission intensities within these ranges were selected arbitrarily and are denoted as solid green circles in FIG. 37. These points correspond to the emission intensities of 418 and 470 nm at 350 nm excitation, 448 nm emission at 380 nm excitation, and 502 nm emission at 400 nm excitation. An algorithm was developed using the same data reduction and classification methods as above based upon this reduced data set. The training performance of the reduced algorithm is 100% sensitivity and 90% specificity, and the cross-validated performance is 90% sensitivity and 90% specificity compared to 100% sensitivity and 88% specificity of for the algorithm based on the entire emission spectra. This algorithm uses a higher ESL of 95% since the reduced data set contains less variance introduced by noise. Motivated by the desire to construct a simple device that could interrogate or image large areas of tissue, a reduced algorithm based upon a single emission wavelength was evaluated. The emission wavelength chosen was common to all three emission spectra, 472 nm. The training performance of this reduced algorithm was 100% sensitivity, 88% specificity, and upon cross validation it was 90% sensitivity and 88% specificity.

Normalization of Each Emission Spectra by its Peak Emission Prior to Concatenation The analysis was repeated using concatenated vectors in which each emission spectrum was normalized to its peak intensity. This method removes relative intensity information and relies on differences in fluorescence lineshape. The maximum difference between training performance and the performance after random diagnosis assignment was 0.58 compared to 0.82 using the other normalization method. Consequently, the top wavelength combination identified (350, 380, 400, 430 nm) showed poor performance upon cross-validation with a sensitivity of 50% and a specificity of 88%. It is interesting to note that the previously identified wavelengths, (350, 380, 400 nm) are also a part of this combination, indicating that the line shape at these wavelengths contains diagnostic information.

Discussion and Conclusions

This Example identified the optimal excitation wavelengths for in vivo detection of oral cancers with fluorescence spectroscopy. The optimal excitation wavelengths were found to be 350, 380 and 400 nm. An unbiased estimate of an algorithm based on the entire emission spectra at these excitation wavelengths yields a sensitivity of 100% and specificity of 88%. Increasing the number of excitation wavelengths did not improve algorithm performance. Better algorithm performance was obtained when data were normalized to the peak emission intensity of the concatenated vector than when each emission spectrum was normalized to its own peak emission wavelength. The discriminating ability of this wavelength combination is due to differences in both relative intensity and spectral line shape. The number of emission wavelengths could be significantly reduced as well without compromising algorithm performance. An algorithm based on four emission intensities: 418 and 470 nm at 350 nm excitation, 448 nm emission at 380 nm excitation, and 502 nm emission at 400 nm excitation yielded 90% sensitivity and 90% specificity upon cross-validation. When only a single emission wavelength of 472 nm, common to all three excitation wavelengths, was used algorithm performance on cross validation was 90% sensitivity and 88% specificity.

The unbiased performance estimate for the diagnostic algorithms based on fluorescence spectroscopy have a higher sensitivity than current visual screening techniques done by experts. In their hands, visual screening has been reported to have a sensitivity of 74% and specificity of 99%. The performance of visual screening by experts in this study was 100% sensitivity, 83% specificity.

It is interesting to note that emission spectra obtained at 400 nm excitation are included in a majority of the top combinations. Hemoglobin has a strong absorption maximum near this location, suggesting that differences in absorption due to perfusion may offer diagnostic information. This suggests that the combinations of reflectance and fluorescence spectroscopy may offer improved diagnostic performance.

Head and Neck Analysis—Reflectance

A FastEEM system was also used to measure tissue reflectance spectra over the visible region of the spectrum at three source-detector fiber separations. We have analyzed these data with at least two goals: (1) to determine the diagnostic potential of reflectance spectroscopy for detection of neoplasia of the oral cavity, and (2) to determine the combined diagnostic potential of fluorescence and reflectance spectroscopy for detection of neoplasia of the oral cavity.

Study Design 9 normal volunteers and 11 patients with a known or suspected premalignant or malignant oral cavity lesion were recruited to participate in the study at the Head and Neck Surgery Clinical at The University of Texas M.D. Anderson Cancer Center. Written informed consent was obtained from each person in the study.

Instrument

The spectroscopic system used to measure reflectance spectra has been described in detail previously and is briefly summarized here. It includes of a Xenon arc lamp and a 295 nm long-pass filter which provides broadband illumination, a fiber optic probe which directs light to the tissue and collects difflusely reflected light from three locations (position 1, position 2, position 3), and an imaging spectrograph and CCD which detects the reflected light intensity as a function of wavelength. Fibers for illumination and collection of diffuse reflectance are arranged in a ring at the edge of the probe. The collection fibers are located 1.1, 2.1 and 3 mm from a single illumination fiber. All fibers have a core diameter of 200 microns. White light from the Xe lamp is coupled to the proximal end of the illumination fiber. The distal ends of the fibers are flush with the probe tip and placed in direct contact with the sample surface. Using this system, oral cavity tissue reflectance spectra from 390–590 nm with a spectral resolution of 4 nm were collected in approximately 30 seconds. The signal to noise ratio exceeded 75:1 for 90% of the data.

Procedure

Reflectance spectra were wavelength calibrated with a mercury light source. Dark current and background were recorded before each measurement with the same settings but with illumination turned off. These background measurements were subtracted from each reflectance measurement offline. Reflectance data are reported relative to a 2.68% by volume solution of 1.072 micron diameter polystyrene microspheres (Polyscience Inc., Warrington, Pa.). The probe was placed on the outside wall of a 1 cm path length cuvette containing the microsphere solution. The total integrated reflectance of this standard was measured on a double beam spectrophotometer (U-3300 Hitachi, Tokyo, Japan) with an integrating sphere attachment (Labsphere Inc., North Sutton, N.H.). This was used to correct the reflectance measurements of the microsphere solution made with the spectroscopic system. Tissue spectra at each collection fiber position were divided pointwise by the corrected standard reflectance spectrum at the corresponding fiber position.

Before the probe was used it was disinfected with Metricide (Metrex Research Corp.) in accordance with standard protocol. The probe was then guided into the oral cavity and its tip positioned flush with the mucosa. Then reflectance spectra were measured.

Reflectance spectra were measured from 9 volunteers with no history of oral cavity neoplasia at 35 clinically normal sites in the oral cavity (see Table 3). No biopsies were obtained from volunteers. Following visual screening in 11 patients with a known or suspected premalignant or malignant oral cavity lesion, reflectance spectra were measured from 27 sites. The physician placed the fiber optic probe on a lesion or suspected lesion and the reflectance of that site was measured. In addition to the three to five visually abnormal sites, reflectance spectra were measured from one to three contralateral normal sites. Post-spectroscopy, abnormal sites were tattooed with India Ink where the probe measured the spectra. A clinical diagnosis of each lesion as normal, abnormal (not dysplastic), abnormal (dysplastic) or cancerous was recorded by an experienced head and neck surgeon (AMG) or dental oncologist (RJ). During follow up surgery, a 2–4 mm biopsy of the tissue was taken from the tattooed area. These specimens were evaluated by an experienced pathologist (BK) using light microscopy and classified as normal, mucosal reactive atypia (MRA), dysplasia or cancer using standard diagnostic criterion. Biopsies with multiple diagnoses were classified according to the most severe pathological diagnosis. The pathologist and clinicians were blinded to the results of the spectroscopic analyses.

Data Analysis

Reflectance spectra were further processed to reduce noise. A moving average with a width of 10 nm was applied to each spectrum; following this, intensities of all reflectance spectra were extracted in 5 nm steps from 400 to 585 nm and individually analyzed. In addition, the first (slope) and second derivatives of the reflectance spectra were calculated between 400 and 580 nm in 5 nm steps.

An exploratory data analysis was carried out to determine which source-detector separations and wavelength regions were useful to separate three tissue categories: normal, dysplasia and cancer. The normal class contained sites which were clinically and/or histologically normal as well as benign changes such as inflammation.

For each diagnostic category (normal, dysplasia, cancer) we calculated the average value and standard deviation of the intensity at each wavelength, and the first and second derivative at each wavelength. These values were calculated separately for each source detector separation. The Student's t-test was used to determine whether differences in these mean values were statistically significant between groups of two categories. We examined normal tissues vs. abnormal tissues (dysplasia and cancer) as well as normal tissues vs. dysplasia.

Parameters which were most statistically significant, corresponding to the lowest p-values, were examined further for diagnostic ability. We constructed two-dimensional scatter plots which showed the most statistically significant parameter values for each site measured to determine which parameters could most effectively discriminate between the two categories of normal and abnormal (dysplasia and cancer). All calculations and graphs were produced with the Matlab® (Mathworks Inc.) and the Statistical Toolbox for Matlab.

Results

Figure 38A:
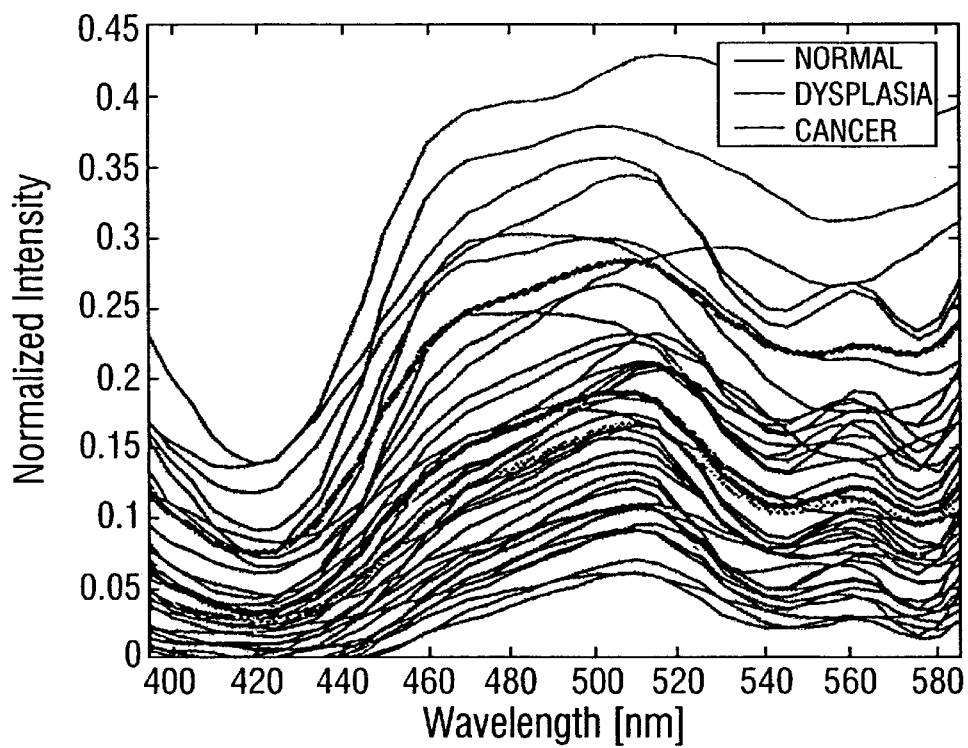
FIGS. 38A–38C Reflectance spectra (A), first (B) and second derivation (C) for position one.
Figure 38B:
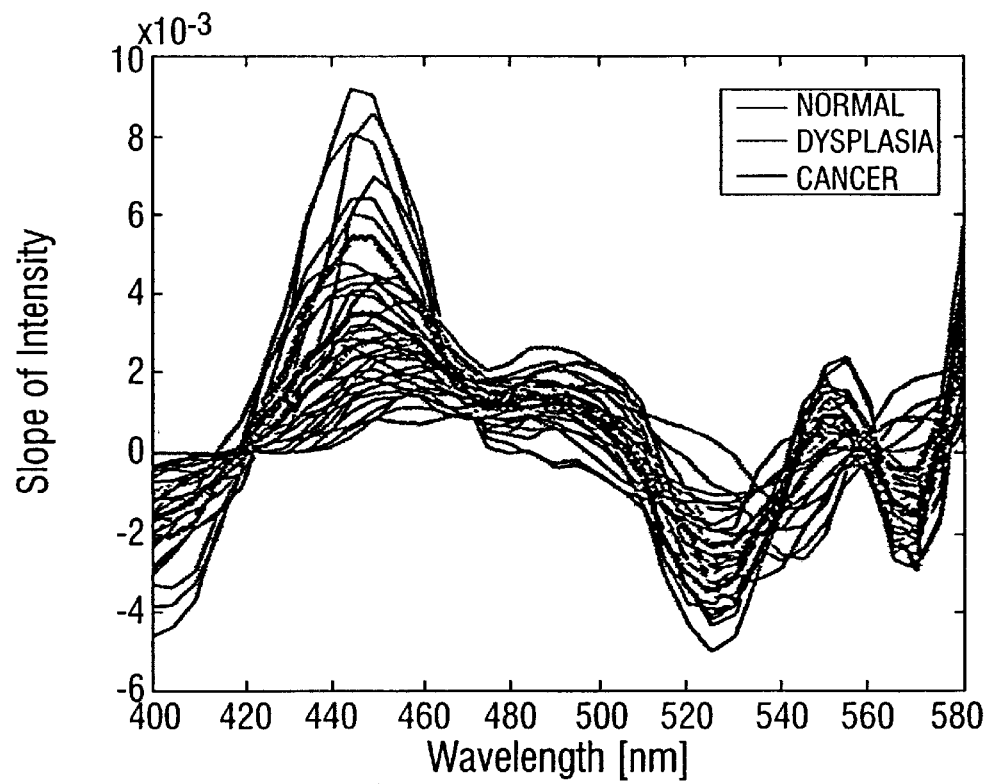
Figure 38C:
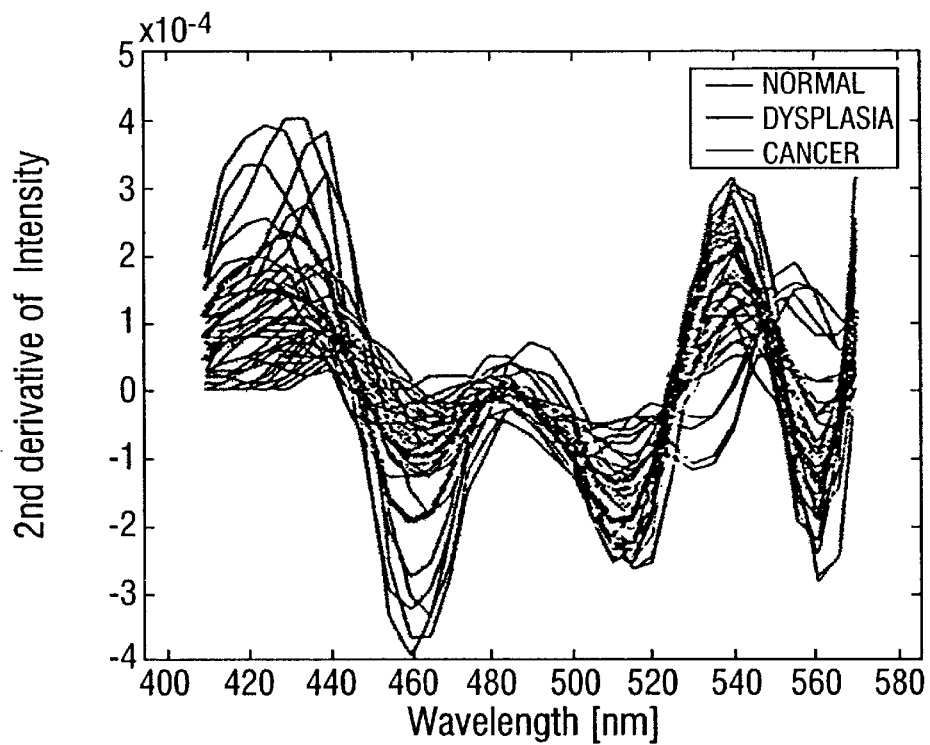
Figure 39A:
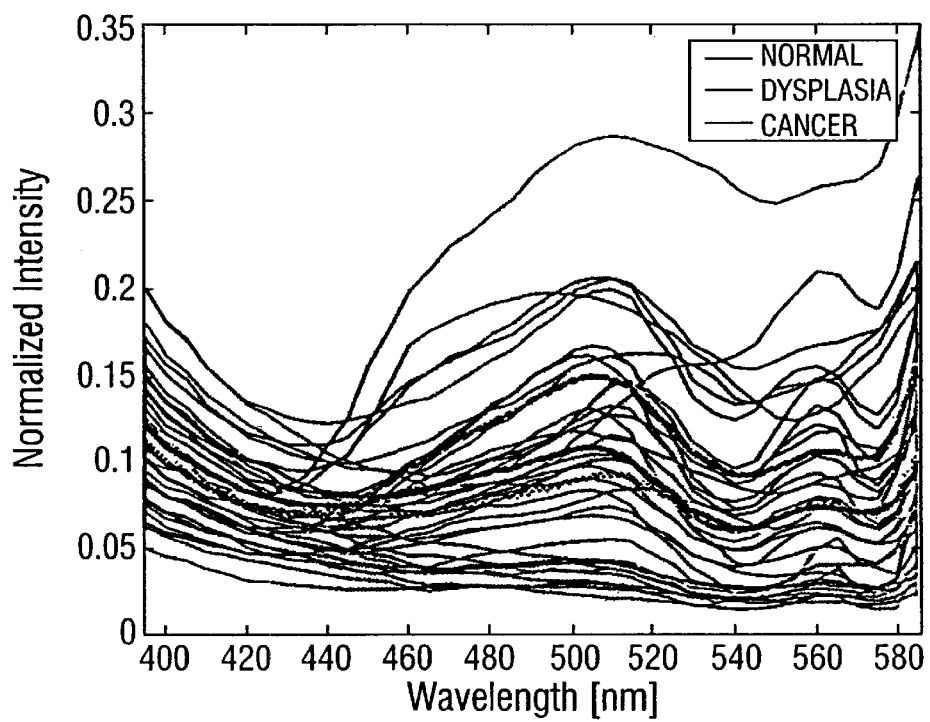
FIGS. 39A–39C Reflectance spectra (top), first (middle) and second derivation (bottom) for position two.
Figure 39B:
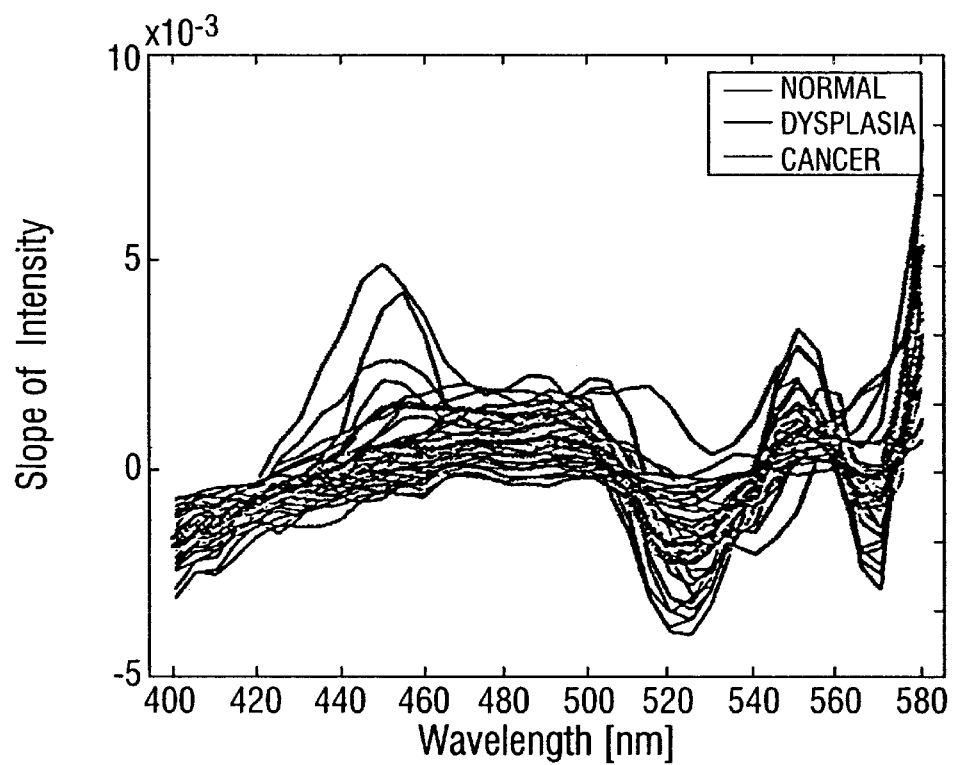
Figure 39C:
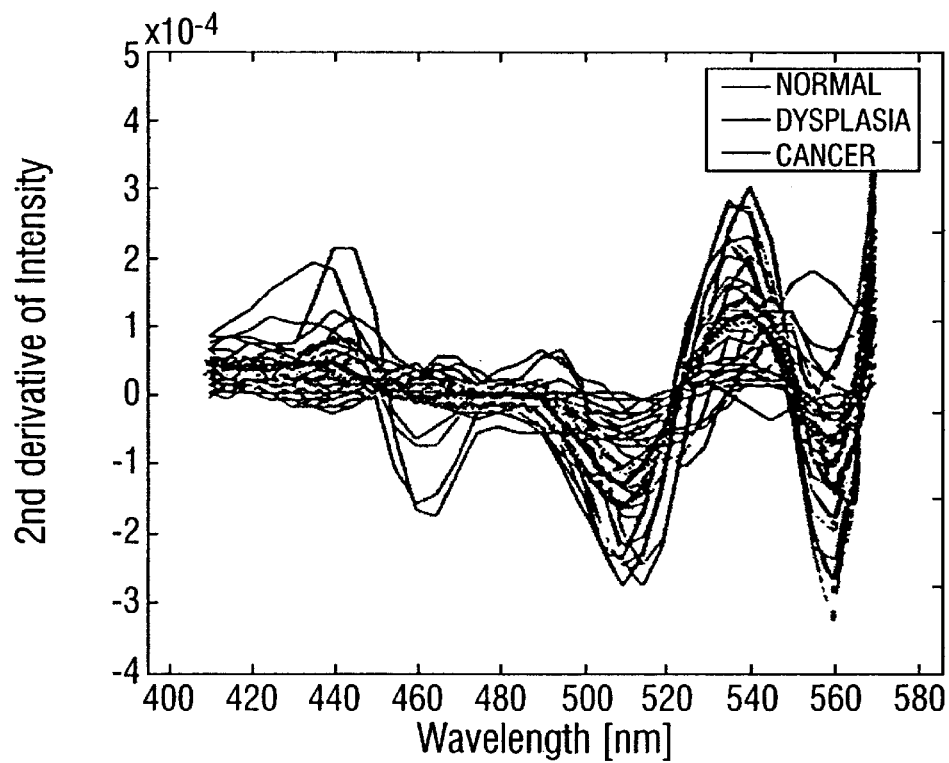
Figure 40A:
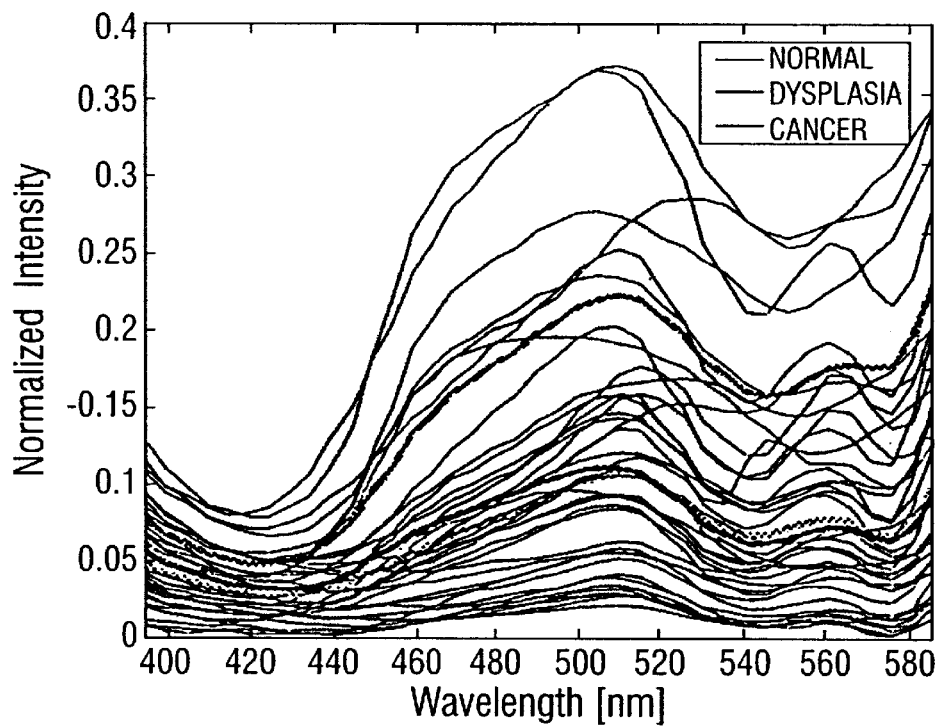
FIGS. 40A–40C Reflectance spectra (top), first (middle) and second derivation (bottom) for position three.
Figure 40B:
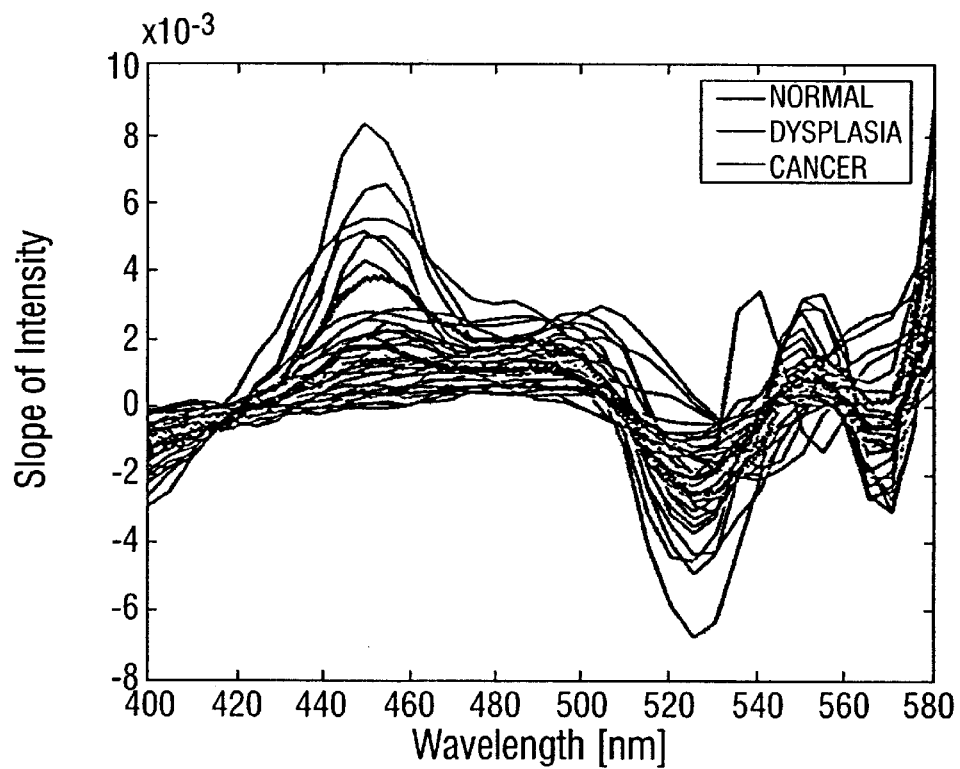
Figure 40C:
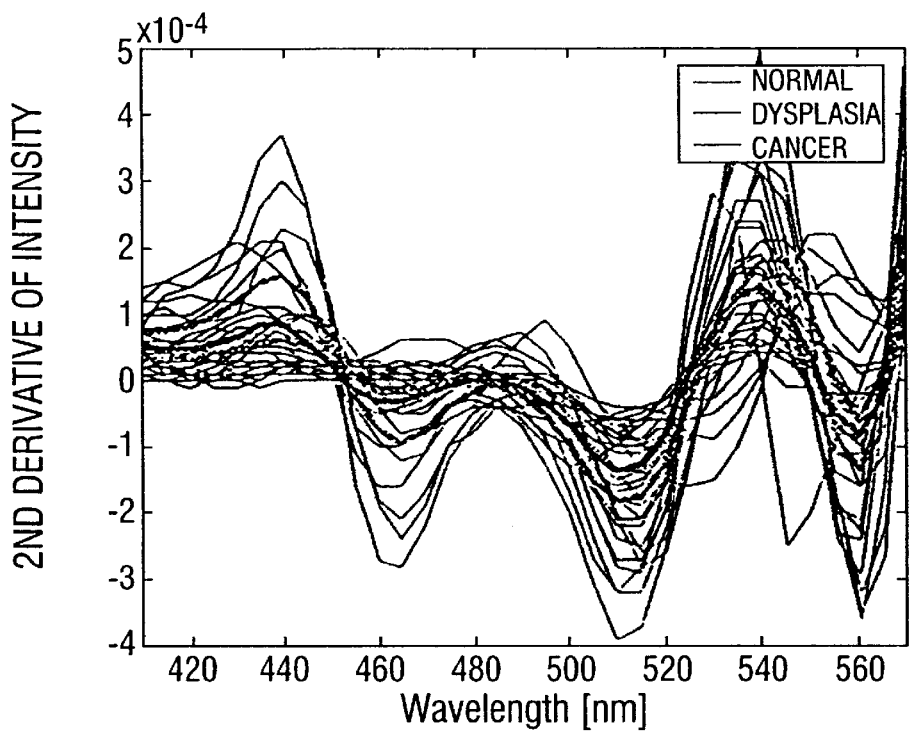
Figure 41A:
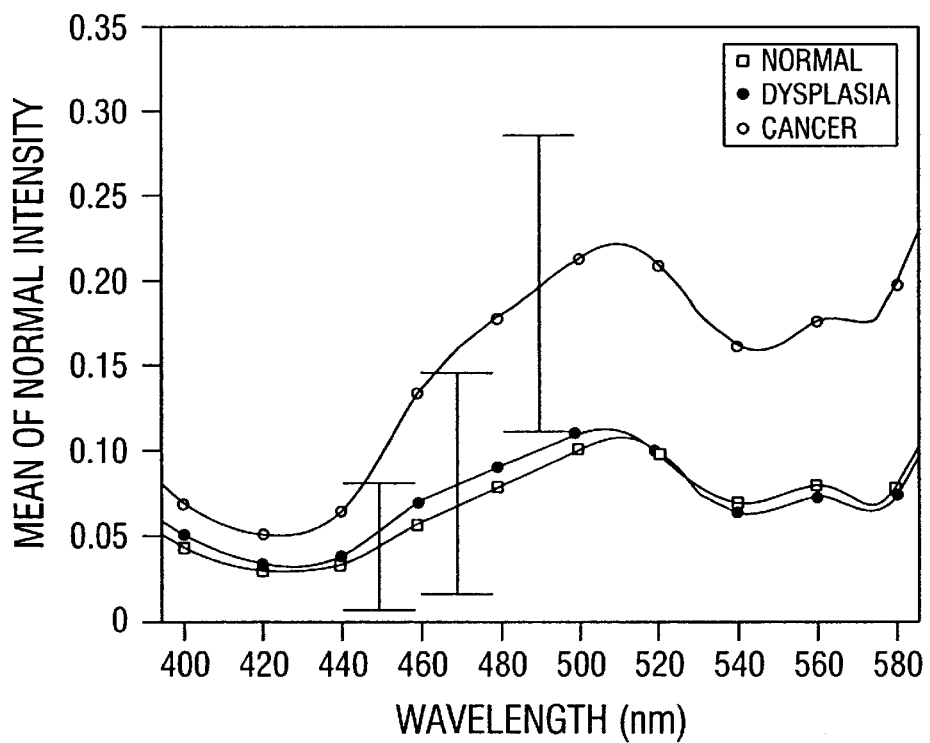
FIGS. 41A–41C Average reflectance spectra (top), first (middle) and second derivation (bottom) for position one. Error bars show standard deviation.
Figure 41B:
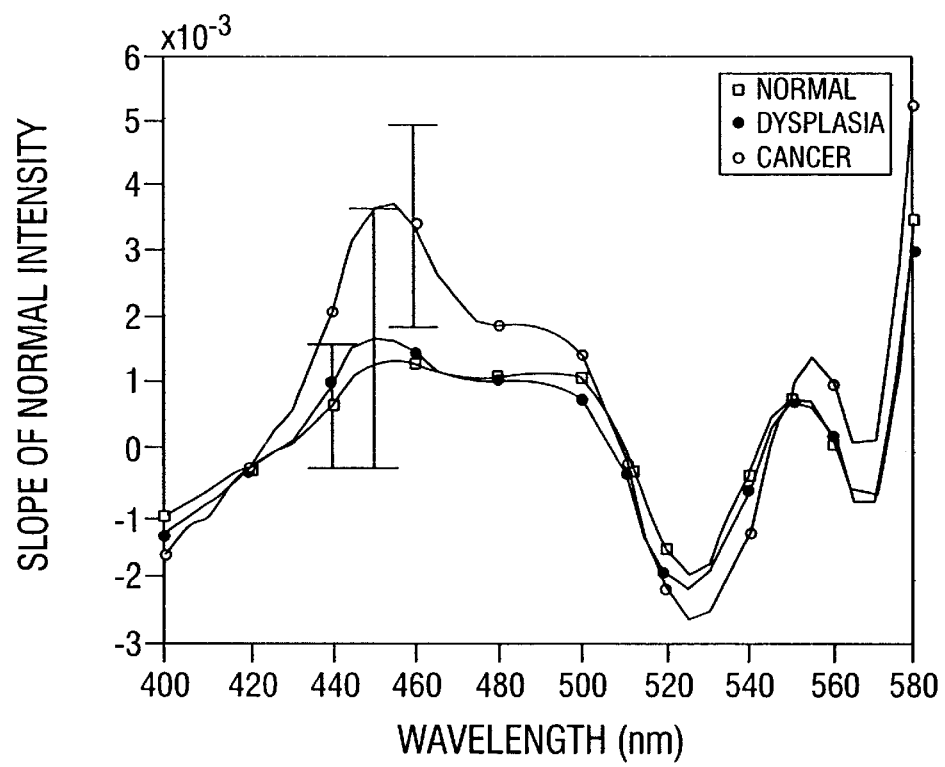
Figure 41C:
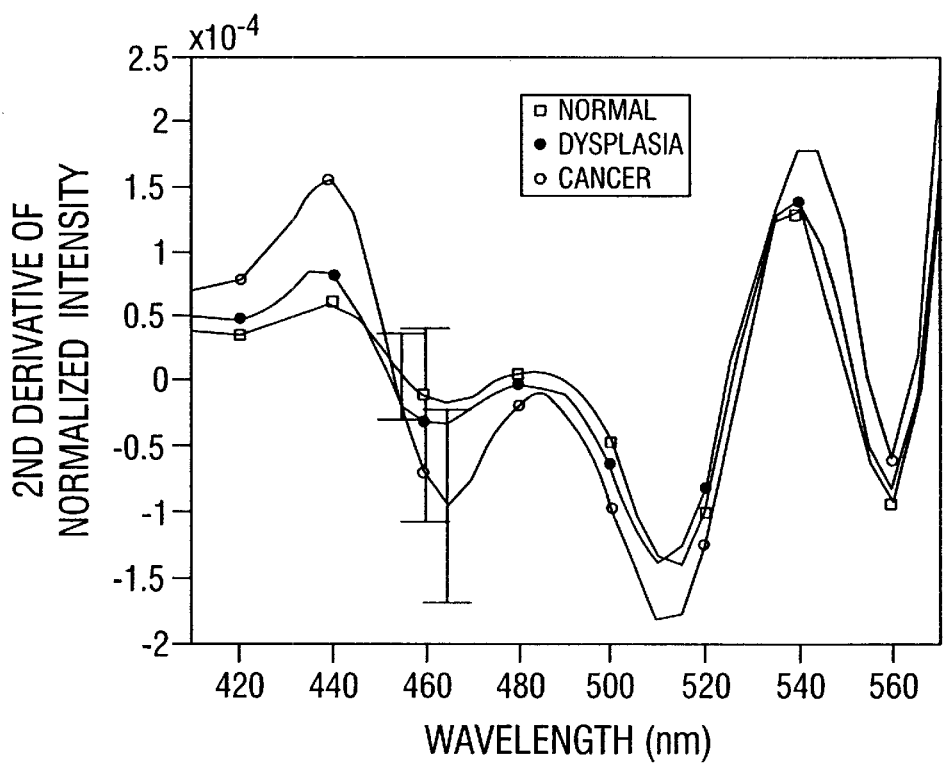
Figure 42A:
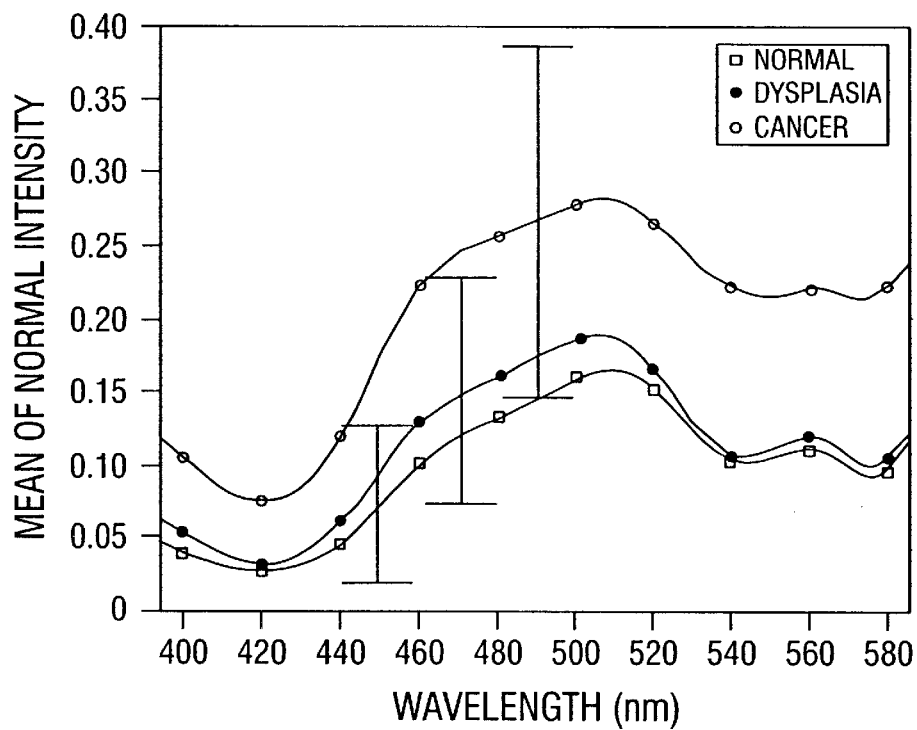
FIGS. 42A–42C Average reflectance spectra (top), first (middle) and second derivation (bottom) for position two. Error bars show standard deviation.
Figure 42B:
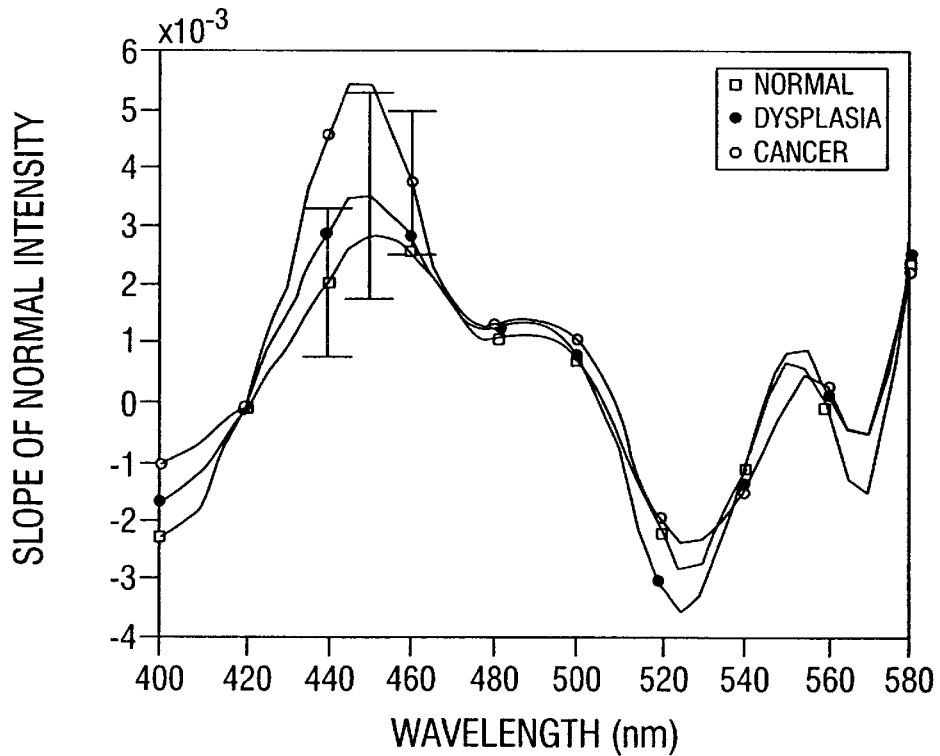
Figure 42C:
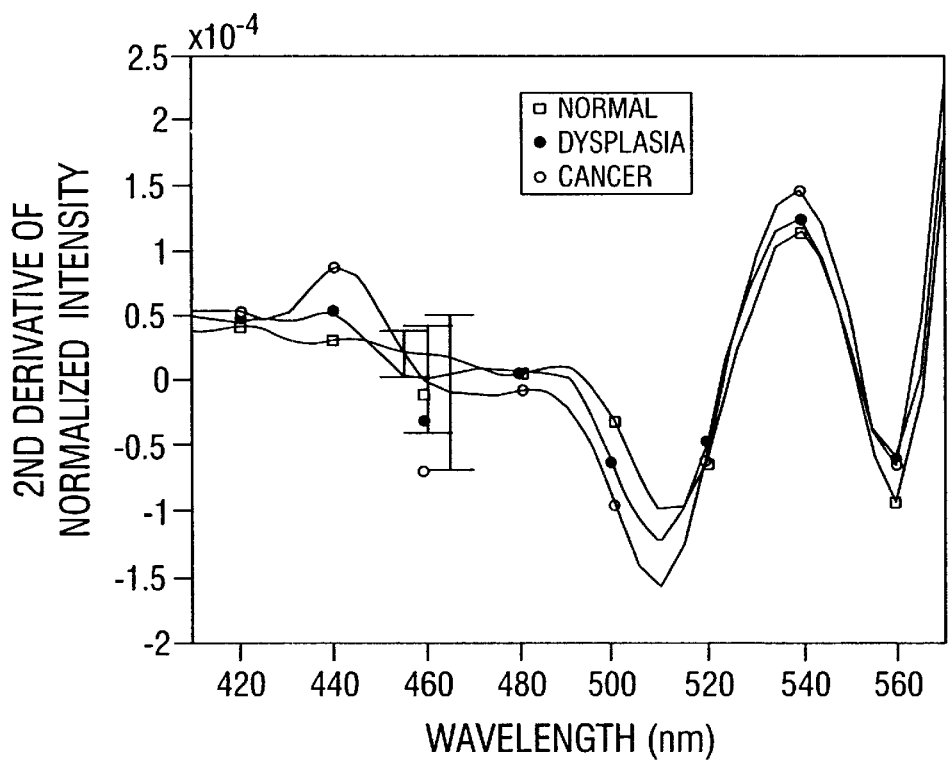
Figure 43A:
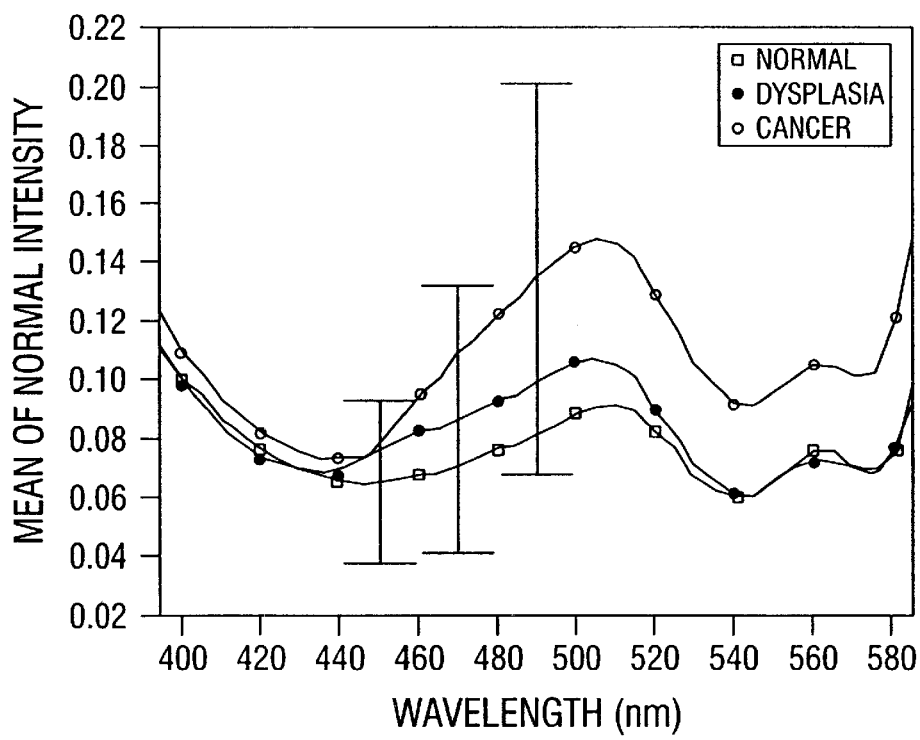
FIGS. 43A–43C Average reflectance spectra (top), first (middle) and second derivation (bottom) for position three. Error bars show standard deviation.
Figure 43B:
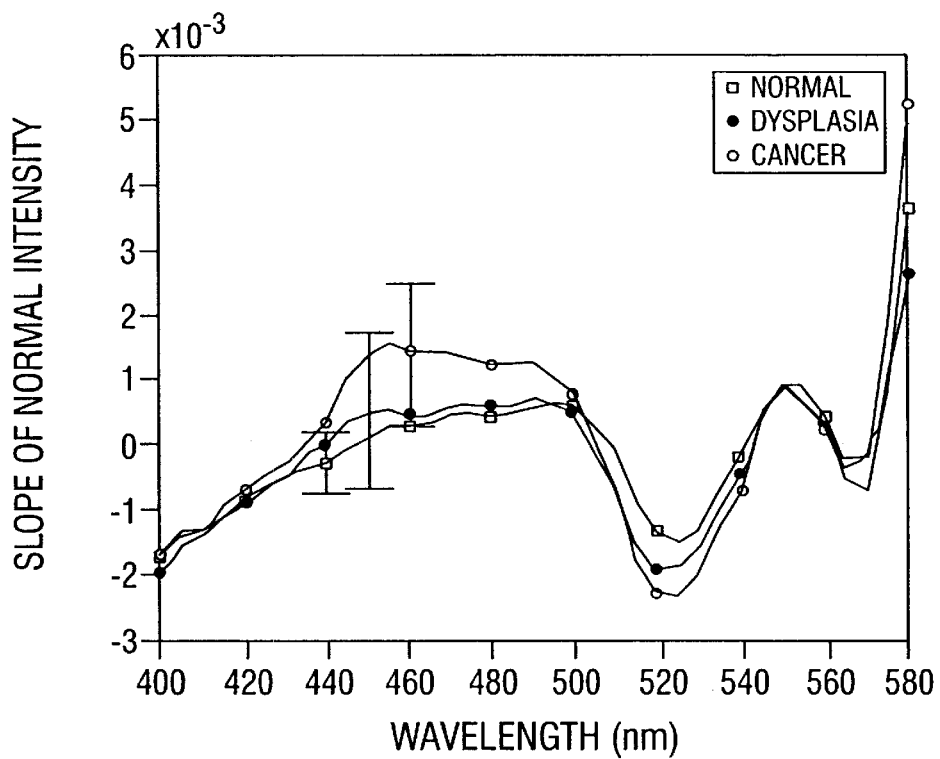
Figure 43C:
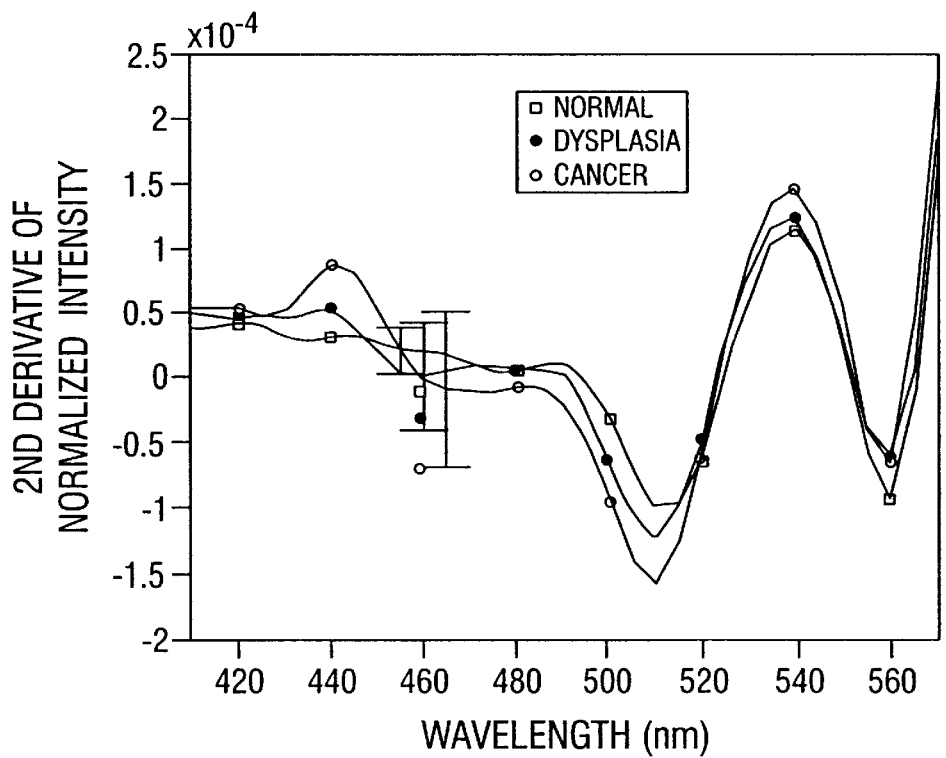

FIGS. 38 through 40 show the reflectance spectra, first and second derivative at each of the three source detector separations for all sites measured. FIGS. 41 through 43 show the average value plus and minus one standard deviation for normal, dysplastic and cancer sites. Normal sites are shown in green, dysplasia in blue and cancer in red. In general, the spectra of cancer sites show the highest reflectance intensity at all wavelengths measured, while spectra of normal and dysplastic sites are lower in intensity and more similar. Differences in intensity are greatest at position 1 and least at position 3. The slope and second derivative of the reflectance spectra are greater (lower) for cancers at 440 and 480 nm (520 nm).

Figure 44A:
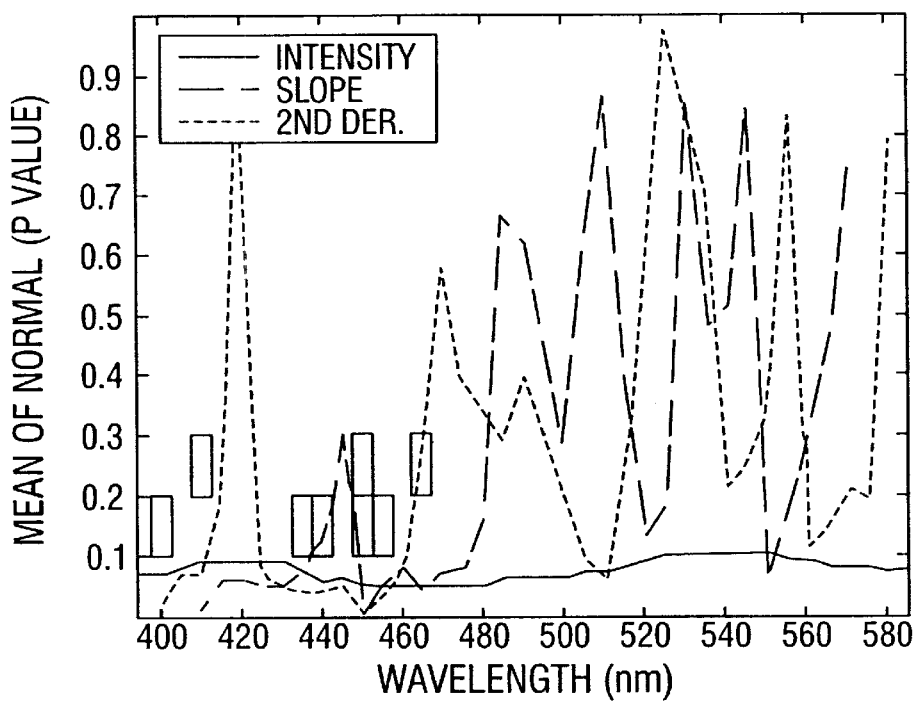
FIGS. 44A–44C p values comparing the mean intensity, mean first and second derivatives of normal tissue versus abnormal tissues, at source detector separation 1 (top), 2 (middle) and 3 (bottom).
Figure 44B:
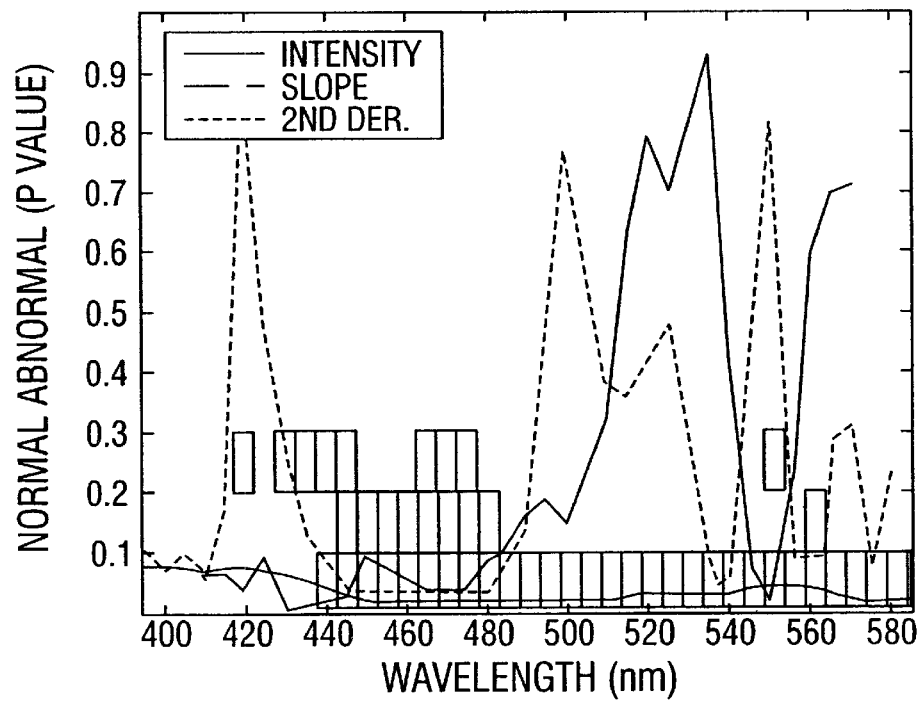
Figure 44C:
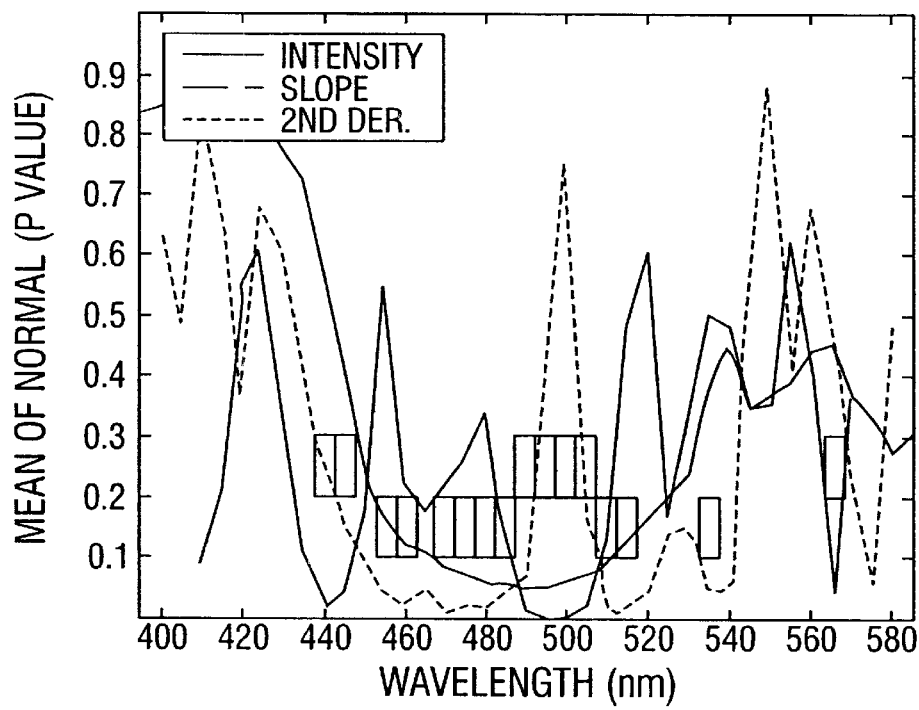
Figure 45A:
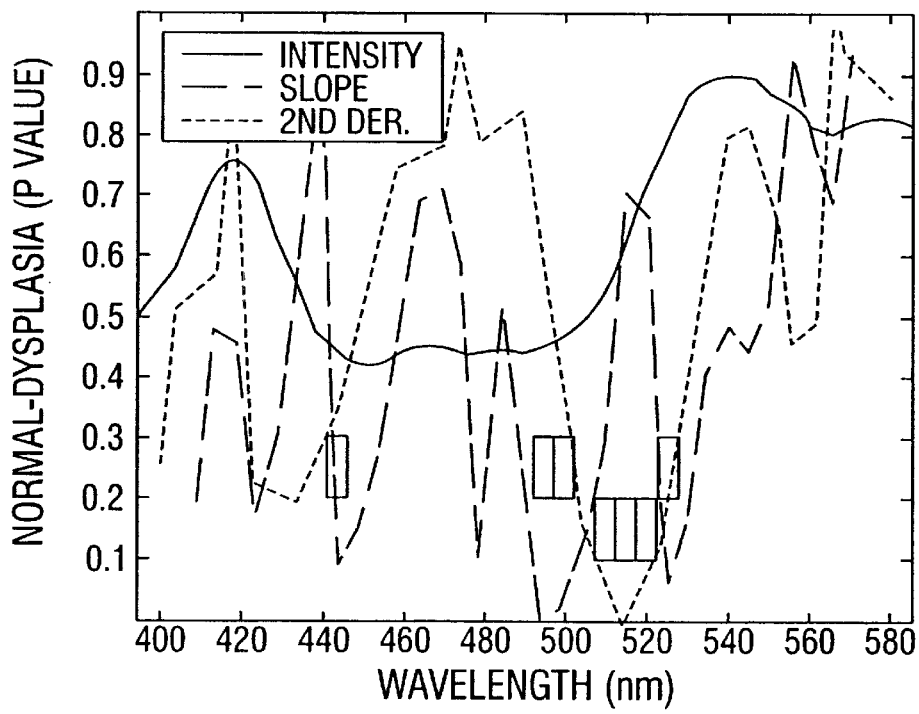
FIGS. 45A–45C p values comparing the mean intensity, mean first and second derivatives of normal tissue versus dysplastic tissues, at source detector separation 1 (top), 2 (middle) and 3 (bottom).
Figure 45B:
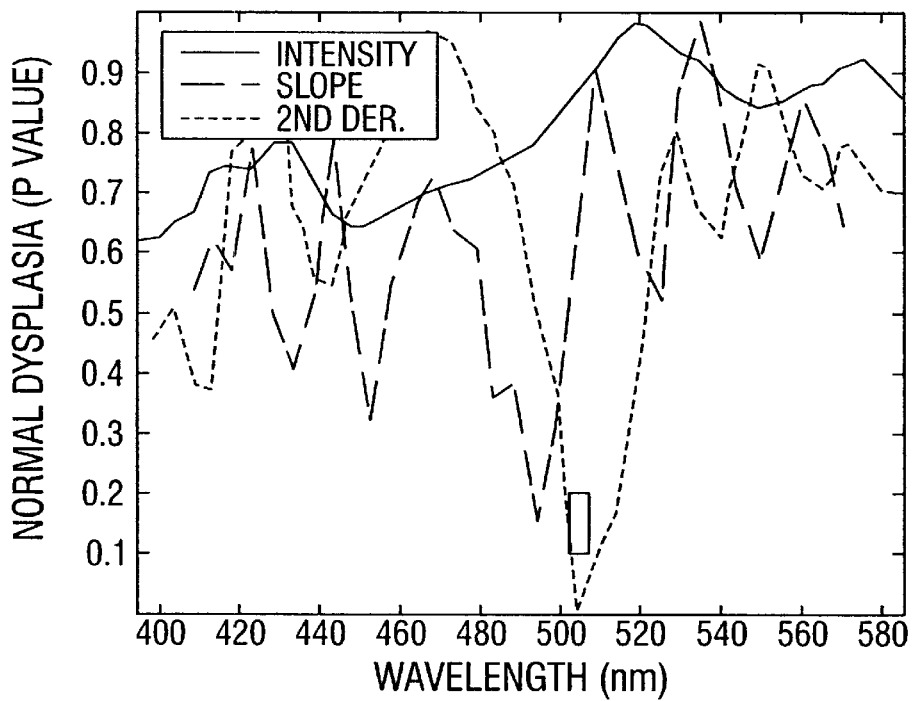
Figure 45C:
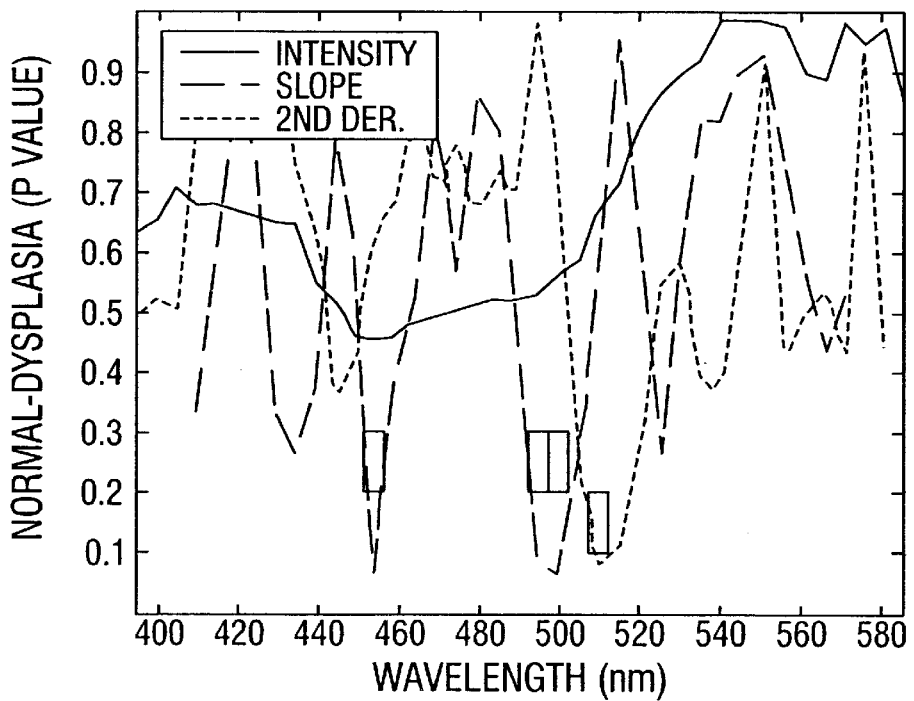

FIG. 44 shows the p values comparing the mean intensity, mean first and second derivatives of normal tissue versus abnormal tissues, at each wavelength at the three different source detector separations. FIG. 45 shows the p values comparing the mean intensity, mean first and second derivatives of normal tissue versus dysplastic tissues, at each wavelength at the three different source detector separations. A low value indicates a statistically significant result; we are particularly interested in those with values less than 0.05.

At each source-detector fiber separation, we ranked the intensity, first and second derivatives at each wavelength in order of increasing p-value. Tables 4–6 show the results when normal and abnormal tissues were compared, Tables 7–9 show the results when normal and dysplastic tissues were compared. Results are shown for p-values less than or equal to 0.05.

In order to explore the diagnostic contributions provided by these wavelength regions, we highlighted all regions where the p-value was less than or equal to 0.01 for first and second derivatives and less than or equal to 0.02 for intensity. These values are highlighted in gray in tables 4–9. This resulted in a total of 15 different parameters. The slope and second derivative near 440–460 nm at positions 1 and 2 were identified as diagnostically useful regions, as was the slope and second derivative near 500–510 nm at position 3. The intensity from 450–51 nm and 570–585 nm at position 2 were also identified as diagnostically useful.

Figure 46:
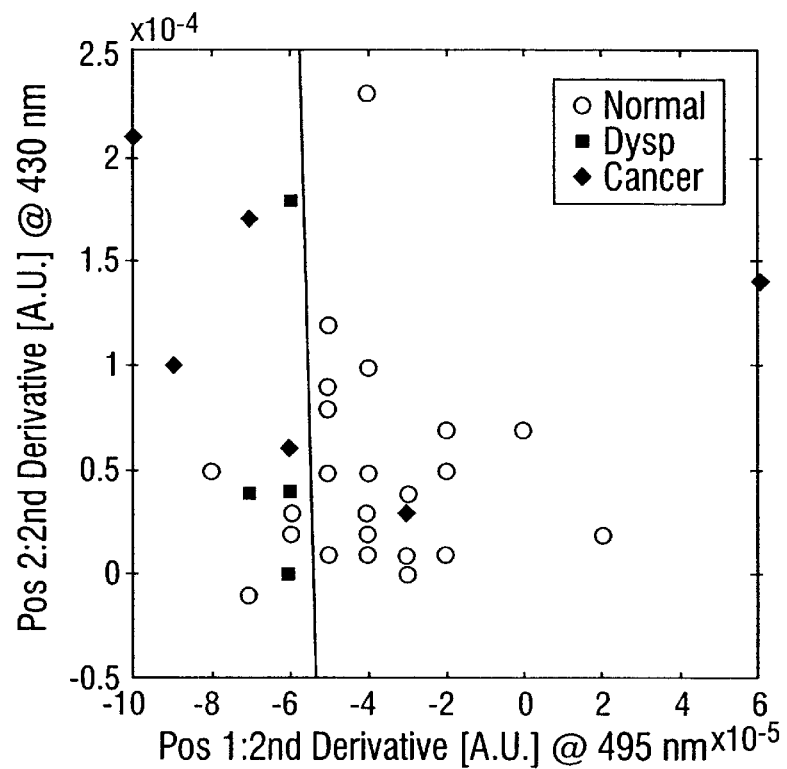
FIG. 46 Scatter plot of the second derivative at 430 nm for position 2 vs. the second derivative at 495 nm for position one. The straight line represents an algorithm to separate normal findings from dysplasias and cancers, and results in a sensitivity of 80% and a specificity of 85%.
Figure 47:
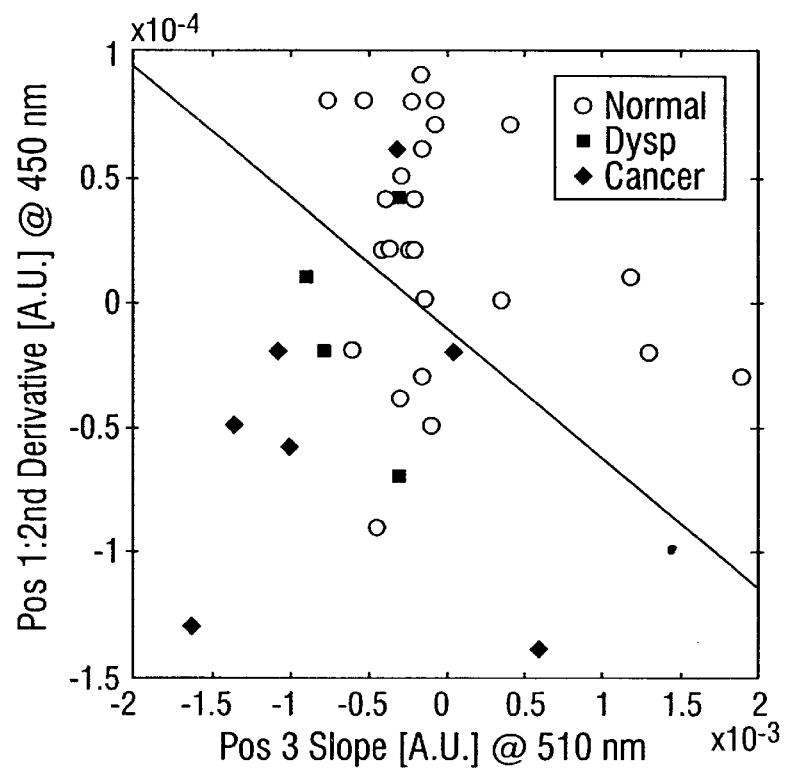
FIG. 47 Scatter plot of the second derivative at 450 nm for position 1 vs. the first derivative at 510 nm for position three. The straight line represents an algorithm to separate normal findings from dysplasias and cancers, and results in a sensitivity of 80% and a specificity of 82%.
Figure 48:
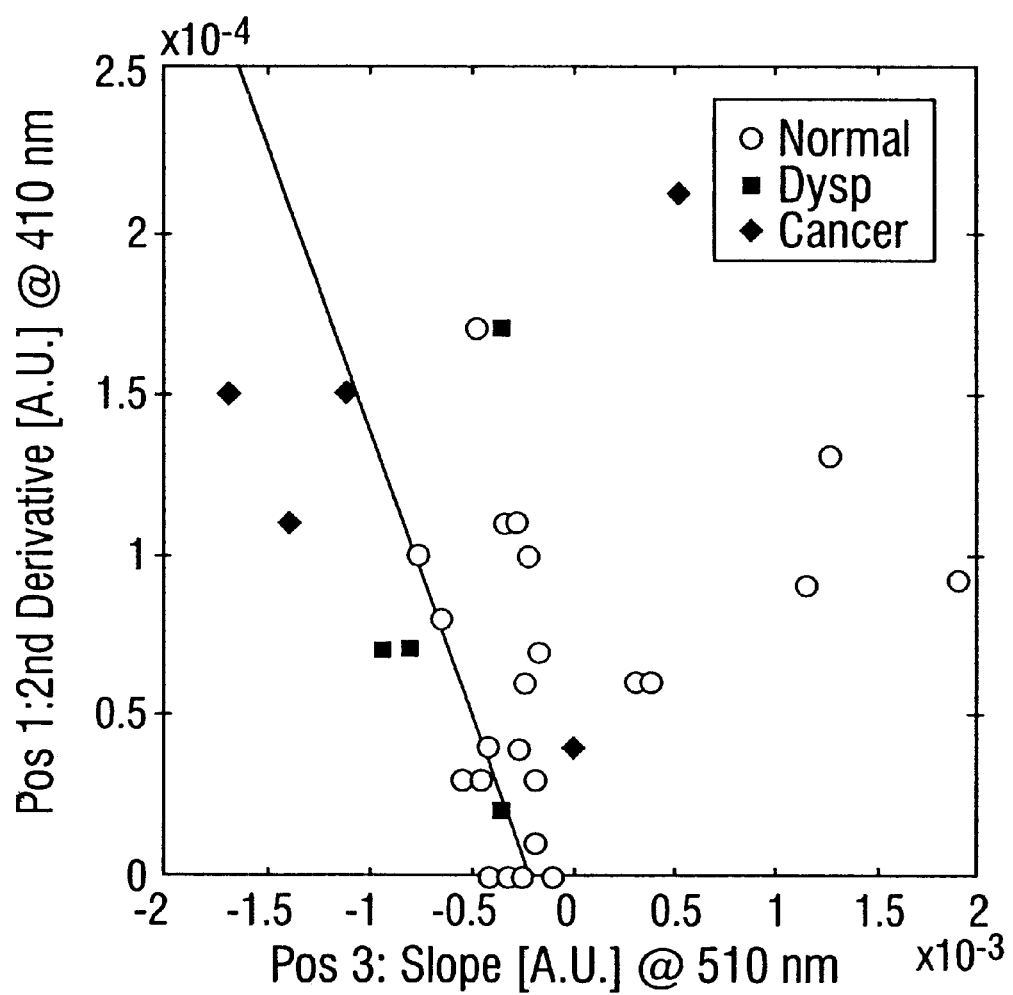
FIG. 48 Scatter plot of the second derivative at 410 nm for position 1 vs. the first derivative at 510 nm for position three. The straight line represents an algorithm to separate normal findings from dysplasias and cancers, and results in a sensitivity of 70% and a specificity of 75%.

Two dimensional scatterplots containing all possible pairwise combinations of these 15 groups of parameters were generated (105 total combinations). FIGS. 46–48 show three representative examples. FIG. 46 shows the second derivative at 430 nm for position 2 vs. the second derivative at 495 nm for position one. The straight line represents an algorithm to separate normal findings from dysplasias and cancers, and results in a sensitivity of 80% and a specificity of 85%. FIG. 47 shows the second derivative at 450 nm for position 1 vs. the first derivative at 510 nm for position three. The straight line represents an algorithm to separate normal findings from dysplasias and cancers, and results in a sensitivity of 80% and a specificity of 82%. FIG. 48 shows the second derivative at 410 nm for position 1 vs. the first derivative at 510 nm for position three. The straight line represents an algorithm to separate normal findings from dysplasias and cancers, and results in a sensitivity of 70% and a specificity of 75%. In each case, the lines were drawn to minimize the total number of samples misclassified. These sensitivity and specificity values are slightly lower than those achieved in the previous section using fluorescence alone, and reflect the greater overlap in the reflectance of tissues from the three groups than is seen in the fluorescence spectra. However, the fluorescence algorithms were based on multi-variate classifiers to enable the use of more than two parameters in the algorithm. These techniques were next pursued using reflectance spectra.

Multi-Variate Discriminant Algorithms

Reflectance spectra were analyzed to determine which wavelength ranges and source-detector fiber separations contained the most diagnostically useful information and to estimate the performance of multi-variate diagnostic algorithms based on this information. We considered algorithms based on multi-variate discriminant analysis. First, we developed algorithms based on reflectance spectra, or their first or second derivatives over various wavelength ranges at each source-detector fiber separation in order to determine which types of spectra, wavelength ranges and fiber separations contained the most diagnostic information. In addition, we developed algorithms using the concatenated spectra (or their first or second derivatives) at all fiber separations over various wavelength ranges. In each case, the algorithm development process, described in detail below, consisted of the following major steps: (1) data reduction to reduce the dimensionality of the data set, (2) feature selection and classification to develop algorithms which maximized diagnostic performance and minimized the likelihood of over-training in a training set, (3) unbiased evaluation of these algorithms using the technique of cross-validation.

Diagnostic Categories

Multi-variate discriminant algorithms were sought to separate two tissue categories: normal and abnormal. The abnormal class contained sites with dysplasia, carcinoma in situ and squamous cell carcinoma; the normal class contained sites which were clinically and/or histologically normal as well as benign changes such as inflammation.

Algorithm Development

For each of the different types of spectra and wavelength ranges, spectra from the entire data set were used as a training set to develop multi-variate algorithms to separate normal and abnormal tissues based on their reflectance. Algorithm development included two steps: (1) data reduction and (2) development of a classification algorithm which maximized diagnostic performance. For each type of data, principal component analysis was performed using the entire dataset and eigenvectors accounting for 65, 75, 85, 95% and 99% of the total variance were retained. Principal component scores associated with these eigenvectors were calculated for each sample. Discriminant functions were then formed to classify each sample as normal or abnormal. The classification was based on the Mahalanobis distance, which is a multivariate measure of the separation of a point from a dataset in n-dimensional space. Each sample was held out one at a time and the Mahalanobis distances between to the held out sample and the remaining normal and abnormal samples were calculated; the sample was classified according to the category corresponding to the smallest distance. The sensitivity and specificity of the algorithm were then evaluated relative to diagnoses based on histopathology (in patients suspected to have oral cavity malignancy) or clinical impression (in normal volunteers). Overall diagnostic performance was evaluated as the sum of the sensitivity and the specificity, thus minimizing the number of misclassifications (when prevalence of disease and normal are approximately equal). The performance of the diagnostic algorithm depended on the principal component scores which were included. Five different diagnostic algorithms were developed using principal component scores derived from eigenvectors accounting for increasing amounts of total variance. From the available pool of principle component scores, the single principal component score yielding the best initial performance was identified, and then the principal component score that most improved this performance was selected. This process was repeated until performance was no longer improved by the addition of principal components scores, or all available scores were selected. The pool of available eigenvectors is specified by a variance criterion, eigenvector significance level (ESL), that represents the minimum variance fraction accounted for by the sum of the n largest eigenvalues. In this work we examined 5 ESLs, corresponding to 65%, 75%, 85%, 95% and 99% of the total variance.

Comparing Performance of Various Data Types and Wavelength Ranges

At each ESL, wavelength range and type of data we calculated the sum of sensitivity and specificity. As the ESL approaches 100%, over-training becomes more likely, since the available pool of eigenvectors will account for nearly 100% of the variance, including variance due to noise. The magnitude of diagnostically important variances is unknown. The risk of over-training risk was assessed for each of the types of input data, by comparing the training set performance to the performance of an algorithm developed from the same data after the diagnoses corresponding to each measurement site had been randomized. This provides a dataset with the same variance structure as the original dataset, but where the diagnostic performance is not expected to exceed that of chance. In order to make equivalent comparisons, the disease prevalence in the real sample was maintained in the randomly assigned diagnoses. Diagnostic algorithms were then developed again which minimized the number of misclassified samples at a specified eigenvector significance level (ESL). Random diagnoses were assigned fifty times for each wavelength combination and the average and standard deviation of the sum of the sensitivity and specificity were calculated. Ideally, for completely normally distributed data, the sum of the sensitivity and specificity should be one for the randomized diagnosis at all levels of training significance. However, if over-training occurs, this sum will be greater than one. At each ESL, wavelength range and type of data we calculated the absolute difference between the training set performance and random diagnosis assignment. This method allows the best types of data and wavelength ranges to be identified based on their robustness, or lack of propensity to over-train. Unlike our analysis of the fluorescence from oral cavity, in this case, all sensitivity and specificity values were calculated for the case of cross-validation. This proved to be necessary since the eigenvectors which contained diagnostically useful information contributed a relatively smaller amount of the total variance for reflectance than for fluorescence. The largest differences, were selected as the optimal data type and wavelength range. This criterion selects the data type and wavelength range that is least prone to over-training.

Results—Multi-Variate Discriminant Algorithms

Tables 10–12 show the absolute difference between the training set performance and random diagnosis assignment for the different data types, wavelength ranges and ESLs. We selected an improvement of 0.5 as significant for first and second derivative data and an improvement of greater than 0.4 as significant for intensity data (since this is easier to measure in a multi-spectral imaging system). Wavelength ranges, data types and ESLs with at least this improvement are highlighted in Tables 10–12. Eight types of data met these criteria; however, the wavelength range associated with several of them overlapped significantly. In this case, the combination with the best performance increase was selected, resulting in the following four combinations: (1) Intensity at position 2 from 395–475 nm at 95% ESL, (2) Intensity at positions 1–3 from 425–500 nm at 99% ESL, (3) Slope at position 1 from 450–525 nm at 65% ESL and (4) Slope at position 3 from 395–550 nm at 95% ESL. Table 13 gives the cross-validated sensitivity and specificity for algorithms based on these data types, wavelength ranges and ESLs. The best performance was achieved using the slope at position 3 from 395–550 nm at 95% ESL, with a cross-validated sensitivity of 70% and a specificity of 100%. This compares favorably to the scatter plot shown in FIG. 47, which shows the second derivative at 450 nm for position 1 vs. the slope at 510 nm for position three, where a simple linear discriminant algorithm resulted in a sensitivity of 80% and a specificity of 82%.

Head and Neck Analysis—Combination of Fluorescence and Reflectance

In general, the performance of multi-variate algorithms based on reflectance spectroscopy alone was somewhat lower than that based on fluorescence spectroscopy alone. However, from an instrumentation point of view, it may be easier to measure reflectance images and spectra since signal to noise ratio is higher. Therefore, we explored the combination of reflectance and fluorescence spectroscopy and wheter it may provide better discrimination. Further, we examined whether the good performance of the fluorescence algorithm may be maintained if the number of fluorescence excitation wavelengths were reduced, but reflectance spectra were measured.

In our previous analyses, we identified a combination of emission spectra at three excitation wavelength as optimal for diagnosis based on fluorescence spectroscopy and four types of reflectance data which were optimal for diagnosis. We evaluated the performance of the following combinations of data at ESLs of 65%, 75%, 85%, 95% and 99%: (a) Fluorescence at three excitation wavelengths +each type of reflectance data, (b) Fluorescence at all combinations of two excitation wavelengths +each type of reflectance data, and (c) Fluorescence at each single excitation wavelength +each type of reflectance data.

The performance of these combinations was compared to that which could be achieved with fluorescence alone. Since the number of samples where both fluorescence and reflectance data were available was smaller than that for either type of data alone, we re-evaluated the performance of algorithms based on reflectance or fluorescence data alone using this reduced dataset. We also evaluated the performance of fluorescence alone at one or two excitation wavelengths using this reduced dataset. Table 14 shows the number of patients and sites where both reflectance and fluorescence data were available. Results, reported as sensitivity and specificity giving best performance under cross validation, are shown in Tables 15–18 for each type of reflectance data.

The performance of the fluorescence algorithm based on three excitation wavelengths does not improve when any of the four types of reflectance data are also incorporated. The performance of fluorescence algorithms based on two excitation wavelengths was lower than that for three excitation wavelengths; incorporation of any of the four types of reflectance spectra did not improve performance. The performance of fluorescence algorithms based on a single excitation wavelength was lower than that for two and three excitation wavelengths. Best results were obtained using spectra at 400 nm excitation. Incorporation of any of the four types of reflectance spectra did not improve performance.

TABLE 2

Ranking of wavelength combinations of three based upon the difference between training and random diagnosis assignment performance, Δ. (ESL = 65%)

| Rank | | Wavelength Combination | | | Performance (Se + Sp) | | |
|---|---|---|---|---|---|---|---|
| Random | Training | | | | Training | Random | Δ |
| 1 | 1 | 350 | 380 | 400 | 1.90 | 1.13 ± 0.17 | 0.77 |
| 2 | 7 | 350 | 380 | 390 | 1.78 | 1.13 ± 0.14 | 0.66 |
| 3 | 2 | 350 | 380 | 460 | 1.87 | 1.25 ± 0.12 | 0.62 |
| 4 | 3 | 350 | 380 | 450 | 1.85 | 1.25 ± 0.12 | 0.59 |
| 5 | 15 | 360 | 370 | 400 | 1.77 | 1.20 ± 0.13 | 0.57 |
| 6 | 12 | 380 | 400 | 430 | 1.78 | 1.23 ± 0.12 | 0.56 |
| 7 | 11 | 380 | 400 | 410 | 1.78 | 1.23 ± 0.12 | 0.55 |
| 8 | 9 | 350 | 400 | 500 | 1.78 | 1.24 ± 0.12 | 0.54 |
| 9 | 23 | 330 | 410 | 430 | 1.77 | 1.23 ± 0.13 | 0.54 |
| 10 | 4 | 360 | 400 | 440 | 1.80 | 1.26 ± 0.14 | 0.54 |
| 11 | 24 | 330 | 410 | 440 | 1.77 | 1.23 ± 0.11 | 0.54 |
| 12 | 10 | 370 | 380 | 400 | 1.78 | 1.25 ± 0.14 | 0.53 |
| 13 | 20 | 330 | 400 | 410 | 1.77 | 1.23 ± 0.14 | 0.53 |
| 14 | 17 | 330 | 350 | 380 | 1.77 | 1.24 ± 0.13 | 0.53 |
| 15 | 8 | 350 | 380 | 430 | 1.78 | 1.26 ± 0.13 | 0.52 |
| 16 | 14 | 420 | 490 | 500 | 1.78 | 1.26 ± 0.12 | 0.52 |
| 17 | 18 | 330 | 350 | 400 | 1.77 | 1.25 ± 0.14 | 0.52 |
| 18 | 22 | 330 | 400 | 440 | 1.77 | 1.26 ± 0.14 | 0.50 |
| 19 | 21 | 330 | 400 | 430 | 1.77 | 1.27 ± 0.13 | 0.50 |
| 20 | 13 | 390 | 400 | 420 | 1.78 | 1.30 ± 0.13 | 0.49 |
| 21 | 5 | 350 | 370 | 430 | 1.79 | 1.31 ± 0.12 | 0.48 |
| 22 | 25 | 350 | 360 | 400 | 1.77 | 1.30 ± 0.11 | 0.47 |
| 23 | 6 | 350 | 360 | 370 | 1.78 | 1.34 ± 0.14 | 0.44 |
| 24 | 16 | 330 | 340 | 400 | 1.77 | 1.32 ± 0.14 | 0.44 |
| 25 | 19 | 330 | 360 | 400 | 1.77 | 1.33 ± 0.14 | 0.44 |

TABLE 1

Summary of sites measured and corresponding clinical or histopathologic diagnosis.

|  | # of sites | # of patients | Tongue | Floor of Mouth | Buccal Mucosa | Gingiva | Palate | Lip |
|---|---|---|---|---|---|---|---|---|
| Total Sites | 62 | 20 | 37 | 8 | 7 | 4 | 1 | 5 |
| Normals | 52 | 20 | 32 | 5 | 7 | 3 | 0 | 5 |
| Normal | 35 | 9 | 25 | 1 | 4 | — | — | 5 |
| Adjacent | 17 | 11 | 7 | 4 | 3 | 3 | — | — |
| Abnormals | 10 | 9 | 5 | 3 | 0 | 1 | 1 | 0 |
| Dysplasia |  |  |  |  |  |  |  |  |
| Mild | 1 | 1 | — | 1 | — | — | — | — |
| Moderate | 1 | 1 | 1 | — | — | — | — | — |
| Severe | 2 | 2 | 1 | — | — | — | 1 | — |
| Cancer |  |  |  |  |  |  |  |  |
| Invasive | 4 | 3 | 2 | 1 | — | 1 | — | — |
| Submucosal | 1 | 1 | 1 | — | — | — | — | — |
| Verrucus | 1 | 1 | — | 1 | — | — | — | — |

TABLE 3

|  | Normal | Dysplasia | Cancer |
|---|---|---|---|
| Position 1 - # Sites | 31 | 4 | 6 |
| Position 1 - # Patients | 16 | 4 | 5 |
| Position 2 - # Sites | 32 | 4 | 6 |
| Position 2 - # Patients | 15 | 4 | 5 |
| Position 3 - # Sites | 31 | 4 | 6 |
| Position 3 - # Patients | 15 | 4 | 5 |
| Position 1–3 - # Sites | 27 | 4 | 6 |
| Position 1–3 - # Patients | 14 | 4 | 5 |

TABLE 4

Normal-Abnormal Position One

| Intensity | p value | Slope | p value | 2nd Derivative | p value |
|---|---|---|---|---|---|
| 450 | 0.05 | 450 | 0.01 | 450 | 0 |
| 455 | 0.05 | 400 | 0.02 | 410 | 0.01 |
| 460 | 0.05 | 455 | 0.03 | 465 | 0.04 |
| 465 | 0.05 | 435 | 0.04 | 425 | 0.05 |
| 470 | 0.05 | 440 | 0.04 | 430 | 0.05 |
| 475 | 0.05 | 430 | 0.05 | 455 | 0.05 |
| 480 | 0.05 | 445 | 0.05 |  |  |

TABLE 5

Normal-Abnormal Position Two

| Intensity | p value | Slope | p value | 2nd Derivative | p value |
|---|---|---|---|---|---|
| 450 | 0.02 | 465 | 0.01 | 430 | 0.01 |
| 455 | 0.02 | 470 | 0.01 | 435 | 0.01 |
| 460 | 0.02 | 560 | 0.01 | 550 | 0.01 |
| 465 | 0.02 | 445 | 0.02 | 440 | 0.02 |
| 470 | 0.02 | 450 | 0.02 | 445 | 0.03 |
| 475 | 0.02 | 455 | 0.02 | 420 | 0.04 |
| 480 | 0.02 | 460 | 0.02 | 465 | 0.04 |
| 485 | 0.02 | 475 | 0.02 | 470 | 0.04 |
| 490 | 0.02 | 480 | 0.04 | 475 | 0.04 |
| 495 | 0.02 | 540 | 0.05 |  |  |
| 500 | 0.02 |  |  |  |  |
| 505 | 0.02 |  |  |  |  |
| 510 | 0.02 |  |  |  |  |

TABLE 5-continued

Normal-Abnormal Position Two

| Intensity | p value | Slope | p value | 2nd Derivative | p value |
|---|---|---|---|---|---|
| 570 | 0.02 |  |  |  |  |
| 575 | 0.02 |  |  |  |  |
| 580 | 0.02 |  |  |  |  |
| 585 | 0.02 |  |  |  |  |
| 445 | 0.03 |  |  |  |  |
| 515 | 0.03 |  |  |  |  |
| 520 | 0.03 |  |  |  |  |
| 525 | 0.03 |  |  |  |  |
| 530 | 0.03 |  |  |  |  |
| 535 | 0.03 |  |  |  |  |
| 540 | 0.03 |  |  |  |  |
| 565 | 0.03 |  |  |  |  |
| 440 | 0.04 |  |  |  |  |
| 545 | 0.04 |  |  |  |  |
| 550 | 0.04 |  |  |  |  |
| 555 | 0.04 |  |  |  |  |
| 560 | 0.04 |  |  |  |  |

TABLE 6

Normal-Abnormal Position Three

| Intensity | p value | Slope | p value | 2nd Derivative | p value |
|---|---|---|---|---|---|
| 490 | 0.05 | 470 | 0.01 | 495 | 0 |
| 495 | 0.05 | 510 | 0.01 | 500 | 0 |
|  |  | 460 | 0.02 | 490 | 0.01 |
|  |  | 475 | 0.02 | 440 | 0.02 |
|  |  | 480 | 0.02 | 505 | 0.02 |
|  |  | 515 | 0.02 | 445 | 0.04 |
|  |  | 455 | 0.04 | 565 | 0.04 |
|  |  | 485 | 0.04 |  |  |
|  |  | 535 | 0.04 |  |  |
|  |  | 465 | 0.05 |  |  |
|  |  | 520 | 0.05 |  |  |
|  |  | 540 | 0.05 |  |  |
|  |  | 575 | 0.05 |  |  |

TABLE 7

Normal-Dysplasia Position One

| Intensity | p value | Slope | p value | 2nd Derivative | p value |
|---|---|---|---|---|---|
| | | 515 | 0 | 495 | 0 |
| | | | | 500 | 0.03 |

TABLE 8

Normal-Dysplasia Position Two

| Intensity | p value | Slope | p value | 2nd Derivative | p value |
|---|---|---|---|---|---|
| | | 505 | 0 | | |

TABLE 9

Normal-Dysplasia Position Three

| Intensity | p value | Slope | p value | 2nd Derivative | p value |
|---|---|---|---|---|---|
| | | | | 455 | 0.05 |

TABLE 10

Absolute difference between the sum of the sensitivity and specificity for cross-validated training set performance and cross-validated random diagnosis assignment for the intensity data at different source-detector fiber separations, wavelength ranges and ESLs.

| Intensity | Wavelength Range | 65% | 75% | 85% | 95% | 99% |
|---|---|---|---|---|---|---|
| Position 1 | 395–475 | +0.182 | +0.141 | +0.213 | +0.219 | +0.101 |
| Position 1 | 425–500 | +0.236 | +0.216 | +0.262 | +0.314 | +0.272 |
| Position 1 | 450–525 | +0.316 | +0.281 | +0.345 | +0.367 | +0.225 |
| Position 1 | 475–550 | +0.262 | +0.231 | +0.311 | +0.305 | +0.286 |
| Position 1 | 500–585 | +0.239 | +0.215 | +0.242 | +0.253 | +0.173 |
| Position 1 | 395–550 | +0.268 | +0.242 | +0.343 | +0.373 | +0.186 |
| Position 1 | 395–585 | +0.283 | +0.273 | +0.305 | +0.346 | +0.083 |
| Position 2 | 395–475 | +0.340 | +0.384 | +0.373 | +0.395 | +0.317 |
| Position 2 | 425–500 | +0.293 | +0.324 | +0.307 | +0.275 | +0.209 |
| Position 2 | 450–525 | +0.256 | +0.257 | +0.265 | +0.242 | +0.229 |
| Position 2 | 475–550 | +0.175 | +0.178 | +0.201 | +0.189 | +0.164 |
| Position 2 | 500–585 | +0.185 | +0.169 | +0.224 | +0.205 | +0.116 |
| Position 2 | 395–550 | +0.271 | +0.296 | +0.326 | +0.288 | +0.120 |
| Position 2 | 395–585 | +0.262 | +0.265 | +0.286 | +0.293 | +0.013 |
| Position 3 | 395–475 | +0.125 | +0.079 | −0.034 | +0.048 | +0.047 |
| Position 3 | 425–500 | +0.116 | +0.076 | +0.145 | +0.348 | +0.174 |
| Position 3 | 450–525 | +0.141 | +0.104 | +0.163 | +0.148 | +0.317 |
| Position 3 | 475–550 | −0.351 | −0.404 | −0.341 | −0.348 | +0.145 |
| Position 3 | 500–585 | −0.260 | −0.313 | −0.281 | −0.299 | +0.155 |
| Position 3 | 395–550 | −0.127 | −0.155 | −0.102 | −0.188 | +0.121 |
| Position 3 | 395–585 | +0.000 | +0.000 | +0.000 | +0.000 | +0.000 |
| Position 123 | 395–475 | +0.386 | +0.417 | +0.402 | +0.269 | +0.243 |
| Position 123 | 425–500 | +0.355 | +0.392 | +0.369 | +0.307 | +0.426 |
| Position 123 | 450–525 | +0.318 | +0.343 | +0.333 | +0.275 | +0.194 |
| Position 123 | 475–550 | +0.267 | +0.265 | +0.273 | +0.193 | +0.341 |
| Position 123 | 500–585 | +0.302 | +0.296 | +0.317 | +0.117 | +0.132 |
| Position 123 | 395–550 | +0.323 | +0.351 | +0.348 | +0.308 | −0.044 |
| Position 123 | 395–585 | +0.300 | +0.308 | +0.310 | +0.130 | +0.030 |

TABLE 11

Absolute difference between the sum of the sensitivity and specificity for cross-validated training set performance and cross-validated random diagnosis assignment for the first derivative data at different source-detector fiber separations, wavelength ranges and ESLs.

| Slope | Wavelength Range | 65% | 75% | 85% | 95% | 99% |
|---|---|---|---|---|---|---|
| Position 1 | 395–475 | +0.411 | +0.370 | +0.351 | +0.201 | +0.089 |
| Position 1 | 425–500 | +0.401 | +0.421 | +0.311 | +0.327 | +0.186 |
| Position 1 | 450–525 | +0.506 | +0.464 | +0.273 | +0.313 | +0.064 |
| Position 1 | 475–550 | +0.244 | +0.277 | +0.270 | +0.158 | −0.048 |
| Position 1 | 500–585 | +0.154 | +0.093 | +0.004 | −0.029 | +0.132 |
| Position 1 | 395–550 | +0.492 | +0.251 | +0.322 | +0.162 | −0.168 |
| Position 1 | 395–585 | +0.323 | +0.285 | +0.252 | +0.190 | +0.282 |
| Position 2 | 395–475 | +0.277 | +0.264 | +0.265 | +0.202 | +0.357 |
| Position 2 | 425–500 | +0.295 | +0.268 | +0.272 | +0.187 | −0.110 |
| Position 2 | 450–525 | +0.239 | +0.203 | +0.215 | −0.012 | +0.109 |
| Position 2 | 475–550 | +0.161 | +0.144 | +0.205 | +0.160 | +0.366 |
| Position 2 | 500–585 | +0.110 | +0.471 | +0.434 | +0.391 | +0.214 |
| Position 2 | 395–550 | +0.224 | +0.168 | +0.224 | +0.123 | −0.044 |
| Position 2 | 395–585 | +0.157 | +0.201 | +0.354 | +0.307 | −0.134 |
| Position 3 | 395–475 | +0.134 | +0.141 | −0.017 | +0.108 | +0.454 |
| Position 3 | 425–500 | −0.116 | −0.146 | −0.152 | +0.296 | +0.288 |
| Position 3 | 450–525 | +0.247 | +0.198 | +0.429 | +0.578 | +0.339 |
| Position 3 | 475–550 | +0.281 | +0.374 | +0.222 | +0.500 | +0.356 |
| Position 3 | 500–585 | +0.156 | +0.492 | +0.498 | +0.426 | +0.326 |
| Position 3 | 395–550 | −0.028 | +0.059 | +0.686 | +0.649 | +0.137 |
| Position 3 | 395–585 | +0.129 | +0.163 | +0.209 | +0.028 | +0.147 |
| Position 123 | 395–475 | +0.329 | +0.326 | +0.383 | −0.053 | +0.222 |
| Position 123 | 425–500 | +0.332 | +0.304 | +0.291 | +0.297 | −0.088 |
| Position 123 | 450–525 | +0.379 | +0.381 | +0.432 | −0.026 | +0.301 |
| Position 123 | 475–550 | +0.036 | +0.207 | +0.264 | +0.203 | +0.249 |
| Position 123 | 500–585 | +0.198 | +0.397 | +0.318 | +0.077 | +0.206 |
| Position 123 | 395–550 | +0.373 | +0.429 | +0.414 | −0.029 | −0.026 |
| Position 123 | 395–585 | +0.211 | +0.383 | +0.145 | −0.125 | −0.039 |

TABLE 12

Absolute difference between the sum of the sensitivity and specificity for cross-validated training set performance and cross-validated random diagnosis assignment for the second derivative data at different source-detector fiber separations, wavelength ranges and ESLs.

| 2nd Derivative | Wavelength Range | 65 | 75 | 85 | 95 | 99 |
|---|---|---|---|---|---|---|
| Position 1 | 395–475 | +0.400 | +0.341 | +0.277 | +0.287 | +0.440 |
| Position 1 | 425–500 | +0.399 | +0.358 | +0.406 | +0.440 | +0.182 |
| Position 1 | 450–525 | +0.420 | +0.272 | +0.195 | +0.082 | +0.053 |
| Position 1 | 475–550 | −0.020 | +0.188 | −0.018 | +0.190 | +0.021 |
| Position 1 | 500–585 | −0.268 | −0.281 | −0.245 | +0.111 | −0.102 |
| Position 1 | 395–550 | +0.369 | +0.294 | +0.112 | +0.065 | +0.282 |
| Position 1 | 395–585 | +0.201 | +0.158 | −0.002 | −0.022 | +0.164 |
| Position 2 | 395–475 | +0.321 | +0.343 | +0.315 | +0.264 | +0.402 |
| Position 2 | 425–500 | +0.300 | +0.363 | +0.248 | +0.068 | +0.010 |
| Position 2 | 450–525 | +0.015 | +0.056 | +0.178 | −0.118 | +0.043 |
| Position 2 | 475–550 | −0.130 | +0.014 | +0.019 | −0.031 | −0.014 |
| Position 2 | 500–585 | −0.153 | +0.181 | +0.028 | +0.037 | +0.117 |
| Position 2 | 395–550 | +0.269 | +0.265 | +0.279 | +0.256 | +0.116 |
| Position 2 | 395–585 | +0.248 | +0.323 | +0.073 | +0.254 | +0.154 |
| Position 3 | 395–475 | +0.081 | +0.129 | +0.259 | +0.402 | +0.372 |
| Position 3 | 425–500 | +0.242 | +0.257 | +0.278 | +0.377 | +0.296 |
| Position 3 | 450–525 | +0.186 | +0.183 | +0.377 | +0.468 | +0.242 |
| Position 3 | 475–550 | +0.032 | +0.124 | −0.031 | +0.314 | +0.265 |
| Position 3 | 500–585 | −0.120 | −0.208 | +0.269 | +0.129 | +0.015 |
| Position 3 | 395–550 | −0.118 | −0.057 | −0.078 | +0.318 | −0.022 |
| Position 3 | 395–585 | +0.141 | +0.168 | +0.338 | +0.290 | +0.406 |
| Position 123 | 395–475 | +0.351 | +0.337 | +0.270 | −0.011 | |
| Position 123 | 425–500 | +0.349 | +0.247 | +0.198 | +0.222 | |
| Position 123 | 450–525 | +0.212 | +0.271 | +0.043 | +0.087 | |
| Position 123 | 475–550 | +0.153 | +0.161 | +0.252 | +0.114 | |
| Position 123 | 500–585 | +0.214 | +0.237 | +0.216 | −0.165 | |

TABLE 12-continued

Absolute difference between the sum of the sensitivity and specificity for cross-validated training set performance and cross-validated random diagnosis assignment for the second derivative data at different source-detector fiber separations, wavelength ranges and ESLs.

| 2nd Derivative | Wavelength Range | 65 | 75 | 85 | 95 | 99 |
|---|---|---|---|---|---|---|
| Position 123 | 395–550 | +0.231 | +0.220 | +0.159 | −0.025 | |
| Position 123 | 395–585 | +0.222 | +0.243 | +0.231 | −0.115 | |

TABLE 13

Cross validated performance of algorithms based on selected data types, wavelength ranges and ESLs. Combinations are ranked in order of decreasing sum of sensitivity plus specificity.

| Position | Data Type | Wavelength Range | ESL | Sensitivity | Specificity |
|---|---|---|---|---|---|
| 3 | Slope | 395–550 | 85% | 70% | 100% |
| 123 | Intensity | 425–500 | 99% | 70% | 78% |
| 1 | Slope | 450–525 | 65% | 80% | 65% |
| 2 | Intensity | 395–475 | 95% | 40% | 91% |

TABLE 14

Patients and sites where fluorescence and reflectance data were measured.

| | Normal | Dysplasia | Cancer |
|---|---|---|---|
| Fluorescence EEM | | | |
| # Sites | 52 | 5 | 5 |
| # Patients | 20 | 5 | 4 |
| Position 1 + Fluorescence EEM | | | |
| # Sites | 29 | 3 | 5 |
| # Patients | 15 | 3 | 4 |
| Position 2 + Fluorescence EEM | | | |
| # Sites | 30 | 3 | 5 |
| # Patients | 15 | 3 | 4 |
| Position 3 + Fluorescence EEM | | | |
| # Sites | 30 | 3 | 5 |
| # Patients | 15 | 3 | 4 |
| Position 1–3 + Fluorescence EEM | | | |
| # Sites | 26 | 3 | 5 |
| # Patients | 14 | 3 | 4 |

TABLE 15

Cross-validated performance of algorithms based on combinations of fluorescence and reflectance data based on the slope at position 3 from 395–550 nm. Strategies based on fluorescence alone are shown with an asterisk; strategies based on fluorescence + reflectance have no asterisk.

| Type of Data | ESL | Sensitivity | Specificity |
|---|---|---|---|
| *Fluorescence at 350, 380 400 nm excitation alone | 65% | 75% | 90% |
| Fluorescence at 350, 380 400 nm excitation + Reflectance Data | 65% | 75% | 90% |
| *Fluorescence at 350, 380 nm excitation alone | 65% | 63% | 86% |
| Fluorescence at 350, 380 nm excitation + Reflectance Data | 65% | 63% | 87% |
| *Fluorescence at 350, 400 nm excitation alone | 65% | 50% | 83% |
| Fluorescence at 350, 400 nm excitation + Reflectance Data | 65% | 50% | 83% |
| *Fluorescence at 380, 400 nm excitation alone | 65% | 63% | 87% |
| Fluorescence at 380, 400 nm excitation + Reflectance Data | 65% | 63% | 87% |
| Fluorescence at 350 nm excitation alone | 65% | 50% | 67% |
| *Fluorescence at 350 nm excitation + Reflectance Data | 65% | 50% | 67% |
| Fluorescence at 380 nm excitation alone | 65% | 50% | 47% |
| *Fluorescence at 380 nm excitation + Reflectance Data | 95% | 50% | 83% |
| Fluorescence at 400 nm excitation alone | 65% | 75% | 70% |
| *Fluorescence at 400 nm excitation + Reflectance Data | 85% | 75% | 73% |

TABLE 16

Cross-validated performance of algorithms based on combinations of fluorescence and reflectance data based on the intensity at position 1–3 from 425–500 nm. Strategies based on fluorescence alone are shown with an asterisk; strategies based on fluorescence + reflectance have no asterisk.

| Type of Data | ESL | Sensitivity | Specificity |
|---|---|---|---|
| *Fluorescence at 350, 380 400 nm excitation alone | 65% | 63% | 89% |
| Fluorescence at 350, 380 400 nm excitation + Reflectance Data | 65% | 63% | 85% |
| *Fluorescence at 350, 380 nm excitation alone | 65% | 63% | 85% |
| Fluorescence at 350, 380 nm excitation + Reflectance Data | 65% | 63% | 85% |
| *Fluorescence at 350, 400 nm excitation alone | 65% | 50% | 81% |
| Fluorescence at 350, 400 nm excitation + Reflectance Data | 65% | 50% | 81% |
| *Fluorescence at 380, 400 nm excitation alone | 65% | 50% | 85% |
| Fluorescence at 380, 400 nm excitation + Reflectance Data | 95% | 50% | 89% |
| Fluorescence at 350 nm excitation alone | 65% | 50% | 62% |
| *Fluorescence at 350 nm excitation + Reflectance Data | 65% | 38% | 73% |
| Fluorescence at 380 nm excitation alone | 65% | 50% | 46% |
| *Fluorescence at 380 nm excitation + Reflectance Data | 65% | 38% | 58% |
| Fluorescence at 400 nm excitation alone | 65% | 75% | 73% |
| *Fluorescence at 400 nm excitation + Reflectance Data | 65% | 88% | 69% |

TABLE 17

Cross-validated performance of algorithms based on combinations of fluorescence and reflectance data based on the slope at position 1 from 450–525 nm. Strategies based on fluorescence alone are shown with an asterisk; strategies based on fluorescence + reflectance have no asterisk.

| Type of Data | ESL | Sensitivity | Specificity |
|---|---|---|---|
| *Fluorescence at 350, 380 400 nm excitation alone | 65% | 75% | 86% |
| Fluorescence at 350, 380 400 nm excitation + Reflectance Data | 65% | 75% | 86% |
| *Fluorescence at 350, 380 nm excitation alone | 65% | 63% | 86% |
| Fluorescence at 350, 380 nm excitation + Reflectance Data | 65% | 63% | 86% |
| *Fluorescence at 350, 400 nm excitation alone | 65% | 50% | 83% |
| Fluorescence at 350, 400 nm excitation + Reflectance Data | 75% | 63% | 83% |
| *Fluorescence at 380, 400 nm excitation alone | 65% | 50% | 86% |
| Fluorescence at 380, 400 nm excitation + Reflectance Data | 95% | 63% | 90% |
| Fluorescence at 350 nm excitation alone | 65% | 50% | 66% |
| *Fluorescence at 350 nm excitation + Reflectance Data | 65% | 50% | 66% |
| Fluorescence at 380 nm excitation alone | 65% | 25% | 48% |
| *Fluorescence at 380 nm excitation + Reflectance Data | 85% | 38% | 66% |
| Fluorescence at 400 nm excitation alone | 65% | 75% | 76% |
| *Fluorescence at 400 nm excitation + Reflectance Data | 65% | 75% | 76% |

TABLE 18

Cross-validated performance of algorithms based on combinations of fluorescence and reflectance data based on the intensity at position 2 from 395–475 nm Strategies based on fluorescence alone are shown with an asterisk; strategies based on fluorescence + reflectance have no asterisk.

| Type of Data | ESL | Sensitivity | Specificity |
|---|---|---|---|
| *Fluorescence at 350, 380 400 nm excitation alone | 65% | 75% | 90% |
| Fluorescence at 350, 380 400 nm excitation + Reflectance Data | 65% | 75% | 90% |
| *Fluorescence at 350, 380 nm excitation alone | 65% | 63% | 87% |
| Fluorescence at 350, 380 nm excitation + Reflectance Data | 65% | 63% | 87% |
| *Fluorescence at 350, 400 nm excitation alone | 65% | 50% | 83% |
| Fluorescence at 350, 400 nm excitation + Reflectance Data | 65% | 50% | 83% |
| *Fluorescence at 380, 400 nm excitation alone | 65% | 63% | 87% |
| Fluorescence at 380, 400 nm excitation + Reflectance Data | 95% | 63% | 87% |
| Fluorescence at 350 nm excitation alone | 65% | 25% | 63% |
| *Fluorescence at 350 nm excitation + Reflectance Data | 99% | 50% | 67% |
| Fluorescence at 380 nm excitation alone | 65% | 50% | 53% |
| *Fluorescence at 380 nm excitation + Reflectance Data | 95% | 50% | 83% |
| Fluorescence at 400 nm excitation alone | 65% | 75% | 70% |
| *Fluorescence at 400 nm excitation + Reflectance Data | 65% | 63% | 83% |

All of the methods and apparatus disclosed and claimed herein can be made and executed without undue experimentation in light of the present disclosure. While the apparatus and methods of this invention have been described in terms of certain embodiments, it will be apparent to those of skill in the art that variations may be applied to the methods and/or apparatus described herein without departing from the concept, spirit and scope of the invention.

REFERENCES

The following references, to the extent that they provide exemplary procedural or other details supplementary to those set forth herein, are specifically incorporated herein by reference.

*An Introduction to Spectroscopy for Biochemists*, Brown, Ed., Academic Press, London; New York, 1980.
Bigio and Mourant, *Physics in Medicine & Biology*, 42:803–814, 1997.
Bohorfoush, *Endoscopy*, 28:372–380, 1996.
Cheng, [Master's Report] The University of Texas at Austin, 1992.
Chung, Schwartz, Gardner, Sawaya, Jacques, *J. Korean Med. Science*, 12:135–142, 1997.
Cothren, Kolubayev, Kjellstrom, Richards-Kortum, Healy, Ratliff, Engelmann, Loop, Kramer, Kittrell, Feld, *Proceedings of the SPIE—The International Society for Optical Engineering*, 906:320.
Cothren, Richards-Kortum, Sivak, Fitzmaurice, Rava, Boyce, Doxtader, Blackman, Ivanc, Hayes, Feld, Petras, *Gastrointestinal Endoscopy*, 36:105–111, 1990.
Deckelbaum, Stetz, O'brien, Cutruzzola, Gmitro, Laifer, Gindi, *Lasers in Surgery and Medicine*, 9:204–214, 1989.
Dhingra et al., "Early diagnosis of upper aerodigestive tract cancer by autofluorescence," *Arch. Otolaryngol Head Nec Surg.*, 122:1181–1186, 1996.
Durkin and Richards-Kortum, *Lasers in Surgery and Medicine*, 19:75–89, 1996.
Durkin, [Dissertation] University of Texas at Austin, 1995.
Durkin, Jaikumar, Ramanujam and Richards-Kortum, *Applied Optics*, 33(3):414–423, 1994.
Durkin, Jaiumar, Richards-Kortum, *Applied Spectroscopy*, 47:2114–2121, 1993.
Farell, Patterson, Wilson, *Med Phys*, 19:879–888, 1992.
Gillenwater, "Noninvasive diagnosis of oral neoplasia based on fluorescence spectroscopy and native tissue autofluorescence," *Intl. Conf on Head and Neck Cancer*, Toronto, Canada, 1996.
Ho, Christian, Davidson, *Analytical Chemistry*, 50(8):1108–1113, 1978.
Holland, Teets, Timmick, *Analytical Chemistry*, 45(1):145–153, 1973.
Ingrams, Dhingra, Roy, Perrault Jr., Bottrill, Kabani, Rebeiz, Pankratov, Shapshay, Manoharan, Itzkan, Feld, "Autofluorescence characteristics of oral mucosa," *Head & Neck*, 19:27–32, 1997.
Koenig, McGovern, Althausen, Deutsch, Schomacker, *J. Urology*, 156:1597–1601, 1996.
Lin, Wang, Jacques, Tittel, *Applied Optics*, 36:136–143, 1997.
Lynn, Oelberg, Jacques, *Biology of the Neonate*, 64:69–75, 1993.
Mahadevan, Mitchell, Silva, Thomsen, Richards-Kortum, *Lasers in Surgery & Medicine*, 13:647–655, 1993.
Mourant, Bigio, Boyer, Conn, Johnson, Shimada, *Lasers in Surgery & Medicine*, 17:350–357, 1995.
Nichols, Hull, Foster, *Applied Optics*, 36:93–104, 1997.
Nishioka, *Gastrointestinal Endoscopy Clinics of North America*, 4:313–326, 1994.
NSF Polar Programs UV Spectroradiometer Network 1994–1995 Operations Report; NSF UV Radiation Monitoring Network 1994 to 1995 Volume 5.0 Data Set. Available at WWW.BIOSPHERICAL.COM.

Ramanujam, Mitchell, Mahadevan-Jansen, Thomsen, Staerkel, Malpica, Wright, Atkinson, Richards-Kortum, *Photochemistry & Photobiology*, 64:720–735, 1996.

Richards-Kortum and Sevick-Muraca, *Annual Review of Physical Chemistry*, 47:555–606, 1996.

Richards-Kortum, In: *Optical-Thermal Response of Laser Irradiated Tissue*, Welch, Van Gemert (Eds.), Plenum Press, New York, Chapter 21, 1994.

Richards-Kortum, Rava, Petras, Fitzmaurice, Sivak, Feld, *Photochemistry & Photobiology* 53:777–786, 1991.

Schomacker, Frisoli, Compton, Flotte, Richter, Deutsch, Nishioka, *Gastroenterology*, 102:1155–1160, 1992.

Schomacker, Frisoli, Compton, Flotte, Richter, Nishioka, Deutsch, *Lasers in Surgery and Medicine*, 12:63–78, 1992.

Sterenborg, Thomsen, Jacques, Duvic, Motamedi, Wagner Jr., *Dermatologic Surgery*, 21:821–822, 1995.

Trujillio, Sandison, Utzinger, Ramanujam, Follen-Mitchell, Richards-Kortum, *Applied Spectroscopy*, In Press, Submitted 1997.

Wang and Jacques, *Applied Optics*, 34:2362–2366, 1995.

Wang, Jacques, University of Texas M.D. Anderson Cancer Center, Houston, Tex., through 1wang@tamu.edu., 1992.

Warner, Callis, Davidsion, Gouterman, Christian, *Analytical Letters*, 8(9):665–681, 1975.

Warner, Christian, Davidson, Callis, *Analytical Chemistry*, 49(4):564–573, 1977.

Warner, Davidson, Christian, *Analytical Chemistry*, 49(14):2155–2159, 1977.

Welch, Gardner, Richards-Kortum, Criswell, Chan, Pfefer, Warren, *Lasers in Surgery and Medicine*, 21:166–178, 1997.

Wilson, Lindberg, Kowalski, *J. of the American Chemical Society*, 111:3797–3804, 1989.

Wu, Feld, Rava, *Applied Optics*, 32:3585–3595, 1993.

Yang, Katz, Celmer, Zurawska-Szczepaniak, Alfano, *Lasers in the Life Sciences*, 7:115–127, 1996.

Zangaro, Silveira Jr., Manoharan, Zonios, Itzkan, Dasari, Van Dam, Feld, *Applied Optics*, 35:5211–5219, 1997.

Zuclich, Shimada, Loree, Biggio, Strobl, Nie, *Lasers in the Life Sciences*, 6:39–53, 1994.

Wright T. C., Kurman R. J., Ferenczy A. (1994) Cervical Intraepithelial Neoplasia. In *Pathology of the Female Genital Tract*. (Edited by A.Blaustein), New York.

American Cancer Society (1995) Cancer Facts and Figures, 12.

Kurman R. J., Henson D. E., Herbst A. L., Noller K. L., Schiffinan M. H. (1994) Interim guidelines of management of abnormal cervical cytology. JAMA 271, 1866–1869.

World Health Organization, Geneva (1988) Cytological Screening in the Control of Cervical Cancer: Technical Guidelines.

Fahey M. T., Irwig L., Macaskill P. (1995) Meta-analysis of pap test accuracy. American J Epidemiology 141(7), 680–689.

Wilkinson E. J. (1990) Pap Smears and screening for cervical neoplasia. Clin Obstet Gynecol 33, 817–825.

Koss L. G. (1989) The Papanicolaou test for cervical cancer detection: a triumph and a tragedy. JAMA, 737–743.

Burke L., Ducatman B. S. (1991) Colposcopy, text and atlas. Appleton and Large, Norwalk, Conn.

Mitchell M F. (1994) Accuracy of Colposcopy. Consultations in Obstetrics and Gynecology 6(1), 70–73.

Richards-Kortum R. R., Rava R. P., Fitzmaurice M., Sivak M. V. (1991) Spectroscopic diagnosis of colonic dysplasia. Photochemistry and Photobiology 53, 777–786.

Kapadia C. R., Cutruzzola F. W., O'Brien K. M., Stetz M. L., Enriquez R., Deckelbaum L. I. (1990) Laser-induced fluorescence spectroscopy of human colonic mucosa, Gastroenterology 99, 150–157.

Marchesini R., Brambilla M., Pignoli E., Bottiroli G., Croce A. C., Dal Fante M., Spinelli P., Di Palma S. (1992) Light-induced fluorescence spectroscopy of adenomas, adenocarcinomas and non-neoplastic mucosa in human colon, J Photochemistry and Photobiology 14(3), 219–30.

Cothren R. M., Richards-Kortum R. R., Rava R. P., Boyce G. A., Doxtader M., Blackman KR. Ivanc T., Hayes G. B., Feld M. S., Petras R. E. (1990) Gastrointestinal tissue diagnosis by laser induced fluorescence spectroscopy at endoscopy. Gatrointestinal Endoscopy 36, 105–111.

Schomacker K. T., Frisoli J. K., Compton C. C., Flotte T. J., Richter J. M., Nishioka N. S., Deutsch T. F. (1992) Ultraviolet laser induced fluorescence of colonic tissue: basic biology and diagnostic potential. Lasers in Surgery and Medicine 12, 63–78.

Hung J., Lam S., LeRiche J. C., Palcic B. (1991) Autofluorescence of normal and malignant bronchial tissue. Lasers in Surgery and Medicine 11(2), 99–105.

Lam S., Hung J. Y. C., Kennedy S. M., Leriche J. C., Vedal R., Nelems B., Macaulay C. E., Palcic B. (1992) Detection of dysplasia and carcinoma in situ by ratio fluorimetry. Am Rev Dis 146, 1458–1461.

Lam S., Macaulay C., Palcic B. (1993) Detection and localization of early lung cancer by imaging techniques. Chest 103, 12s–14s.

Yuanlong Y., Yanning Y., Fuming L., Yufen L., Paozhong M. (1987) Characteristic autofluorescence for cancer diagnosis and its origin, Lasers in Surgery and Medicine 7, 528–532.

Montan S., Stromblad L. G. (1987) Spectral characterization of brain tumors utilizing laser-induced fluorescence. Lasers in Life Sciences 1(4), 275–285.

Liu C. H., Das B. B., Sha Glassman W. L., Tang G. C., Yoo K. M., Zhu H. R., Akins D. L., Lubicz S. S., Cleary J., Prudente R. (1992) Raman, fluorescence and time-resolved light scattering as optical diagnostic techniques to separate diseased and normal biomedical media. J Photochemistry and Photobiology 16(2), 187–209.

Glassman W. S. Liu C. H., Tang G. C., Lubicz S., Alfano R. R. (1992) Ultraviolet excited fluorescence spectra from non-malignant and malignant tissues of the gynecologic tract. Lasers in Life Sciences 5, 49–58.

Lohmann W., Mußmann J., Lohmann C., Kunzel W. (1989) Fluorescence of the cervix uteri as a marker for dysplasia and invasive carcinoma. European Journal of Obstetrics and Gynecology and Reproductive Biology 131, 249–253.

Mahadevan A., Mitchell M., Silva E., Thomsen S., Richards-Kortum R. R. (1993) Study of the fluorescence properties of normal and neoplastic human cervical tissue. Lasers in Surgery and Medicine 13, 647–655.

Braichofte D. R., Wagnieres G. A., Bays R., Monnier P., Van den Bergh H. E. (1995) Clinical pharmacokinetic studies of photofrin by fluorescence spectroscopy in the oral cavity, the esophagus and the bronchi. Cancer 75(11), 2768–78.

Gray M. J., Lipson R., Maeck J. V. S., Parker L., Romeyn D. (1967) Use of hematoporphyrin derivative in detection and management of cervical cancer. Am J Obst & Gynec, 766–770.

Kennedy J. C. Pottier R. H. (1992) Endogenous protoporphyrin IX, a clinical useful photosensitizer for photodynarnic therapy. J Photochem Photobiol B:Biol 14, 275–292.

Loh C. S., MacRobert A. J., Bedwell J., Regula J., Krasner N., Bown S. G. (1993) Oral versus intravenous administration of 5-aminolaevulinic acid for photodynamic therapy. British Journal of Cancer 68(1), 41–51.

Ramanujam N., Mitchell M. F., Mahadevan A., Thomsen S., Malpica A., Wright T., Atkinson N., Richards-Kortum R. R. (1995) Development of a multivariate statistical algorithm to analyze human cervical tissue fluorescence spectra acquired in vivo. Lasers Surg Med, 19 (1), 46–62, 1996.

Ramanujam N., Mitchell M. F., Mahadevan A., Thomsen S., Malpica A., Wright T., Atkinson N., Richards-Kortum R. R. (1995) Spectroscopic diagnosis of cervical Squamous intraepithelial neoplasia in vivo using laser-induced fluorescence spectra at multiple excitation wavelengths. Lasers Surg Med, 19 (1), 63–74, 1996.

Dillon R. W., Goldstein M. (1984) *Mutlivariate Analysis: Methods and Applications*. John Wiley and Sons, New York.

Walpole R. E., Myers R. H. (1987) *Probability and Statistics for Engineers and Scientists*. Decker, New York.

Albert A., Harris E. K. (1987) *Multivariate Interpretation of Clinical Laboratory Data*. Marcel Dekker, New York.

Devore J. L. (1992) *Probability and Statistics for Engineering and the Science*. Brooks/Cole, Pacific Grove.

Cancer Facts and Figures, Publication No. 93-400M, No. 5008-03, Washington, S.C. American Cancer Society, 1993.

Boring C C, Squires T S, Tong T, Montgomery S, Cancer Statistics, 1994, C—A Cancer Journal for Clinicians, 44:7–26, 1994.

Strong M S, Incze J, Vaughan C N. Field Cancerization in the Aerodigestive Tract—Its Etiology, Manifestation, and Significance. J Otolaryngol 13:1–6, 1984.

Blair E A, Callendar D L. Head and Neck Cancer—the Problem. Clinics in Plastic Surgery, 21:1–7, 1994.

WHO Collaborating Centre for Oral Precancerous Lesions. Definition of Leukoplakia and Related Lesions: An Aid to Studies on Oral Precancer. Oral Surg Oral Med Oral Pathol 46:518–39, 1978.

"Leukoplakia", "Keratosis", and Intra-Epithelial Squamous Cell Carcinoma of the Head and Neck. In: Batsakis J G, ed, Tumors of the Head and Neck—Clinical and Pathological Considerations. Baltimore, Md., pp. 68–71, 1974.

Silverman S, Gorsky M, Lozada F. Oral Leukoplakia and Malignant Transformation. A Follow Up Study of 257 Patients. Cancer 53:563–68, 1984.

Roed-Peterson B. Cancer Development in Oral Leukoplakia: Follow Up of 331 Patients. J. Dent Research, 50:711, 1971.

Silverman S, Migliorati C, Barbarosa J. toluidine Blue Staining in the Detection of Oral Precancerous and Malignant Lesions. Oral Surg Oral Med Oral Pathol 57:379–82, 1984.

Reddy C R M, Rarnilu C, Sundareshwar B, Raju M V S, Gopal R, Sarma R. Toluidine Blue Staining or Oral Cancer and Precancerous Lesions, Indian J Med Res, 61:1161–4, 1973.

Rpsemberg D, Cretin S. Use of Meta-Analysis to Evaluate Tolniun Chloride in Oral Cancer Screening. Oral Surg Oral Med Oral Pathol 67:621–7, 1987.

Epstein Review.

Sevick-Muraca E, Richards-Kortum R; Quantitative Optical Spectroscopy for Tissue Diagnosis, Ann Rev Phys Chem, 47:555–606, 1996.

Wagnieres G A, Star W M, Wilson B C. In Vivo Fluorescence Spectroscopy and Imaging for Oncological Applications. Photochemistry and Photobiology, 68:603–32, 1998.

N. Ramanujam, M. Follen-Mitchell, A. Mahadevan-Jansen, S. Thomsen, G. Staerkel, A. Malpica, T. Wright, N. Atkinson and R. Richards-Kortum (1996) Cervical precancer detection using multivariate statistical algorithm based on laser-induced fluorescence spectra at multiple excitation wavelengths. *Photochemistry and Photobiology* 64(4), 720–735.

R. Cothren, R. Richards-Kortum, M. Sivak, M. Fitzmaurice, R. Rava, G. Boyce, G. Hayes, M. Doxtader, R. Blackman, T. Ivanc, M. Feld and R. Petras (1990) Gastrointestinal tissue diagnosis by laser induced fluorescence spectroscopy at endoscopy. *Gastrointestinal Endoscopy* 36, 105–111.

Schantz, S. P., Kolli, V., Savage, H. E., Yu, G., Shah, J. P., Harris, D. E., Katz, A., Alfano, R. R., Huvos, A.G. In vivo native cellular fluorescence and histological characteristics of head and neck cancer. Clinical Cancer Research, 4: 1177–1182, 1998.

Kolli, V., Savage, H. E., Yao, T. J., Schantz, S. P. Native cellular fluorescence of neoplastic upper aerodigestive mucosa. Arch. Otolaryng. Head Neck Surg., 121(11): 1287–92, 1995.

Chen, C. T., Wang, C. Y., Kuo, Y. S., Chiang, H. H., Chow, S. N., Hsiao, I. Y., Chiang, C. P. Light-induced fluorescence spectroscopy: a potential diagnostic tool for oral neoplasia. Proceed. Nat. Scien. Council, Rep. of China- Part B, Life Sci., 20(4): 123–30, 1996.

Roy, K., Bottrill, I. D., Ingrams, D. R., Pankratov, M. M., Rebeiz, E. E., Woo, P., Kabani, S., Shapshey, S. M., Manoharan, R., Itzkan, I., Feld, M. S. Diagnostic fluorescence spectroscopy of oral mucosa. SPIE, 2395: 135–142, 1995.

Ingrams, D. R., Dhingra, J. K., Roy, K., Perrault, D. F. Jr., Bottrill, I. D., Kabani, S., Rebeiz, E. E., Pankratov, M. M., Shapshay, S. M., Manoharan, R., Itzkan, I., Feld, M. S. Autofluorescence characteristics of oral mucosa. Head & Neck, 19(1): 27–32, 1997.

Dhingra, J. K., Zahng, X., McMillan, K., Kabani, S., Manoharan, R., Itzkan, I., Feld, M. S., Shapshay, S. M. Diagnosis of head and neck precancerous lesions in an animal model using fluorescence spectroscopy. Laryngoscope, 108: 471–5, 1998.

Dhingra, J. K., Perrault, D. F. Jr., McMillan, K., Rebeiz, E. E, Kabani, S., Manoharan, R., Itzkan, I., Feld, M. S., Shapshay, S. M. Early diagnosis of upper aerodigestive tract cancer by autofluorescence. Arch. Otolaryng. Head Neck Surg., 122(11): 1181–6, 1996.

Gillenwater, A., Jacob, R., Ganeshappa, R., Kemp, B., El-Naggar, A. K., Palmer, J. L., Clayman, G., Mitchell, M. F., Richards-Kortum, R. Noninvasive diagnosis of oral neoplasia based on fluorescence spectroscopy and native tissue autofluorescence.

Kulapaditharom, B., Boonkitticharoen, V. Laser-induced fluorescence imaging in localization of head and neck cancers. Ann. Otol. Rhinol. Laryngol., 107: 241–246, 1998.

Onizawa, K., Saginoya, H., Furuya, Y., Yoshida, H. Fluorescence photography as a diagnostic method for oral cancer. Cancer Lett., 108(1): 61–6, 1996.

NADH, Fad change with oxidation.

K. Schomacker, J. Frisoli, C. Compton, T. Flotte, J. Richter, N. Nishioka and T. Deutsch (1992) Ultraviolet laser-induced fluorescence of colonic tissue: basic biology and diagnostic potential. *Lasers in Surgery & Medicine*. 12(1), 63–78.

Welch A J, Gardner C, Richards-Kortum R, Chan E, Criswell G, Pfefer J, Warren S; Propagation of Fluorescent Light, Lasers in Surgery and Medicine, 21:166–78, 1997.

A. F. Zuluaga, U. Utzinger, A. Durkin, H. Fuchs, A. Gillenwater, R. Jacob, B. Kemp, J. Fan, R. Richards-Kortum, "Fluorescence Excitation Emission Matrices of human tissue: A system for in vivo measurement and method of data analysis," in press, *Applied Spectroscopy*, 1999.

Utzinger U, Trujillo V, Atkinson E N, Mitchell M F, Cantor S B, Richards-Kortum R; Performance Estimation of Diagnostic Tests for Cervical Pre-Cancer Based on Fluorescence Spectroscopy: Effects of Tissue Type, Sample Size, Population and Signal-to-Noise Ratio, IEEE Trans BME, in press, 1999.

N. Cliff, Analyzing Multivariate Data, Harcourt Brace Jovanovich, Orlando, Fla., 1987.

Lachenbruch P A, Discriminant Analysis, Hafner Press, New York, 1975.

J. A. Jullien, M. C. Downer, J. M. Zakrzewska, P. M. Speight, "Evaluation of a screening test for the early detection of oral cancer and precancer," *Community Dental Health*, 12(1): 3–7, 1995.

Fuchs, H., Utzinger, U., Zuluaga, A. F., Gillenwater, A., Jacob, R., Kemp, B., Richards-Kortum, R. Combined fluorescence and reflectance spectroscopy: in vivo assessment of oral cavity epithelial neoplasia. IEEE Opt. Soc. America., 6:306–7, 1998.

What is claimed is:

1. An apparatus for performing fluorescence and spatially resolved reflectance spectroscopy on a sample, comprising:
   a light source;
   a monochromator in optical communication with said light source;
   a reflectance illumination fiber in optical communication with said light source;
   a fluorescence excitation fiber in optical communication with said monochromator;
   an imaging spectrograph;
   a fluorescence collection fiber in optical communication with said imaging spectrograph;
   a reflectance collection fiber in optical communication with said imaging spectrograph and in spaced relation with said reflectance illumination fiber; and
   a detector in optical communication with said imaging spectrograph;
   wherein said reflectance illumination fiber, said fluorescence excitation fiber, said fluorescence collection fiber, and said reflectance collection fiber define a fiber optic probe, said probe comprising a center section and an outer section, said fluorescence excitation fiber and said fluorescence collection fiber being positioned in said center section, and said reflectance illumination fiber and said reflectance collection fiber being positioned in said outer section.

2. The apparatus of claim 1, wherein said light source comprises a Xe arc lamp.

3. The apparatus of claim 1, wherein said monochromator comprises a double monochromator.

4. The apparatus of claim 1, wherein said detector comprises a thermo-electrically cooled CCD camera.

5. The apparatus of claim 1, wherein said fluorescence excitation fiber and said fluorescence collection fiber are integral.

6. The apparatus of claim 1, wherein one or more of said fibers are positioned flush with said sample.

7. The apparatus of claim 1, further comprising a spacer positioned between one or more of said fibers and said sample.

8. The apparatus of claim 1, wherein said reflectance illumination fiber, said fluorescence excitation fiber, said fluorescence collection fiber, and said reflectance collection fiber define a fiber optic probe.

9. The apparatus of claim 8, wherein said probe is configured to be positioned within a trocar.

10. The apparatus of claim 8, wherein said probe comprises a center section and an outer section, said fluorescence excitation fiber and said fluorescence collection fiber being positioned in said center section, and said reflectance illumination fiber and said reflectance collection fiber being positioned in said outer section.

11. The apparatus of claim 1, comprising a plurality of fluorescence excitation and collection fibers arranged in a circular bundle.

12. The apparatus of claim 1, comprising a plurality of reflectance collection fibers defming a plurality of collection positions.

13. The apparatus of claim 12, wherein said plurality of collection positions are spaced between about 0 and about 10 millimeters from said reflectance illumination fiber.

14. The apparatus of claim 1, wherein said reflectance collection fiber defines a collection position at about 180 degrees relative to said reflectance illumination fiber.

15. The apparatus of claim 1, wherein said reflectance collection fiber defines a collection position at about 90 degrees relative to said reflectance illumination fiber.

16. The apparatus of claim 1, wherein said reflectance collection fiber defines a collection position at about 45 degrees relative to said reflectance illumination fiber.

17. The apparatus of claim 1, further comprising a one or more fibers in optical communication with said light source and configured to illuminate said sample during operation of said apparatus.

18. The apparatus of claim 1, comprising a plurality of fluorescence excitation fibers arranged in one or more rows adjacent said monochromator.

19. The apparatus of claim 1, comprising a plurality of fluorescence excitation fibers and a plurality of reflectance collection fibers arranged in a single row adjacent said imaging spectrograph.

20. The apparatus of claim 19, further comprising one or more unconnected fibers interspersed with said plurality of fluorescence excitation fibers and said plurality of reflectance collection fibers.

21. The apparatus of claim 1, further comprising a fiber connected from said light source to said imaging spectrograph to monitor spectral output of said light source.

22. The apparatus of claim 1, further comprising a controller coupled to said detector.

23. The apparatus of claim 1, wherein said center and outer sections are circular.

24. An apparatus for measuring fluorescence and spatially resolved reflectance spectra of a sample, comprising:
   a light source;
   a monochromator in optical communication with said light source;
   a fiber optic probe in optical communication with said light source and with said monochromator, said probe comprising a plurality of fluorescence excitation and collection fibers in spaced relation and surrounded at least partially by a plurality of reflectance collection fibers in spaced relation with a reflectance illumination fiber;
   an imaging spectrograph in optical communication with said plurality of fluorescence collection fibers and with said plurality of reflectance collection fibers; and a detector in optical communication with said imaging spectrograph.

25. The apparatus of claim 24, wherein said plurality of reflectance collection fibers and said reflectance illumination fiber are positioned concentrically about said plurality of fluorescence excitation and collection fibers.

26. The apparatus of claim 24, wherein at least one of said plurality of reflectance collection fibers defines a collection position at about 180 degrees relative to said reflectance illumination fiber.

27. The apparatus of claim 24, wherein at least one of said plurality of reflectance collection fibers defines a collection position at about 90 degrees relative to said reflectance illumination fiber.

28. The apparatus of claim 24, wherein at least one of said plurality of reflectance collection fibers defines a collection position at about 45 degrees relative to said reflectance illumination fiber.

29. The apparatus of claim 24, wherein said plurality of collection positions are spaced between about 0 and about 10 millimeters from said reflectance illumination fiber.

30. The apparatus of claim 24, wherein said probe comprises between twenty-one and forty-six optical fibers.

31. A method for combined fluorescence and spatially resolved reflectance spectroscopy of a sample, comprising:
providing a reflectance illumination fiber, a fluorescence excitation fiber, a fluorescence collection fiber, and a reflectance collection fiber that define a fiber optic probe comprising a center section and an outer section, said fluorescence excitation fiber and said fluorescence collection fiber being positioned in said center section, and said reflectance illumination fiber and said reflectance collection fiber being positioned in said outer section;
directing radiation to said sample with said fluorescence excitation fiber;
collecting radiation from said sample with said fluorescence collection fiber;
directing said radiation from said sample to an imaging spectrograph and a detector;
illuminating said sample with said reflectance illumination fiber;
collecting reflected light from said sample with said reflectance collection fiber; and
directing said reflected light from said sample to an imaging spectrograph and a detector.

32. The method of claim 31, wherein said collecting reflected light comprises collecting reflected light from a plurality of collection positions with a plurality of reflectance collection fibers.

33. The method of claim 31, wherein said collecting reflected light comprises collecting reflected light from said sample with a reflectance collection fiber defming a collection position at about 180 degrees relative to said reflectance illumination fiber.

34. The method of claim 31, wherein said collecting reflected light comprises collecting reflected light from said sample with a reflectance collection fiber defining a collection position at about 90 degrees relative to said reflectance illumination fiber.

35. The method of claim 31, wherein said collecting reflected light comprises collecting reflected light from said sample with a reflectance collection fiber defining a collection position at about 45 degrees relative to said reflectance illumination fiber.

36. The method of claim 31, wherein said sample comprises ovarian, head and neck, or cervical tissue.

37. The method of claim 31, further comprising analyzing spectral data from said detector to characterize said sample.

38. The method of claim 37, wherein said analyzing comprises pre-processing said data and reducing a dimension of said data using principal component analysis.

39. The method of claim 38, wherein said analyzing further comprises selecting one or more diagnostic principal components of said data and forming one or more algorithms.

40. The method of claim 40, wherein said analyzing further comprises forming one or more composite algorithms.

41. The method of claim 39, wherein said analyzing further comprises evaluating at least one of said algorithms using a cross-validation technique.

42. The method of claim 31, further comprising correcting said radiation collected with said fluorescence collection fiber using a measured background fluorescence.

43. The method of claim 31, wherein said center and outer sections are circular.

44. A method for combined fluorescence and spatially resolved reflectance spectroscopy of a sample, comprising:
providing a probe comprising a plurality of fluorescence excitation and collection fibers in spaced relation surrounded at least partially by a plurality of reflectance collection fibers in spaced relation with a reflectance illumination fiber;
directing radiation to said sample with a fluorescence excitation fiber;
collecting radiation from said sample with a fluorescence collection fiber;
directing said radiation from said sample to an imaging spectrograph and a detector;
illuminating said sample with a reflectance illumination fiber;
collecting reflected light at a plurality of collection positions from said sample with said plurality of reflectance collection fibers arranged in spaced relation;
directing said reflected light from said sample to an imaging spectrograph and a detector to produce spectral data;
pre-processing said data; and
reducing a dimension of said data using principal component analysis.

45. The method of claim 44, further comprising selecting one or more diagnostic principal components of said data and forming one or more algorithms.

46. The method of claim 45, further comprising forming one or more composite algorithms.

47. The method of claim 46, further comprising evaluating at least one of said algorithms using a cross-validation technique.

48. The method of claim 44, further comprising correcting said radiation collected with said fluorescence collection fiber using a measured background fluorescence.

* * * * *